US009707223B2

(12) United States Patent
Hunt et al.

(10) Patent No.: US 9,707,223 B2
(45) Date of Patent: Jul. 18, 2017

(54) HETEROARYL-KETONE FUSED AZADECALIN GLUCOCORTICOID RECEPTOR MODULATORS

(71) Applicant: Corcept Therapeutics, Inc., Menlo Park, CA (US)

(72) Inventors: Hazel Hunt, West Sussex (GB); Tony Johnson, Essex (GB); Nicholas Ray, Essex (GB); Iain Walters, Nottingham (GB)

(73) Assignee: CORCEPT THERAPEUTICS, INC., Menlo Park, CA (US)

( * ) Notice: Subject to any disclaimer, the term of this patent is extended or adjusted under 35 U.S.C. 154(b) by 0 days.

(21) Appl. No.: 15/013,218

(22) Filed: Feb. 2, 2016

(65) Prior Publication Data
US 2017/0020860 A1    Jan. 26, 2017

Related U.S. Application Data

(62) Division of application No. 14/487,347, filed on Sep. 16, 2014, now Pat. No. 9,273,047, which is a division of application No. 13/901,946, filed on May 24, 2013, now Pat. No. 8,859,774.

(60) Provisional application No. 61/781,269, filed on Mar. 14, 2013, provisional application No. 61/759,520, filed on Feb. 1, 2013, provisional application No. 61/715,907, filed on Oct. 19, 2012, provisional application No. 61/691,083, filed on Aug. 20, 2012, provisional application No. 61/651,669, filed on May 25, 2012.

(51) Int. Cl.
| | |
|---|---|
| A61K 31/56 | (2006.01) |
| A61K 31/4745 | (2006.01) |
| C07D 471/04 | (2006.01) |
| A61K 31/506 | (2006.01) |
| A61K 31/5377 | (2006.01) |
| A61K 31/497 | (2006.01) |
| C07D 498/04 | (2006.01) |
| A61K 31/5383 | (2006.01) |
| C07D 519/00 | (2006.01) |
| A61K 45/06 | (2006.01) |

(52) U.S. Cl.
CPC ........ *A61K 31/4745* (2013.01); *A61K 31/497* (2013.01); *A61K 31/506* (2013.01); *A61K 31/5377* (2013.01); *A61K 31/5383* (2013.01); *A61K 31/56* (2013.01); *A61K 45/06* (2013.01); *C07D 471/04* (2013.01); *C07D 498/04* (2013.01); *C07D 519/00* (2013.01)

(58) Field of Classification Search
CPC .................................................. A61K 31/4745
USPC ........................................................ 514/171
See application file for complete search history.

(56) References Cited

U.S. PATENT DOCUMENTS

| | | | |
|---|---|---|---|
| 4,963,558 A | 10/1990 | Hotten et al. | |
| 6,680,310 B2 * | 1/2004 | Belanoff ................ | A61K 31/00 |
| | | | 514/172 |
| 7,678,813 B2 | 3/2010 | Clark et al. | |
| 7,790,745 B2 | 9/2010 | Yang et al. | |
| 7,928,237 B2 | 4/2011 | Clark et al. | |
| 8,461,172 B2 | 6/2013 | Clark et al. | |
| 8,598,154 B2 | 12/2013 | Clark et al. | |
| 8,859,774 B2 | 10/2014 | Hunt et al. | |
| 8,969,557 B2 | 3/2015 | Harriman et al. | |
| 9,273,047 B2 * | 3/2016 | Hunt ................... | C07D 471/04 |
| 9,422,323 B2 | 8/2016 | Houpis et al. | |
| 2007/0281928 A1 | 12/2007 | Clark et al. | |
| 2008/0070950 A1 | 3/2008 | Benjamin et al. | |
| 2010/0179115 A1 | 7/2010 | Belanoff | |
| 2010/0292477 A1 | 11/2010 | Clark et al. | |
| 2011/0166110 A1 | 7/2011 | Clark et al. | |
| 2012/0220565 A1 | 8/2012 | Clark et al. | |
| 2013/0225633 A1 | 8/2013 | Hunt et al. | |

FOREIGN PATENT DOCUMENTS

| | | |
|---|---|---|
| EP | 0145121 A2 | 6/1985 |
| EP | 0375210 A1 | 6/1990 |
| JP | 9-505030 A | 5/1997 |
| JP | 2002-506032 A | 2/2002 |
| JP | 2002-544271 A | 12/2002 |
| WO | 94/04734 A1 | 2/1995 |
| WO | 99/45925 A1 | 9/1999 |
| WO | 00/69846 A1 | 11/2000 |
| WO | 03/015692 A2 | 2/2003 |
| WO | 03/061651 A1 | 7/2003 |
| WO | 2005/087769 A1 | 9/2005 |
| WO | 2012027702 A1 | 3/2012 |

OTHER PUBLICATIONS

EP13793417.0 , "Extended European Search Report", Jan. 4, 2016, 7 pages.
Clark, et al., "1H-Pyrazolo[3,4-g]hexahydro-isoquinolines as selective glucocorticoid receptor antagonists with high functional activity," 2008, *Bioorganic & Medical Chemistry Letters*, 18, pp. 1312-1317.
Wayne Genck. 2004, Chemical Processing.com.
JP Office Action from JP Application No. 2007-503030, dated Feb. 23, 2011, 8 pages.
International Search Report dated Jun. 15, 2005, issued in related International Application No. PCT/US2005/0008049, filed Mar. 9, 2005.
International Search Report and Written Opinion, dated Jul. 9, 2010, issued in related International Patent Application No. PCT/US2010/034382, filed May 11, 2010.

(Continued)

*Primary Examiner* — Nizal Chandrakumar
(74) *Attorney, Agent, or Firm* — Kilpatrick Townsend & Stockton LLP

(57) ABSTRACT

The present invention provides heteroaryl ketone fused azadecalin compounds and methods of using the compounds as glucocorticoid receptor modulators.

19 Claims, 2 Drawing Sheets

(56) References Cited

OTHER PUBLICATIONS

International Search Report and Written Opinion dated Jan. 30, 2012, issued in related International Patent Appln. No. PCT/US11/49408, filed Aug. 26, 2011.

International Search Report and Written Opinion dated Jun. 17, 2013, issued in related International Patent Appln. No. PCT/US13/27720 filed Feb. 26, 2013.

\* cited by examiner

HETEROARYL-KETONE FUSED AZADECALIN GLUCOCORTICOID RECEPTOR MODULATORS

CROSS-REFERENCES TO RELATED APPLICATIONS

This application is a divisional of U.S. application Ser. No. 14/487,347, filed Sep. 16, 2014, which is a divisional of U.S. application Ser. No. 13/901,946, filed May 24, 2013, which claims priority to U.S. Provisional Application No. 61/781,269, filed Mar. 14, 2013, 61/759,520, filed Feb. 1, 2013, 61/715,907, filed Oct. 19, 2012, 61/691,083, filed Aug. 20, 2012, and 61/651,669, filed May 25, 2012, each of which is incorporated in its entirety herein for all purposes.

BACKGROUND OF THE INVENTION

In most species, including man, the physiological glucocorticoid is cortisol (hydrocortisone). Glucocorticoids are secreted in response to ACTH (corticotropin), which shows both circadian rhythm variation and elevations in response to stress and food. Cortisol levels are responsive within minutes to many physical and psychological stresses, including trauma, surgery, exercise, anxiety and depression. Cortisol is a steroid and acts by binding to an intracellular, glucocorticoid receptor (GR). In man, glucocorticoid receptors are present in two forms: a ligand-binding GR-alpha of 777 amino acids; and, a GR-beta isoform which lacks the 50 carboxy terminal residues. Since these include the ligand binding domain, GR-beta is unable to bind ligand, is constitutively localized in the nucleus, and is transcriptionally inactive. The GR is also known as the GR-II receptor.

The biologic effects of cortisol, including those caused by hypercortisolemia, can be modulated at the GR level using receptor modulators, such as agonists, partial agonists and antagonists. Several different classes of agents are able to block the physiologic effects of GR-agonist binding. These antagonists include compositions which, by binding to GR, block the ability of an agonist to effectively bind to and/or activate the GR. One such known GR antagonist, mifepristone, has been found to be an effective anti-glucocorticoid agent in humans (Bertagna (1984) *J. Clin. Endocrinol. Metab.* 59:25). Mifepristone binds to the GR with high affinity, with a dissociation constant ($K_d$) of $10^{-9}$M (Cadepond (1997) *Annu. Rev. Med.* 48:129). What is needed in the art are new compositions and methods for modulating GR receptors. Surprisingly, the present invention meets these and other needs.

BRIEF SUMMARY OF THE INVENTION

The present invention provides many fused azadecalin compounds. In some embodiments, the present invention provides compounds having the structure of formula I:

(I)

wherein $R^1$ of formula I is a heteroaryl ring having from 5 to 6 ring members and from 1 to 4 heteroatoms which can each independently be N, O or S, optionally substituted with 1-4 groups which can each independently be $R^{1a}$. Each $R^{1a}$ of formula I can independently be hydrogen, $C_{1-6}$ alkyl, halogen, $C_{1-6}$ haloalkyl, $C_{1-6}$ alkoxy, $C_{1-6}$ haloalkoxy, —CN, N-oxide, $C_{3-8}$ cycloalkyl, or $C_{3-8}$ heterocycloalkyl. Ring J of formula I can be a cycloalkyl ring, a heterocycloalkyl ring, an aryl ring or a heteroaryl ring, wherein the heterocycloalkyl and heteroaryl rings have from 5 to 6 ring members and from 1 to 4 heteroatoms which can each independently be N, O or S. Each $R^2$ of formula I can independently be hydrogen, $C_{1-6}$ alkyl, halogen, $C_{1-6}$ haloalkyl, $C_{1-6}$ alkoxy, $C_{1-6}$ haloalkoxy, $C_{1-6}$ alkyl-$C_{1-6}$ alkoxy, —CN, —OH, —$NR^{2a}R^{2b}$, —$C(O)R^{2a}$, —$C(O)OR^{2a}$, —$C(O)NR^{2a}R^{2b}$, —$SR^{2a}$, —$S(O)R^{2a}$, —$S(O)_2R^{2a}$, $C_{3-8}$ cycloalkyl, and $C_{3-8}$ heterocycloalkyl, wherein the heterocycloalkyl groups are optionally substituted with 1-4 $R^{2c}$ groups. Alternatively, two $R^2$ groups linked to the same carbon can be combined to form an oxo group (=O). Alternatively, two $R^2$ groups can be combined to form a heterocycloalkyl ring having from 5 to 6 ring members and from 1 to 3 heteroatoms wherein each can independently be N, O or S, wherein the heterocycloalkyl ring is optionally substituted with from 1 to 3 $R^{2d}$ groups. $R^{2a}$ and $R^{2b}$ of formula I can each independently be hydrogen or $C_{1-6}$ alkyl. Each $R^{2c}$ can independently be hydrogen, halogen, hydroxy, $C_{1-6}$ alkoxy, $C_{1-6}$ haloalkoxy, —CN, or —$NR^{2a}R^{2b}$. Each $R^{2d}$ can independently be hydrogen or $C_{1-6}$ alkyl, or two $R^{2d}$ groups attached to the same ring atom can be combined to form (=O). $R^3$ of formula I can be phenyl or pyridyl, each optionally substituted with 1-4 $R^{3a}$ groups. Each $R^{3a}$ of formula I can independently be hydrogen, halogen, or $C_{1-6}$ haloalkyl. Subscript n of formula I can be an integer from 0 to 3. The compounds of formula I can also be the salts and isomers thereof.

In some embodiments, the present invention provides a pharmaceutical composition including a pharmaceutically acceptable excipient and the compound of formula I.

In some embodiments, the present invention provides a method of modulating a glucocorticoid receptor, the method including contacting a glucocorticoid receptor with a compound of formula I, thereby modulating the glucocorticoid receptor.

In some embodiments, the present invention provides a method of treating a disorder through modulating a glucocorticoid receptor, the method including administering to a subject in need of such treatment, a therapeutically effective amount of a compound of formula I, thereby treating the disorder.

In some embodiments, the present invention provides a method of treating a disorder through antagonizing a glucocorticoid receptor, the method including administering to a subject in need of such treatment, an effective amount of the compound of formula I, thereby treating the disorder.

DETAILED DESCRIPTION OF THE INVENTION

I. General

Figure 1:
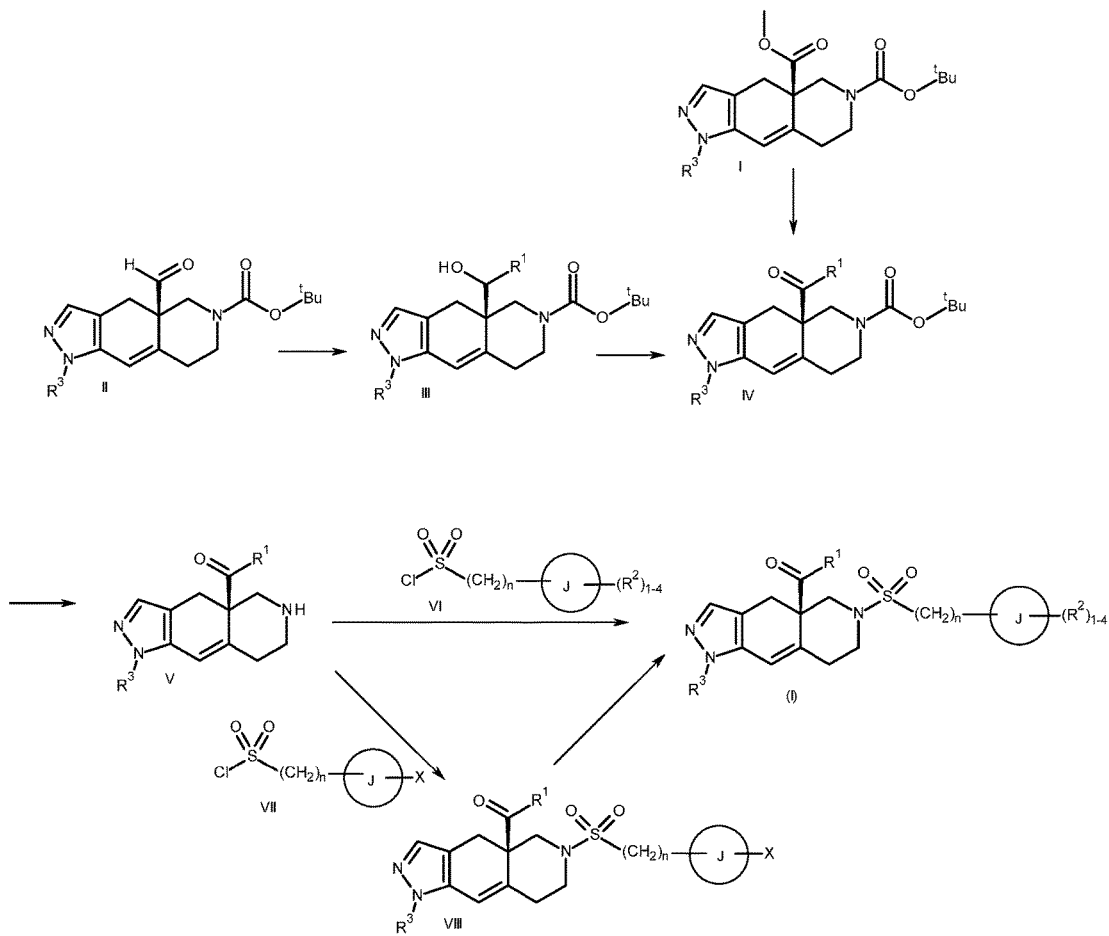
FIGS. 1 and 2 show various synthetic schemes for making the compounds of the present invention.

The present invention provides compounds capable of modulating a glucocorticoid receptor (GR) and thereby providing beneficial therapeutic effects. The compounds include heteroaryl ketone fused azadecalins. The present invention also provides methods of treating diseases and disorders by modulating a GR receptor with the compounds of the present invention.

II. Definitions

The abbreviations used herein have their conventional meaning within the chemical and biological arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

"Alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, decyl, etc.

"Alkylene" refers to a straight or branched, saturated, aliphatic radical having the number of carbon atoms indicated, and linking at least two other groups, i.e., a divalent hydrocarbon radical. The two moieties linked to the alkylene can be linked to the same atom or different atoms of the alkylene group. For instance, a straight chain alkylene can be the bivalent radical of —(CH$_2$)$_n$—, where n is 1, 2, 3, 4, 5 or 6. Representative alkylene groups include, but are not limited to, methylene, ethylene, propylene, isopropylene, butylene, isobutylene, sec-butylene, pentylene and hexylene.

"Alkoxy" refers to an alkyl group having an oxygen atom that connects the alkyl group to the point of attachment: alkyl-O—. As for the alkyl group, alkoxy groups can have any suitable number of carbon atoms, such as $C_{1-6}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc.

"Alkyl-Alkoxy" refers to a radical having an alkyl component and an alkoxy component, where the alkyl component links the alkoxy component to the point of attachment. The alkyl component is as defined above, except that the alkyl component is at least divalent, an alkylene, to link to the alkoxy component and to the point of attachment. The alkyl component can include any number of carbons, such as $C_{0-6}$, $C_{1-2}$, $C_{1-3}$, $C_{1-4}$, $C_{1-5}$, $C_{1-6}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. In some instances, the alkyl component can be absent. The alkoxy component is as defined above.

"Halogen" refers to fluorine, chlorine, bromine and iodine.

"Haloalkyl" refers to alkyl, as defined above, where some or all of the hydrogen atoms are replaced with halogen atoms. As for the alkyl group, haloalkyl groups can have any suitable number of carbon atoms, such as $C_{1-6}$. For example, haloalkyl includes trifluoromethyl, fluoromethyl, etc. In some instances, the term "perfluoro" can be used to define a compound or radical where all the hydrogens are replaced with fluorine. For example, perfluoromethane includes 1,1,1-trifluoromethyl.

"Haloalkoxy" refers to an alkoxy group where some or all of the hydrogen atoms are substituted with halogen atoms. As for the alkyl group, haloalkoxy groups can have any suitable number of carbon atoms, such as $C_{1-6}$. The alkoxy groups can be substituted with 1, 2, 3, or more halogens. When all the hydrogens are replaced with a halogen, for example by fluorine, the compounds are per-substituted, for example, perfluorinated. Haloalkoxy includes, but is not limited to, trifluoromethoxy, 2,2,2,-trifluoroethoxy, perfluoroethoxy, etc.

"Cycloalkyl" refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2] bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. When cycloalkyl is a saturated monocyclic $C_{3-8}$ cycloalkyl, exemplary groups include, but are not limited to cyclopropyl, cyclobutyl, cyclopentyl, cyclohexyl, cycloheptyl and cyclooctyl. When cycloalkyl is a saturated monocyclic $C_{3-6}$ cycloalkyl, exemplary groups include, but are not limited to cyclopropyl, cyclobutyl, cyclopentyl, and cyclohexyl.

"Alkyl-cycloalkyl" refers to a radical having an alkyl component and a cycloalkyl component, where the alkyl component links the cycloalkyl component to the point of attachment. The alkyl component is as defined above, except that the alkyl component is at least divalent, an alkylene, to link to the cycloalkyl component and to the point of attachment. In some instances, the alkyl component can be absent. The alkyl component can include any number of carbons, such as $C_{1-6}$, $C_{1-2}$, $C_{1-3}$, $C_{1-4}$, $C_{1-5}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. The cycloalkyl component is as defined within. Exemplary alkyl-cycloalkyl groups include, but are not limited to, methyl-cyclopropyl, methyl-cyclobutyl, methyl-cyclopentyl and methyl-cyclohexyl.

"Heterocycloalkyl" refers to a saturated ring system having from 3 to 12 ring members and from 1 to 4 heteroatoms of N, O and S. Additional heteroatoms can also be useful, including, but not limited to, B, Al, Si and P. The heteroatoms can also be oxidized, such as, but not limited to, —S(O)— and —S(O)$_2$—. Heterocycloalkyl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocycloalkyl groups, such as 1, 2, 3, or 4, or 1 to 2, 1 to 3, 1 to 4, 2 to 3, 2 to 4, or 3 to 4. The heterocycloalkyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxalidine, thiazolidine, isothiazolidine, dioxolane, dithiolane, morpholine, thiomorpholine, dioxane, or dithiane. The heterocycloalkyl groups can also be fused to aromatic or non-aromatic ring systems to form members including, but not limited to, indoline.

When heterocycloalkyl includes 3 to 8 ring members and 1 to 3 heteroatoms, representative members include, but are not limited to, pyrrolidine, piperidine, tetrahydrofuran, oxane, tetrahydrothiophene, thiane, pyrazolidine, imidazolidine, piperazine, oxazolidine, isoxazolidine, thiazolidine, isothiazolidine, morpholine, thiomorpholine, dioxane and dithiane. Heterocycloalkyl can also form a ring having 5 to 6 ring members and 1 to 2 heteroatoms, with representative members including, but not limited to, pyrrolidine, piperidine, tetrahydrofuran, tetrahydrothiophene, pyrazolidine, imidazolidine, piperazine, oxazolidine, isoxazolidine, thiazolidine, isothiazolidine, and morpholine.

"Aryl" refers to an aromatic ring system having any suitable number of ring atoms and any suitable number of rings. Aryl groups can include any suitable number of ring atoms, such as, 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be substituted or unsubstituted.

"Arylene" refers to an aryl group, as defined above, linking at least two other groups. The two moieties linked to the aryl are linked to different atoms of the aryl. Arylene groups can be substituted or unsubstituted.

"Heteroaryl" refers to a monocyclic or fused bicyclic or tricyclic aromatic ring assembly containing 5 to 16 ring atoms, where from 1 to 5 of the ring atoms are a heteroatom such as N, O or S. Additional heteroatoms can also be useful, including, but not limited to, B, Al, Si and P. The heteroatoms can also be oxidized, such as, but not limited to, —S(O)— and —S(O)$_2$—. Heteroaryl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. The heteroaryl group can include groups such as pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl groups can be substituted or unsubstituted.

The heteroaryl groups can be linked via any position on the ring. For example, pyrrole includes 1-, 2- and 3-pyrrole, pyridine includes 2-, 3- and 4-pyridine, imidazole includes 1-, 2-, 4- and 5-imidazole, pyrazole includes 1-, 3-, 4- and 5-pyrazole, triazole includes 1-, 4- and 5-triazole, tetrazole includes 1- and 5-tetrazole, pyrimidine includes 2-, 4-, 5- and 6-pyrimidine, pyridazine includes 3- and 4-pyridazine, 1,2,3-triazine includes 4- and 5-triazine, 1,2,4-triazine includes 3-, 5- and 6-triazine, 1,3,5-triazine includes 2-triazine, thiophene includes 2- and 3-thiophene, furan includes 2- and 3-furan, thiazole includes 2-, 4- and 5-thiazole, isothiazole includes 3-, 4- and 5-isothiazole, oxazole includes 2-, 4- and 5-oxazole, isoxazole includes 3-, 4- and 5-isoxazole, indole includes 1-, 2- and 3-indole, isoindole includes 1- and 2-isoindole, quinoline includes 2-, 3- and 4-quinoline, isoquinoline includes 1-, 3- and 4-isoquinoline, quinazoline includes 2- and 4-quinazoline, cinnoline includes 3- and 4-cinnoline, benzothiophene includes 2- and 3-benzothiophene, and benzofuran includes 2- and 3-benzofuran.

Some heteroaryl groups include those having from 5 to 10 ring members and from 1 to 3 ring atoms including N, O or S, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, isoxazole, indole, isoindole, quinoline, isoquinoline, quinoxaline, quinazoline, phthalazine, cinnoline, benzothiophene, and benzofuran. Other heteroaryl groups include those having from 5 to 8 ring members and from 1 to 3 heteroatoms, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, and isoxazole. Some other heteroaryl groups include those having from 9 to 12 ring members and from 1 to 3 heteroatoms, such as indole, isoindole, quinoline, isoquinoline, quinoxaline, quinazoline, phthalazine, cinnoline, benzothiophene, benzofuran and bipyridine. Still other heteroaryl groups include those having from 5 to 6 ring members and from 1 to 2 ring heteroatoms including N, O or S, such as pyrrole, pyridine, imidazole, pyrazole, pyrazine, pyrimidine, pyridazine, thiophene, furan, thiazole, isothiazole, oxazole, and isoxazole.

Some heteroaryl groups include from 5 to 10 ring members and only nitrogen heteroatoms, such as pyrrole, pyridine, imidazole, pyrazole, triazole, pyrazine, pyrimidine, pyridazine, triazine (1,2,3-, 1,2,4- and 1,3,5-isomers), indole, isoindole, quinoline, isoquinoline, quinoxaline, quinazoline, phthalazine, and cinnoline. Other heteroaryl groups include from 5 to 10 ring members and only oxygen heteroatoms, such as furan and benzofuran. Some other heteroaryl groups include from 5 to 10 ring members and only sulfur heteroatoms, such as thiophene and benzothiophene. Still other heteroaryl groups include from 5 to 10 ring members and at least two heteroatoms, such as imidazole, pyrazole, triazole, pyrazine, pyrimidine, pyridazine, triazine (1,2,3-, 1,2,4- and 1,3,5-isomers), thiazole, isothiazole, oxazole, isoxazole, quinoxaline, quinazoline, phthalazine, and cinnoline.

"Heteroarylene" refers to a heteroaryl group, as defined above, linking at least two other groups. The two moieties linked to the heteroaryl are linked to different atoms of the heteroaryl. Heteroarylene groups can be substituted or unsubstituted.

"Salt" refers to acid or base salts of the compounds used in the methods of the present invention. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

"Hydrate" refers to a compound that is complexed to at least one water molecule. The compounds of the present invention can be complexed with from 1 to 10 water molecules.

"Isomers" refers to compounds with the same chemical formula but which are structurally distinguishable.

"Tautomer" refers to one of two or more structural isomers which exist in equilibrium and which are readily converted from one form to another.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors and colors, and the like. One of skill in the art will recognize that other pharmaceutical excipients are useful in the present invention.

"Modulating a glucocorticoid receptor" refers to methods for adjusting the response of a glucocorticoid receptor towards glucocorticoids, glucocorticoid antagonists, agonists, and partial agonists. The methods include contacting a glucocorticoid receptor with an effective amount of either an antagonist, an agonist, or a partial agonist and detecting a change in GR activity.

"Glucocorticoid receptor" ("GR") refers to a family of intracellular receptors which specifically bind to cortisol and/or cortisol analogs (e.g. dexamethasone). The glucocorticoid receptor is also referred to as the cortisol receptor. The term includes isoforms of GR, recombinant GR and mutated GR.

"Glucocorticoid receptor antagonist" refers to any composition or compound which partially or completely inhibits (antagonizes) the binding of a glucocorticoid receptor (GR) agonist, such as cortisol, or cortisol analogs, synthetic or natural, to a GR. A "specific glucocorticoid receptor antagonist" refers to any composition or compound which inhibits any biological response associated with the binding of a GR to an agonist. By "specific," we intend the drug to preferentially bind to the GR rather than other nuclear receptors, such as mineralocorticoid receptor (MR) or progesterone receptor (PR).

"GR modulator" refers to compounds that agonize and/or antagonize the glucocorticoid receptor and are defined as compounds of Formula I below.

"Anti-inflammatory glucocorticosteroid" refers to a class of steroid hormones that bind to the glucocorticoid receptor and reduce inflammation. Examples of anti-inflammatory glucocorticosteroids include, but are not limited to, cortisol (the physiological glucocorticoid) as well as alclometasone, betamethasone, budesonide, ciclesonide, clobetasol, clocortolone, deprodone, desonide, dexamethasone, difluprednate, flunisolide, fluocinolone, fluticasone, halcinonide, halometasone, halopredone, hydrocortisone, loteprednol, methylprednisolone, mometasone, naflocort, oxazacort, paramethasone, prednicarbate, prednisolone, prednisone, triamcinolone, trimexolone, and ulobetasol. Glucocorticosteroids are part of a class of compounds called corticosteroids that also includes mineralocorticosteroids. The anti-inflammatory glucocorticosteroids of the present invention bind to glucocorticoid receptor and not to the mineralocorticoid receptor, also known as the glucocorticoid receptor I (GRI).

"GR induced transactivation" refers to gene expression induced by binding of a GR agonist to a glucocorticoid receptor. For example, GR induced transactivation can occur when an anti-inflammatory glucocorticosteroid, such as dexamethasone, binds to a glucocorticoid receptor. In the present invention, inhibition of GR induced transactivation occurs with at least 25% inhibition of the GR induced transactivation activity.

"GR induced transrepression" refers to inhibition of gene expression induced by binding of a GR agonist to a glucocorticoid receptor. The GR modulators of the present invention can have minimal effect on GR induced transrepression. In the present invention, substantially not inhibiting GR-induced transrepression is when GR-induced transrepression activity in the presence of the GR modulator is at least 50% of the activity observed in the absence of the GR modulator.

"Contacting" refers to the process of bringing into contact at least two distinct species such that they can react with one another or interact such that one has an effect on the other.

"Treat", "treating" and "treatment" refer to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation.

"Patient" or "subject in need thereof" refers to a living organism suffering from or prone to a condition that can be treated by administration of a pharmaceutical composition as provided herein. Non-limiting examples include humans, other mammals and other non-mammalian animals.

"Disorder" or "condition" refer to a state of being or health status of a patient or subject capable of being treated with the glucocorticoid receptor modulators of the present invention. Examples of disorders or conditions include, but are not limited to, obesity, hypertension, depression, anxiety, and Cushing's Syndrome.

"Antagonizing" refers to blocking the binding of an agonist at a receptor molecule or to inhibiting the signal produced by a receptor-agonist. A receptor antagonist blocks or dampens agonist-mediated responses.

"Therapeutically effective amount" refers to an amount of a conjugated functional agent or of a pharmaceutical composition useful for treating or ameliorating an identified disease or condition, or for exhibiting a detectable therapeutic or inhibitory effect. The effect can be detected by any assay method known in the art.

Description of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, or physiological conditions.

III. Compounds

The present invention provides many fused azadecalin compounds. In some embodiments, the present invention provides compounds having the structure of formula I:

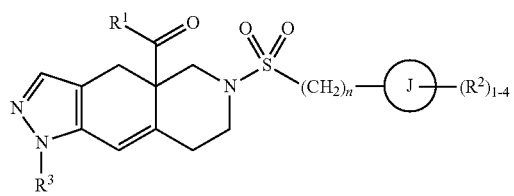

(I)

wherein $R^1$ of formula I is a heteroaryl ring having from 5 to 6 ring members and from 1 to 4 heteroatoms which can each independently be N, O or S, optionally substituted with 1-4 groups which can each independently be $R^{1a}$. Each $R^{1a}$ of formula I can independently be hydrogen, $C_{1-6}$ alkyl, halogen, $C_{1-6}$ haloalkyl, $C_{1-6}$ alkoxy, $C_{1-6}$ haloalkoxy, —CN, N-oxide, $C_{3-8}$ cycloalkyl, or $C_{3-8}$ heterocycloalkyl. Ring J of formula I can be a cycloalkyl ring, a heterocycloalkyl ring, an aryl ring or a heteroaryl ring, wherein the heterocycloalkyl and heteroaryl rings have from 5 to 6 ring members and from 1 to 4 heteroatoms which can each independently be N, O or S. Each $R^2$ of formula I can independently be hydrogen, $C_{1-6}$ alkyl, halogen, $C_{1-6}$ haloalkyl, $C_{1-6}$ alkoxy, $C_{1-6}$ haloalkoxy, $C_{1-6}$ alkyl-$C_{1-6}$ alkoxy, —CN, —OH, —$NR^{2a}R^{2b}$, —$C(O)R^{2a}$, —$C(O)OR^{2a}$, —$C(O)NR^{2a}R^{2b}$, —$SR^{2a}$, —$S(O)R^{2a}$, —$S(O)_2R^{2a}$, $C_{3-8}$ cycloalkyl, and $C_{3-8}$ heterocycloalkyl, wherein the heterocycloalkyl groups are optionally substituted with 1-4 $R^{2c}$ groups. Alternatively, two $R^2$ groups linked to the same carbon can be combined to form an oxo group (=O). Alternatively, two $R^2$ groups can be combined to form a heterocycloalkyl ring having from 5 to 6 ring members and from 1 to 3 heteroatoms wherein each can independently be N, O or S, wherein the heterocycloalkyl ring is optionally substituted with from 1 to 3 $R^{2d}$ groups. $R^{2a}$ and $R^{2b}$ of formula I can each independently be hydrogen or $C_{1-6}$ alkyl. Each $R^{2c}$ can independently be hydrogen, halogen, hydroxy, $C_{1-6}$ alkoxy, $C_{1-6}$ haloalkoxy, —CN, or —$NR^{2a}R^{2b}$. Each $R^{2d}$ can independently be hydrogen or $C_{1-6}$ alkyl, or two $R^{2d}$ groups attached to the same ring atom can be combined to form (=O). $R^3$ of formula I can be phenyl or pyridyl, each optionally substituted with 1-4 $R^{3a}$ groups. Each $R^{3a}$ of formula I can independently be hydrogen, halogen, or $C_{1-6}$ haloalkyl. Subscript n of formula I can be an integer from 0 to 3. The compounds of formula I can also be the salts and isomers thereof.

In some embodiments, wherein $R^1$ of formula I can be a heteroaryl ring having from 5 to 6 ring members and from 1 to 4 heteroatoms which can each independently be N, O or S, optionally substituted with 1-4 groups which can each independently be $R^{1a}$. Each $R^{1a}$ of formula I can independently be hydrogen, $C_{1-6}$ alkyl, halogen, $C_{1-6}$ haloalkyl, $C_{1-6}$ alkoxy, $C_{1-6}$ haloalkoxy, —CN, $C_{3-8}$ cycloalkyl, or $C_{3-8}$ heterocycloalkyl. Ring J of formula I can be a cycloalkyl ring, a heterocycloalkyl ring, an aryl ring or a heteroaryl ring, wherein the heterocycloalkyl and heteroaryl rings have from 5 to 6 ring members and from 1 to 3 heteroatoms which can each independently be N, O or S. Each $R^2$ of formula I can independently be hydrogen, $C_{1-6}$ alkyl, halogen, $C_{1-6}$ haloalkyl, $C_{1-6}$ alkoxy, $C_{1-6}$ haloalkoxy, —CN, —$NR^{2a}R^{2b}$, $C_{3-8}$ cycloalkyl, or $C_{3-8}$ heterocycloalkyl, wherein the heterocycloalkyl groups are optionally substituted with 1-4 $R^{2c}$ groups. $R^{2a}$ and $R^{2b}$ of formula I can each independently be hydrogen or $C_{1-6}$ alkyl. Each $R^{2c}$ can independently be hydrogen, halogen, hydroxy, $C_{1-6}$ alkoxy, $C_{1-6}$ haloalkoxy, —CN, or —$NR^{2a}R^{2b}$. $R^3$ of formula I can be phenyl or pyridyl, each optionally substituted with 1-4 $R^{3a}$ groups. Each $R^{3a}$ of formula I can independently be hydrogen, halogen, or $C_{1-6}$ haloalkyl. Subscript n of formula I can be an integer from 0 to 3. The compounds of formula I can also be the salts and isomers thereof.

In some embodiments, $R^1$ can be a heteroaryl ring having from 5 to 6 ring members and from 1 to 3 heteroatoms which each can independently be N, O or S, optionally substituted with 1-4 groups which can each independently be $R^{1a}$. Each $R^{1a}$ can independently be hydrogen or $C_{1-6}$ alkyl. Ring J can be tetrahydrofuran, phenyl or pyridyl. Each $R^2$ can independently be hydrogen, $C_{1-6}$ alkyl, halogen, $C_{1-6}$ haloalkyl, $C_{1-6}$ alkoxy, $C_{1-6}$ haloalkoxy, —CN, —$NR^{2a}R^{2b}$, $C_{3-8}$ cycloalkyl, or $C_{3-8}$ heterocycloalkyl. $R^{2a}$ and $R^{2b}$ can each independently be hydrogen or $C_{1-6}$ alkyl. $R^3$ can be phenyl or pyridyl. $R^{3a}$ can be F. Subscript n can be 0 or 1. In some embodiments, each $R^{1a}$ can independently be hydrogen, $C_{1-6}$ alkyl, $C_{1-6}$ haloalkyl, or $C_{1-6}$ alkoxy.

In some embodiments, $R^1$ can be a heteroaryl ring having from 5 to 6 ring members and from 1 to 3 heteroatoms which can each independently be N, O or S, optionally substituted with 1-4 groups which can each independently be $R^{1a}$. Each $R^{1a}$ can independently be hydrogen or $C_{1-6}$ alkyl. Ring J can be phenyl or pyridyl. Each $R^2$ can independently be hydrogen, halogen, $C_{1-6}$ haloalkyl, —CN or $C_{5-6}$ heterocycloalkyl. $R^3$ can be phenyl or pyridyl. $R^{3a}$ can be F. In some embodiments, each $R^{1a}$ can independently be hydrogen, $C_{1-6}$ alkyl, $C_{1-6}$ haloalkyl, or $C_{1-6}$ alkoxy.

The compounds of the present invention include at least one stereogenic center at the bridgehead carbon. Accordingly, the compounds can include a mixture of isomers, including enantiomers in a racemic mixture, or in enantiomerically pure mixtures that are substantially the R- or S-isomer. In some embodiments, the compounds of formula I can have the following structure:

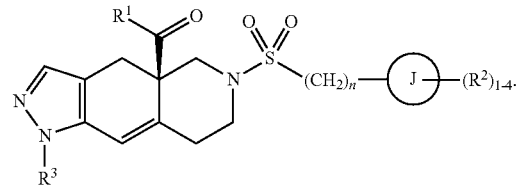

Any suitable heteroaryl can be used for $R^1$ in the compounds of the present invention, as defined in the definitions above. In some embodiments, the heteroaryl of $R^1$ can have from 5 to 6 ring members and from 1 to 4 heteroatoms which can each independently be N, O or S, optionally substituted with 1-4 groups which can each independently be $R^{1a}$. In some embodiments, the heteroaryl of $R^1$ can be pyrrole, pyrazole, imidazole, triazole, tetrazole, furan, oxazole, isoxazole, oxadiazole, thiophene, thiazole, isothiazole, thiadiazole, pyridine, pyrazine, pyrimidine, or pyridazine. In some embodiments, the heteroaryl of $R^1$ can be 2-pyrrole, 3-pyrrole, 1-pyrazole, 3-pyrazole, 4-pyrazole, 5-pyrazole, 2-imidazole, 4-imidazole, 5-imidazole, 1,2,3-triazol-4-yl, 1,2,3,-triazol-5-yl, 1,2,4-triazol-3-yl, 1,2,4-triazol-5-yl, 1,2,3,4-tetrazol-1-yl, 1,2,3,4,tetrazol-5-yl, 2-furan, 3-furan, 2-oxazole, 4-oxazole, 5-oxazole, 3-isoxazole, 4-isooxazole, 5-isooxazole, 1,2,4-oxadiazol-3-yl, 1,2,4-oxadiazol-5-yl, 1,2,5-oxadiazol-3-yl, 1,3,4-oxadiazol-2-yl, 2-thiophene, 3-thiophene, 2-thiazole, 4-thiazole, 5-thiazole, 3-isothiazole, 4-isothiazole, 5-isothiazole, 1,2,3-thiadiazol-4-yl, 1,2,3-thiadiazol-5-yl, 1,2,4-thiadiazol-3-yl, 1,2,4-thiadiazol-5-yl, 1,2,5-thiadiazol-3-yl, 1,3,4-thiadiazol-2-yl, 2-pyridine, 3-pyridine, 4-pyridine, pyrazine, 2-pyrimidine, 4-pyrimidine, 5-pyrimidine, 6-pyrimidine, 3-pyridazine, 4-pyridazine, 5-pyridazine, or 6-pyridazine. In some embodiments, the heteroaryl of $R^1$ can be pyrazole, imidazole, triazole, furan, oxazole, oxadiazole, thiophene, thiazole, pyridine, pyrazine or pyrimidine. In some embodiments, the heteroaryl of $R^1$ can be imidazole, furan, oxazole, oxadiazole, thiophene, thiazole, or pyridine. In some embodiments, the heteroaryl of $R^1$ can be 1-pyrazole, 3-pyrazole, 4-pyrazole, 5-pyrazole, 2-imidazole, 4-imidazole, 5-imidazole, 1,2,3-triazol-4-yl, 1,2,3,-triazol-5-yl, 1,2,4-triazol-3-yl, 1,2,4-triazol-5-yl, 2-furan, 3-furan, 2-oxazole, 4-oxazole, 5-oxazole, 1,2,4-oxadiazol-3-yl, 1,2,4-oxadiazol-5-yl, 1,2,5-oxadiazol-3-yl, 1,3,4-oxadiazol-2-yl, 2-thiophene, 3-thiophene, 2-thiazole, 4-thiazole, 5-thiazole, 2-pyridine, 3-pyridine, 4-pyridine, pyrazine, 2-pyrimidine, 4-pyrimidine, 5-pyrimidine, or 6-pyrimidine. In some embodiments, the heteroaryl of $R^1$ can be 3-pyrazole, 4-pyrazole, 2-imidazole, 1,2,4-triazol-5-yl, 2-furan, 2-oxazole, 4-oxazole, 1,3,4-oxadiazol-2-yl, 2-thiophene, 2-thiazole, 4-thiazole, 5-thiazole, 2-pyridine, 3-pyridine, 4-pyridine, pyrazine, or 2-pyrimidine. In some embodiments, the heteroaryl of $R^1$ can be 2-imidazole, 4-imidazole, 5-imidazole, 2-furan, 3-furan, 2-oxazole, 4-oxazole, 5-oxazole, 1,2,4-oxadiazol-3-yl, 1,2,4-oxadiazol-5-yl, 1,2,5-oxadiazol-3-yl, 1,3,4-oxadiazol-2-yl, 2-thiophene, 3-thiophene, 2-thiazole, 4-thiazole, 5-thiazole, 2-pyridine, 3-pyridine, or 4-pyridine.

In some embodiments, the heteroaryl of $R^1$ can be optionally substituted with 1-4 groups which can each independently be $R^{1a}$. In some embodiments, each $R^{1a}$ can independently be hydrogen, $C_{1-6}$ alkyl, halogen, $C_{1-6}$ haloalkyl, $C_{1-6}$ alkoxy, $C_{1-6}$ haloalkoxy, —CN, N-oxide, $C_{3-8}$ cycloalkyl, or $C_{3-8}$ heterocycloalkyl. In some embodiments, each $R^{1a}$ can independently be hydrogen, $C_{1-6}$ alkyl, $C_{1-6}$ haloalkyl, $C_{1-6}$ alkoxy or $C_{3-8}$ heterocycloalkyl. In some embodiments, each $R^{1a}$ can independently be hydrogen, $C_{1-6}$ alkyl, $C_{1-6}$ haloalkyl, or $C_{1-6}$ alkoxy. In some embodiments, each $R^{1a}$ can independently be hydrogen, $C_{1-6}$ alkyl, or $C_{1-6}$ haloalkyl. In some embodiments, each $R^{1a}$ can independently be hydrogen or $C_{1-6}$ alkyl. The alkyl of $R^{1a}$ can be any suitable alkyl group, such as methyl, ethyl, propyl, butyl, pentyl, and hexyl, among others. In some embodiments, each $R^{1a}$ can independently be hydrogen, methyl, ethyl, trifluoromethyl, methoxy, or pyrrolidinyl. In some embodiments, each $R^{1a}$ can independently be hydrogen, methyl, ethyl, trifluoromethyl, or methoxy. In some embodiments, each $R^{1a}$ can independently be hydrogen or methyl.

Ring J of formula I can be any suitable ring. In some embodiments, ring J of formula I can be a cycloalkyl ring, a heterocycloalkyl ring, an aryl ring or a heteroaryl ring, wherein the heterocycloalkyl and heteroaryl rings can have from 5 to 6 ring members and from 1 to 4 heteroatoms which can each independently be N, O or S. In some embodiments, ring J can be heterocycloalkyl, aryl or heteroaryl. Suitable heterocycloalkyl groups include those defined in the definitions above. In some embodiments, the heterocycloalkyl can tetrahydrofuran. Suitable aryl groups for ring J include those defined in the definitions above. Representative aryl groups include phenyl and naphthyl. In some embodiments, the aryl group of ring J can be phenyl. Suitable heteroaryl groups for ring J include those defined in the definitions above. Representative heteroaryl groups include pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. In some embodiments, the heteroaryl can be pyridyl or thiophene. In some embodiments, ring J can be aryl or heteroaryl. In some embodiments, ring J can be phenyl, pyridine, imidazole, pyrazole, triazole, tetrazole, thiadiazole, isothiazole, isoxazole, cyclohexyl, tetrahydrofuran and tetrahydro-2H-pyran. In some embodiments, ring J can be phenyl, pyridine, or pyrazole. In some embodiments, ring J can be tetrahydrofuran, phenyl, pyridyl or thiophene. In some embodiments, ring J can be phenyl. In some embodiments, ring J can be pyridyl. In some embodiments, ring J can be pyrazole.

In some embodiments, the heteroaryl of $R^1$ can be 3-pyrazole, 4-pyrazole, 2-imidazole, 1,2,4-triazol-5-yl, 2-furan, 2-oxazole, 4-oxazole, 1,3,4-oxadiazol-2-yl, 2-thiophene, 2-thiazole, 4-thiazole, 5-thiazole, 2-pyridine, 3-pyridine, 4-pyridine, pyrazine, or 2-pyrimidine, and Ring J can be 2-pyridine, 3-pyridine, 4-pyridine, imidazol-2-yl, imidazol-4-yl, imidazol-5-yl, pyrazol-3-yl, pyrazol-4-yl, pyrazol-5-yl, 1,2,3-triazol-4-yl, 1,2,3-triazol-5-yl, isoxazol-4-yl, cyclohexyl, tetrahydrofuran or tetrahydro-2H-pyran.

Ring J of formula I can be substituted with any suitable number of $R^2$ groups. Each $R^2$ of formula I can independently be hydrogen, $C_{1-6}$ alkyl, halogen, $C_{1-6}$ haloalkyl, $C_{1-6}$ alkoxy, $C_{1-6}$ haloalkoxy, $C_{1-6}$ alkyl-$C_{1-6}$ alkoxy, —CN, —OH, —$NR^{2a}R^{2b}$, —$C(O)R^{2a}$, —$C(O)OR^{2a}$, —$C(O)NR^{2a}R^{2b}$, —$SR^{2a}$, —$S(O)R^{2a}$, —$S(O)_2R^{2a}$, $C_{3-8}$ cycloalkyl, or $C_{3-8}$ heterocycloalkyl, wherein the heterocycloalkyl groups are optionally substituted with 1-4 $R^{2c}$ groups. In some embodiments, each $R^2$ of formula I can independently be hydrogen, $C_{1-6}$ alkyl, halogen, $C_{1-6}$ haloalkyl, $C_{1-6}$ alkoxy, $C_{1-6}$ haloalkoxy, $C_{1-6}$ alkyl-$C_{1-6}$ alkoxy, —CN, —$NR^{2a}R^{2b}$, —$C(O)OR^{2a}$, —$S(O)_2R^{2a}$, $C_{3-8}$ cycloalkyl, or $C_{3-8}$ heterocycloalkyl, wherein the heterocycloalkyl group has 5-6 ring members and 1 to 2 heteroatoms. In some embodiments, each $R^2$ of formula I can independently be hydrogen, $C_{1-6}$ alkyl, halogen, $C_{1-6}$ haloalkyl, $C_{1-6}$ alkoxy, $C_{1-6}$ haloalkoxy, $C_{1-6}$ alkyl-$C_{1-6}$ alkoxy, —CN, —$NR^{2a}R^{2b}$, —$S(O)_2R^{2a}$, $C_{3-8}$ cycloalkyl, or $C_{3-8}$ heterocycloalkyl, wherein the heterocycloalkyl group has 5-6 ring members and 1 to 2 heteroatoms. Each $R^2$ of formula I can independently be hydrogen, $C_{1-6}$ alkyl, halogen, $C_{1-6}$ haloalkyl, $C_{1-6}$ alkoxy, $C_{1-6}$ haloalkoxy, —CN, —$NR^{2a}R^{2b}$, $C_{3-8}$ cycloalkyl, or $C_{3-8}$ heterocycloalkyl, wherein the heterocycloalkyl groups are optionally substituted with 1-4 $R^{2c}$ groups. In some embodiments, each $R^2$ can independently be hydrogen, halogen, $C_{1-6}$ haloalkyl, —CN, or heterocycloalkyl having 5-6 ring members and 1 to 2 heteroatoms wherein at least one heteroatom is N. Heterocycloalkyl groups having 5-6 ring members and 1 to 2 heteroatoms with at least one nitrogen include, but are not limited to, pyrrolidine, piperidine, pyrazolidine, imidazolidine, piperazine (1,2-, 1,3- and 1,4-isomers), oxazolidine, isoxalidine, thiazolidine, isothiazolidine, morpholine, or thiomorpholine. In some embodiments, each $R^2$ can independently be hydrogen, methyl, ethyl, propyl, isopropyl, F, Cl, —$CF_3$, $CH_2OMe$, OMe, $OCHF_2$, —CN, —$NMe_2$, —C(O)OH, —$C(O)NMe_2$, —$S(O)_2Me$, pyrrolidine, piperidine or morpholine. In some embodiments, each $R^2$ can independently be hydrogen, methyl, ethyl, F, Cl, —$CF_3$, OMe, $OCHF_2$, —CN, —$NMe_2$, —$S(O)_2Me$, pyrrolidine, piperidine or morpholine. In some embodiments, each $R^2$ can independently be hydrogen, F, —CF$_3$, —CN, pyrrolidine, piperidine or morpholine. In some embodiments, R$^2$ can be —CF$_3$. Ring J can be substituted with 1, 2, 3 or 4 R$^2$ groups. In some embodiments, ring J is substituted with 1 R$^2$ group.

Several R$^2$ groups can be further substituted with one or more of R$^{2a}$, R$^{2b}$ and R$^{2c}$. R$^{2a}$ and R$^{2b}$ can each independently be hydrogen or C$_{1-6}$ alkyl. Each R$^{2c}$ can independently be hydrogen, halogen, hydroxy, C$_{1-6}$ alkoxy, C$_{1-6}$ haloalkoxy, —CN, or —NR$^{2a}$R$^{2b}$.

R$^3$ of formula I can be phenyl or pyridyl, each optionally substituted with 1-4 R$^{3a}$ groups. In some embodiments, R$^3$ can be substituted with 1 R$^{3a}$ group. Each R$^{3a}$ group can independently be hydrogen, halogen, or C$_{1-6}$ haloalkyl. In some embodiments, each R$^{3a}$ group can independently be H, F, Cl, Br, or —CF$_3$. In some embodiments, each R$^{3a}$ group can independently be F or —CF$_3$. In some embodiments, R$^{3a}$ can be F. The R$^{3a}$ group can be present at any position on the phenyl or pyridyl ring to form a 2-, 3- or 4-substituted ring. In some embodiments, the phenyl or pyridyl ring is substituted at the 4-position. In some embodiments, R$^3$ can be 4-F-phenyl.

When R$^3$ of formula I is 4-F-phenyl, the compounds of the present invention can have the following structure:

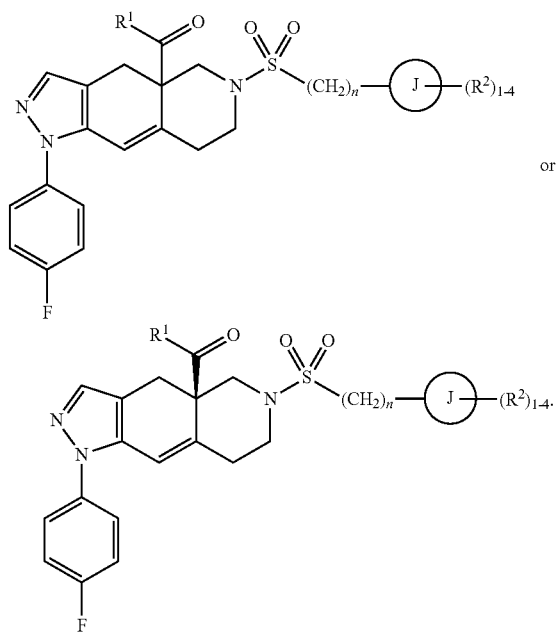

Alternatively, the compounds of the present invention can have the following structure:

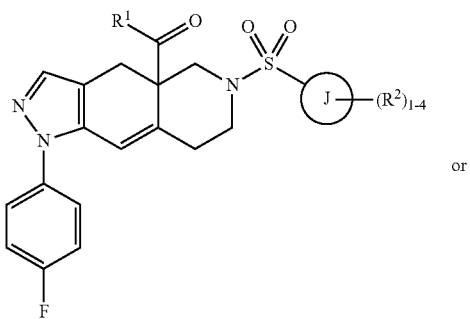

or

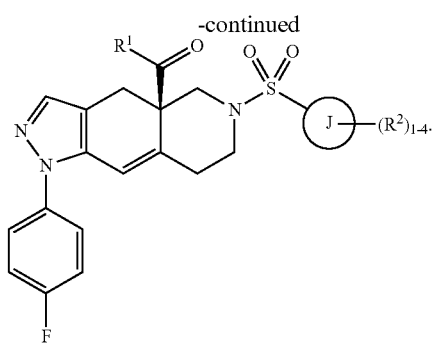

Subscript n of formula I can be an integer from 0 to 3. In some embodiments, subscript n can be 0, 1, 2, or 3. In some embodiments, subscript n can be 0 or 1. In some embodiments, subscript n can be 0. In some embodiments, subscript n can be 1.

In some embodiments, the compound of formula I can be:

Intermediate 13. (R)-(6-((6-chloropyridin-3-yl)sulfonyl)-1-(4-fluorophenyl)-4,4a,5,6,7,8-hexahydro-1H-pyrazolo[3,4-g]isoquinolin-4a-yl)(pyridin-2-yl)methanone, Intermediate 14. (R)-(6-((6-chloropyridin-3-yl)sulfonyl)-1-(4-fluorophenyl)-4,4a,5,6,7,8-hexahydro-1H-pyrazolo[3,4-g]isoquinolin-4a-yl)(thiazol-2-yl)methanone, Example 1. (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(pyridin-2-yl)methanone, Example 1A. (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(1-methyl-1H-imidazol-2-yl)methanone, Example 1B. (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(pyridin-3-yl)methanone, Example 1C. (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(thiazol-2-yl)methanone, Example 1D. (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(5-methyl-1,3,4-oxadiazol-2-yl)methanone, Example 1E. (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(oxazol-4-yl)methanone, Example 1F. (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(oxazol-2-yl)methanone, Example 1G. (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(furan-2-yl)methanone, Example 1H. (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(thiophen-2-yl)methanone, Example 1I. (R)-(1-(4-fluorophenyl)-6-(m-tolylsulfonyl)-4,4a,5,6,7,8-hexahydro-1H-pyrazolo[3,4-g]isoquinolin-4a-yl)(oxazol-2-yl)methanone, Example 1J. (R)-(1-(4-fluorophenyl)-6-(m-tolylsulfonyl)-4,4a,5,6,7,8-hexahydro-1H-pyrazolo[3,4-g]isoquinolin-4a-yl)(pyrimidin-2-yl)methanone, Example 1K. (R)-(6-((3,5-difluorophenyl)sulfonyl)-1-(4-fluorophenyl)-4,4a,5,6,7,8-hexahydro-1H-pyrazolo[3,4-g]isoquinolin-4a-yl)(4-methoxypyridin-2-yl)methanone, Example 1L. (R)-(4-ethylpyridin-2-yl)(1-(4-fluorophenyl)-6-((3,4,5-trifluorophenyl)sulfonyl)-4,4a,5,6,7,8-hexahydro-1H-pyrazolo[3,4-g]isoquinolin-4a-yl)methanone, Example 1M. (R)-(1-(4-fluorophenyl)-6-((3,4,5-trifluorophenyl)sulfonyl)-4,4a,5,6,7,8-hexahydro-1H-pyrazolo[3,4-g]isoquinolin-4a-yl)(4-methoxypyridin-2-yl)methanone, Example 2. (R)-(1-(4-fluorophenyl)-6-((4-fluorophenyl)sulfonyl)-4,4a,5,6,7,8-hexahydro-1H-pyrazolo[3,4-g]isoquinolin-4a-yl)(pyridin-2-yl)methanone, Example 2A. (R)-(6-((3-fluorobenzyl)sulfonyl)-1-(4-fluorophenyl)-4,4a,5,6,7,8-hexahydro-1H-pyrazolo[3,4-g]isoquinolin-4a-yl)(thiazol-2-yl)methanone, Example 2B. ((4aR)-1-(4-fluorophenyl)-6-(((((R/S)-tetrahydrofuran-2-yl)methyl)sulfonyl)-4,4a,5,6,7,8-hexahydro-1H-pyrazolo[3,4-g]isoquinolin-4a-yl)(thiazol-2-yl)methanone, Example 2C. (R)-(1-(4-fluorophenyl)-6-(o-tolylsulfonyl)-4,4a,5,6,7,8-hexahydro-1H-pyrazolo[3,4-g]isoquinolin-4a-yl)(pyridin-2-yl)methanone, Example 2D. (R)-(6-((4-ethylphenyl)sulfonyl)-1-(4-fluorophenyl)-4,4a,5,6,7,8-hexahydro-1H-pyrazolo[3,4-g]isoquinolin-4a-yl)(pyridin-2-yl)methanone, Example 2E. (R)-(1-(4-fluorophenyl)-6-(m-tolylsulfonyl)-4,4a,5,6,7,8-hexahydro-1H-pyrazolo[3,4-g]isoquinolin-4a-yl)(pyridin-2-yl)methanone, Example 2F. (R)-(6-((3-chlorophenyl)sulfonyl)-1-(4-fluorophenyl)-4,4a,5,6,7,8-hexahydro-1H-pyrazolo[3,4-g]isoquinolin-4a-yl)(pyridin-2-yl)methanone, Example 2G. (R)-(1-(4-fluorophenyl)-6-((3-methoxyphenyl)sulfonyl)-4,4a,5,6,7,8-hexahydro-1H-pyrazolo[3,4-g]isoquinolin-4a-yl)(pyridin-2-yl)methanone, Example 2H. (R)-(6-((4-chloro-3-fluorophenyl)sulfonyl)-1-(4-fluorophenyl)-4,4a,5,6,7,8-hexahydro-1H-pyrazolo[3,4-g]isoquinolin-4a-yl)(pyridin-2-yl)methanone, Example 2I. (R)-(1-(4-fluorophenyl)-6-((4-methoxyphenyl)sulfonyl)-4,4a,5,6,7,8-hexahydro-1H-pyrazolo[3,4-g]isoquinolin-4a-yl)(pyridin-2-yl)methanone, Example 2J. (R)-(6-((3-fluoro-4-methylphenyl)sulfonyl)-1-(4-fluorophenyl)-4,4a,5,6,7,8-hexahydro-1H-pyrazolo[3,4-g]isoquinolin-4a-yl)(pyridin-2-yl)methanone, Example 2K. (R)-(1-(4-fluorophenyl)-6-(phenylsulfonyl)-4,4a,5,6,7,8-hexahydro-1H-pyrazolo[3,4-g]isoquinolin-4a-yl)(pyridin-2-yl)methanone, Example 2L. (R)-(1-(4-fluorophenyl)-6-((2-fluorophenyl)sulfonyl)-4,4a,5,6,7,8-hexahydro-1H-pyrazolo[3,4-g]isoquinolin-4a-yl)(pyridin-2-yl)methanone, Example 2M. (R)-(1-(4-fluorophenyl)-6-((1-methyl-1H-pyrazol-4-yl)sulfonyl)-4,4a,5,6,7,8-hexahydro-1H-pyrazolo[3,4-g]isoquinolin-4a-yl)(pyridin-2-yl)methanone, Example 2N. (R)-(1-(4-fluorophenyl)-6-((6-(trifluoromethyl)pyridin-3-yl)sulfonyl)-4,4a,5,6,7,8-hexahydro-1H-pyrazolo[3,4-g]isoquinolin-4a-yl)(pyridin-2-yl)methanone, Example 2O. (R)-(1-(4-fluorophenyl)-6-tosyl-4,4a,5,6,7,8-hexahydro-1H-pyrazolo[3,4-g]isoquinolin-4a-yl)(pyridin-2-yl)methanone, Example 2P. (R)-(6-((4-fluoro-3-(trifluoromethyl)phenyl)sulfonyl)-1-(4-fluorophenyl)-4,4a,5,6,7,8-hexahydro-1H-pyrazolo[3,4-g]isoquinolin-4a-yl)(pyridin-2-yl)methanone, Example 2Q. (R)-4-((1-(4-fluorophenyl)-4a-picolinoyl-4a,5,7,8-tetrahydro-1H-pyrazolo[3,4-g]isoquinolin-6(4H)-yl)sulfonyl)benzonitrile, Example 2R. (R)-(1-(4-fluorophenyl)-6-((6-methoxypyridin-3-yl)sulfonyl)-4,4a,5,6,7,8-hexahydro-1H-pyrazolo[3,4-g]isoquinolin-4a-yl)(pyridin-2-yl)methanone, Example 2S. (R)-(1-(4-fluorophenyl)-6-((tetrahydro-2H-pyran-4-yl)sulfonyl)-4,4a,5,6,7,8-hexahydro-1H-pyrazolo[3,4-g]isoquinolin-4a-yl)(pyridin-2-yl)methanone, Example 2T. (R)-(6-(cyclohexylsulfonyl)-1-(4-fluorophenyl)-4,4a,5,6,7,8-hexahydro-1H-pyrazolo[3,4-g]isoquinolin-4a-yl)(pyridin-2-yl)methanone, Example 2U. (R)-(6-((1-ethyl-1H-pyrazol-5-yl)sulfonyl)-1-(4-fluorophenyl)-4,4a,5,6,7,8-hexahydro-1H-pyrazolo[3,4-g]isoquinolin-4a-yl)(4-(trifluoromethyl)pyridin-2-yl)methanone, Example 2V. (R)-(6-((3,5-dimethyl-1H-pyrazol-4-yl)sulfonyl)-1-(4-fluorophenyl)-4,4a,5,6,7,8-hexahydro-1H-pyrazolo[3,4-g]isoquinolin-4a-yl)(4-(trifluoromethyl)pyridin-2-yl)methanone, Example 2W. (R)-(6-((1H-imidazol-4-yl)sulfonyl)-1-(4-fluorophenyl)-4,4a,5,6,7,8-hexahydro-1H-pyrazolo[3,4-g]isoquinolin-4a-yl)(4-(trifluoromethyl)pyridin-2-yl)methanone, Example 3. (R)-(1-(4-fluorophenyl)-6-((6-morpholinopyridin-3-yl)sulfonyl)-4,4a,5,6,7,8-hexahydro-1H-pyrazolo[3,4-g]isoquinolin-4a-yl)(pyridin-2-yl)methanone, Example 4. (R)-(1-(4-fluorophenyl)-6-((6-(pyrrolidin-1-yl)pyridin-3-yl)sulfonyl)-4,4a,5,6,7,8-hexahydro-1H-pyrazolo[3,4-g]isoquinolin-4a-yl)(thiazol-2-yl)methanone, Example 5. (R)-(1-(4-fluorophenyl)-6-((4-fluorophenyl)sulfonyl)-4,4a,5,6,7,8-hexahydro-1H-pyrazolo[3,4-g]isoquinolin-4a-yl)(thiazol-2-yl)methanone, Example 5A. (R)-(1-(4-fluorophenyl)-6-((3-fluorophenyl)sulfonyl)-4,4a,5,6,7,8-hexahydro-1H-pyrazolo[3,4-g]isoquinolin-4a-yl)(thiazol-2-yl)methanone, Example 5B. (R)-4-(((1-(4-fluorophenyl)-4a-(thiazole-2-carbonyl)-4a,5,7,8-tetrahydro-1H-pyrazolo[3,4-g]isoquinolin-6(4H)-yl)sulfonyl)methyl)benzonitrile, Example 5C. (R)-(1-(4-fluorophenyl)-6-((3-(trifluoromethyl)phenyl)sulfonyl)-4,4a,5,6,7,8-hexahydro-1H-pyrazolo[3,4-g]isoquinolin-4a-yl)methanone, Example 5D. (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(1-methyl-1H-1,2,4-triazol-5-yl)methanone, Example 5E. (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(pyrazin-2-yl)methanone, Example 5F. (R)-(1-(4-fluorophenyl)-6-((5-fluoropyridin-3-yl)sulfonyl)-4,4a,5,6,7,8-hexahydro-1H-pyrazolo[3,4-g]isoquinolin-4a-yl)(pyridin-2-yl)methanone, Example 5G. (R)-(1-(4-fluorophenyl)-6-((3-fluorophenyl)sulfonyl)-4,4a,5,6,7,8-hexahydro-1H-pyrazolo[3,4-g]isoquinolin-4a-yl)(pyridin-2-yl)methanone, Example 5H. (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(5-methoxypyridin-2-yl)methanone, Example 5I. (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(thiazol-5-yl)methanone, Example 5J. (R)-(1-(4-fluorophenyl)-6-((5-fluoropyridin-3-yl)sulfonyl)-4,4a,5,6,7,8-hexahydro-1H-pyrazolo[3,4-g]isoquinolin-4a-yl)(thiazol-2-yl)methanone, Example 6. (R)-(1-(4-fluorophenyl)-6-((4-(pyrrolidin-1-yl)phenyl)sulfonyl)-4,4a,5,6,7,8-hexahydro-1H-pyrazolo[3,4-g]isoquinolin-4a-yl)(thiazol-2-yl)methanone, Example 6A. (R)-(1-(4-fluorophenyl)-6-((3-(pyrrolidin-1-yl)phenyl)sulfonyl)-4,4a,5,6,7,8-hexahydro-1H-pyrazolo[3,4-g]isoquinolin-4a-yl)(thiazol-2-yl)methanone, Example 7. (R)-(1-(4-fluorophenyl)-6-((5-(piperidin-1-yl)pyridin-3-yl)sulfonyl)-4,4a,5,6,7,8-hexahydro-1H-pyrazolo[3,4-g]isoquinolin-4a-yl)(thiazol-2-yl)methanone, Example 7A. (R)-(1-(4-fluorophenyl)-6-((5-(pyrrolidin-1-yl)pyridin-3-yl)sulfonyl)-4,4a,5,6,7,8-hexahydro-1H-pyrazolo[3,4-g]isoquinolin-4a-yl)(thiazol-2-yl)methanone, Example 8. (R)-(1-(4-fluorophenyl)-6-((6-(pyrrolidin-1-yl)pyridin-3-yl)sulfonyl)-4,4a,5,6,7,8-hexahydro-1H-pyrazolo[3,4-g]isoquinolin-4a-yl)(pyridin-2-yl)methanone, Example 9. ((R)-1-(4-fluorophenyl)-6-((6-((R)-3-fluoropyrrolidin-1-yl)pyridin-3-yl)sulfonyl)-4,4a,5,6,7,8-hexahydro-1H-pyrazolo[3,4-g]isoquinolin-4a-yl)(thiazol-2-yl)methanone, Example 10. (R)-(1-(4-fluorophenyl)-6-((4-(pyrrolidin-1-yl)phenyl)sulfonyl)-4,4a,5,6,7,8-hexahydro-1H-pyrazolo[3,4-g]isoquinolin-4a-yl)(pyridin-2-yl)methanone, Example 10A. (R)-(1-(4-fluorophenyl)-6-((5-(piperidin-1-yl)pyridin-3-yl)sulfonyl)-4,4a,5,6,7,8-hexahydro-1H-pyrazolo[3,4-g]isoquinolin-4a-yl)(pyridin-2-yl)methanone, Example 10B. (R)-(1-(4-fluorophenyl)-6-((5-(pyrrolidin-1-yl)pyridin-3-yl)sulfonyl)-4,4a,5,6,7,8-hexahydro-1H-pyrazolo[3,4-g]isoquinolin-4a-yl)(pyridin-2-yl)methanone, Example 11. (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(thiazol-4-yl)methanone, Example 11A. (R)-(6-((4-chlorophenyl)sulfonyl)-1-(4-fluorophenyl)-4,4a,5,6,7,8-hexahydro-1H-pyrazolo[3,4-g]isoquinolin-4a-yl)(pyridin-2-yl)methanone, Example 11B. (R)-(1-(4-fluorophenyl)-6-((4-methoxy-3-methylphenyl)sulfonyl)-4,4a,5,6,7,8-hexahydro-1H-pyrazolo[3,4-g]isoquinolin-4a-yl)(pyridin-2-yl)methanone, Example 11C. (R)-(6-((3-chloro-4-methoxyphenyl)sulfonyl)-1-(4-fluorophenyl)-4,4a,5,6,7,8-hexahydro-1H-pyrazolo[3,4-g]isoquinolin-4a-yl)(pyridin-2-yl)methanone, Example 11D. (R)-(6-((3-fluoro-4-methoxyphenyl)sulfonyl)-1-(4-fluorophenyl)-4,4a,5,6,7,8-hexahydro-1H-pyrazolo[3,4-g]isoquinolin-4a-yl)(pyridin-2-yl)methanone, Example 11E. (R)-(6-((2-fluoro-4-methylphenyl)sulfonyl)-1-(4-fluorophenyl)-4,4a,5,6,7,8-hexahydro-1H-pyrazolo[3,4-g]isoquinolin-4a-yl)(pyridin-2-yl)methanone, Example 11F. (R)-(1-(4-fluorophenyl)-6-(m-tolylsulfonyl)-4,4a,5,6,7,8-hexahydro-1H-pyrazolo[3,4-g]isoquinolin-4a-yl)(thiazol-4-yl)methanone, Example 11G. (R)-3-((1-(4-fluorophenyl)-4a-picolinoyl-4a,5,7,8-tetrahydro-1H-pyrazolo[3,4-g]isoquinolin-6(4H)-yl)sulfonyl)benzonitrile, Example 11H. (R)-(6-((4-(difluoromethoxy)phenyl)sulfonyl)-1-(4-fluorophenyl)-4,4a,5,6,7,8-hexahydro-1H-pyrazolo[3,4-g]isoquinolin-4a-yl)(pyridin-2-yl)methanone, Example 11I. (R)-(1-(4-fluorophenyl)-6-((3-(trifluoromethoxy)phenyl)sulfonyl)-4,4a,5,6,7,8-hexahydro-1H-pyrazolo[3,4-g]isoquinolin-4a-yl)(pyridin-2-yl)methanone, Example 11J. (R)-(6-((3,5-difluorophenyl)sulfonyl)-1-(4-fluorophenyl)-4,4a,5,6,7,8-hexahydro-1H-pyrazolo[3,4-g]isoquinolin-4a-yl)(pyridin-2-yl)methanone, Example 11K. (R)-(1-(4-fluorophenyl)-6-tosyl-4,4a,5,6,7,8-hexahydro-1H-pyrazolo[3,4-g]isoquinolin-4a-yl)(thiazol-4-yl)methanone, Example 11L. (R)-(6-((3-(difluoromethoxy)phenyl)sulfonyl)-1-(4-fluorophenyl)-4,4a,5,6,7,8-hexahydro-1H-pyrazolo[3,4-g]isoquinolin-4a-yl)(pyridin-2-yl)methanone, Example 11M. (R)-(6-((3,4-dimethylphenyl)sulfonyl)-1-(4-fluorophenyl)-4,4a,5,6,7,8-hexahydro-1H-pyrazolo[3,4-g]isoquinolin-4a-yl)(pyridin-2-yl)methanone, Example 11N. (R)-(6-((3,5-dimethylphenyl)sulfonyl)-1-(4-fluorophenyl)-4,4a,5,6,7,8-hexahydro-1H-pyrazolo[3,4-g]isoquinolin-4a-yl)(pyridin-2-yl)methanone, Example 11O. (R)-(1-(4-fluorophenyl)-6-((6-methylpyridin-2-yl)sulfonyl)-4,4a,5,6,7,8-hexahydro-1H-pyrazolo[3,4-g]isoquinolin-4a-yl)(pyridin-2-yl)methanone, Example 11P. (R)-(6-((3,4-difluorophenyl)sulfonyl)-1-(4-fluorophenyl)-4,4a,5,6,7,8-hexahydro-1H-pyrazolo[3,4-g]isoquinolin-4a-yl)(pyridin-2-yl)methanone, Example 11Q. (R)-(1-(4-fluorophenyl)-6-((3,4,5-trifluorophenyl)sulfonyl)-4,4a,5,6,7,8-hexahydro-1H-pyrazolo[3,4-g]isoquinolin-4a-yl)(pyridin-2-yl)methanone, Example 11R. (R)-(6-((3-chloro-4-fluorophenyl)sulfonyl)-1-(4-fluorophenyl)-4,4a,5,6,7,8-hexahydro-1H-pyrazolo[3,4-g]isoquinolin-4a-yl)(pyridin-2-yl)methanone, Example 11S. (R)-3-((1-(4-fluorophenyl)-4a-(4-methylpicolinoyl)-4a,5,7,8-tetrahydro-1H-pyrazolo[3,4-g]isoquinolin-6(4H)-yl)sulfonyl)benzonitrile, Example 11T. (R)-(1-(4-fluorophenyl)-6-((1-methyl-1H-pyrazol-4-yl)sulfonyl)-4,4a,5,6,7,8-hexahydro-1H-pyrazolo[3,4-g]isoquinolin-4a-yl)(4-methylpyridin-2-yl)methanone, Example 11U. (R)-(6-((3,4-difluorophenyl)sulfonyl)-1-(4-fluorophenyl)-4,4a,5,6,7,8-hexahydro-1H-pyrazolo[3,4-g]isoquinolin-4a-yl)(4-methylpyridin-2-yl)methanone, Example 11V. (R)-(1-(4-fluorophenyl)-6-((1-methyl-1H-imidazol-4-yl)sulfonyl)-4,4a,5,6,7,8-hexahydro-1H-pyrazolo[3,4-g]isoquinolin-4a-yl)(4-methylpyridin-2-yl)methanone, Example 11W. (R)-(6-((3,5-difluorophenyl)sulfonyl)-1-(4-fluorophenyl)-4,4a,5,6,7,8-hexahydro-1H-pyrazolo[3,4-g]isoquinolin-4a-yl)(4-methylpyridin-2-yl)methanone, Example 11X. (R)-(1-(4-fluorophenyl)-6-((3,4,5-trifluorophenyl)sulfonyl)-4,4a,5,6,7,8-hexahydro-1H-pyrazolo[3,4-g]isoquinolin-4a-yl)(4-methylpyridin-2-yl)methanone, Example 11Y. (R)-(1-(4-fluorophenyl)-6-((3-(methylsulfonyl)phenyl)sulfonyl)-4,4a,5,6,7,8-hexahydro-1H-pyrazolo[3,4-g]isoquinolin-4a-yl)(pyridin-2-yl)methanone, Example 11Z. (R)-3-((1-(4-fluorophenyl)-4a-picolinoyl-4a,5,7,8-tetrahydro-1H-pyrazolo[3,4-g]isoquinolin-6(4H)-yl)sulfonyl)benzoic acid, Example 11AA. (R)-(1-(4-fluorophenyl)-6-((3-(methoxymethyl)phenyl)sulfonyl)-4,4a,5,6,7,8-hexahydro-1H-pyrazolo[3,4-g]isoquinolin-4a-yl)(pyridin-2-yl)methanone, Example 11AB. (R)-(1-(4-fluorophenyl)-6-((4-methyl-3,4-dihydro-2H-pyrido[3,2-b][1,4]oxazin-7-yl)sulfonyl)-4,4a,5,6,7,8-hexahydro-1H-pyrazolo[3,4-g]isoquinolin-4a-yl)(pyridin-2-yl)methanone, Example 11AC. (R)-(1-(4-fluorophenyl)-6-((2,3,4-trifluorophenyl)sulfonyl)-4,4a,5,6,7,8-hexahydro-1H-pyrazolo[3,4-g]isoquinolin-4a-yl)(pyridin-2-yl)methanone, Example 11AD. (R)-(1-(4-fluorophenyl)-6-((6-(trifluoromethyl)pyridin-2-yl)sulfonyl)-4,4a,5,6,7,8-hexahydro-1H-pyrazolo[3,4-g]isoquinolin-4a-yl)(pyridin-2-yl)methanone, Example 11AE. (R)-(1-(4-fluorophenyl)-6-((6-(trifluoromethyl)pyridin-2-yl)sulfonyl)-4,4a,5,6,7,8-hexahydro-1H-pyrazolo[3,4-g]isoquinolin-4a-yl)(4-methylpyridin-2-yl)methanone, Example 11AF. (R)-(6-((3,4-dichlorophenyl)sulfonyl)-1-(4-fluorophenyl)-4,4a,5,6,7,8-hexahydro-1H-pyrazolo[3,4-g]isoquinolin-4a-yl)(pyridin-2-yl)methanone, Example 11AG. (R)-(1-(4-fluorophenyl)-6-((3-(trifluoromethyl)phenyl)sulfonyl)-4,4a,5,6,7,8-hexahydro-1H-pyrazolo[3,4-g]isoquinolin-4a-yl)(4-methylpyridin-2-yl)methanone, Example 11AH. (R)-(6-((1-ethyl-1H-pyrazol-4-yl)sulfonyl)-1-(4-fluorophenyl)-4,4a,5,6,7,8-hexahydro-1H-pyrazolo[3,4-g]isoquinolin-4a-yl)(4-methylpyridin-2-yl)methanone, Example 11AI. (R)-(6-((1,5-dimethyl-1H-pyrazol-4-yl)sulfonyl)-1-(4-fluorophenyl)-4,4a,5,6,7,8-hexahydro-1H-pyrazolo[3,4-g]isoquinolin-4a-yl)(4-methylpyridin-2-yl)methanone, Example 11AJ. (R)-(1-(4-fluorophenyl)-6-((1-methyl-1H-pyrazol-5-yl)sulfonyl)-4,4a,5,6,7,8-hexahydro-1H-pyrazolo[3,4-g]isoquinolin-4a-yl)(4-methylpyridin-2-yl)methanone, Example 11AK. (R)-(1-(4-fluorophenyl)-6-((1-methyl-1H-pyrazol-3-yl)sulfonyl)-4,4a,5,6,7,8-hexahydro-1H-pyrazolo[3,4-g]isoquinolin-4a-yl)(4-methylpyridin-2-yl)methanone, Example 11AL. (R)-(6-((4-fluoro-3-methylphenyl)sulfonyl)-1-(4-fluorophenyl)-4,4a,5,6,7,8-hexahydro-1H-pyrazolo[3,4-g]isoquinolin-4a-yl)(4-methylpyridin-2-yl)methanone, Example 11AM. (R)-(1-(4-fluorophenyl)-6-((4-methyl-3,4-dihydro-2H-pyrido[3,2-b][1,4]oxazin-7-yl)sulfonyl)-4,4a,5,6,7,8-hexahydro-1H-pyrazolo[3,4-g]isoquinolin-4a-yl)(4-methylpyridin-2-yl)methanone, Example 11AN. (R)-(6-((2,3-dihydrobenzofuran-5-yl)sulfonyl)-1-(4-fluorophenyl)-4,4a,5,6,7,8-hexahydro-1H-pyrazolo[3,4-g]isoquinolin-4a-yl)(4-methylpyridin-2-yl)methanone, Example 11AO. (R)-5-((1-(4-fluorophenyl)-4a-(4-methylpicolinoyl)-4a,5,7,8-tetrahydro-1H-pyrazolo[3,4-g]isoquinolin-6(4H)-yl)sulfonyl)-1-methylindolin-2-one, Example 11AP. (R)-(1-(4-fluorophenyl)-6-((3-(methylsulfonyl)phenyl)sulfonyl)-4,4a,5,6,7,8-hexahydro-1H-pyrazolo[3,4-g]isoquinolin-4a-yl)(4-methylpyridin-2-yl)methanone, Example 11AQ. (R)-(6-((1,3-dimethyl-1H-pyrazol-4-yl)sulfonyl)-1-(4-fluorophenyl)-4,4a,5,6,7,8-hexahydro-1H-pyrazolo[3,4-g]isoquinolin-4a-yl)(4-methylpyridin-2-yl)methanone, Example 11AR. (R)-(6-((2,3-dihydrobenzo[b][1,4]dioxin-6-yl)sulfonyl)-1-(4-fluorophenyl)-4,4a,5,6,7,8-hexahydro-1H-pyrazolo[3,4-g]isoquinolin-4a-yl)(4-methylpyridin-2-yl)methanone, Example 11AS. (R)-(6-((3-fluoro-4-(trifluoromethyl)phenyl)sulfonyl)-1-(4-fluorophenyl)-4,4a,5,6,7,8-hexahydro-1H-pyrazolo[3,4-g]isoquinolin-4a-yl)(4-methylpyridin-2-yl)methanone, Example 11AT. (R)-(6-((3-fluoro-4-(trifluoromethyl)phenyl)sulfonyl)-1-(4-fluorophenyl)-4,4a,5,6,7,8-hexahydro-1H-pyrazolo[3,4-g]isoquinolin-4a-yl)(pyridin-2-yl)methanone, Example 11AU. (R)-3-((4a-(4-ethylpicolinoyl)-1-(4-fluorophenyl)-4a,5,7,8-tetrahydro-1H-pyrazolo[3,4-g]isoquinolin-6(4H)-yl)sulfonyl)benzonitrile, Example 11AV. (R)-(4-ethylpyridin-2-yl)(1-(4-fluorophenyl)-6-((6-(trifluoromethyl)pyridin-2-yl)sulfonyl)-4,4a,5,6,7,8-hexahydro-1H-pyrazolo[3,4-g]isoquinolin-4a-yl)methanone, Example 11AW. (R)-3-((1-(4-fluorophenyl)-4a-(4-methylpicolinoyl)-4a,5,7,8-tetrahydro-1H-pyrazolo[3,4-g]isoquinolin-6(4H)-yl)sulfonyl)benzoic acid, Example 11AX. (R)-(6-((3,5-dimethylisoxazol-4-yl)sulfonyl)-1-(4-fluorophenyl)-4,4a,5,6,7,8-hexahydro-1H-pyrazolo[3,4-g]isoquinolin-4a-yl)(4-methylpyridin-2-yl)methanone, Example 11AY. (R)-(6-((1-ethyl-1H-pyrazol-4-yl)sulfonyl)-1-(4-fluorophenyl)-4,4a,5,6,7,8-hexahydro-1H-pyrazolo[3,4-g]isoquinolin-4a-yl)(pyridin-2-yl)methanone, Example 11AZ. (R)-(1-phenyl-6-((3-(trifluoromethyl)phenyl)sulfonyl)-4,4a,5,6,7,8-hexahydro-1H-pyrazolo[3,4-g]isoquinolin-4a-yl)(pyridin-2-yl)methanone, Example 11BA. (R)-(6-((1,3-dimethyl-1H-pyrazol-5-yl)sulfonyl)-1-(4-fluorophenyl)-4,4a,5,6,7,8-hexahydro-1H-pyrazolo[3,4-g]isoquinolin-4a-yl)(4-methylpyridin-2-yl)methanone, Example 11BB. (R)-(1-(4-fluorophenyl)-6-((2-(trifluoromethyl)pyridin-4-yl)sulfonyl)-4,4a,5,6,7,8-hexahydro-1H-pyrazolo[3,4-g]isoquinolin-4a-yl)(4-methylpyridin-2-yl)methanone, Example 11BC. (R)-(1-(4-fluorophenyl)-6-((4-(trifluoromethyl)pyridin-2-yl)sulfonyl)-4,4a,5,6,7,8-hexahydro-1H-pyrazolo[3,4-g]isoquinolin-4a-yl)(4-methylpyridin-2-yl)methanone, Example 11BD. (R)-(1-(4-fluorophenyl)-6-((5-methyl-1H-pyrazol-4-yl)sulfonyl)-4,4a,5,6,7,8-hexahydro-1H-pyrazolo[3,4-g]isoquinolin-4a-yl)(4-methylpyridin-2-yl)methanone, Example 11BE. (R)-(1-(4-fluorophenyl)-6-((2-(trifluoromethyl)pyridin-4-yl)sulfonyl)-4,4a,5,6,7,8-hexahydro-1H-pyrazolo[3,4-g]isoquinolin-4a-yl)(pyridin-2-yl)methanone, Example 11BF. (R)-(6-((4-chloro-3-(trifluoromethyl)phenyl)sulfonyl)-1-(4-fluorophenyl)-4,4a,5,6,7,8-hexahydro-1H-pyrazolo[3,4-g]isoquinolin-4a-yl)(pyridin-2-yl)methanone, Example 11BG. (R)-(6-((3-chloro-4-methylphenyl)sulfonyl)-1-(4-fluorophenyl)-4,4a,5,6,7,8-hexahydro-1H-pyrazolo[3,4-g]isoquinolin-4a-yl)(pyridin-2-yl)methanone, Example 11BH. (R)-(6-((3,4-difluorophenyl)sulfonyl)-1-(4-fluorophenyl)-4,4a,5,6,7,8-hexahydro-1H-pyrazolo[3,4-g]isoquinolin-4a-yl)(2-(pyrrolidin-1-yl)pyridin-4-yl)methanone, Example 11BI. (R)-(1-(4-fluorophenyl)-6-((1-methyl-1H-pyrazol-3-yl)sulfonyl)-4,4a,5,6,7,8-hexahydro-1H-pyrazolo[3,4-g]isoquinolin-4a-yl)(4-(trifluoromethyl)pyridin-2-yl)methanone, Example 11BJ. (R)-(1-(4-fluorophenyl)-6-((1-methyl-1H-pyrazol-3-yl)sulfonyl)-4,4a,5,6,7,8-hexahydro-1H-pyrazolo[3,4-g]isoquinolin-4a-yl)(pyridin-2-yl)methanone, Example 11BK. (R)-(1-(4-fluorophenyl)-6-((5-methyl-1H-pyrazol-4-yl)sulfonyl)-4,4a,5,6,7,8-hexahydro-1H-pyrazolo[3,4-g]isoquinolin-4a-yl)(4-(trifluoromethyl)pyridin-2-yl)methanone, Example 11BL. (R)-3-((1-(4-fluorophenyl)-4a-(4-(trifluoromethyl)picolinoyl)-4a,5,7,8-tetrahydro-1H-pyrazolo[3,4-g]isoquinolin-6(4H)-yl)sulfonyl)benzonitrile, Example 11BM. (R)-(1-(4-fluorophenyl)-6-((1-methyl-1H-pyrazol-5-yl)sulfonyl)-4,4a,5,6,7,8-hexahydro-1H-pyrazolo[3,4-g]isoquinolin-4a-yl)(4-(trifluoromethyl)pyridin-2-yl)methanone, Example 11BN. (R)-(6-((1,5-dimethyl-1H-pyrazol-4-yl)sulfonyl)-1-(4-fluorophenyl)-4,4a,5,6,7,8-hexahydro-1H-pyrazolo[3,4-g]isoquinolin-4a-yl)(4-(trifluoromethyl)pyridin-2-yl)methanone, Example 11BO. (R)-(6-((1H-pyrazol-4-yl)sulfonyl)-1-(4-fluorophenyl)-4,4a,5,6,7,8-hexahydro-1H-pyrazolo[3,4-g]isoquinolin-4a-yl)(4-(trifluoromethyl)pyridin-2-yl)methanone, Example 11BP. (R)-(1-(4-fluorophenyl)-6-((1-methyl-3-(trifluoromethyl)-1H-pyrazol-4-yl)sulfonyl)-4,4a,5,6,7,8-hexahydro-1H-pyrazolo[3,4-g]isoquinolin-4a-yl)(pyridin-2-yl)methanone, Example 11BQ. (R)-(1-(4-fluorophenyl)-6-((3,4,5-trifluorophenyl)sulfonyl)-4,4a,5,6,7,8-hexahydro-1H-pyrazolo[3,4-g]isoquinolin-4a-yl)(4-(trifluoromethyl)pyridin-2-yl)methanone, Example 11BR. (R)-(1-(4-chlorophenyl)-6-((1-methyl-1H-pyrazol-3-yl)sulfonyl)-4,4a,5,6,7,8-hexahydro-1H-pyrazolo[3,4-g]isoquinolin-4a-yl)(4-(trifluoromethyl)pyridin-2-yl)methanone, Example 11BS. (R)-(6-((1H-pyrazol-4-yl)sulfonyl)-1-(4-fluorophenyl)-4,4a,5,6,7,8-hexahydro-1H-pyrazolo[3,4-g]isoquinolin-4a-yl)(pyridin-2-yl)methanone, Example 11BT. (R)-(6-((1-methyl-1H-pyrazol-3-yl)sulfonyl)-1-(4-(trifluoromethyl)phenyl)-4,4a,5,6,7,8-hexahydro-1H-pyrazolo[3,4-g]isoquinolin-4a-yl)(pyridin-2-yl)methanone, Example 11BU. (R)-(6-((3,4-difluorophenyl)sulfonyl)-1-(4-fluorophenyl)-4,4a,5,6,7,8-hexahydro-1H-pyrazolo[3,4-g]isoquinolin-4a-yl)(thiazol-4-yl)methanone, Example 11BV. (R)-(6-((1,2-dimethyl-1H-imidazol-4-yl)sulfonyl)-1-(4-fluorophenyl)-4,4a,5,6,7,8-hexahydro-1H-pyrazolo[3,4-g]isoquinolin-4a-yl)(4-(trifluoromethyl)pyridin-2-yl)methanone, Example 11BW. (R)-(6-((1,2-dimethyl-1H-imidazol-5-yl)sulfonyl)-1-(4-fluorophenyl)-4,4a,5,6,7,8-hexahydro-1H-pyrazolo[3,4-g]isoquinolin-4a-yl)(4-(trifluoromethyl)pyridin-2-yl)methanone, Example 11BX. (R)-(1-(4-fluorophenyl)-6-((1-methyl-1H-imidazol-2-yl)sulfonyl)-4,4a,5,6,7,8-hexahydro-1H-pyrazolo[3,4-g]isoquinolin-4a-yl)(4-(trifluoromethyl)pyridin-2-yl)methanone, Example 11BY. (R)-(6-((1-ethyl-1H-imidazol-4-yl)sulfonyl)-1-(4-fluorophenyl)-4,4a,5,6,7,8-hexahydro-1H-pyrazolo[3,4-g]isoquinolin-4a-yl)(4-(trifluoromethyl)pyridin-2-yl)methanone, Example 11BZ. (R)-(6-((1-ethyl-1H-pyrazol-4-yl)sulfonyl)-1-(4-fluorophenyl)-4,4a,5,6,7,8-hexahydro-1H-pyrazolo[3,4-g]isoquinolin-4a-yl)(thiazol-4-yl)methanone, Example 11CA. (R)-(1-(4-fluorophenyl)-6-((1-propyl-1H-pyrazol-4-yl)sulfonyl)-4,4a,5,6,7,8-hexahydro-1H-pyrazolo[3,4-g]isoquinolin-4a-yl)(pyridin-2-yl)methanone, Example 11CB. (R)-(1-(4-fluorophenyl)-6-((1-(2-methoxyethyl)-1H-pyrazol-4-yl)sulfonyl)-4,4a,5,6,7,8-hexahydro-1H-pyrazolo[3,4-g]isoquinolin-4a-yl)(pyridin-2-yl)methanone, Example 11CC. (R)-(6-((3,4-dichlorophenyl)sulfonyl)-1-(4-fluorophenyl)-4,4a,5,6,7,8-hexahydro-1H-pyrazolo[3,4-g]isoquinolin-4a-yl)(1-methyl-1H-pyrazol-4-yl)methanone, Example 11CD. (R)-(1-(4-fluorophenyl)-6-((1-isopropyl-1H-pyrazol-4-yl)sulfonyl)-4,4a,5,6,7,8-hexahydro-1H-pyrazolo[3,4-g]isoquinolin-4a-yl)(pyridin-2-yl)methanone, Example 11CE. (R)-(1-(4-fluorophenyl)-6-((2-methyl-2H-1,2,3-triazol-4-yl)sulfonyl)-4,4a,5,6,7,8-hexahydro-1H-pyrazolo[3,4-g]isoquinolin-4a-yl)(4-(trifluoromethyl)pyridin-2-yl)methanone, Example 11CF. (R)-(1-(4-fluorophenyl)-6-((1-methyl-1H-1,2,3-triazol-5-yl)sulfonyl)-4,4a,5,6,7,8-hexahydro-1H-pyrazolo[3,4-g]isoquinolin-4a-yl)(4-(trifluoromethyl)pyridin-2-yl)methanone, Example 11CG. (R)-(1-(4-fluorophenyl)-6-((1-methyl-1H-1,2,3-triazol-4-yl)sulfonyl)-4,4a,5,6,7,8-hexahydro-1H-pyrazolo[3,4-g]isoquinolin-4a-yl)(4-(trifluoromethyl)pyridin-2-yl)methanone, Example 11CH. (R)-(6-((2-ethyl-2H-1,2,3-triazol-4-yl)sulfonyl)-1-(4-fluorophenyl)-4,4a,5,6,7,8-hexahydro-1H-pyrazolo[3,4-g]isoquinolin-4a-yl)(pyridin-2-yl)methanone, Example 11CI. (R)-(6-((1-ethyl-1H-1,2,3-triazol-5-yl)sulfonyl)-1-(4-fluorophenyl)-4,4a,5,6,7,8-hexahydro-1H-pyrazolo[3,4-g]isoquinolin-4a-yl)(pyridin-2-yl)methanone, Example 11CJ. (R)-(6-((1-ethyl-1H-1,2,3-triazol-4-yl)sulfonyl)-1-(4-fluorophenyl)-4,4a,5,6,7,8-hexahydro-1H-pyrazolo[3,4-g]isoquinolin-4a-yl)(pyridin-2-yl)methanone, Example 11CK. (R)-(6-((2-ethyl-2H-1,2,3-triazol-4-yl)sulfonyl)-1-(4-fluorophenyl)-4,4a,5,6,7,8-hexahydro-1H-pyrazolo[3,4-g]isoquinolin-4a-yl)(4-(trifluoromethyl)pyridin-2-yl)methanone, Example 11CL. (R)-(6-((1-ethyl-1H-1,2,3-triazol-5-yl)sulfonyl)-1-(4-fluorophenyl)-4,4a,5,6,7,8-hexahydro-1H-pyrazolo[3,4-g]isoquinolin-4a-yl)(4-(trifluoromethyl)pyridin-2-yl)methanone, Example 11CM. (R)-(6-((1-ethyl-1H-1,2,3-triazol-4-yl)sulfonyl)-1-(4-fluorophenyl)-4,4a,5,6,7,8-hexahydro-1H-pyrazolo[3,4-g]isoquinolin-4a-yl)(4-(trifluoromethyl)pyridin-2-yl)methanone, Example 11CN. (R)-(1-(4-fluorophenyl)-6-((2-propyl-2H-1,2,3-triazol-4-yl)sulfonyl)-4,4a,5,6,7,8-hexahydro-1H-pyrazolo[3,4-g]isoquinolin-4a-yl)(pyridin-2-yl)methanone, Example 11CO. (R)-(1-(4-fluorophenyl)-6-((1-propyl-1H-1,2,3-triazol-5-yl)sulfonyl)-4,4a,5,6,7,8-hexahydro-1H-pyrazolo[3,4-g]isoquinolin-4a-yl)(pyridin-2-yl)methanone, Example 11CP. (R)-(1-(4-fluorophenyl)-6-((1-propyl-1H-1,2,3-triazol-4-yl)sulfonyl)-4,4a,5,6,7,8-hexahydro-1H-pyrazolo[3,4-g]isoquinolin-4a-yl)(pyridin-2-yl)methanone, Example 11CQ. (R)-(1-(4-fluorophenyl)-6-((2-propyl-2H-1,2,3-triazol-4-yl)sulfonyl)-4,4a,5,6,7,8-hexahydro-1H-pyrazolo[3,4-g]isoquinolin-4a-yl)(thiazol-4-yl)methanone, Example 11CR. (R)-(1-(4-fluorophenyl)-6-((1-propyl-1H-1,2,3-triazol-5-yl)sulfonyl)-4,4a,5,6,7,8-hexahydro-1H-pyrazolo[3,4-g]isoquinolin-4a-yl)(thiazol-4-yl)methanone, Example 11CS. (R)-(1-(4-fluorophenyl)-6-((1-propyl-1H-1,2,3-triazol-4-yl)sulfonyl)-4,4a,5,6,7,8-hexahydro-1H-pyrazolo[3,4-g]isoquinolin-4a-yl)(thiazol-4-yl)methanone, Example 11CT. (R)-(1-(4-fluorophenyl)-6-((2-isopropyl-2H-1,2,3-triazol-4-yl)sulfonyl)-4,4a,5,6,7,8-hexahydro-1H-pyrazolo[3,4-g]isoquinolin-4a-yl)(pyridin-2-yl)methanone, Example 11CU. (R)-(1-(4-fluorophenyl)-6-((1-isopropyl-1H-1,2,3-triazol-5-yl)sulfonyl)-4,4a,5,6,7,8-hexahydro-1H-pyrazolo[3,4-g]isoquinolin-4a-yl)(pyridin-2-yl)methanone, Example 11CV. (R)-(1-(4-fluorophenyl)-6-((1-isopropyl-1H-1,2,3-triazol-4-yl)sulfonyl)-4,4a,5,6,7,8-hexahydro-1H-pyrazolo[3,4-g]isoquinolin-4a-yl)(pyridin-2-yl)methanone, Example 11CW. (R)-(6-((1-ethyl-1H-pyrazol-5-yl)sulfonyl)-1-(4-fluorophenyl)-4,4a,5,6,7,8-hexahydro-1H-pyrazolo[3,4-g]isoquinolin-4a-yl)(thiazol-4-yl)methanone, Example 11CX. (R)-(1-(4-fluorophenyl)-6-((1-propyl-1H-pyrazol-4-yl)sulfonyl)-4,4a,5,6,7,8-hexahydro-1H-pyrazolo[3,4-g]isoquinolin-4a-yl)(4-(trifluoromethyl)pyridin-2-yl)methanone, Example 11CY. (R)-(1-(4-fluorophenyl)-6-((1-methyl-1H-pyrazol-4-yl)sulfonyl)-4,4a,5,6,7,8-hexahydro-1H-pyrazolo[3,4-g]isoquinolin-4a-yl)(thiazol-4-yl)methanone, Example 11CZ. (R)-(1-(4-fluorophenyl)-6-((1-propyl-1H-pyrazol-4-yl)sulfonyl)-4,4a,5,6,7,8-hexahydro-1H-pyrazolo[3,4-g]isoquinolin-4a-yl)(thiazol-4-yl)methanone, Example 12. (R)-(1-(4-fluorophenyl)-6-((3-(trifluoromethyl)phenyl)sulfonyl)-4,4a,5,6,7,8-hexahydro-1H-pyrazolo[3,4-g]isoquinolin-4a-yl)(thiazol-2-yl)methanone, Example 12A. (R)-(1-(4-fluorophenyl)-6-(m-tolylsulfonyl)-4,4a,5,6,7,8-hexahydro-1H-pyrazolo[3,4-g]isoquinolin-4a-yl)(thiazol-2-yl)methanone, Example 12B. (R)-(1-(4-fluorophenyl)-6-((3-methoxyphenyl)sulfonyl)-4,4a,5,6,7,8-hexahydro-1H-pyrazolo[3,4-g]isoquinolin-4a-yl)(thiazol-2-yl)methanone, Example 12C. (R)-(6-((3-fluoro-4-methylphenyl)sulfonyl)-1-(4-fluorophenyl)-4,4a,5,6,7,8-hexahydro-1H-pyrazolo[3,4-g]isoquinolin-4a-yl)(thiazol-2-yl)methanone, Example 12D. (R)-(1-(4-fluorophenyl)-6-(phenylsulfonyl)-4,4a,5,6,7,8-hexahydro-1H-pyrazolo[3,4-g]isoquinolin-4a-yl)(thiazol-2-yl)methanone, Example 12E. (R)-(6-((3-chlorophenyl)sulfonyl)-1-(4-fluorophenyl)-4,4a,5,6,7,8-hexahydro-1H-pyrazolo[3,4-g]isoquinolin-4a-yl)(thiazol-2-yl)methanone, Example 12F. (R)-(1-(4-fluorophenyl)-6-(m-tolylsulfonyl)-4,4a,5,6,7,8-hexahydro-1H-pyrazolo[3,4-g]isoquinolin-4a-yl)(5-methylpyridin-2-yl)methanone, Example 12G. (R)-(1-(4-fluorophenyl)-6-(m-tolylsulfonyl)-4,4a,5,6,7,8-hexahydro-1H-pyrazolo[3,4-g]isoquinolin-4a-yl)(4-methylpyridin-2-yl)methanone, Example 12H. (R)-(1-(4-fluorophenyl)-6-(m-tolylsulfonyl)-4,4a,5,6,7,8-hexahydro-1H-pyrazolo[3,4-g]isoquinolin-4a-yl)(6-methylpyridin-2-yl)methanone, Example 12I. (R)-(6-((4-fluoro-3-(trifluoromethyl)phenyl)sulfonyl)-1-(4-fluorophenyl)-4,4a,5,6,7,8-hexahydro-1H-pyrazolo[3,4-g]isoquinolin-4a-yl)(thiazol-2-yl)methanone, Example 12J. (R)-(1-(4-fluorophenyl)-6-((3,4,5-trifluorophenyl)sulfonyl)-4,4a,5,6,7,8-hexahydro-1H-pyrazolo[3,4-g]isoquinolin-4a-yl)(thiazol-2-yl)methanone, Example 12K. (R)-(6-((3-fluoro-4-(trifluoromethyl)phenyl)sulfonyl)-1-(4-fluorophenyl)-4,4a,5,6,7,8-hexahydro-1H-pyrazolo[3,4-g]isoquinolin-4a-yl)(thiazol-2-yl)methanone, Example 12L. (R)-(1-(4-fluorophenyl)-6-((3-(trifluoromethyl)phenyl)sulfonyl)-4,4a,5,6,7,8-hexahydro-1H-pyrazolo[3,4-g]isoquinolin-4a-yl)(5-methylthiazol-2-yl)methanone, Example 12M. (R)-(1-(4-fluorophenyl)-6-((3-(trifluoromethyl)phenyl)sulfonyl)-4,4a,5,6,7,8-hexahydro-1H-pyrazolo[3,4-g]isoquinolin-4a-yl)(4-methylthiazol-2-yl)methanone, Example 12N. (R)-(6-((3,4-dichlorophenyl)sulfonyl)-1-(4-fluorophenyl)-4,4a,5,6,7,8-hexahydro-1H-pyrazolo[3,4-g]isoquinolin-4a-yl)(thiazol-2-yl)methanone, Example 12O. (R)-(6-((3,4-dichlorophenyl)sulfonyl)-1-(4-fluorophenyl)-4,4a,5,6,7,8-hexahydro-1H-pyrazolo[3,4-g]isoquinolin-4a-yl)(5-methylthiazol-2-yl)methanone, Example 12P. (R)-(6-((3,4-difluorophenyl)sulfonyl)-1-(4-fluorophenyl)-4,4a,5,6,7,8-hexahydro-1H-pyrazolo[3,4-g]isoquinolin-4a-yl)(thiazol-2-yl)methanone, Example 12Q. (R)-(6-((3,4-difluorophenyl)sulfonyl)-1-(4-fluorophenyl)-4,4a,5,6,7,8-hexahydro-1H-pyrazolo[3,4-g]isoquinolin-4a-yl)(5-methylthiazol-2-yl)methanone, Example 12R. (R)-(6-((4-chloro-3-fluorophenyl)sulfonyl)-1-(4-fluorophenyl)-4,4a,5,6,7,8-hexahydro-1H-pyrazolo[3,4-g]isoquinolin-4a-yl)(5-methylthiazol-2-yl)methanone, Example 12S. (R)-(1-(4-fluorophenyl)-6-((1-methyl-1H-pyrazol-3-yl)sulfonyl)-4,4a,5,6,7,8-hexahydro-1H-pyrazolo[3,4-g]isoquinolin-4a-yl)(5-methylthiazol-2-yl)methanone, Example 12T. (R)-(1-(4-fluorophenyl)-6-((1-methyl-1H-pyrazol-4-yl)sulfonyl)-4,4a,5,6,7,8-hexahydro-1H-pyrazolo[3,4-g]isoquinolin-4a-yl)(5-methylthiazol-2-yl)methanone, Example 12U. (R)-(6-((1,3-dimethyl-1H-pyrazol-5-yl)sulfonyl)-1-(4-fluorophenyl)-4,4a,5,6,7,8-hexahydro-1H-pyrazolo[3,4-g]isoquinolin-4a-yl)(5-methylthiazol-2-yl)methanone, Example 12V. (R)-(1-(4-fluorophenyl)-6-((1-methyl-1H-pyrazol-5-yl)sulfonyl)-4,4a,5,6,7,8-hexahydro-1H-pyrazolo[3,4-g]isoquinolin-4a-yl)(5-methylthiazol-2-yl)methanone, Example 12W. (R)-(6-((1-ethyl-1H-pyrazol-5-yl)sulfonyl)-1-(4-fluorophenyl)-4,4a,5,6,7,8-hexahydro-1H-pyrazolo[3,4-g]isoquinolin-4a-yl)(thiazol-2-yl)methanone, Example 12X. (R)-(6-((1-ethyl-1H-pyrazol-4-yl)sulfonyl)-1-(4-fluorophenyl)-4,4a,5,6,7,8-hexahydro-1H-pyrazolo[3,4-g]isoquinolin-4a-yl)(thiazol-2-yl)methanone, Example 12Y. (R)-(1-(4-fluorophenyl)-6-((1-propyl-1H-pyrazol-4-yl)sulfonyl)-4,4a,5,6,7,8-hexahydro-1H-pyrazolo[3,4-g]isoquinolin-4a-yl)(thiazol-2-yl)methanone, Example 13. (R)-(1-(4-fluorophenyl)-6-tosyl-4,4a,5,6,7,8-hexahydro-1H-pyrazolo[3,4-g]isoquinolin-4a-yl)(1-methyl-1H-imidazol-2-yl)methanone, Example 13A. (R)-(1-(4-fluorophenyl)-6-(m-tolylsulfonyl)-4,4a,5,6,7,8-hexahydro-1H-pyrazolo[3,4-g]isoquinolin-4a-yl)(1-methyl-1H-imidazol-2-yl)methanone, Example 14. (R)-3-((1-(4-fluorophenyl)-4a-picolinoyl-4a,5,7,8-tetrahydro-1H-pyrazolo[3,4-g]isoquinolin-6(4H)-yl)sulfonyl)-N,N-dimethylbenzamide, Example 15. (R)-(6-((1-ethyl-1H-pyrazol-4-yl)sulfonyl)-1-(4-fluorophenyl)-4,4a,5,6,7,8-hexahydro-1H-pyrazolo[3,4-g]isoquinolin-4a-yl)(4-(trifluoromethyl)pyridin-2-yl)methanone, Example 15A. (R)-pyridin-2-yl(1-(pyridin-3-yl)-6-((3-(trifluoromethyl)phenyl)sulfonyl)-4,4a,5,6,7,8-hexahydro-1H-pyrazolo[3,4-g]isoquinolin-4a-yl)methanone, Example 15B. (R)-(6-((3,4-dichlorophenyl)sulfonyl)-1-phenyl-4,4a,5,6,7,8-hexahydro-1H-pyrazolo[3,4-g]isoquinolin-4a-yl)(pyridin-2-yl)methanone, Example 15C. (R)-(6-((3,4-dichlorophenyl)sulfonyl)-1-(3,4-difluorophenyl)-4,4a,5,6,7,8-hexahydro-1H-pyrazolo[3,4-g]isoquinolin-4a-yl)(pyridin-2-yl)methanone, Example 15D. (R)-(6-((3,5-difluoro-4-methoxyphenyl)sulfonyl)-1-(4-fluorophenyl)-4,4a,5,6,7,8-hexahydro-1H-pyrazolo[3,4-g]isoquinolin-4a-yl)(pyridin-2-yl)methanone, Example 16. (R)-(6-((6-(dimethylamino)pyridin-3-yl)sulfonyl)-1-(4-fluorophenyl)-4,4a,5,6,7,8-hexahydro-1H-pyrazolo[3,4-g]isoquinolin-4a-yl)(pyridin-2-yl)methanone, Example 17. (R)-5-((1-(4-fluorophenyl)-4a-picolinoyl-4a,5,7,8-tetrahydro-1H-pyrazolo[3,4-g]isoquinolin-6(4H)-yl)sulfonyl)-1-methylpyridin-2(1H)-one, Example 18. (R)-(1-(4-fluorophenyl)-6-((1-methyl-1H-pyrazol-4-yl)sulfonyl)-4,4a,5,6,7,8-hexahydro-1H-pyrazolo[3,4-g]isoquinolin-4a-yl)(4-(trifluoromethyl)pyridin-2-yl)methanone, Example 19. (R)-(6-((3,4-dichlorophenyl)sulfonyl)-1-(4-fluorophenyl)-4,4a,5,6,7,8-hexahydro-1H-pyrazolo[3,4-g]isoquinolin-4a-yl)(thiazol-4-yl)methanone, or salts and isomers thereof.

In some embodiments, the compound of formula I can be
(R)-(1-(4-fluorophenyl)-6-((2-methyl-2H-1,2,3-triazol-4-yl)sulfonyl)-4,4a,5,6,7,8-hexahydro-1H-pyrazolo[3,4-g]isoquinolin-4a-yl)(thiazol-4-yl)methanone,
(R)-(1-(4-fluorophenyl)-6-((1-methyl-1H-1,2,3-triazol-5-yl)sulfonyl)-4,4a,5,6,7,8-hexahydro-1H-pyrazolo[3,4-g]isoquinolin-4a-yl)(thiazol-4-yl)methanone, or
(R)-(1-(4-fluorophenyl)-6-((1-methyl-1H-1,2,3-triazol-4-yl)sulfonyl)-4,4a,5,6,7,8-hexahydro-1H-pyrazolo[3,4-g]isoquinolin-4a-yl)(thiazol-4-yl)methanone.

In some embodiments, the compound of formula I can be
(R)-(1-(4-fluorophenyl)-6-((2-methyl-2H-1,2,3-triazol-4-yl)sulfonyl)-4,4a,5,6,7,8-hexahydro-1H-pyrazolo[3,4-g]isoquinolin-4a-yl)(pyridin-2-yl)methanone,
(R)-(1-(4-fluorophenyl)-6-((1-methyl-1H-1,2,3-triazol-5-yl)sulfonyl)-4,4a,5,6,7,8-hexahydro-1H-pyrazolo[3,4-g]isoquinolin-4a-yl)(pyridin-2-yl)methanone, or
(R)-(1-(4-fluorophenyl)-6-((1-methyl-1H-1,2,3-triazol-4-yl)sulfonyl)-4,4a,5,6,7,8-hexahydro-1H-pyrazolo[3,4-g]isoquinolin-4a-yl)(pyridin-2-yl)methanone.

In some embodiments, the compound of formula I can be
(R)-(1-(4-fluorophenyl)-6-((2-propyl-2H-1,2,3-triazol-4-yl)sulfonyl)-4,4a,5,6,7,8-hexahydro-1H-pyrazolo[3,4-g]isoquinolin-4a-yl)(4-(trifluoromethyl)pyridin-2-yl)methanone,
(R)-(1-(4-fluorophenyl)-6-((1-propyl-1H-1,2,3-triazol-5-yl)sulfonyl)-4,4a,5,6,7,8-hexahydro-1H-pyrazolo[3,4-g]isoquinolin-4a-yl)(4-(trifluoromethyl)pyridin-2-yl)methanone, or
(R)-(1-(4-fluorophenyl)-6-((1-propyl-1H-1,2,3-triazol-4-yl)sulfonyl)-4,4a,5,6,7,8-hexahydro-1H-pyrazolo[3,4-g]isoquinolin-4a-yl)(4-(trifluoromethyl)pyridin-2-yl)methanone.

In some embodiments, the compound of formula I can be
(R)-(1-(4-fluorophenyl)-6-((2-methyl-2H-1,2,3-triazol-4-yl)sulfonyl)-4,4a,5,6,7,8-hexahydro-1H-pyrazolo[3,4-g]isoquinolin-4a-yl)(thiazol-2-yl)methanone,
(R)-(1-(4-fluorophenyl)-6-((1-methyl-1H-1,2,3-triazol-5-yl)sulfonyl)-4,4a,5,6,7,8-hexahydro-1H-pyrazolo[3,4-g]isoquinolin-4a-yl)(thiazol-2-yl)methanone, or
(R)-(1-(4-fluorophenyl)-6-((1-methyl-1H-1,2,3-triazol-4-yl)sulfonyl)-4,4a,5,6,7,8-hexahydro-1H-pyrazolo[3,4-g]isoquinolin-4a-yl)(thiazol-2-yl)methanone.

In some embodiments, the compound of formula I can be
(R)-(1-(4-fluorophenyl)-6-((2-propyl-2H-1,2,3-triazol-4-yl)sulfonyl)-4,4a,5,6,7,8-hexahydro-1H-pyrazolo[3,4-g]isoquinolin-4a-yl)(thiazol-2-yl)methanone,
(R)-(1-(4-fluorophenyl)-6-((1-propyl-1H-1,2,3-triazol-5-yl)sulfonyl)-4,4a,5,6,7,8-hexahydro-1H-pyrazolo[3,4-g]isoquinolin-4a-yl)(thiazol-2-yl)methanone, or
(R)-(1-(4-fluorophenyl)-6-((1-propyl-1H-1,2,3-triazol-4-yl)sulfonyl)-4,4a,5,6,7,8-hexahydro-1H-pyrazolo[3,4-g]isoquinolin-4a-yl)(thiazol-2-yl)methanone.

In some embodiments, the compound of formula I can be
(R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(pyridin-2-yl)methanone,
(R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(thiazol-2-yl)methanone,
(R)-(6-((3,4-difluorophenyl)sulfonyl)-1-(4-fluorophenyl)-4,4a,5,6,7,8-hexahydro-1H-pyrazolo[3,4-g]isoquinolin-4a-yl)(pyridin-2-yl)methanone,
(R)-(6-((3,4-dichlorophenyl)sulfonyl)-1-(4-fluorophenyl)-4,4a,5,6,7,8-hexahydro-1H-pyrazolo[3,4-g]isoquinolin-4a-yl)(pyridin-2-yl)methanone,
(R)-(1-(4-fluorophenyl)-6-((1-methyl-1H-pyrazol-4-yl)sulfonyl)-4,4a,5,6,7,8-hexahydro-1H-pyrazolo[3,4-g]isoquinolin-4a-yl)(4-(trifluoromethyl)pyridin-2-yl)methanone,
(R)-(6-((3,4-dichlorophenyl)sulfonyl)-1-(4-fluorophenyl)-4,4a,5,6,7,8-hexahydro-1H-pyrazolo[3,4-g]isoquinolin-4a-yl)(thiazol-2-yl)methanone,
(R)-(6-((3,4-dichlorophenyl)sulfonyl)-1-(4-fluorophenyl)-4,4a,5,6,7,8-hexahydro-1H-pyrazolo[3,4-g]isoquinolin-4a-yl)(5-methylthiazol-2-yl)methanone,
(R)-(6-((3-fluoro-4-(trifluoromethyl)phenyl)sulfonyl)-1-(4-fluorophenyl)-4,4a,5,6,7,8-hexahydro-1H-pyrazolo[3,4-g]isoquinolin-4a-yl)(pyridin-2-yl)methanone,
(R)-(1-(4-fluorophenyl)-6-((1-methyl-1H-pyrazol-3-yl)sulfonyl)-4,4a,5,6,7,8-hexahydro-1H-pyrazolo[3,4-g]isoquinolin-4a-yl)(4-(trifluoromethyl)pyridin-2-yl)methanone,
(R)-(1-(4-fluorophenyl)-6-((1-methyl-1-pyrazol-5-yl)sulfonyl)-4,4a,5,6,7,8-hexahydro-1H-pyrazolo[3,4-g]isoquinolin-4a-yl)(4-(trifluoromethyl)pyridin-2-yl)methanone,
(R)-(6-((1-ethyl-1H-pyrazol-5-yl)sulfonyl)-1-(4-fluorophenyl)-4,4a,5,6,7,8-hexahydro-1H-pyrazolo[3,4-g]isoquinolin-4a-yl)(4-(trifluoromethyl)pyridin-2-yl)methanone, or
(R)-(6-((3,4-dichlorophenyl)sulfonyl)-1-(4-fluorophenyl)-4,4a,5,6,7,8-hexahydro-1H-pyrazolo[3,4-g]isoquinolin-4a-yl)(thiazol-4-yl)methanone.

The compounds of the present invention can also include compounds of formula II:

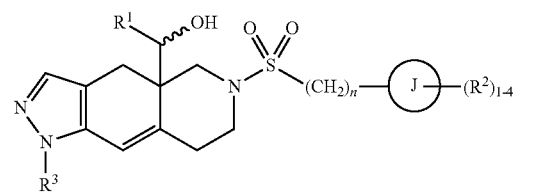

wherein $R^1$, $R^2$, $R^3$, ring J and subscript n are as described above.

When $R^3$ of formula II is 4-F-phenyl, the compounds of formula II can have the following structure:

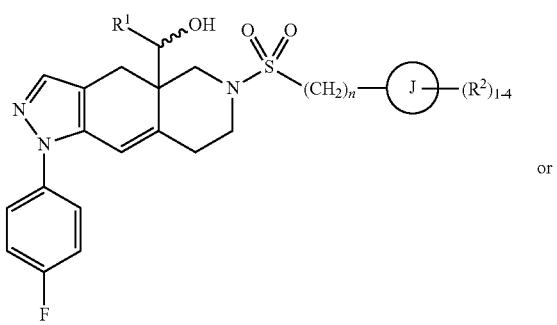

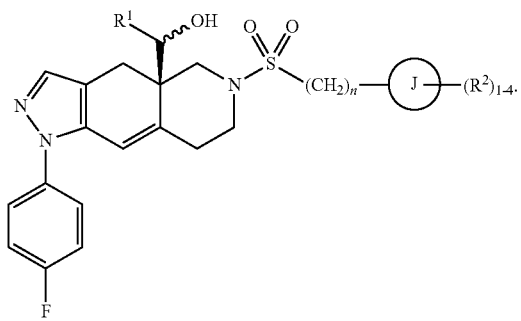

Alternatively, the compounds of formula II can have the following structure:

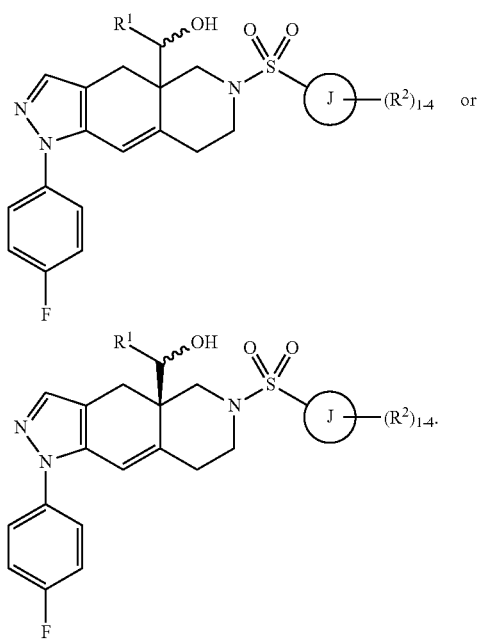

In some embodiments, the compound of formula II can be

Intermediate 3. (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(pyridin-2-yl)-(R/S)-methanol, Intermediate 4. (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(pyridin-3-yl)-(R/S)-methanol, Intermediate 5. (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(1-methyl-1H-imidazol-2-yl)-(R/S)-methanol, Intermediate 6. (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(thiazol-2-yl)-(R/S)-methanol, Intermediate 7. (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(oxazol-4-yl)-(R/S)-methanol, Intermediate 8. (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(furan-2-yl)-(R/S)-methanol, Intermediate 9. (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(thiophen-2-yl)-(R/S)-methanol, Intermediate 15. (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(5-methyl-1,3,4-oxadiazol-2-yl)-(R/S)-methanol, Intermediate 16. (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(oxazol-2-yl)-(R/S)-methanol, Intermediate 17. (R)-(1-(4-fluorophenyl)-6-(m-tolylsulfonyl)-4,4a,5,6,7,8-hexahydro-1H-pyrazolo[3,4-g]isoquinolin-4a-yl)(oxazol-2-yl)-(R/S)-methanol, Intermediate 18. (R)-(6-((3,5-difluorophenyl)sulfonyl)-1-(4-fluorophenyl)-4,4a,5,6,7,8-hexahydro-1H-pyrazolo[3,4-g]isoquinolin-4a-yl)(4-methoxypyridin-2-yl)-(R/S)-methanol, Intermediate 19. (R)-(4-ethylpyridin-2-yl)(1-(4-fluorophenyl)-6-((3,4,5-trifluorophenyl)sulfonyl)-4,4a,5,6,7,8-hexahydro-1H-pyrazolo[3,4-g]isoquinolin-4a-yl)-(R/S)-methanol, Intermediate 20. (R)-(1-(4-fluorophenyl)-6-((3,4,5-trifluorophenyl)sulfonyl)-4,4a,5,6,7,8-hexahydro-1H-pyrazolo[3,4-g]isoquinolin-4a-yl)(4-methoxypyridin-2-yl)-(R/S)-methanol, or Intermediate 62. (R)-(1-(4-fluorophenyl)-6-(m-tolylsulfonyl)-4,4a,5,6,7,8-hexahydro-1H-pyrazolo[3,4-g]isoquinolin-4a-yl)(pyrimidin-2-yl)-(R/S)-methanol.

Compounds of Formula II

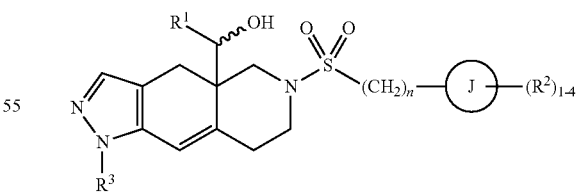

(II)

| Intermediate Compound | $R^1$ | $R^{1a}$ | Ring J | $R^2$ | n | $R^3$ |
|---|---|---|---|---|---|---|
| 3 | pyridin-2-yl | | phenyl | 4-$CF_3$ | 0 | 4-F-phenyl |
| 4 | pyridin-3-yl | | phenyl | 4-$CF_3$ | 0 | 4-F-phenyl |
| 5 | 1H-imidazol-2-yl | 1-Me | phenyl | 4-$CF_3$ | 0 | 4-F-phenyl |

-continued

Compounds of Formula II (II)

[Structure showing R¹, OH, pyrazole fused bicyclic with sulfonamide group, (CH₂)ₙ, Ring J, (R²)₁₋₄, and R³]

| Intermediate Compound | R¹ | R¹ᵃ | Ring J | R² | n | R³ |
|---|---|---|---|---|---|---|
| 6 | thiazol-2-yl | | phenyl | 4-CF₃ | 0 | 4-F-phenyl |
| 7 | oxazol-4-yl | | phenyl | 4-CF₃ | 0 | 4-F-phenyl |
| 8 | furan-2-yl | | phenyl | 4-CF₃ | 0 | 4-F-phenyl |
| 9 | thiophen-2-yl | | phenyl | 4-CF₃ | 0 | 4-F-phenyl |
| 15 | 1,3,4-oxadiazol-2-yl | 5-Me | phenyl | 4-CF₃ | 0 | 4-F-phenyl |
| 16 | oxazol-2-yl | | phenyl | 4-CF₃ | 0 | 4-F-phenyl |
| 17 | oxazol-2-yl | | phenyl | 3-Me | 0 | 4-F-phenyl |
| 18 | pyridin-2-yl | 4-OMe | phenyl | 3,5-difluoro | 0 | 4-F-phenyl |
| 19 | pyridin-2-yl | 4-Et | phenyl | 3,4,5-trifluoro | 0 | 4-F-phenyl |
| 20 | pyridin-2-yl | 4-OMe | phenyl | 3,4,5-trifluoro | 0 | 4-F-phenyl |
| 62 | pyrimidin-2-yl | | phenyl | 3-Me | 0 | 4-F-phenyl |

The compounds of the present invention can also be the salts and isomers thereof. In some embodiments, the compounds of the present invention include the salt forms thereof. Examples of applicable salt forms include hydrochlorides, hydrobromides, sulfates, methanesulfonates, nitrates, maleates, acetates, citrates, fumarates, tartrates (e.g. (+)-tartrates, (−)-tartrates or mixtures thereof including racemic mixtures), succinates, benzoates and salts with amino acids such as glutamic acid. These salts may be prepared by methods known to those skilled in art. When compounds of the present invention contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present invention contain basic acidic functionalities that allow the compounds to be converted into base addition salts. Additional information on suitable pharmaceutically acceptable salts can be found in Remington's Pharmaceutical Sciences, 17th ed., Mack Publishing Company, Easton, Pa., 1985, which is incorporated herein by reference.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the enantiomers, racemates, diastereomers, tautomers, geometric isomers, stereoisomeric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques.

Isomers include compounds having the same number and kind of atoms, and hence the same molecular weight, but differing in respect to the structural arrangement or configuration of the atoms.

It will be apparent to one skilled in the art that certain compounds of this invention may exist in tautomeric forms, all such tautomeric forms of the compounds being within the scope of the invention. Tautomer refers to one of two or more structural isomers which exist in equilibrium and which are readily converted from one isomeric form to another.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, the compounds of the present invention may also contain unnatural proportions of atomic isotopes at one or more of the atoms that constitute such compounds. For example, the compounds of the present invention may be radiolabeled with radioactive isotopes, such as for example deuterium ($^2$H), tritium ($^3$H), iodine-125 ($^{125}$I), carbon-13 ($^{13}$C), or carbon-14 ($^{14}$C). All isotopic variations of the compounds of the present invention, whether radioactive or not, are encompassed within the scope of the present invention.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

The compounds of the invention can be synthesized by a variety of methods known to one of skill in the art (see

*Comprehensive Organic Transformations* Richard C. Larock, 1989) or by an appropriate combination of generally well known synthetic methods. Techniques useful in synthesizing the compounds of the invention are both readily apparent and accessible to those of skill in the relevant art. The discussion below is offered to illustrate certain of the diverse methods available for use in assembling the compounds of the invention. However, the discussion is not intended to define the scope of reactions or reaction sequences that are useful in preparing the compounds of the present invention. One of skill in the art will appreciate that other methods of making the compounds are useful in the present invention. Although some compounds in FIG. 1, FIG. 2, and Table 1 may indicate relative stereochemistry, the compounds may exist as a racemic mixture or as either enantiomer.

Compounds of the present invention can be prepared as shown in FIG. 1. Starting materials can be obtained from commercial sources, by employing known synthetic methods, and by employing methods described in U.S. Pat. No. 7,928,237, incorporated herein by reference. Esters I are converted to ketones IV by reaction with an appropriate organometallic reagent such as a Grignard reagent, an organolithium reagent, an organoboron reagent, an organocerium reagent or an organozinc reagent in a solvent such as ether or tetrahydrofuran, or a similar aprotic solvent. Ketones of formula IV are also prepared by reaction of an aldehyde of formula II with an appropriate organometallic reagent followed by oxidation of the resultant alcohols of formula III with a suitable oxidizing agent such as the Dess-Martin periodinane reagent in an inert solvent such as dichloromethane. The tert-butoxycarbonyl protecting group is removed from IV by treatment with an acid, such as HCl, HBr, trifluoroacetic acid, p-toluenesulfonic acid or methanesulfonic acid, preferably HCl or trifluoroacetic acid, optionally in a solvent such as dioxane, ethanol or tetrahydrofuran, preferably dioxane, either under anhydrous or aqueous conditions. Amines V are converted to the compounds of formula (1) by treatment with an appropriate substituted sulfonyl halide, such as the sulfonyl chloride VI, in an inert solvent such as dichloromethane, toluene or tetrahydrofuran, preferably dichloromethane, in the presence of a base such as N,N-di-isopropylethylamine or triethylamine. It may be convenient to carry out the sulfonylation reaction in situ, without isolation of the amine V. Compounds of formula (1) can also be prepared from amines of formula V in a two-step sequence beginning with reaction of amines V with a halo-substituted sulfonyl chloride, VII, to afford a halo-substituted sulfonamide derivative exemplified by VIII (in which X represents a halogen). The halogen substituent X can be converted in a substituent $R^2$ by any standard method known to those skilled in the art. For example, if $R^2$ represents an amino substituent NR'R" (in which NR'R" can be either an acyclic or cyclic amine), this can be introduced by treating a compound of formula VIII with an amine HNR'R" in an inert solvent, such as tetrahydrofuran, toluene or N,N-dimethylformamide, in the presence of a palladium catalyst (e.g. BINAP/Pd$_2$(dba)$_3$) and a base (e.g. sodium or potassium tert-butoxide), optionally under microwave conditions, to afford compounds of formula (1). Alternatively, if X represents a fluorine or chlorine and $R^2$ represents an amino substituent NR'R", $R^2$ may be introduced by direct nucleophilic displacement of X. This may be accomplished using any standard method known to those skilled in the art, such as by reacting a compound of formula VIII with an amine, optionally at elevated temperature, optionally under microwave conditions, optionally in an appropriate solvent such as acetonitrile or N-methylpyrrolidine.

Figure 2:
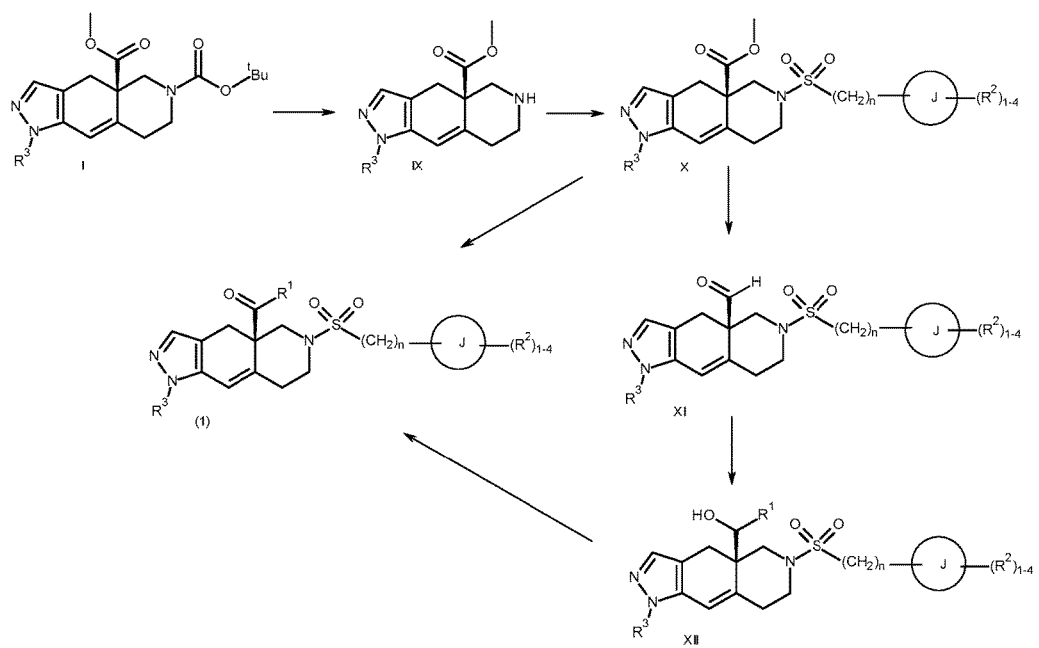

Alternatively, compounds of formula (1) are prepared as shown FIG. 2. The tert-butoxycarbonyl protecting group is removed from I by treatment with an acid, such as HCl, HBr, trifluoroacetic acid, p-toluenesulfonic acid or methanesulfonic acid, preferably HCl or trifluoroacetic acid, optionally in a solvent such as dioxane, ethanol or tetrahydrofuran, preferably dioxane, either under anhydrous or aqueous conditions. Amines IX are converted to the sulfonamides of formula X as described for the conversion of amines of formula V into sulfonamides of formula (1). The ester group in compounds of formula X is converted to an aldehyde of formula XI by using a reducing agent such as DIBAL-H, LiAlH$_4$ or RED-AL, preferably DIBAL-H in an inert solvent such as dichloromethane, tetrahydrofuran, benzene or toluene, preferably dichloromethane. It may be convenient to convert X into XI using a two-step process involving reduction of the ester to an alcohol and subsequent oxidation of the alcohol to an aldehyde of formula XI. The oxidation can be carried out using any suitable procedure, such as the Swern reaction, or an oxidizing reagent such as the Dess-Martin periodinane reagent in a suitable solvent, such as dichloromethane. Aldehydes of formula XI are converted into alcohols of formula XII using a suitable organometallic reagent, such as a Grignard reagent, an organolithium reagent, an organoboron reagent, an organocerium reagent or an organozinc reagent. Alcohols of formula XII are converted into ketones of formula (1) by oxidation. Suitable oxidation conditions include the Swern reaction and the use of the Dess-Martin periodinane reagent. Alternatively, esters of formula X are converted directly to ketones of formula (1) using an appropriate organometallic reagent.

IV. Pharmaceutical Compositions

In some embodiments, the present invention provides a pharmaceutical composition including a pharmaceutically acceptable excipient and a compound of the present invention. In some embodiments, the composition also includes an anti-inflammatory glucocorticosteroid.

Anti-Inflammatory Glucocorticosteroids

Anti-inflammatory glucocorticosteroids suitable for use with the present invention include those glucocorticosteroids that bind GR and include, but are not limited to, alclometasone, alclometasone dipropionate, beclometasone, beclometasone dipropionate, betamethasone, betamethasone butyrate proprionate, betamethasone dipropionate, betamethasone valerate, budesonide, ciclesonide, clobetasol, clobetasol propionate, clocortolone, clocortolone pivalate, cortexolone, cortisol, cortisporin, cortivazol, deflazacort, deprodone, deprodone propionate, desonide, dexamethasone, dexamethasone acetate, dexamethasone cipecilate, dexamethasone palmitate, difluprednate, fludroxycortide, flunisolide, fluocinolone, fluocinolone acetonide, fluocinonide, fluocortolone, fluorometholone, fluticasone, fluticasone propionate, fluticasone furoate, halcinonide, halometasone, halopredone, halopredone acetate, hydrocortisone, hydrocortisone 17-butyrate, hydrocortisone aceponate, hydrocortisone acetate, hydrocortisone probutate, hydrocortisone sodium succinate, loteprednol, loteprednol etabonate, meprednisone, methylprednisolone, methylprednisolone aceponate, methylprednisolone suleptanate, mometasone, mometasone furoate, naflocort, 19-nordeoxycorticosterone, 19-norprogesterone, otobiotic, oxazacort, paramethasone, prednicarbate, prednisolone, prednisolone farnesylate, prednisone, prednisone sodium phosphate, prednylidene, proctosedyl, rimexolone, tobradex, triamcinolone, triamcinolone hexacetonide, trimexolone, ulobetasol, ulobetasol propionate, 11β-(4-dimethylaminoethoxyphenyl)-17α-propynyl-17β-hydroxy-4,9estradien-3-one (RU009), 17β-hydroxy-17α-19-(4-methylphenyl)androsta-4,9(11)-dien-3-one (RU044), and the salt and esters forms thereof.

Additional anti-inflammatory glucocorticosteroids suitable for use with the present invention include, but are not limited to, a naturally occurring or synthetic steroid glucocorticoid which can be derived from cholesterol and is characterized by a hydrogenated cyclopentanoperhydrophenanthrene ring system. Suitable glucocorticosteroids also include, but are not limited to, 11-alpha,17-alpha,21-trihydroxypregn-4-ene-3,20-dione; 11-beta,16-alpha,17,21-tetrahydroxypregn-4-ene-3,20-dione; 11-beta,16-alpha,17,21-tetrahydroxypregn-1,4-diene-3,20-dione; 11-beta,17-alpha,21-trihydroxy-6-alpha-methylpregn-4-ene-3,20-dione; 11-dehydrocorticosterone; 11-deoxycortisol; 11-hydroxy-1,4-androstadiene-3,17-dione; 11-ketotestosterone; 14-hydroxyandrost-4-ene-3,6,17-trione; 15,17-dihydroxyprogesterone; 16-methylhydrocortisone; 17,21-dihydroxy-16-alpha-methylpregna-1,4,9(11)-triene-3,20-dione; 17-alpha-hydroxypregn-4-ene-3,20-dione; 17-alpha-hydroxypregnenolone; 17-hydroxy-16-beta-methyl-5-beta-pregn-9(11)-ene-3,20-dione; 17-hydroxy-4,6,8(14)-pregnatriene-3,20-dione; 17-hydroxypregna-4,9(11)-diene-3,20-dione; 18-hydroxycorticosterone; 18-hydroxycortisone; 18-oxocortisol; 21-acetoxypregnenolone; 21-deoxyaldosterone; 21-deoxycortisone; 2-deoxyecdysone; 2-methylcortisone; 3-dehydroecdysone; 4-pregnene-17-alpha,20-beta,21-triol-3,11-dione; 6,17,20-trihydroxypregn-4-ene-3-one; 6-alpha-hydroxycortisol; 6-alphafluoroprednisolone; 6-alpha-methylprednisolone; 6-alpha-methylprednisolone-21-acetate; 6-alpha-methylprednisolone 21-hemisuccinate sodium salt, 6-betahydroxy cortisol, 6-alpha, 9-alpha-difluoroprednisolone 21-acetate 17-butyrate, 6-hydroxycorticosterone; 6-hydroxydexamethasone; 6-hydroxyprednisolone; 9-fluorocortisone; alclomethasone dipropionate; algestone; alphaderm; amadinone; amcinonide; anagestone; androstenedione; anecortave acetate; beclomethasone; beclomethasone dipropionate; betamethasone 17-valerate; betamethasone sodium acetate; betamethasone sodium phosphate; betamethasone valerate; bolasterone; budesonide; calusterone; chlormadinone; chloroprednisone; chloroprednisone acetate; cholesterol; ciclesonide; clobetasol; clobetasol propionate; clobetasone; clocortolone; clocortolone pivalate; clogestone; cloprednol; corticosterone; cortisol; cortisol acetate; cortisol butyrate; cortisol cypionate; cortisol octanoate; cortisol sodium phosphate; cortisol sodium succinate; cortisol valerate; cortisone; cortisone acetate; cortivazol; cortodoxone; daturaolone; deflazacort, 21-deoxycortisol, dehydroepiandrosterone; delmadinone; deoxycorticosterone; deprodone; descinolone; desonide; desoximethasone; dexafen; dexamethasone; dexamethasone 21-acetate; dexamethasone acetate; dexamethasone sodium phosphate; dichlorisone; diflorasone; diflorasone diacetate; diflucortolone; difluprednate; dihydroelatericin a; domoprednate; doxibetasol; ecdysone; ecdysterone; emoxolone; endrysone; enoxolone; fluazacort; flucinolone; flucloronide; fludrocortisone; fludrocortisone acetate; flugestone; flumethasone; flumethasone pivalate; flumoxonide; flunisolide; fluocinolone; fluocinolone acetonide; fluocinonide; fluocortin butyl; 9-fluorocortisone; fluocortolone; fluorohydroxyandrostenedione; fluorometholone; fluorometholone acetate; fluoxymesterone; fluperolone acetate; fluprednidene; fluprednisolone; flurandrenolide; fluticasone; fluticasone propionate; fonnebolone; fonnestane; fonnocortal; gestonorone; glyderinine; halcinonide; halobetasol propionate; halometasone; halopredone; haloprogesterone; hydrocortamate; hydrocortisone cypionate; hydrocortisone; hydrocortisone; 21-butyrate; hydrocortisone aceponate; hydrocortisone acetate; hydrocortisone buteprate; hydrocortisone butyrate; hydrocortisone cypionate; hydrocortisone hemisuccinate; hydrocortisone probutate; hydrocortisone sodium phosphate; hydrocortisone sodium succinate; hydrocortisone valerate; hydroxyprogesterone; inokosterone; isoflupredone; isoflupredone acetate; isoprednidene; loteprednol etabonate; meclorisone; mecortolon; medrogestone; medroxyprogesterone; medrysone; megestrol; megestrol acetate; melengestrol; meprednisone; methandrostenolone; methylprednisolone; methylprednisolone aceponate; methylprednisolone acetate; methylprednisolone hemisuccinate; methylprednisolone sodium succinate; methyltestosterone; metribolone; mometasone; mometasone furoate; mometasone furoate monohydrate; nisone; nomegestrol; norgestomet; norvinisterone; oxymesterone; paramethasone; paramethasone acetate; ponasterone; prednicarbate; prednisolamate; prednisolone; prednisolone 21-diethylaminoacetate; prednisolone 21-hemisuccinate; prednisolone acetate; prednisolone famesylate; prednisolone hemisuccinate; prednisolone-21 (beta-D-glucuronide); prednisolone metasulphobenzoate; prednisolone sodium phosphate; prednisolone steaglate; prednisolone tebutate; prednisolone tetrahydrophthalate; prednisone; prednival; prednylidene; pregnenolone; procinonide; tralonide; progesterone; promegestone; rhapontisterone; rimexolone; roxibolone; rubrosterone; stizophyllin; tixocortol; topterone; triamcinolone; triamcinolone acetonide; triamcinolone acetonide 21-palmitate; triamcinolone benetonide; triamcinolone diacetate; triamcinolone hexacetonide; trimegestone; turkesterone; and wortmannin.

Additional anti-inflammatory glucocorticosteroids suitable for use with the present invention include, but are not limited to, alclometasone, beclometasone, betamethasone, budesonide, ciclesonide, clobetasol, clocortolone, cortexolone, cortisol, cortisporin, cortivazol, deflazacort, deprodone, desonide, dexamethasone, difluprednate, fludroxycortide, flunisolide, fluocinolone, fluocinonide, fluocortolone, fluorometholone, fluticasone, halcinonide, halometasone, halopredone, hydrocortisone, loteprednol, meprednisone, methylprednisolone, mometasone, naflocort, 19-nordeoxycorticosterone, 19-norprogesterone, otobiotic, oxazacort, paramethasone, prednicarbate, prednisolone, prednisone, prednylidene, proctosedyl, rimexolone, tobradex, triamcinolone, trimexolone, ulobetasol, 11β-(4-dimethylaminoethoxyphenyl)-17α-propynyl-17β-hydroxy-4,9estradien-3-one (RU009), and 17β-hydroxy-17α-19-(4-methylphenyl)androsta-4,9(11)-dien-3-one (RU044).

The anti-inflammatory glucocorticosteroids of the present invention also include the salts, hydrates, solvates and prodrug forms. The anti-inflammatory glucocorticosteroids of the present invention also include the isomers and metabolites of those described above.

Salts include, but are not limited, to sulfate, citrate, acetate, oxalate, chloride, bromide, iodide, nitrate, bisulfate, phosphate, acid phosphate, phosphonic acid, isonicotinate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. Other salts include, but are not limited to, salts with inorganic bases including alkali metal salts such as sodium salts, and potassium salts; alkaline earth metal salts such as calcium salts, and magnesium salts; aluminum salts; and ammonium salts. Other salts with organic bases include salts with diethylamine, diethanolamine, meglumine, and N,N'-dibenzylethylenediamine.

The neutral forms of the anti-inflammatory glucocorticosteroids can be regenerated by contacting the salt with a base or acid and isolating the parent anti-inflammatory glucocorticosteroid in the conventional manner. The parent form of the anti-inflammatory glucocorticosteroid differs from the various salt forms in certain physical properties, such as solubility in polar solvents, but otherwise the salts are equivalent to the parent form of the compound for the purposes of the present invention.

Certain anti-inflammatory glucocorticosteroids of the present invention can exist in unsolvated forms as well as solvated forms, including hydrated forms. In general, the solvated forms are equivalent to unsolvated forms and are encompassed within the scope of the present invention. Certain anti-inflammatory glucocorticosteroids of the present invention may exist in multiple crystalline or amorphous forms. In general, all physical forms are equivalent for the uses contemplated by the present invention and are intended to be within the scope of the present invention.

Certain anti-inflammatory glucocorticosteroids of the present invention possess asymmetric carbon atoms (optical centers) or double bonds; the enantiomers, racemates, diastereomers, tautomers, geometric isomers, stereoisomeric forms that may be defined, in terms of absolute stereochemistry, as (R)- or (S)- or, as (D)- or (L)- for amino acids, and individual isomers are encompassed within the scope of the present invention. The anti-inflammatory glucocorticosteroids of the present invention do not include those which are known in art to be too unstable to synthesize and/or isolate. The present invention is meant to include anti-inflammatory glucocorticosteroids in racemic and optically pure forms. Optically active (R)- and (S)-, or (D)- and (L)-isomers may be prepared using chiral synthons or chiral reagents, or resolved using conventional techniques.

The present invention also provides anti-inflammatory glucocorticosteroids which are in a prodrug form. Prodrugs of the anti-inflammatory glucocorticosteroids described herein are those anti-inflammatory glucocorticosteroids that readily undergo chemical changes under physiological conditions to provide the compounds of the present invention. Additionally, prodrugs can be converted to the anti-inflammatory glucocorticosteroids of the present invention by chemical or biochemical methods in an ex vivo environment. For example, prodrugs can be slowly converted to the anti-inflammatory glucocorticosteroids of the present invention when placed in a transdermal patch reservoir with a suitable enzyme or chemical reagent.

V. Formulation

The compositions of the present invention can be prepared in a wide variety of oral, parenteral and topical dosage forms. Oral preparations include tablets, pills, powder, dragees, capsules, liquids, lozenges, cachets, gels, syrups, slurries, suspensions, etc., suitable for ingestion by the patient. The compositions of the present invention can also be administered by injection, that is, intravenously, intramuscularly, intracutaneously, subcutaneously, intraduodenally, or intraperitoneally. Also, the compositions described herein can be administered by inhalation, for example, intranasally. Additionally, the compositions of the present invention can be administered transdermally. The compositions of this invention can also be administered by intraocular, intravaginal, and intrarectal routes including suppositories, insufflation, powders and aerosol formulations (for examples of steroid inhalants, see Rohatagi, *J. Clin. Pharmacol.* 35:1187-1193, 1995; Tjwa, *Ann. Allergy Asthma Immunol.* 75:107-111, 1995). Accordingly, the present invention also provides pharmaceutical compositions including a pharmaceutically acceptable carrier or excipient and a compound of the present invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Maack Publishing Co, Easton Pa. ("Remington's").

In powders, the carrier is a finely divided solid, which is in a mixture with the finely divided active component. In tablets, the active component is mixed with the carrier having the necessary binding properties in suitable proportions and compacted in the shape and size desired. The powders and tablets preferably contain from 5% or 10% to 70% of the compounds of the present invention.

Suitable solid excipients include, but are not limited to, magnesium carbonate; magnesium stearate; talc; pectin; dextrin; starch; tragacanth; a low melting wax; cocoa butter; carbohydrates; sugars including, but not limited to, lactose, sucrose, mannitol, or sorbitol, starch from corn, wheat, rice, potato, or other plants; cellulose such as methyl cellulose, hydroxypropylmethyl-cellulose, or sodium carboxymethyl-cellulose; and gums including arabic and tragacanth; as well as proteins including, but not limited to, gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain the compounds of the present invention mixed with a filler or binders such as lactose or starches, lubricants such as talc or magnesium stearate, and, optionally, stabilizers. In soft capsules, the compounds of the present invention may be dissolved or suspended in suitable liquids, such as fatty oils, liquid paraffin, or liquid polyethylene glycol with or without stabilizers.

For preparing suppositories, a low melting wax, such as a mixture of fatty acid glycerides or cocoa butter, is first melted and the compounds of the present invention are dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the compounds of the present invention in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can be formulated by suspending the compounds of the present invention in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, J. Pharmacol. Exp. Ther. 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The compositions of the present invention can also be delivered as microspheres for slow release in the body. For example, microspheres can be formulated for administration via intradermal injection of drug-containing microspheres, which slowly release subcutaneously (see Rao, J. Biomater Sci. Polym. Ed. 7:623-645, 1995; as biodegradable and injectable gel formulations (see, e.g., Gao Pharm. Res. 12:857-863, 1995); or, as microspheres for oral administration (see, e.g., Eyles, J. Pharm. Pharmacol. 49:669-674, 1997). Both transdermal and intradermal routes afford constant delivery for weeks or months.

In another embodiment, the compositions of the present invention can be formulated for parenteral administration, such as intravenous (IV) administration or administration into a body cavity or lumen of an organ. The formulations for administration will commonly comprise a solution of the compositions of the present invention dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of the compositions of the present invention in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In another embodiment, the formulations of the compositions of the present invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the compositions of the present invention into the target cells in vivo. (See, e.g., Al-Muhammed, J. Microencapsul. 13:293-306, 1996; Chonn, Curr. Opin. Biotechnol. 6:698-708, 1995; Ostro, Am. J. Hosp. Pharm. 46:1576-1587, 1989).

Lipid-based drug delivery systems include lipid solutions, lipid emulsions, lipid dispersions, self-emulsifying drug delivery systems (SEDDS) and self-microemulsifying drug delivery systems (SMEDDS). In particular, SEDDS and SMEDDS are isotropic mixtures of lipids, surfactants and co-surfactants that can disperse spontaneously in aqueous media and form fine emulsions (SEDDS) or microemulsions (SMEDDS). Lipids useful in the formulations of the present invention include any natural or synthetic lipids including, but not limited to, sesame seed oil, olive oil, castor oil, peanut oil, fatty acid esters, glycerol esters, Labrafil®, Labrasol®, Cremophor®, Solutol®, Tween®, Capryol®, Capmul®, Captex®, and Peceol®.

VI. Administration

The compounds and compositions of the present invention can be delivered by any suitable means, including oral, parenteral and topical methods. Transdermal administration methods, by a topical route, can be formulated as applicator sticks, solutions, suspensions, emulsions, gels, creams, ointments, pastes, jellies, paints, powders, and aerosols.

The pharmaceutical preparation is preferably in unit dosage form. In such form the preparation is subdivided into unit doses containing appropriate quantities of the compounds and compositions of the present invention. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The compounds and compositions of the present invention can be co-administered with other agents. Co-administration includes administering the compound or composition of the present invention within 0.5, 1, 2, 4, 6, 8, 10, 12, 16, 20, or 24 hours of the other agent. Co-administration also includes administering simultaneously, approximately simultaneously (e.g., within about 1, 5, 10, 15, 20, or 30 minutes of each other), or sequentially in any order. Moreover, the compounds and compositions of the present invention can each be administered once a day, or two, three, or more times per day so as to provide the preferred dosage level per day.

In some embodiments, co-administration can be accomplished by co-formulation, i.e., preparing a single pharmaceutical composition including the compounds and compositions of the present invention and any other agent. Alternatively, the various components can be formulated separately.

The compounds and compositions of the present invention, and any other agents, can be present in any suitable amount, and can depend on various factors including, but not limited to, weight and age of the subject, state of the disease, etc. Suitable dosage ranges include from about 0.1 mg to about 10,000 mg, or about 1 mg to about 1000 mg, or about 10 mg to about 750 mg, or about 25 mg to about 500 mg, or about 50 mg to about 250 mg. Suitable dosages also include about 1 mg, 5, 10, 20, 30, 40, 50, 60, 70, 80, 90, 100, 200, 300, 400, 500, 600, 700, 800, 900 or 1000 mg.

The composition can also contain other compatible therapeutic agents. The compounds described herein can be used in combination with one another, with other active agents known to be useful in modulating a glucocorticoid receptor, or with adjunctive agents that may not be effective alone, but may contribute to the efficacy of the active agent.

VII. Methods of Modulating a Glucocorticoid Receptor and Treating a Disorder In some embodiments, the present invention provides a method of modulating a glucocorticoid receptor, the method including contacting a glucocorticoid receptor with a compound of the present invention, thereby modulating the glucocorticoid receptor.

In some embodiments, the present invention provides a method of treating a disorder through modulating a glucocorticoid receptor, the method including administering to a subject in need of such treatment, a therapeutically effective amount of a compound of the present invention, thereby treating the disorder.

In some other embodiments, the present invention provides a method of treating a disorder through antagonizing a glucocorticoid receptor, the method including administering to a subject in need of such treatment, an effective amount of the compound of the present invention, thereby treating the disorder.

In another embodiment, the present invention provides methods of modulating glucocorticoid receptor activity using the techniques described herein. In an exemplary embodiment, the method includes contacting a GR with an effective amount of a compound of the present invention, such as the compound of the present invention, and detecting a change in GR activity.

In an exemplary embodiment, the GR modulator is an antagonist of GR activity (also referred to herein as "a glucocorticoid receptor antagonist"). A glucocorticoid receptor antagonist, as used herein, refers to any composition or compound which partially or completely inhibits (antagonizes) the binding of a glucocorticoid receptor (GR) agonist (e.g. cortisol and synthetic or natural cortisol analog) to a GR thereby inhibiting any biological response associated with the binding of a GR to the agonist.

In a related embodiment, the GR modulator is a specific glucocorticoid receptor antagonist. As used herein, a specific glucocorticoid receptor antagonist refers to a composition or compound which inhibits any biological response associated with the binding of a GR to an agonist by preferentially binding to the GR rather than another nuclear receptor (NR). In some embodiments, the specific glucocorticoid receptor antagonist binds preferentially to GR rather than the mineralocorticoid receptor (MR) or progesterone receptor (PR). In an exemplary embodiment, the specific glucocorticoid receptor antagonist binds preferentially to GR rather than the mineralocorticoid receptor (MR). In another exemplary embodiment, the specific glucocorticoid receptor antagonist binds preferentially to GR rather than the progesterone receptor (PR).

In a related embodiment, the specific glucocorticoid receptor antagonist binds to the GR with an association constant ($K_d$) that is at least 10-fold less than the $K_d$ for other nuclear receptor. In another embodiment, the specific glucocorticoid receptor antagonist binds to the GR with an association constant ($K_d$) that is at least 100-fold less than the $K_d$ for the other nuclear receptor. In another embodiment, the specific glucocorticoid receptor antagonist binds to the GR with an association constant ($K_d$) that is at least 1000-fold less than the $K_d$ for the other nuclear receptor.

Examples of disorders or conditions suitable for use with present invention include, but are not limited to, obesity, diabetes, cardiovascular disease, hypertension, Syndrome X, depression, anxiety, glaucoma, human immunodeficiency virus (HIV) or acquired immunodeficiency syndrome (AIDS), neurodegeneration, Alzheimer's disease, Parkinson's disease, cognition enhancement, Cushing's Syndrome, Addison's Disease, osteoporosis, frailty, muscle frailty, inflammatory diseases, osteoarthritis, rheumatoid arthritis, asthma and rhinitis, adrenal function-related ailments, viral infection, immunodeficiency, immunomodulation, autoimmune diseases, allergies, wound healing, compulsive behavior, multi-drug resistance, addiction, psychosis, anorexia, cachexia, post-traumatic stress syndrome, post-surgical bone fracture, medical catabolism, major psychotic depression, mild cognitive impairment, psychosis, dementia, hyperglycemia, stress disorders, antipsychotic induced weight gain, delirium, cognitive impairment in depressed patients, cognitive deterioration in individuals with Down's syndrome, psychosis associated with interferon-alpha therapy, chronic pain, pain associated with gastroesophageal reflux disease, postpartum psychosis, postpartum depression, neurological disorders in premature infants, and migraine headaches. In some embodiments, the disorder or condition can be major psychotic depression, stress disorders or antipsychotic induced weight gain. In other embodiments, the disorder or condition can be Cushing's Syndrome.

A. Binding Assays

GR modulators of this invention can be tested for binding activity in a variety of assays. For example, by screening for the ability to compete with a GR ligand, such as dexamethasone, for binding to the glucocorticoid receptor. Those of skill in the art will recognize that there are a number of ways to perform such competitive binding assays. In some embodiments, GR is pre-incubated with a labeled GR ligand and then contacted with a test compound. This type of competitive binding assay may also be referred to herein as a binding displacement assay. Alteration (e.g., a decrease) of the quantity of ligand bound to GR indicates that the molecule is a potential GR modulator. Alternatively, the binding of a test compound to GR can be measured directly with a labeled test compound. This latter type of assay is called a direct binding assay.

Both direct binding assays and competitive binding assays can be used in a variety of different formats. The formats may be similar to those used in immunoassays and receptor binding assays. For a description of different formats for binding assays, including competitive binding assays and direct binding assays, see *Basic and Clinical Immunology* 7th Edition (D. Stites and A. Terr ed.) 1991; *Enzyme Immunoassay*, E. T. Maggio, ed., CRC Press, Boca Raton, Fla. (1980); and "Practice and Theory of Enzyme Immunoassays," P. Tijssen, *Laboratory Techniques in Biochemistry and Molecular Biology*, Elsevier Science Publishers B.V. Amsterdam (1985), each of which is incorporated herein by reference.

In solid phase competitive binding assays, for example, the sample compound can compete with a labeled analyte for specific binding sites on a binding agent bound to a solid surface. In this type of format, the labeled analyte can be a GR ligand and the binding agent can be GR bound to a solid phase. Alternatively, the labeled analyte can be labeled GR and the binding agent can be a solid phase GR ligand. The concentration of labeled analyte bound to the capture agent is inversely proportional to the ability of a test compound to compete in the binding assay.

Alternatively, the competitive binding assay may be conducted in liquid phase, and any of a variety of techniques known in the art may be used to separate the bound labeled protein from the unbound labeled protein. For example, several procedures have been developed for distinguishing between bound ligand and excess bound ligand or between bound test compound and the excess unbound test compound. These include identification of the bound complex by sedimentation in sucrose gradients, gel electrophoresis, or gel isoelectric focusing; precipitation of the receptor-ligand complex with protamine sulfate or adsorption on hydroxylapatite; and the removal of unbound compounds or ligands by adsorption on dextran-coated charcoal (DCC) or binding to immobilized antibody. Following separation, the amount of bound ligand or test compound is determined.

Alternatively, a homogenous binding assay may be performed in which a separation step is not needed. For example, a label on the GR may be altered by the binding of the GR to its ligand or test compound. This alteration in the labeled GR results in a decrease or increase in the signal emitted by label, so that measurement of the label at the end of the binding assay allows for detection or quantitation of the GR in the bound state. A wide variety of labels may be used. The component may be labeled by any one of several methods. Useful radioactive labels include those incorporating $^3$H, $^{125}$I, $^{35}$S, $^{14}$C, or $^{32}$P. Useful non-radioactive labels include those incorporating fluorophores, chemiluminescent agents, phosphorescent agents, electrochemiluminescent agents, and the like. Fluorescent agents are especially useful in analytical techniques that are used to detect shifts in protein structure such as fluorescence anisotropy and/or fluorescence polarization. The choice of label depends on sensitivity required, ease of conjugation with the compound, stability requirements, and available instrumentation. For a review of various labeling or signal producing systems which may be used, see U.S. Pat. No. 4,391,904, which is incorporated herein by reference in its entirety for all purposes. The label may be coupled directly or indirectly to the desired component of the assay according to methods well known in the art.

High-throughput screening methods may be used to assay a large number of potential modulator compounds. Such "compound libraries" are then screened in one or more assays, as described herein, to identify those library members (particular chemical species or subclasses) that display a desired characteristic activity. Preparation and screening of chemical libraries is well known to those of skill in the art. Devices for the preparation of chemical libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.).

B. Cell-Based Assays

Cell-based assays involve whole cells or cell fractions containing GR to assay for binding or modulation of activity of GR by a compound of the present invention. Exemplary cell types that can be used according to the methods of the invention include, e.g., any mammalian cells including leukocytes such as neutrophils, monocytes, macrophages, eosinophils, basophils, mast cells, and lymphocytes, such as T cells and B cells, leukemias, Burkitt's lymphomas, tumor cells (including mouse mammary tumor virus cells), endothelial cells, fibroblasts, cardiac cells, muscle cells, breast tumor cells, ovarian cancer carcinomas, cervical carcinomas, glioblastomas, liver cells, kidney cells, and neuronal cells, as well as fungal cells, including yeast. Cells can be primary cells or tumor cells or other types of immortal cell lines. Of course, GR can be expressed in cells that do not express an endogenous version of GR.

In some cases, fragments of GR, as well as protein fusions, can be used for screening. When molecules that compete for binding with GR ligands are desired, the GR fragments used are fragments capable of binding the ligands (e.g., dexamethasone). Alternatively, any fragment of GR can be used as a target to identify molecules that bind GR. GR fragments can include any fragment of, e.g., at least 20, 30, 40, 50 amino acids up to a protein containing all but one amino acid of GR.

In some embodiments, signaling triggered by GR activation is used to identify GR modulators. Signaling activity of GR can be determined in many ways. For example, downstream molecular events can be monitored to determine signaling activity. Downstream events include those activities or manifestations that occur as a result of stimulation of a GR receptor. Exemplary downstream events useful in the functional evaluation of transcriptional activation and antagonism in unaltered cells include upregulation of a number of glucocorticoid response element (GRE)-dependent genes (PEPCK, tyrosine amino transferase, aromatase). In addition, specific cell types susceptible to GR activation may be used, such as osteocalcin expression in osteoblasts which is downregulated by glucocorticoids; primary hepatocytes which exhibit glucocorticoid mediated upregulation of PEPCK and glucose-6-phosphate (G-6-Pase)). GRE-mediated gene expression has also been demonstrated in transfected cell lines using well-known GRE-regulated sequences (e.g. the mouse mammary tumor virus promoter (MMTV) transfected upstream of a reporter gene construct). Examples of useful reporter gene constructs include luciferase (luc), alkaline phosphatase (ALP) and chloramphenicol acetyl transferase (CAT). The functional evaluation of transcriptional repression can be carried out in cell lines such as monocytes or human skin fibroblasts. Useful functional assays include those that measure IL-1beta stimulated IL-6 expression; the downregulation of collagenase, cyclooxygenase-2 and various chemokines (MCP-1, RANTES); LPS stimulated cytokine release, e.g., TNFα; or expression of genes regulated by NFkB or AP-1 transcription factors in transfected cell-lines.

Typically, compounds that are tested in whole-cell assays are also tested in a cytotoxicity assay. Cytotoxicity assays are used to determine the extent to which a perceived modulating effect is due to non-GR binding cellular effects. In an exemplary embodiment, the cytotoxicity assay includes contacting a constitutively active cell with the test compound. Any decrease in cellular activity indicates a cytotoxic effect.

C. Specificity

The compounds of the present invention may be subject to a specificity assay (also referred to herein as a selectivity assay). Typically, specificity assays include testing a compound that binds GR in vitro or in a cell-based assay for the degree of binding to non-GR proteins. Selectivity assays may be performed in vitro or in cell based systems, as described above. Binding may be tested against any appropriate non-GR protein, including antibodies, receptors, enzymes, and the like. In an exemplary embodiment, the non-GR binding protein is a cell-surface receptor or nuclear receptor. In another exemplary embodiment, the non-GR protein is a steroid receptor, such as estrogen receptor, progesterone receptor, androgen receptor, or mineralocorticoid receptor.

The terms and expressions which have been employed herein are used as terms of description and not of limitation, and there is no intention in the use of such terms and expressions of excluding equivalents of the features shown and described, or portions thereof, it being recognized that various modifications are possible within the scope of the invention claimed. Moreover, any one or more features of any embodiment of the invention may be combined with any one or more other features of any other embodiment of the invention, without departing from the scope of the invention. For example, the features of the GR modulator compounds are equally applicable to the methods of treating disease states and/or the pharmaceutical compositions described herein. All publications, patents, and patent applications cited herein are hereby incorporated by reference in their entirety for all purposes.

VIII. Methods of Treating and Reducing Steroid Side Effects

The compounds and compositions of the present invention are useful in a variety of methods such as treating a disorder or condition or reducing the side effects of glucocorticosteroid treatment.

In some embodiments, the present invention provides a method of inhibiting glucocorticoid receptor (GR) induced transactivation without substantially inhibiting GR-induced transrepression, wherein the method includes contacting a GR with a composition including an anti-inflammatory glucocorticosteroid able to induce both GR transactivation and GR transrepression, and a GR modulator of the present invention, in an amount sufficient to inhibit GR induced transactivation without substantially inhibiting GR-induced transrepression, thereby inhibiting GR induced transactivation without substantially inhibiting GR-induced transrepression. In some embodiments, the method of inhibiting glucocorticoid receptor (GR) induced transactivation without substantially inhibiting GR-induced transrepression, includes contacting the GR with a composition including the compound (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(thiazol-2-yl)methanone.

For those GR modulators of the present invention that can inhibit transactivation, the compounds can inhibit transactivation when GR induced transactivation of gene expression is reduced by at least about 50%, relative to the level of gene expression observed in the absence of the GR modulator. For example, GR induced transactivation can be inhibited by at least about 50, 55, 60, 65, 70, 75, 80, 85, 90, 95, 96, 97, 98 or 99%. In some embodiments, glucocorticoid receptor induced transactivation is inhibited by at least about 50%. In other embodiments, glucocorticoid receptor induced transactivation is inhibited by at least about 65%. In some other embodiments, glucocorticoid receptor induced transactivation is inhibited by at least about 75%. In still other embodiments, glucocorticoid receptor induced transactivation is inhibited by at least about 85%. In yet other embodiments, glucocorticoid receptor induced transactivation is inhibited by at least about 95%.

For those GR modulators of the present invention that can inhibit transactivation, some of the GR modulators may be able do so while not substantially inhibiting GR-induced transrepression activity. For example, GR-induced transrepression is considered not substantially inhibited when, in the presence of the composition of the present invention, the GR-induced transrepression activity is inhibited by less than about 75%, relative to the level of GR-induced transrepression activity in the absence of the GR modulator of the present invention. GR-induced transrepression is also considered not substantially inhibited when the GR-induced transrepression activity is inhibited by less than about 70, 60, 50, 40, 35, 30, 25, 20, 15, 10, 5, 4, 3, 2 or 1%, relative to the level of GR-induced transrepression activity in the absence of the GR modulator of the present invention. In some embodiments, GR-induced transrepression activity is inhibited by less than about 50%. In other embodiments, GR-induced transrepression activity is inhibited by less than about 25%. In some other embodiments, GR-induced transrepression activity is inhibited by less than about 10%.

In other embodiments, the ratio of percent inhibition of GR induced transactivation inhibition to percent inhibition of GR-induced transrepression inhibition can be from about 1000 to 1. For example, the ratio of percent inhibition of GR induced transactivation inhibition to percent inhibition of GR-induced transrepression inhibition can be about 1000, 500, 100, 90, 80, 70, 60, 50, 40, 30, 25, 20, 15, 10, 5, 4, 3, 2, or 1.

In some other embodiments, the GR induced transactivation is caused by the anti-inflammatory glucocorticosteroid described above.

In some embodiments, the present invention provides a method of treating a disorder or condition, including administering to a subject in need thereof, a therapeutically effective amount of a composition including an anti-inflammatory glucocorticosteroid and a GR modulator of the present invention. In some other embodiments, the anti-inflammatory glucocorticosteroid and GR modulator of the present invention modulate the activity of a GR. The diseases and conditions include, among other, inflammatory conditions and autoimmune diseases. In some embodiments, the disorder or condition can be glaucoma, inflammatory diseases, rheumatoid arthritis, asthma and rhinitis, allergies and autoimmune diseases. Representative autoimmune disease include, but are not limited to, obstructive airways disease, including conditions such as COPD, asthma (e.g. intrinsic asthma, extrinsic asthma, dust asthma, infantile asthma), bronchitis, including bronchial asthma, systemic lupus erythematosus (SLE), multiple sclerosis, type I diabetes mellitus and complications associated therewith, atopic eczema (atopic dermatitis), contact dermatitis and further eczematous dermatitis, inflammatory bowel disease (e.g. Crohn's disease and ulcerative colitis), atherosclerosis and amyotrophic lateral sclerosis. Other autoimmune diseases include tissue and organ transplants, and allergies.

In some embodiments, the present invention provides a method of reducing the side effects of glucocorticosteroid treatment, including administering to a subject in need thereof, a therapeutically effective amount of a composition including an anti-inflammatory glucocorticosteroid and a GR modulator having the structure of the present invention. In some embodiments, the side effects of glucocorticosteroid treatment can be weight gain, glaucoma, fluid retention, increased blood pressure, mood swings, cataracts, high blood sugar, diabetes, infection, loss of calcium from bones, osteoporosis, or menstrual irregularities. Additional side effects include muscle wasting, fat redistribution, growth retardation and cushingoid appearance.

Other conditions that can be treated using the compounds of the present invention include alcohol dependence, symptoms of alcohol withdrawal, and cognitive deficits associated with excess alcohol consumption. The compounds of the present invention can also be used to treat cancer, such as cancer of the bone, breast, prostate, ovary, skin, brain, bladder, cervix, liver, lung, etc. Other cancers that can be treated using the compounds of the present invention include leukemia, lymphoma, neuroblastoma, among others. When administered for the treatment of cancer, the compounds of the present invention can be administered separately or in combination with an antineoplastic agent such as taxanes, taxol, docetaxel, paclitaxel, actinomycin, anthracyclines, doxorubicin, daunorubicin, valrubicin, bleomycin, cisplatin, among others.

Assays to Identify GR Modulators

GR modulators of this invention can be tested for inhibition of GR induced transactivation while not substantially inhibiting GR-induced transrepression in a variety of assays. GR modulators of the present invention that inhibit GR induced transactivation can be identified by measuring the amount of tyrosine amino transferase expressed in the presence of the GR induced transactivation in a cell model (human liver hepatocytes). GR modulators useful in the present invention can be those that inhibit GR induced transactivation by at least about 50%.

Moreover, for the GR modulators of the present invention that induce transactivation, some may be able to do so while not inhibiting the GR-induced transrepression activity by more than about 50%. Specifically, the compositions of the present invention that can induce transactivation while not substantially inhibiting the GR-induced transrepression activity of dexamethasone with regard to LPS activated TNFα release (NFκB responsive gene), can be identified using a cell-based model (human peripheral blood mononuclear cells), dexamethasone can be administered to the cells and the release of TNFα can be measured. After addition of the GR modulator of the present invention, the release of TNFα can be again measured and compared to the amount released in the absence of the GR modulator. A GR modulator of the present invention that does not substantially block the effect of dexamethasone, does not substantially inhibit GR-induced transrepression.

IX. Examples

Structures are named according to standard IUPAC nomenclature using the CambridgeSoft ChemDraw naming package.

$^1$H NMR spectra were recorded at ambient temperature using a Varian Unity Inova spectrometer (400 MHz) with a 5 mm inverse detection triple resonance probe for detection of H1, C13 and P31 or a Bruker Avance DRX spectrometer (400 MHz) with a 5 mm inverse detection triple resonance TXI probe, or a Bruker Avance III spectrometer (400 MHz).

Mass spectrometry (LCMS) experiments to determine retention times and associated mass ions were performed using the following methods:

Method A: experiments were performed using a Waters Platform LC quadrupole mass spectrometer with positive and negative ion electrospray and ELS/Diode array detection using a Phenomenex Luna 3 micron C18 (2) 30×4.6 mm column and a 2 mL/minute flow rate. The solvent system was 95% water containing 0.1% formic acid (solvent A) and 5% acetonitrile containing 0.1% formic acid (solvent B) for the first 50 seconds followed by a gradient up to 5% solvent A and 95% solvent B over the next 4 minutes. The final solvent system was held constant for a further 1 minute.

Method B: experiments were performed using a VG Platform II quadrupole mass spectrometer with a positive and negative ion electrospray and ELS/Diode array detection using a Phenomenex Luna 3 micron C18 (2) 30×4.6 mm column and a 2 mL/minute flow rate. The initial solvent system was 95% water containing 0.1% formic acid (solvent A) and 5% acetonitrile containing 0.1% formic acid (solvent B) for the first 30 seconds followed by a gradient up to 5% solvent A and 95% solvent B over the next 4 minutes. The final solvent system was held constant for a further 2 minutes.

Method C: experiments were performed using a Waters ZMD quadrupole mass spectrometer with positive and negative ion electrospray and ELS/Diode array detection using a Phenomenex Luna 3 micron C18 (2) 30×4.6 mm column and a 2 mL/minute flow rate. The solvent system was 95% water containing 0.1% formic acid (solvent A) and 5% acetonitrile containing 0.1% formic acid (solvent B) for the first 50 seconds followed by a gradient up to 5% solvent A and 95% solvent B over the next 4 minutes. The final solvent system was held constant for a further 1 minute.

Method D: experiments were performed using a Waters Micromass ZQ2000 quadrupole mass spectrometer linked to a Waters Acquity UPLC system with a PDA UV detector using an Acquity UPLC BEH C18 1.7 micron 100×2.1 mm, maintained at 40° C. The spectrometer has an electrospray source operating in positive and negative ion mode. The initial solvent system was 95% water containing 0.1% formic acid (solvent A) and 5% acetonitrile containing 0.1% formic acid (solvent B) for 0.4 minutes followed by a gradient up to 5% solvent A and 95% solvent B over the next 6.4 minutes.

Method E: experiments were performed using a Waters Micromass ZQ2000 quadrupole mass spectrometer linked to a Hewlett Packard HP1100 LC system with a DAD UV detector using a Higgins Clipeus 5 micron C18 100×3.0 mm, maintained at 40° C. The spectrometer has an electrospray source operating in positive and negative ion mode. The initial solvent system was 95% water containing 0.1% formic acid (solvent A) and 5% acetonitrile containing 0.1% formic acid (solvent B) for 1.0 minutes followed by a gradient up to 5% solvent A and 95% solvent B over the next 15 minutes. The final solvent system was held constant for a further 5 minutes.

Method F: experiments were performed using an Agilent Infinity 1260 LC 6120 quadrupole mass spectrometer with positive and negative ion electrospray and ELS/UV @ 254 nm detection using an Agilent Zorbax Extend C18, Rapid Resolution HT 1.8 micron C18 30×4.6 mm column and a 2.5 mL/minute flow rate. The initial solvent system was 95% water containing 0.1% formic acid (solvent A) and 5% acetonitrile containing 0.1% formic acid (solvent B) ramping up to 5% solvent A and 95% solvent B over the next 3.0 minutes, the flow rate was then increased to 4.5 mL/minute and held for 0.5 minutes at 95% B. Over 0.1 minute the gradient was returned to 95% A and 5% B and 3.5 mL/minute and was held at these conditions for 0.3 minutes; the final 0.1 minute resulted in the return to the initial starting conditions, 95% A 5% B at 2.5 mL/minute.

Intermediate 1. (R)-1-(4-fluorophenyl)-6-((4-(trifluoromethyl)phenyl)sulfonyl)-4,4a,5,6,7,8-hexahydro-1H-pyrazolo[3,4-g]isoquinoline-4a-carbaldehyde and Intermediate 2. (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)methanol Intermediate 1

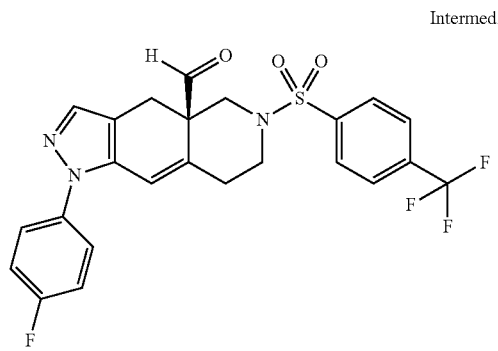

Intermediate 2

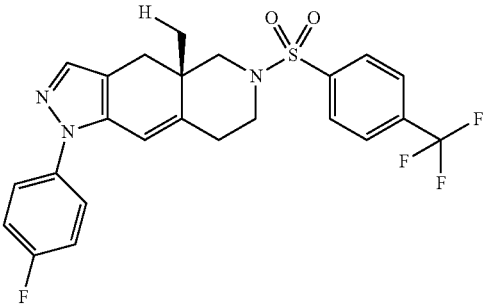

A solution of (R)-methyl 1-(4-fluorophenyl)-6-((4-(trifluoromethyl)phenyl)sulfonyl)-4,4a,5,6,7,8-hexahydro-1H-pyrazolo[3,4-g]isoquinoline-4a-carboxylate (2.12 g, 3.96 mmol) was dissolved in dry dichloromethane and cooled to −78° C. under nitrogen. A solution of diisobutylaluminum hydride (1.0 M in dichloromethane, 16 mmol, 16 mL) was added dropwise maintaining the reaction temperature at <−70° C. and the reaction mixture was stirred at −78° C. for 1 hour. The reaction mixture was treated with water (6 mL), stirred at −78° C. for 5 minutes then warmed to >0° C. over 15 minutes. Solid sodium bicarbonate (5.5 g) was added and the mixture stirred vigorously for 5 minutes. Excess sodium sulfate was added (~20 g) and the resultant mixture was stirred vigorously for a further 15 minutes. The solid materials were removed by filtration and rinsed with a little dichloromethane. The filtrate was concentrated under reduced pressure and the residue purified by column chromatography on silica gel eluting with a mixture of ethyl acetate and cyclohexane (3:7 by volume) followed by ethyl acetate to afford (R)-1-(4-fluorophenyl)-6-((4-(trifluoromethyl)phenyl)sulfonyl)-4,4a,5,6,7,8-hexahydro-1H-pyrazolo[3,4-g]isoquinoline-4a-carbaldehyde as a white foam (0.62 g). 1H NMR (400 MHz, CDCl$_3$): 9.48 (s, 1H); 7.93 (d, J=8.2 Hz, 2H); 7.84 (d, J=8.3 Hz, 2H); 7.39-7.40 (m, 3H); 7.17 (t, J=8.5 Hz, 2H); 6.52 (d, J=2.5 Hz, 1H); 4.32 (d, J=12.3 Hz, 1H); 3.90 (br s, 1H); 3.14 (d, J=16.4 Hz, 1H); 2.65-2.80 (m, 1H); 2.51-2.52 (m, 4H) and (R)-(1-(4-fluorophenyl)-6-((4-(trifluoromethyl)phenyl) sulfonyl)-4,4a,5,6,7,8-hexahydro-1H-pyrazolo[3,4-g]isoquinolin-4a-yl)methanol as a white solid (1.0 g). 1H NMR (400 MHz, CDCl$_3$): δ 7.94 (d, J=8.2 Hz, 2H); 7.83 (d, J=8.3 Hz, 2H); 7.40-7.41 (m, 3H); 7.14-7.15 (m, 2H); 6.31 (d, J=2.4 Hz, 1H); 4.11-4.12 (m, 1H); 4.02 (dd, J=11.4, 5.9 Hz, 1H); 3.78 (dd, J=11.5, 5.6 Hz, 1H); 3.34 (dd, J=11.4, 8.1 Hz, 1H); 3.13 (d, J=15.8 Hz, 1H); 2.74-2.76 (m, 1H); 2.59-2.60 (m, 1H); 2.41 (d, J=15.5 Hz, 1H); 2.24-2.25 (m, 2H); 2.04 (s, 1H).

Intermediate 1. (R)-1-(4-fluorophenyl)-6-((4-(trifluoromethyl)phenyl)sulfonyl)-4,4a,5,6,7,8-hexahydro-1H-pyrazolo[3,4-g]isoquinoline-4a-carbaldehyde A solution of oxalyl chloride (7.35 g, 58.8 mmol) in dry dichloromethane (160 mL) was cooled to −60° C. under nitrogen and treated dropwise with dry dimethyl sulfoxide (9.55 g, 122.5 mmol) such that the temperature did not rise above −50° C. The mixture was stirred at −55° C. for 15 minutes. A solution of (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)methanol (12.40 g, 24.5 mmol) in dry dichloromethane (140 mL) was added such that the temperature did not rise above −50° C. The mixture was stirred for 2 hours allowing the temperature to rise to −15° C. Triethylamine (12.64 g, 125 mmol) was added dropwise such that the temperature did not rise above −5° C. and the resultant mixture was stirred until the temperature reached 0° C. Water (100 mL) was added, the phases were separated, the aqueous phase was extracted with further dichloromethane (×2) and the combined organic phases were dried over sodium sulfate. The solids were removed by filtration, the filtrate was concentrated under reduced pressure and the residue was purified by column chromatography on silica gel eluting with a mixture of ethyl acetate and dichloromethane (1:1 by volume) followed by ethyl acetate to afford (R)-1-(4-fluorophenyl)-6-((4-(trifluoromethyl)phenyl)sulfonyl)-4,4a,5,6,7, 8-hexahydro-1H-pyrazolo[3,4-g]isoquinoline-4a-carbaldehyde as a white foam (11.8 g). 1H NMR (400 MHz, CDCl₃): δ 9.48 (s, 1H); 7.93 (d, J=8.2 Hz, 2H); 7.84 (d, J=8.3 Hz, 2H); 7.39-7.40 (m, 3H); 7.15-7.16 (m, 2H); 6.52 (d, J=2.4 Hz, 1H); 4.32 (dd, J=12.2, 2.1 Hz, 1H); 3.90 (dd, J=11.0, 5.6 Hz, 1H); 3.14 (d, J=16.4 Hz, 1H); 2.71-2.73 (m, 1H); 2.60 (d, J=16.4 Hz, 1H); 2.49-2.51 (m, 3H).

Intermediate 3. (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(pyridin-2-yl)-(R/S)-methanol

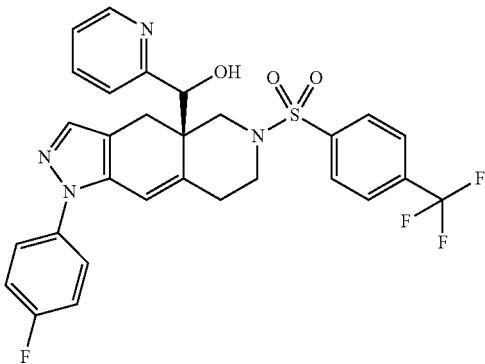 [SMILES: O=S(=O)(c1ccc(C(F)(F)F)cc1)N1CCC2=Cc3c(cnn3-c3ccc(F)cc3)C[C@]2(C(O)c2ccccn2)C1]

2-Bromopyridine (6.50 g, 40 mmol) was added to isopropyl magnesium chloride (2.0 M solution in tetrahydrofuran, 20 mL, 40 mmol) at room temperature. The mixture was stirred for 10 minutes then warmed to 30° C. and stirred for 105 minutes. The mixture was cooled to −10° C. and a solution of (R)-1-(4-fluorophenyl)-6-((4-(trifluoromethyl)phenyl)sulfonyl)-4,4a,5,6,7,8-hexahydro-1H-pyrazolo[3,4-g]isoquinoline-4a-carbaldehyde (5.5 g, 10 mmol) in tetrahydrofuran (9 mL) was added dropwise. The reaction mixture was stirred for 15 minutes at −10° C. followed by stirring at room temperature for 1 hour. The reaction mixture was cooled and treated with water (20 mL) followed by aqueous hydrochloric acid (1.0 M, 40 mL). The mixture was stirred for 10 minutes then extracted with dichloromethane (×2) and the combined organic phases dried over sodium sulfate. The solids were removed by filtration, the filtrate was concentrated under reduced pressure and the residue purified by column chromatography on silica gel (gradient: 20-80% ethyl acetate in cyclohexane) to afford the diastereoisomeric (2:1) mixture (R)-1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(pyridin-2-yl)-(R/S)-methanol as an off-white foam (3.25 g). 1H NMR (400 MHz, CDCl₃): δ 8.29 (d, J=4.8 Hz, 1H); 8.00 (d, J=8.2 Hz, 2H); 7.84-7.86 (m, 3H); 7.44-7.46 (m, 1H); 7.29-7.30 (m, 1.5H); 7.09-7.10 (m, 3.5H); 6.95-6.97 (m, 2.5 H); 6.41 (s, 0.5H); 6.18 (s, 1H); 5.11 (s, 0.5H); 5.04 (s, 1H); 4.87 (s, 1H); 4.50 (d, J=11.8 Hz, 1H); 4.10 (d, J=13.3 Hz, 2.5H); 3.80 (d, J=12.1 Hz, 0.5H); 3.69 (s, 0.5H); 3.24 (d, J=16.6 Hz, 1H); 3.09-3.13 (m, 1.5H); 2.54-2.58 (m, 2.5H); 2.25-2.27 (m, 1H); 2.11 (d, J=16.6 Hz, 1H); 1.43 (s, 0.5H).

The following intermediate 4 was similarly prepared from the appropriate starting materials:

Intermediate 4. (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(pyridin-3-yl)-(R/S)-methanol

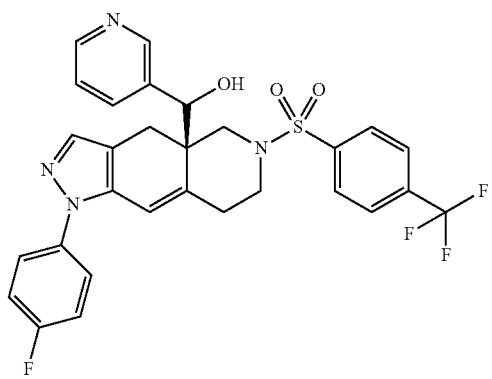 [SMILES: O=S(=O)(c1ccc(C(F)(F)F)cc1)N1CCC2=Cc3c(cnn3-c3ccc(F)cc3)C[C@]2(C(O)c2cccnc2)C1]

LCMS (Method C, ESI): RT 2.84 min, m+H=585.1; 1H NMR (400 MHz, CDCl₃): δ 8.33 (d, J=2.2 Hz, 1H); 8.18 (dd, J=4.8, 1.7 Hz, 1H); 7.97 (d, J=8.2 Hz, 2H); 7.85 (d, J=8.2 Hz, 2H); 7.69 (d, J=8.0 Hz, 1H); 7.04-7.05 (m, 4H); 6.92 (dd, J=7.9, 4.8 Hz, 1H); 6.10 (d, J=2.3 Hz, 1H); 5.18 (s, 1H); 4.34 (dd, J=12.3, 2.3 Hz, 1H); 4.15 (d, J=11.2 Hz, 1H); 3.42 (d, J=16.8 Hz, 1H); 3.25 (s, 1H); 2.66 (t, J=12.0 Hz, 1H); 2.52 (d, J=15.4 Hz, 1H); 2.34 (d, J=12.3 Hz, 1H); 2.17 (d, J=16.8 Hz, 1H).

Intermediate 5. (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(1-methyl-1H-imidazol-2-yl)-(R/S)-methanol

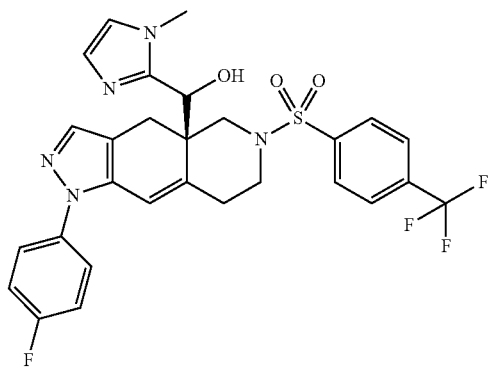 [SMILES: Cn1ccnc1C(O)[C@]12Cc3cnn(-c4ccc(F)cc4)c3C=C1CCN(S(=O)(=O)c1ccc(C(F)(F)F)cc1)C2]

2-Bromo-1-methyl-1H-imidazole (47 μL, 0.48 mmol) was dissolved in diethyl ether (2 mL) and cooled to −75° C. under argon. Butyl lithium (2.5 M in hexanes; 192 μL, 0.48 mmol) was added dropwise and the mixture stirred at −75° C. for 1 hour. A solution of (R)-1-(4-fluorophenyl)-6-((4-(trifluoromethyl)phenyl)sulfonyl)-4,4a,5,6,7,8-hexahydro-1H-pyrazolo[3,4-g]isoquinoline-4a-carbaldehyde (252 mg, 0.5 mmol) in diethyl ether (2 mL) was added dropwise. The reaction mixture was stirred for 16 hours whilst warming slowly to room temperature. The reaction mixture was cooled and treated with water (10 mL) and the phases separated. The organic phase was extracted with further diethyl ether (×2) followed by dichloromethane (×2). The combined organic phases were dried over sodium sulfate, the solids were removed by filtration and the filtrate was concentrated under reduced pressure. The residue was purified by column chromatography on silica gel (gradient: 17.5 to 25% acetone in cyclohexane) to afford (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(1-methyl-1H-imidazol-2-yl)-(R/S)-methanol as a white powder (82 mg) LCMS (Method A, ESI): RT 2.74 min, m+H=588.1

The following intermediates 6-9 were similarly prepared from the appropriate starting material:

Intermediate 6. (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(thiazol-2-yl)-(R/S)-methanol

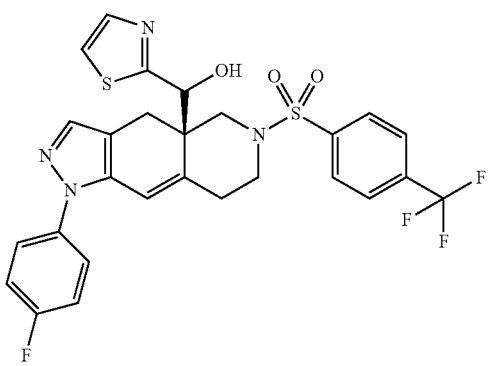 [SMILES: O=S(=O)(c1ccc(C(F)(F)F)cc1)N1CCC2=Cc3c(cnn3-c3ccc(F)cc3)C[C@]2(C(O)c2nccs2)C1]

LCMS (Method C, ESI): RT 3.83 min, m+H=591.0; 1H NMR (400 MHz, CDCl$_3$): δ 7.95 (t, J=9.5 Hz, 4H); 7.83 (t, J=8.6 Hz, 4H); 7.71 (d, J=3.2 Hz, 1H); 7.39-7.40 (m, 2H); 7.35 (s, 1H); 7.30 (d, J=3.2 Hz, 1H); 7.21-7.22 (m, 2H); 7.13-7.15 (m, 4H); 7.03-7.04 (m, 2H); 6.43 (s, 1H); 6.28 (d, J=2.3 Hz, 1H); 5.47 (d, J=5.5 Hz, 1H); 5.27 (d, J=5.4 Hz, 1H); 4.34 (d, J=12.2 Hz, 1H); 4.13 (t, J=8.8 Hz, 0.5H); 3.85 (d, J=5.6 Hz, 1H); 3.60-3.65 (m, 1H); 3.40 (s, 0.5H); 3.37 (d, J=6.1 Hz, 1H); 3.15 (d, J=16.3 Hz, 1H); 2.74 (d, J=12.3 Hz, 1H); 2.67 (dd, J=11.7, 3.8 Hz, 1H); 2.59 (d, J=16.7 Hz, 1H); 2.38 (d, J=11.8 Hz, 1H); 2.19 (d, J=16.8 Hz, 1H); 1.43 (s, 3H).

Intermediate 7. (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(oxazol-4-yl)-(R/S)-methanol

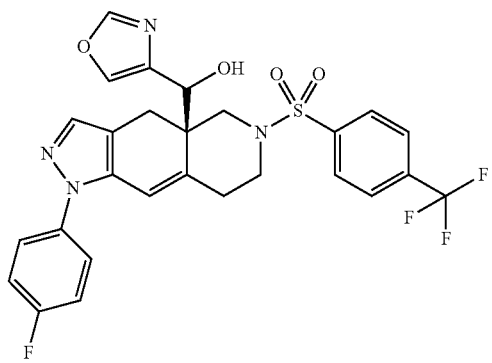 [SMILES: O=S(=O)(c1ccc(C(F)(F)F)cc1)N1CCC2=Cc3c(cnn3-c3ccc(F)cc3)C[C@]2(C(O)c2cocn2)C1]

LCMS (Method A, ESI): RT 3.77 min, m+H=575.2.

Intermediate 8. (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(furan-2-yl)-(R/S)-methanol

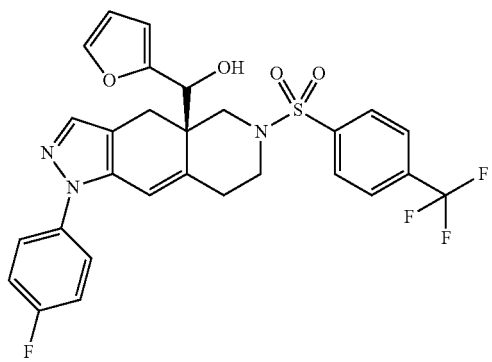 [SMILES: O=S(=O)(c1ccc(C(F)(F)F)cc1)N1CCC2=Cc3c(cnn3-c3ccc(F)cc3)C[C@]2(C(O)c2ccco2)C1]

LCMS (Method A, ESI): RT 4.04 min, m+H=574.1.

Intermediate 9. (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(thiophen-2-yl)-(R/S)-methanol

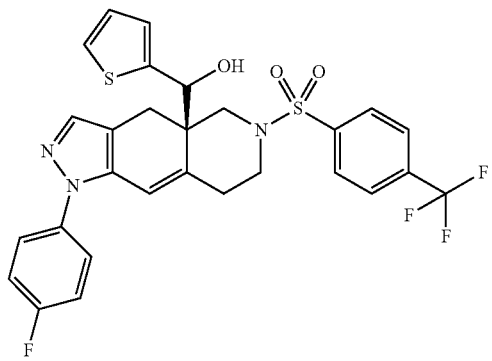 [SMILES: O=S(=O)(c1ccc(C(F)(F)F)cc1)N1CCC2=Cc3c(cnn3-c3ccc(F)cc3)C[C@]2(C(O)c2cccs2)C1]

LCMS (Method A, ESI): RT 4.11 min, m+H=590.1.

Intermediate 10. (R)-tert-butyl 1-(4-fluorophenyl)-4a-(R/S)-(hydroxy(pyridin-2-yl)methyl)-4a,5,7,8-tetrahydro-1H-pyrazolo[3,4-g]isoquinoline-6(4H)-carboxylate

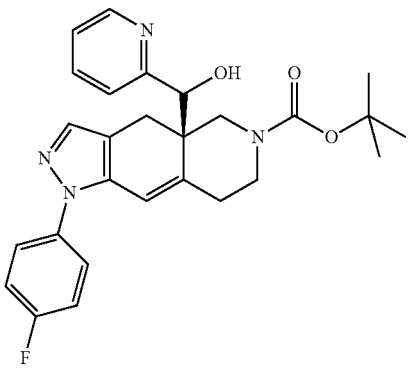 [SMILES: CC(C)(C)OC(=O)N1CCC2=Cc3c(cnn3-c3ccc(F)cc3)C[C@]2(C(O)c2ccccn2)C1]

A solution of 2-bromopyridine (182 μL, 1.82 mmol) in dry diethyl ether (10 mL) was cooled to −78° C. and butyl lithium (2.5 M in hexanes, 730 μL, 1.82 mmol) added dropwise. The mixture was stirred for 1 hour at −78° C. A solution of (R)-tert-butyl 1-(4-fluorophenyl)-4a-formyl-4a,5,7,8-tetrahydro-1H-pyrazolo[3,4-g]isoquinoline-6(4H)-carboxylate (800 mg, 2 mmol) in dry diethyl ether (10 mL) was added dropwise and the reaction mixture was stirred for 1 hour at −78° C. The reaction mixture was stirred and warmed to 0° C. over 1 hour following which the reaction was quenched by the addition of water (10 mL). The resultant mixture was stirred for 30 minutes then extracted with dichloromethane (×2) and the combined organic phases were dried over sodium sulfate. The solids were removed by filtration, the filtrate was concentrated under reduced pressure and the residue was purified by column chromatography on silica gel (gradient: 30-50% ethyl acetate in cyclohexane) to afford the diastereoisomeric mixture (R)-tert-butyl 1-(4-fluorophenyl)-4a-(R/S)-(hydroxy(pyridin-2-yl)methyl)-4a,5,7,8-tetrahydro-1H-pyrazolo[3,4-g]isoquinoline-6(4H)-carboxylate as a straw-coloured foam (410 mg). LCMS (Method C, ESI): RT 2.64/2.81 min, m+H=477.3.

Intermediate 11. (R)-tert-butyl 1-(4-fluorophenyl)-4a-picolinoyl-4a,5,7,8-tetrahydro-1H-pyrazolo[3,4-g]isoquinoline-6(4H)-carboxylate

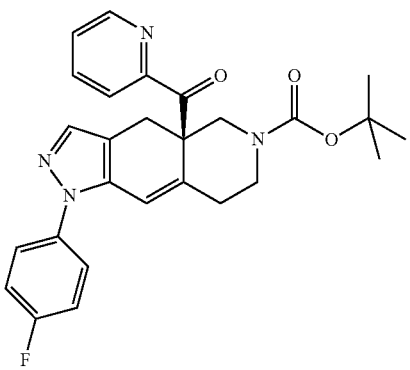 [SMILES: CC(C)(C)OC(=O)N1CCC2=Cc3c(cnn3-c3ccc(F)cc3)C[C@]2(C(=O)c2ccccn2)C1]

A solution of (R)-tert-butyl 1-(4-fluorophenyl)-4a-(R/S)-(hydroxy(pyridin-2-yl)methyl)-4a,5,7,8-tetrahydro-1H-pyrazolo[3,4-g]isoquinoline-6(4H)-carboxylate (410 mg, 0.86 mmol) in dry dichloromethane (10 mL) was treated with 1,1,1-triacetoxy-1,1-dihydro-1,2-benziodoxol-3(1H)-one (547 mg, 1.29 mmol; Dess-Martin periodinane) and the reaction mixture was stirred for 1 hour at room temperature. The reaction mixture was cooled and treated with saturated sodium hydrogen carbonate solution (20 mL) followed by dichloromethane (10 mL). The mixture was stirred for 10 minutes and the phases were separated. The aqueous phase was extracted with further dichloromethane (×2) and the combined organic phases dried over sodium sulfate. The solids were removed by filtration, the filtrate was concentrated under reduced pressure and the residue was purified by column chromatography on silica gel (gradient: 20-40% ethyl acetate in cyclohexane) to afford (R)-tert-butyl 1-(4-fluorophenyl)-4a-picolinoyl-4a,5,7,8-tetrahydro-1H-pyrazolo[3,4-g]isoquinoline-6(4H)-carboxylate as a pale yellow foam (185 mg). LCMS (Method B, ESI): RT 4.13 min, m+H=475.5; 1H NMR (400 MHz, CDCl$_3$): δ 8.68 (d, J=4.8 Hz, 2H); 7.44-7.45 (m, 5H); 7.15-7.16 (m, 3H); 6.51 (s, 2H); 2.83 (br s, 5H); 2.49 (s, 1H); 1.43 (s, 9H).

Alternative Procedure:

2-Bromopyridine (110.0 g, 690 mmole) as a solution in diethyl ether (200 mL) was added to a cooled (−65° C.) solution of 2.5 M n-BuLi (275 mL, 690 mmol) in diethyl ether (200 mL). The mixture was stirred for 1 h at −70° C. to −65° C. To this solution was then added a suspension of (R)-6-tert-butyl 4a-methyl 1-(4-fluorophenyl)-4a,5,7,8-tetrahydro-1H-pyrazolo[3,4-g]isoquinoline-4a,6(4H)-dicarboxylate (100.0 g, 230 mmol) in diethyl ether (1.0 L), keeping the temperature below −65° C. The resulting solution was stirred for 2 hours at −70° C. to −65° C. The reaction mixture was quenched with glacial acetic acid (50 mL) and diluted with water (200 mL). The organic layer was washed with 20% aqueous sodium chloride solution (250 mL), dried over magnesium sulphate and concentrated to give a yellow foam. The crude product was purified over silica gel (350 g, 240-400 mesh) by elution with heptane/ethyl acetate (8:1 to 2:1) to give (R)-tert-butyl 1-(4-fluorophenyl)-4a-picolinoyl-4a,5,7,8-tetrahydro-1H-pyrazolo[3,4-g]isoquinoline-6(4H)-carboxylate (109.5 g) as a yellow foam.

Intermediate 12. (R)-(1-(4-fluorophenyl)-4,4a,5,6,7,8-hexahydro-1H-pyrazolo[3,4-g]isoquinolin-4a-yl)(pyridin-2-yl)methanone

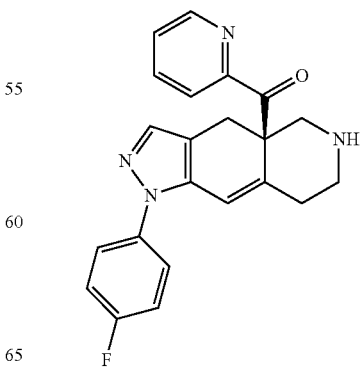

(R)-tert-butyl 1-(4-fluorophenyl)-4a-picolinoyl-4a,5,7,8-tetrahydro-1H-pyrazolo[3,4-g]isoquinoline-6(4H)-carboxylate (180 mg, 0.39 mmol) was dissolved in HCl-dioxan (4 M, 4 mL) and the resultant solution was stirred vigorously at room temperature for 1.5 hours. The reaction mixture was evaporated to afford (R)-(1-(4-fluorophenyl)-4,4a,5,6,7,8-hexahydro-1H-pyrazolo[3,4-g]isoquinolin-4a-yl)(pyridin-2-yl)methanone as a yellow solid. LCMS (Method B, ESI): RT 0.30 and 2.01 min, m+H=375.2.

Intermediate 13. (R)-(6-(((6-chloropyridin-3-yl)sulfonyl)-1-(4-fluorophenyl)-4,4a,5,6,7,8-hexahydro-1H-pyrazolo[3,4-g]isoquinolin-4a-yl)(pyridin-2-yl)methanone

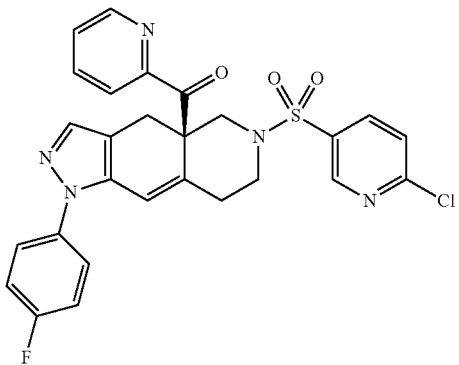 [SMILES: O=C(c1ccccn1)[C@]12Cc3cnn(-c4ccc(F)cc4)c3C=C1CCN(S(=O)(=O)c1ccc(Cl)nc1)C2]

A solution of (R)-(1-(4-fluorophenyl)-4,4a,5,6,7,8-hexahydro-1H-pyrazolo[3,4-g]isoquinolin-4a-yl)(pyridin-2-yl)methanone in dichloromethane (2.5 mL) (2.7 mL, 0.2 mmol) containing diisopropylamine (174 µL, 1 mmol) was added to 6-chloro-pyridine-3-sulfonyl chloride (53 mg, 0.25 mmol) and diisopropylethylamine (100 µL, 0.57 mmol) and the mixture stirred for 16 hours. The reaction mixture was concentrated and the residue was purified by column chromatography on silica gel (gradient: 20-30% ethyl acetate in cyclohexane) to afford (R)-(6-(((6-chloropyridin-3-yl)sulfonyl)-1-(4-fluorophenyl)-4,4a,5,6,7,8-hexahydro-1H-pyrazolo[3,4-g]isoquinolin-4a-yl)(pyridin-2-yl)methanone as a white solid (85 mg). LCMS (Method B ESI): RT 3.92 min, m+H=550.0; 1H NMR (400 MHz, CDCl$_3$): δ 8.66 (d, J=2.5 Hz, 1H); 8.61 (d, J=4.7 Hz, 1H); 7.85-7.86 (m, 3H); 7.48-7.49 (m, 1H); 7.42-7.43 (m, 2H); 7.35 (d, J=8.4 Hz, 1H); 7.27 (s, 1H); 7.15-7.16 (m, 2H); 6.50 (s, 1H); 5.57 (d, J=12.4 Hz, 1H); 4.23 (d, J=16.9 Hz, 1H); 3.85-3.95 (m, 1H); 2.86-2.87 (m, 3H); 2.66 (d, J=11.9 Hz, 1H); 2.53 (d, J=15.1 Hz, 1H).

The following intermediate 14 was similarly prepared from the appropriate starting materials:

Intermediate 14. (R)-(6-(((6-chloropyridin-3-yl)sulfonyl)-1-(4-fluorophenyl)-4,4a,5,6,7,8-hexahydro-1H-pyrazolo[3,4-g]isoquinolin-4a-yl)(thiazol-2-yl)methanone

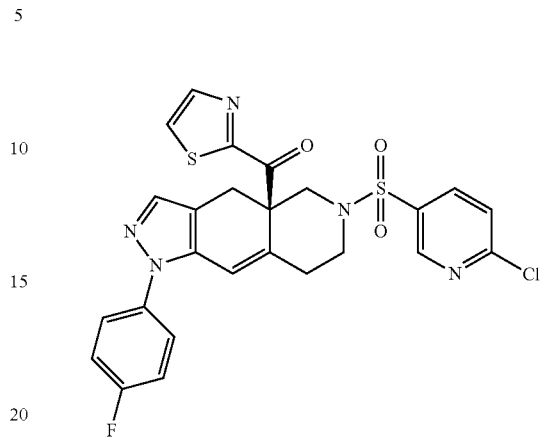

LCMS (Method F, ES-API): RT 2.46 min, m+H=555.8; 1H NMR (400 MHz, CDCl$_3$): δ 8.68 (1H, dd, J=2.6, 0.7 Hz), 8.00 (1H, d, J=3.0 Hz), 7.89 (1H, dd, J=8.3, 2.6 Hz), 7.69 (1H, d, J=3.0 Hz), 7.46-7.40 (2H, m), 7.37 (1H, dd, J=8.3, 0.7 Hz), 7.29 (1H, s), 7.20-7.14 (2H, m), 6.55 (1H, d, J=2.2 Hz), 5.50 (1H, dd, J=12.5, 2.0 Hz), 4.17 (1H, d, J=16.7 Hz), 3.97-3.91 (1H, m), 2.92-2.83 (3H, m), 2.69-2.63 (1H, m), 2.60-2.54 (1H, m).

Intermediate 15. (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(5-methyl-1,3,4-oxadiazol-2-yl)-(R/S)-methanol

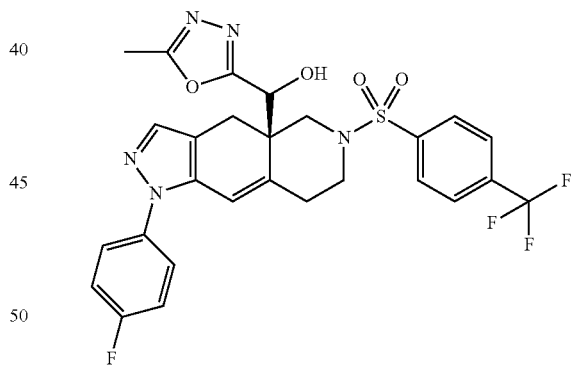

2-Methyl-[1,3,4]-oxadiazole (140 mg, 1.67 mmol) in dry tetrahydrofuran (5 mL) was cooled to −78° C. and butyl lithium (2.5 M solution in hexanes, 600 µL, 1.5 mmol) was added dropwise. The resultant reaction mixture was stirred for 10 minutes at −78° C. Magnesium bromide diethyl etherate (400 mg, 1.55 mmol) was added in one portion and the mixture was warmed to −45° C. over 1.5 hours where the temperature was maintained for 20 minutes. The reaction was re-cooled to −78° C. and a solution of (R)-1-(4-fluorophenyl)-6-((4-(trifluoromethyl)phenyl)sulfonyl)-4,4a,5,6,7,8-hexahydro-1H-pyrazolo[3,4-g]isoquinoline-4a-carbaldehyde (100 mg, 0.4 mmol) in dry tetrahydrofuran (5 mL) was added dropwise and the reaction mixture was stirred whilst allowing the reaction mixture to warm to −5° C. slowly. The reaction mixture was treated with saturated ammonium chloride solution (6 mL) and sufficient water to dissolve precipitated salts. The mixture was extracted with dichloromethane (3×10 mL) and the combined organic phases were dried over sodium sulfate. The solids were removed by filtration, the filtrate was concentrated under reduced pressure and the residue was purified by column chromatography on silica gel (gradient: 50-100% ethyl acetate in cyclohexane) to afford, as a (~2:1) mixture of diastereoisomers, (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(5-methyl-1,3,4-oxadiazol-2-yl)-(R/S)-methanol as an off-white foam (50 mg). LCMS (Method A, ESI): RT 3.38 min, m+H=590.4; 1H NMR (400 MHz, CDCl$_3$): δ 8.33 (s, 0.5H); 7.96 (d, J=8.2 Hz, 2H); 7.85-7.87 (m, 3H); 7.42-7.43 (m, 1H); 7.30 (s, 1H); 7.20-7.21 (m, 2H); 7.12-7.13 (m, 2.5H); 6.43 (s, 0.4H); 6.18 (d, J=2.3 Hz, 1H); 5.43 (d, J=4.4 Hz, 1H); 4.99 (s, 0.4H); 4.30-4.32 (m, 1H); 3.68-3.75 (m, 1H); 3.48 (d, J=16.7 Hz, 1H); 3.29 (d, J=16.2 Hz, 0.4H); 3.02-3.05 (m, 1H); 2.57 (d, J=12.0 Hz, 3H); 2.43-2.48 (m, 2H); 2.35-2.37 (m, 2H); 2.20 (s, 2H).

Intermediate 16. (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(oxazol-2-yl)-(R/S)-methanol

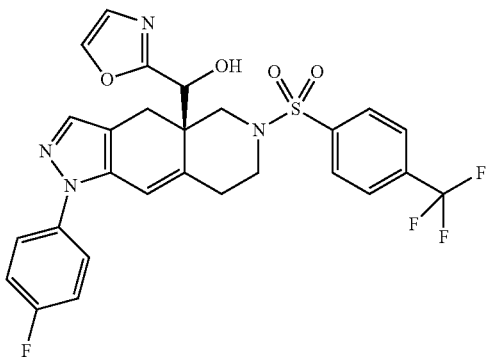 [SMILES: O=S(=O)(c1ccc(C(F)(F)F)cc1)N1CCC2=Cc3c(cnn3-c3ccc(F)cc3)C[C@]2(C(O)c2ncco2)C1]

To a solution of oxazole (99 μL, 0.5 mmol) in dry tetrahydrofuran (2.5 mL) was added borane-tetrahydrofuran complex (1.0 M in tetrahydrofuran, 1.65 mmol, 1.65 mL) and the mixture was stirred at room temperature for 1 hour. The mixture was cooled to −78° C. and butyl lithium (1.6 M solution in hexanes, 1.20 mL, 1.95 mmol) was added dropwise. The reaction mixture was stirred for 40 minutes at −78° C. A solution of (R)-1-(4-fluorophenyl)-6-((4-(trifluoromethyl)phenyl)sulfonyl)-4,4a,5,6,7,8-hexahydro-1H-pyrazolo[3,4-g]isoquinoline-4a-carbaldehyde (250 mg, 0.5 mmol) in dry tetrahydrofuran (3 mL) was added dropwise and the reaction mixture was stirred at −78° C. for 2 hours. The reaction mixture was warmed to room temperature and stirred for 2 hours. The reaction mixture was poured into ethanol/acetic acid mixture (95:5, v/v; 50 mL) and stirred at room temperature for 18 hours. The solvent was evaporated and the residue was dissolved in ethyl acetate (30 mL). The organic phase was washed with water (20 mL), saturated sodium bicarbonate (2×20 mL) and brine (20 mL). The organic phase was dried over sodium sulfate, the solids were removed by filtration and the filtrate was concentrated under reduced pressure. The residue was purified by column chromatography on silica gel (gradient: 0-4% methanol in dichloromethane) to afford, as a mixture of diastereoisomers, (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(oxazol-2-yl)-(R/S)-methanol as a white foam (136 mg). LCMS (Method A, ESI): RT 3.68 min, m+H=575.0.

The following intermediates 17-20 were similarly prepared from the appropriate starting material:

Intermediate 17. (R)-(1-(4-fluorophenyl)-6-(m-tolylsulfonyl)-4,4a,5,6,7,8-hexahydro-1H-pyrazolo[3,4-g]isoquinolin-4a-yl)(oxazol-2-yl)-(R/S)-methanol

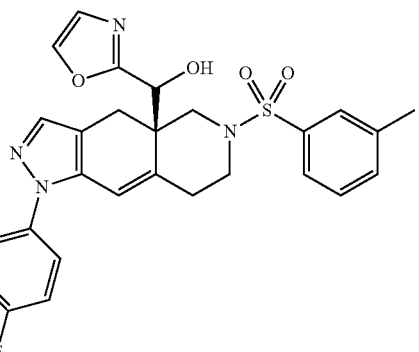

LCMS (Method F, ES-API): RT 2.26 min, m+H=521.1.

Intermediate 18. (R)-(6-((3,5-difluorophenyl)sulfonyl)-1-(4-fluorophenyl)-4,4a,5,6,7,8-hexahydro-1H-pyrazolo[3,4-g]isoquinolin-4a-yl)(4-methoxypyridin-2-yl)-(R/S)-methanol

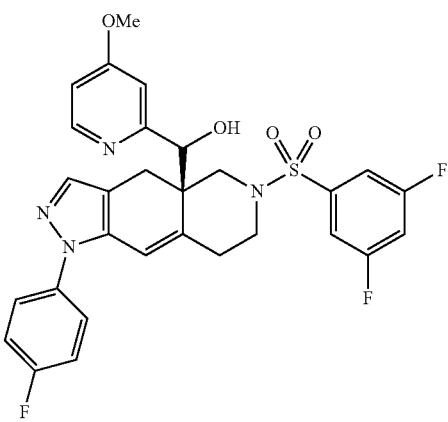 [SMILES: COc1ccnc(C(O)[C@]23Cc4cnn(-c5ccc(F)cc5)c4C=C2CCN(S(=O)(=O)c2cc(F)cc(F)c2)C3)c1]

LCMS (Method F, ES-API): RT 1.70, 1.76 min, m+H=583.2.

Intermediate 19. (R)-(4-ethylpyridin-2-yl)(1-(4-fluorophenyl)-6-((3,4,5-trifluorophenyl)sulfonyl)-4,4a,5,6,7,8-hexahydro-1H-pyrazolo[3,4-g]isoquinolin-4a-yl)-(R/S)-methanol

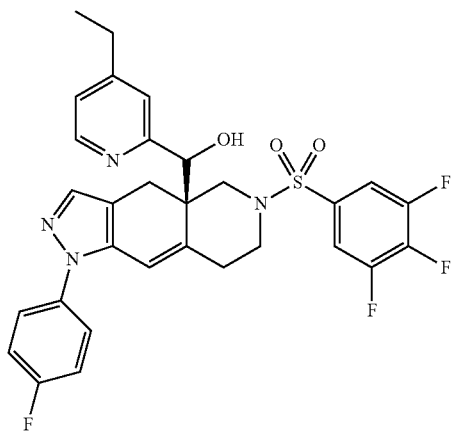 [SMILES: CCc1ccnc(C(O)[C@]23Cc4cnn(-c5ccc(F)cc5)c4C=C2CCN(S(=O)(=O)c2cc(F)c(F)c(F)c2)C3)c1]

LCMS (Method F, ES-API): RT 1.97/2.10 min (mixture of diastereomers), m+H=599.2.

Intermediate 20. (R)-(1-(4-fluorophenyl)-6-((3,4,5-trifluorophenyl)sulfonyl)-4,4a,5,6,7,8-hexahydro-1H-pyrazolo[3,4-g]isoquinolin-4a-yl)(4-methoxypyridin-2-yl)-(R/S)-methanol

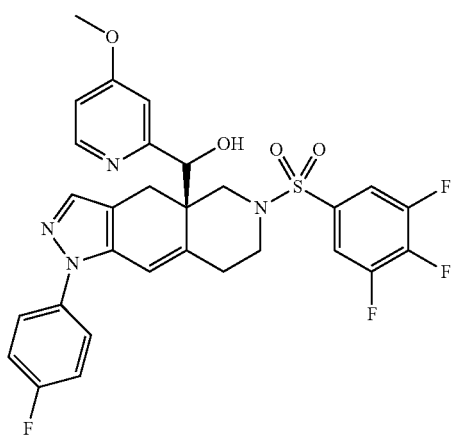 [SMILES: COc1ccnc(C(O)[C@]23Cc4cnn(-c5ccc(F)cc5)c4C=C2CCN(S(=O)(=O)c2cc(F)c(F)c(F)c2)C3)c1]

LCMS (Method F, ES-API): RT 1.90 min, m+H=601.2.

Intermediate 21. (R)-tert-butyl 1-(4-fluorophenyl)-4a-(thiazole-2-carbonyl)-4a,5,7,8-tetrahydro-1H-pyrazolo[3,4-g]isoquinoline-6(4H)-carboxylate

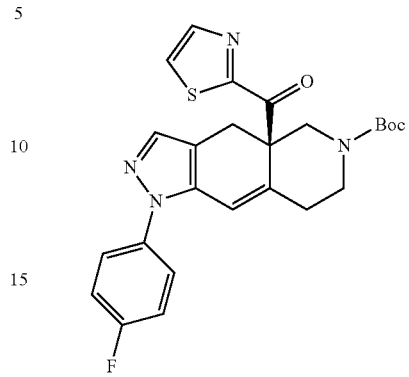

2-Bromothiazole (0.643 mL, 7.14 mmol) in dry ether (7 mL) was added to n-butyllithium (2.5 M in Hexanes) (2.92 mL, 7.31 mmol) in dry ether (5 mL) at −78° C. The reaction mixture was stirred at −78° C. for 45 minutes. A solution of (R)-6-tert-butyl 4a-methyl 1-(4-fluorophenyl)-4a,5,7,8-tetrahydro-1H-pyrazolo[3,4-g]isoquinoline-4a,6(4H)-dicarboxylate (1.0 g, 2.339 mmol) in dry ether (15 mL) was added dropwise and the reaction mixture was stirred for 0.5 hour at −78° C. Water (60 mL) was added and the reaction mixture was stirred at room temperature for 10 minutes. The aqueous layer was extracted with dichloromethane (3×75 mL). The combined organic extracts were washed with brine (100 mL), dried over magnesium sulfate, filtered and concentrated in vacuo to give a dark orange oil. The crude product was purified by column chromatography on silica gel (gradient: 0-40% ethyl acetate in isohexane) to afford (R)-tert-butyl 1-(4-fluorophenyl)-4a-(thiazole-2-carbonyl)-4a,5,7,8-tetrahydro-1H-pyrazolo[3,4-g]isoquinoline-6(4H)-carboxylate as an off-white solid (984 mg). LCMS (Method F, ES-API): RT 2.64 min, m+H=480.9; 1H NMR (400 MHz, CDCl$_3$): δ 8.06 (1H, d, J=3.0 Hz), 7.64 (1H, s), 7.48-7.43 (2H, m), 7.31 (1H, s), 7.20-7.14 (2H, m), 6.55 (1H, s), 5.60 (1H, br s), 4.49 (1H, d, J=15.0 Hz), 4.21 (1H, br s), 3.28-3.25 (1H, m), 2.86-2.81 (3H, m), 2.49 (1H, d, J=14.5 Hz), 1.55 (9H, s).

The following intermediates 22-30 were similarly prepared starting from the appropriate starting material:

Intermediate 22. (R)-tert-butyl 1-(4-fluorophenyl)-4a-(1-methyl-1H-1,2,4-triazole-5-carbonyl)-4a,5,7,8-tetrahydro-1H-pyrazolo[3,4-g]isoquinoline-6(4H)-carboxylate

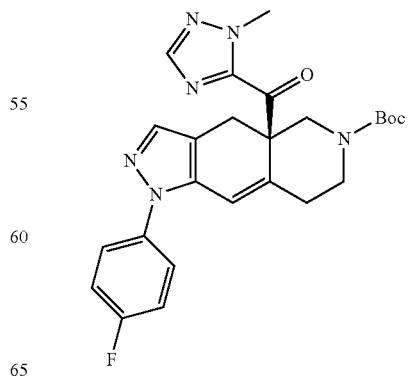

LCMS (Method F, ES-API): RT 2.51 min, m+H=479.3.

Intermediate 23. (R)-tert-butyl 1-(4-fluorophenyl)-4a-(pyrazine-2-carbonyl)-4a,5,7,8-tetrahydro-1H-pyrazolo[3,4-g]isoquinoline-6(4H)-carboxylate

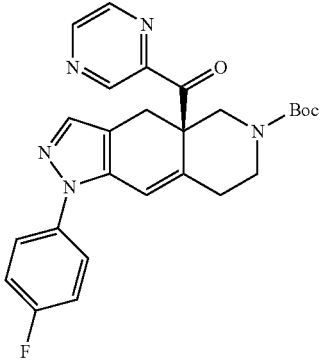 [SMILES: CC(C)(C)OC(=O)N1CCC2=Cc3c(cnn3-c3ccc(F)cc3)C[C@]2(C(=O)c2cnccn2)C1]

LCMS (Method F, ES-API): RT 2.48 min, m+H=476.3.

Intermediate 24. (R)-tert-butyl 1-(4-fluorophenyl)-4a-(5-methoxypicolinoyl)-4a,5,7,8-tetrahydro-1H-pyrazolo[3,4-g]isoquinoline-6(4H)-carboxylate

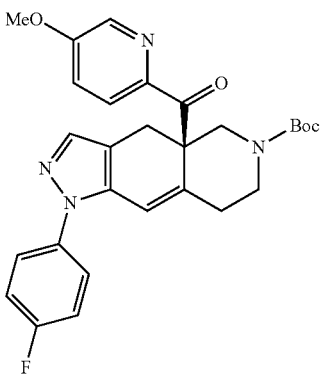 [SMILES: COc1ccc(C(=O)[C@]23Cc4cnn(-c5ccc(F)cc5)c4C=C2CCN(C(=O)OC(C)(C)C)C3)nc1]

LCMS (Method F, ES-API): RT 2.67 min, m+H=505.2.

Intermediate 25. (R)-tert-butyl 1-(4-fluorophenyl)-4a-(4-methylpicolinoyl)-4a,5,7,8-tetrahydro-1H-pyrazolo[3,4-g]isoquinoline-6(4H)-carboxylate

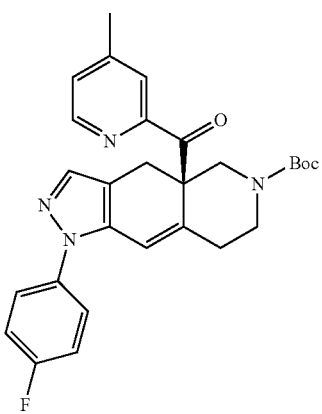 [SMILES: Cc1ccnc(C(=O)[C@]23Cc4cnn(-c5ccc(F)cc5)c4C=C2CCN(C(=O)OC(C)(C)C)C3)c1]

LCMS (Method F, ES-API): RT 2.82 min, m+H=489.3.

Intermediate 26. (R)-tert-butyl 4a-(4-ethylpicolinoyl)-1-(4-fluorophenyl)-4a,5,7,8-tetrahydro-1H-pyrazolo[3,4-g]isoquinoline-6(4H)-carboxylate

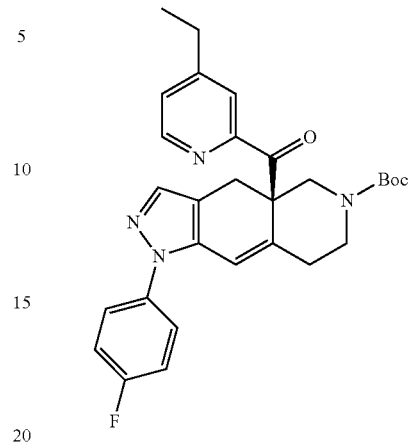

LCMS (Method F, ES-API): RT 3.05 min, m+H=503.3.

Intermediate 27. (R)-tert-butyl 1-phenyl-4a-picolinoyl-4a,5,7,8-tetrahydro-1H-pyrazolo[3,4-g]isoquinoline-6(4H)-carboxylate

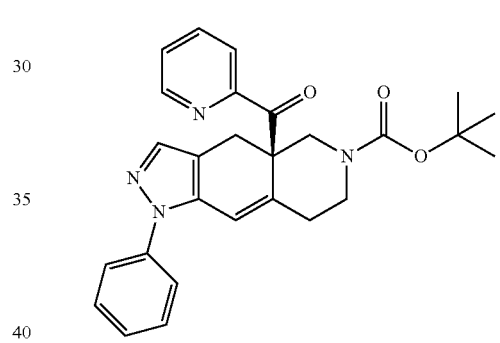

LCMS (Method F, ES-API): RT 2.65 min, m+H=457.

Intermediate 28. (R)-tert-butyl 1-(4-fluorophenyl)-4a-(2-(pyrrolidin-1-yl)isonicotinoyl)-4a,5,7,8-tetrahydro-1H-pyrazolo[3,4-g]isoquinoline-6(4H)-carboxylate

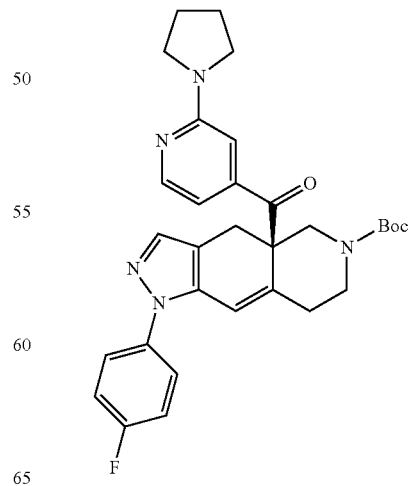

LCMS (Method F, ES-API): RT 2.06 min, m+H=544.0.

Intermediate 29. (R)-tert-butyl 1-(4-chlorophenyl)-4a-(4-(trifluoromethyl)picolinoyl)-4a,5,7,8-tetrahydro-1H-pyrazolo[3,4-g]isoquinoline-6(4H)-carboxylate

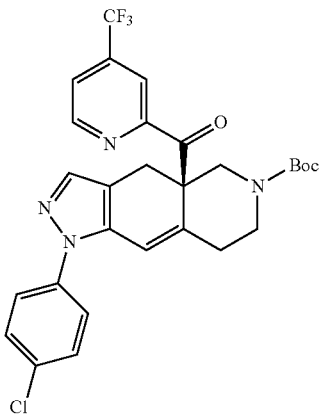 [SMILES: CC(C)(C)OC(=O)N1CCC2=Cc3c(cnn3-c3ccc(Cl)cc3)C[C@]2(C(=O)c2cc(C(F)(F)F)ccn2)C1]

LCMS (Method F, ES-API): RT 3.02 min, m+H=559.2.

Intermediate 30. (R)-tert-butyl 4a-picolinoyl-1-(4-(trifluoromethyl)phenyl)-4a,5,7,8-tetrahydro-1H-pyrazolo[3,4-g]isoquinoline-6(4H)-carboxylate

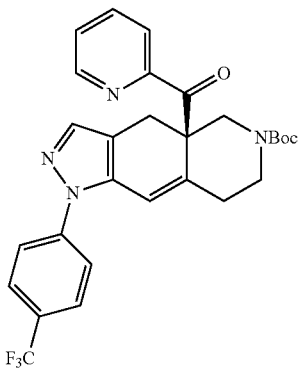 [SMILES: CC(C)(C)OC(=O)N1CCC2=Cc3c(cnn3-c3ccc(C(F)(F)F)cc3)C[C@]2(C(=O)c2ccccn2)C1]

LCMS (Method F, ES-API): RT 2.90 min, m+H=525.

Intermediate 31. (R)-(1-(4-fluorophenyl)-4,4a,5,6,7,8-hexahydro-1H-pyrazolo[3,4-g]isoquinolin-4a-yl)(thiazol-2-yl)methanone 2,2,2-trifluoroacetate

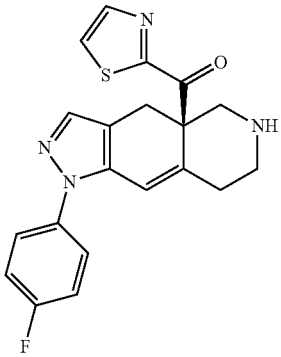 [SMILES: O=C(c1nccs1)[C@@]12CNCCC1=Cc1c(cnn1-c1ccc(F)cc1)C2]

A solution of (R)-tert-butyl 1-(4-fluorophenyl)-4a-(thiazole-2-carbonyl)-4a,5,7,8-tetrahydro-1H-pyrazolo[3,4-g]isoquinoline-6(4H)-carboxylate (1.0 g, 1.561 mmol) in 20% trifluoroacetic acid/dichloromethane (100 mL) was stirred at room temperature for 30 minutes. The solvent was removed in vacuo then the crude residue azeotroped twice with toluene to give (R)-(1-(4-fluorophenyl)-4,4a,5,6,7,8-hexahydro-1H-pyrazolo[3,4-g]isoquinolin-4a-yl)(thiazol-2-yl)methanone trifluoroacetate as an orange solid (0.584 g). LCMS (Method F, ES-API): RT 1.30 min, m+H=381.0; 1H NMR (400 MHz, CDCl$_3$): δ 8.02 (1H, d, J=2.7 Hz), 7.78 (1H, d, J=2.7 Hz), 7.48 (1H, s), 7.46-7.41 (2H, m), 7.24-7.16 (2H, m), 6.57 (1H, s), 4.45 (1H, d, J=12.5 Hz), 3.86 (1H, d, J=16.2 Hz), 3.74-3.65 (2H, m), 3.34 (1H, d, J=13.2 Hz), 3.12 (1H, br t, J=10.6 Hz), 2.89 (1H, d, J=16.2 Hz), 2.82 (1H, d, J=13.1 Hz), 2.62 (1H, d, J=15.4 Hz).

Intermediate 32. (R)-tert-butyl 1-(4-fluorophenyl)-4a-(2-(trimethylsilyl)thiazole-4-carbonyl)-4a,5,7,8-tetrahydro-1H-pyrazolo[3,4-g]isoquinoline-6(4H)-carboxylate

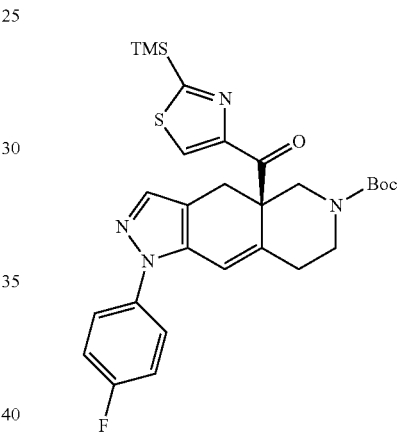

A solution of 4-bromo-2-(trimethylsilyl)thiazole (304 μl, 1.784 mmol) in dry ether (2 mL) was added to a solution of butyllithium (2.5 M in Hexanes) (731 μl, 1.828 mmol) in dry ether (1 mL) at −78° C. The reaction mixture was stirred at −78° C. for 30 minutes. A solution of (R)-6-tert-butyl 4a-methyl 1-(4-fluorophenyl)-4a,5,7,8-tetrahydro-1H-pyrazolo[3,4-g]isoquinoline-4a,6(4H)-dicarboxylate (250 mg, 0.585 mmol) in dry ether (5 mL) was added dropwise and the reaction mixture was stirred for 0.5 hour at −78° C. then slowly warmed to −50° C. over 2 hours. Water (10 mL) was added and the reaction mixture was stirred at room temperature for 10 minutes. The aqueous layer was extracted with ethyl acetate (3×15 mL). The combined organic extracts were washed with brine (20 mL), dried over magnesium sulfate, filtered and concentrated in vacuo to give a dark orange oil. The crude product was purified by column chromatography on silica gel (gradient: 0-40% ethyl acetate in isohexane) to afford (R)-tert-butyl 1-(4-fluorophenyl)-4a-(2-(trimethylsilyl)thiazole-4-carbonyl)-4a,5,7,8-tetrahydro-1H-pyrazolo[3,4-g]isoquinoline-6(4H)-carboxylate as a pale yellow foamy solid (76 mg). LCMS (Method F, ES-API): RT 2.65 min, m+H=553.3.

Intermediate 33. (R)-methyl 1-(4-fluorophenyl)-6-((3-(trifluoromethyl)phenyl)sulfonyl)-4,4a,5,6,7,8-hexahydro-1H-pyrazolo[3,4-g]isoquinoline-4a-carboxylate

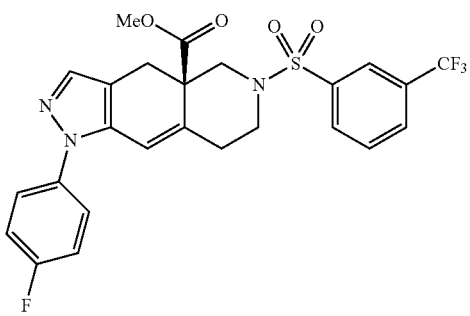 [SMILES: COC(=O)[C@]12Cc3cnn(-c4ccc(F)cc4)c3C=C1CCN(S(=O)(=O)c1cccc(C(F)(F)F)c1)C2]

A solution of (R)-6-tert-butyl 4a-methyl 1-(4-fluorophenyl)-4a,5,7,8-tetrahydro-1H-pyrazolo[3,4-g]isoquinoline-4a,6(4H)-dicarboxylate (2.0 g, 4.68 mmol) in 20% trifluoroacetic acid/dichloromethane (50 mL) was stirred at room temperature for 1 hour. The solvent was removed in vacuo, azeotroping three times with toluene (~20 mL), to give a dark orange oil. The oil was dissolved in dichloromethane (50 mL) and 3-(trifluoromethyl)benzene-1-sulfonyl chloride (0.900 ml, 5.61 mmol) was added followed by diisopropylethylamine (4.09 ml, 23.39 mmol). The reaction mixture was stirred at room temperature for 20 minutes, and then solvent removed in vacuo to give a dark orange oil. The crude product was purified by chromatography on silica gel (gradient: 0-45% ethyl acetate in isohexane) to afford (R)-methyl 1-(4-fluorophenyl)-6-((3-(trifluoromethyl)phenyl)sulfonyl)-4,4a,5,6,7,8-hexahydro-1H-pyrazolo[3,4-g]isoquinoline-4a-carboxylate (931 mg) as a pale yellow solid. LCMS (Method F, ES-API): RT 2.62 min, m+H=536.2.

The following intermediates 34-54 were similarly prepared from the appropriate starting material:

Intermediate 34. (R)-methyl 1-(4-fluorophenyl)-6-(m-tolylsulfonyl)-4,4a,5,6,7,8-hexahydro-1H-pyrazolo[3,4-g]isoquinoline-4a-carboxylate

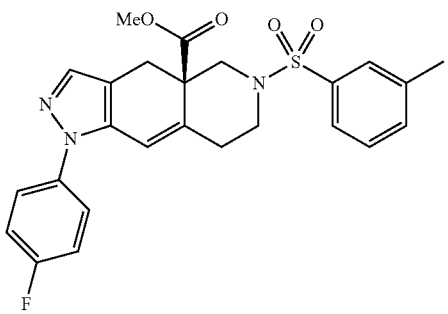 [SMILES: COC(=O)[C@]12Cc3cnn(-c4ccc(F)cc4)c3C=C1CCN(S(=O)(=O)c1cccc(C)c1)C2]

LCMS (Method F, ES-API): RT 2.52 min, m+H=482.2.

Intermediate 35. (R)-methyl 1-(4-fluorophenyl)-6-((3-methoxyphenyl)sulfonyl)-4,4a,5,6,7,8-hexahydro-1H-pyrazolo[3,4-g]isoquinoline-4a-carboxylate

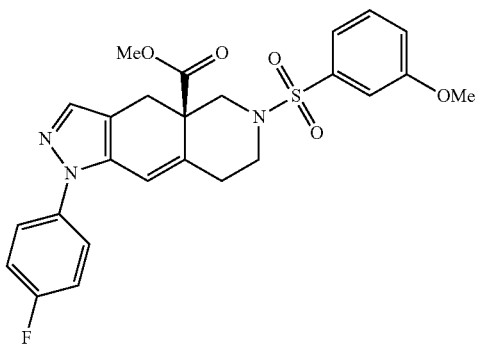 [SMILES: COC(=O)[C@]12Cc3cnn(-c4ccc(F)cc4)c3C=C1CCN(S(=O)(=O)c1cccc(OC)c1)C2]

LCMS (Method F, ES-API): RT 2.44 min, m+H=498.

Intermediate 36. (R)-methyl 6-((3-fluoro-4-methylphenyl)sulfonyl)-1-(4-fluorophenyl)-4,4a,5,6,7,8-hexahydro-1H-pyrazolo[3,4-g]isoquinoline-4a-carboxylate

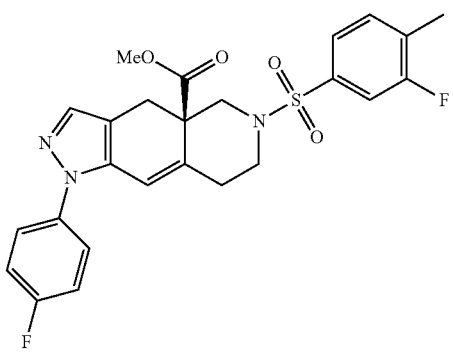 [SMILES: COC(=O)[C@]12Cc3cnn(-c4ccc(F)cc4)c3C=C1CCN(S(=O)(=O)c1ccc(C)c(F)c1)C2]

LCMS (Method F, ES-API): RT 2.57 min, m+H=500.

Intermediate 37. (R)-methyl 1-(4-fluorophenyl)-6-(phenylsulfonyl)-4,4a,5,6,7,8-hexahydro-1H-pyrazolo[3,4-g]isoquinoline-4a-carboxylate

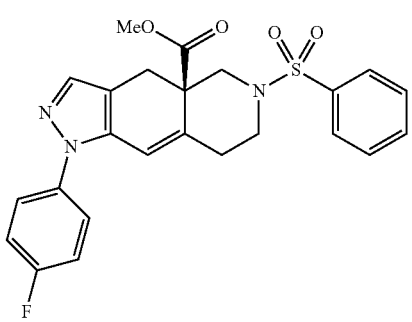 [SMILES: COC(=O)[C@]12Cc3cnn(-c4ccc(F)cc4)c3C=C1CCN(S(=O)(=O)c1ccccc1)C2]

LCMS (Method F, ES-API): RT 2.40 min, m+H=468.2.

Intermediate 38. (R)-methyl 6-((3-chlorophenyl)sulfonyl)-1-(4-fluorophenyl)-4,4a,5,6,7,8-hexahydro-1H-pyrazolo[3,4-g]isoquinoline-4a-carboxylate

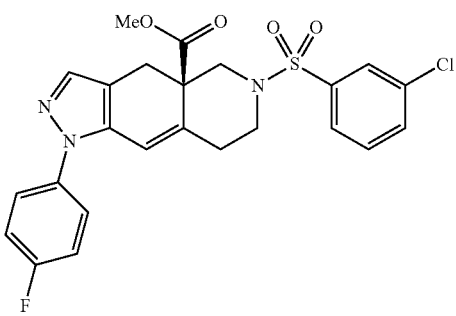 [SMILES: COC(=O)[C@]12Cc3cnn(-c4ccc(F)cc4)c3C=C1CCN(S(=O)(=O)c1cccc(Cl)c1)C2]

LCMS (Method F, ES-API): RT 2.58 min, m+H=502.2.

Intermediate 39. (R)-methyl 1-(4-fluorophenyl)-6-tosyl-4,4a,5,6,7,8-hexahydro-1H-pyrazolo[3,4-g]isoquinoline-4a-carboxylate

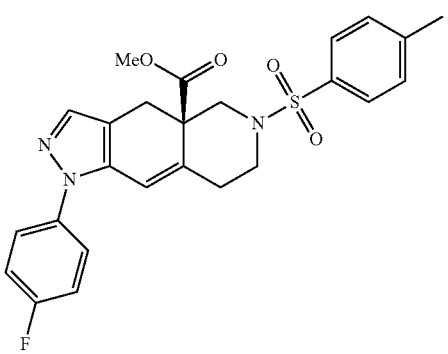 [SMILES: COC(=O)[C@]12Cc3cnn(-c4ccc(F)cc4)c3C=C1CCN(S(=O)(=O)c1ccc(C)cc1)C2]

LCMS (Method F, ES-API): RT 2.51 min, m+H=482.

Intermediate 40. (R)-methyl 6-((4-fluoro-3-(trifluoromethyl)phenyl)sulfonyl)-1-(4-fluorophenyl)-4,4a,5,6,7,8-hexahydro-1H-pyrazolo[3,4-g]isoquinoline-4a-carboxylate

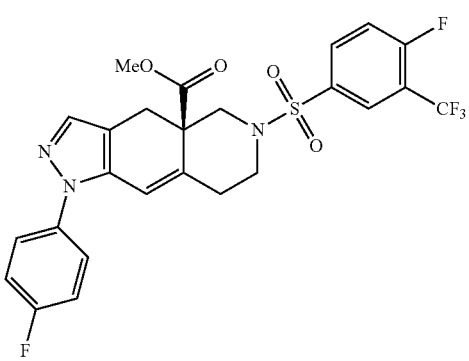 [SMILES: COC(=O)[C@]12Cc3cnn(-c4ccc(F)cc4)c3C=C1CCN(S(=O)(=O)c1ccc(F)c(C(F)(F)F)c1)C2]

Using HCl (4M solution in dioxane) in place of trifluoroacetic acid/dichloromethane. LCMS (Method F, ES-API): RT 2.66 min, m+H=554.

Intermediate 41. (R)-methyl 1-(4-fluorophenyl)-6-((3,4,5-trifluorophenyl)sulfonyl)-4,4a,5,6,7,8-hexahydro-1H-pyrazolo[3,4-g]isoquinoline-4a-carboxylate

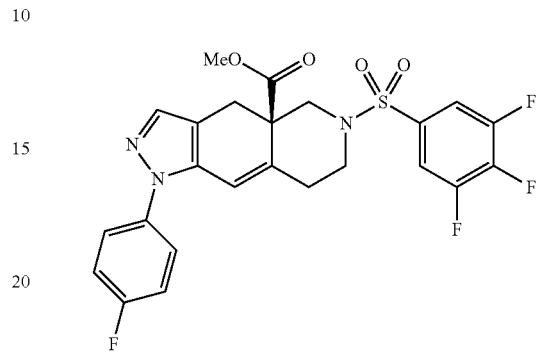

Using HCl (4M solution in dioxane) in place of trifluoroacetic acid/dichloromethane. LCMS (Method F, ES-API): RT 2.59 min, m+H=522.1.

Intermediate 42. (R)-methyl 6-((3-fluoro-4-(trifluoromethyl)phenyl)sulfonyl)-1-(4-fluorophenyl)-4,4a,5,6,7,8-hexahydro-1H-pyrazolo[3,4-g]isoquinoline-4a-carboxylate

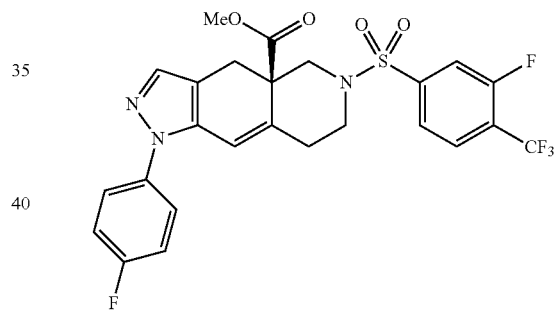

Using HCl (4M solution in dioxane) in place of trifluoroacetic acid/dichloromethane. LCMS (Method F, ES-API): RT 2.88 min, m+H=554.2.

Intermediate 43. (R)-methyl 6-((1-ethyl-1H-pyrazol-4-yl)sulfonyl)-1-(4-fluorophenyl)-4,4a,5,6,7,8-hexahydro-1H-pyrazolo[3,4-g]isoquinoline-4a-carboxylate

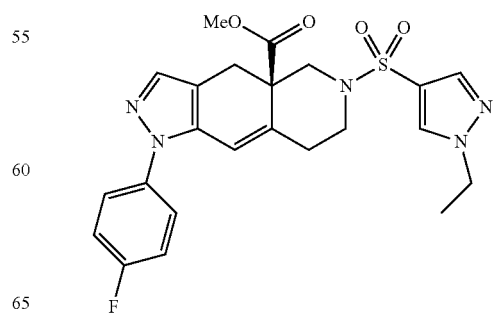

Using HCl (4M solution in dioxane) in place of trifluoroacetic acid/dichloromethane. LCMS (Method F, ES-API): RT 2.38 min, m+H=486.2.

Intermediate 44. (R)-methyl 6-((3,4-dichlorophenyl)sulfonyl)-1-(4-fluorophenyl)-4,4a,5,6,7,8-hexahydro-1H-pyrazolo[3,4-g]isoquinoline-4a-carboxylate

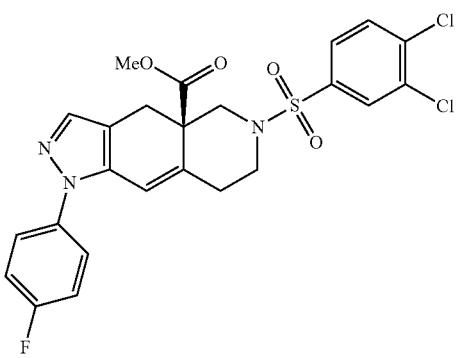 [SMILES: COC(=O)[C@]12Cc3cnn(-c4ccc(F)cc4)c3C=C1CCN(S(=O)(=O)c1ccc(Cl)c(Cl)c1)C2]

Using HCl (4M solution in dioxane) in place of trifluoroacetic acid/dichloromethane. LCMS (Method F, ES-API): RT 2.71 min, m+H=536.

Intermediate 45. (R)-methyl 1-(pyridin-3-yl)-6-((3-(trifluoromethyl)phenyl)sulfonyl)-4,4a,5,6,7,8-hexahydro-1H-pyrazolo[3,4-g]isoquinoline-4a-carboxylate

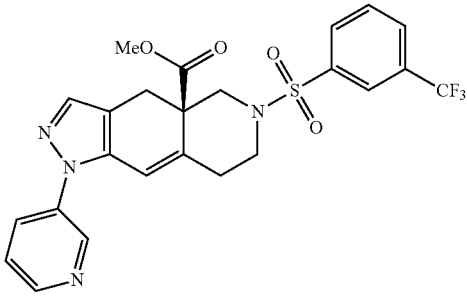 [SMILES: COC(=O)[C@]12Cc3cnn(-c4cccnc4)c3C=C1CCN(S(=O)(=O)c1cccc(C(F)(F)F)c1)C2]

Using HCl (4M solution in dioxane) in place of trifluoroacetic acid/dichloromethane. LCMS (Method F, ES-API): RT 2.24 min, m+H=519.

Intermediate 46. (R)-methyl 6-((3,4-dichlorophenyl)sulfonyl)-1-phenyl-4,4a,5,6,7,8-hexahydro-1H-pyrazolo[3,4-g]isoquinoline-4a-carboxylate

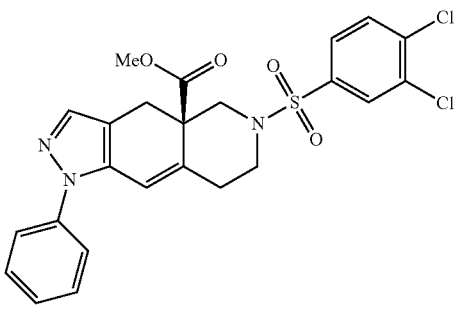 [SMILES: COC(=O)[C@]12Cc3cnn(-c4ccccc4)c3C=C1CCN(S(=O)(=O)c1ccc(Cl)c(Cl)c1)C2]

Using HCl (4M solution in dioxane) in place of trifluoroacetic acid/dichloromethane. LCMS (Method F, ES-API): RT 2.68 min, m+H=519.

Intermediate 47. (R)-methyl 6-((3,4-difluorophenyl)sulfonyl)-1-(4-fluorophenyl)-4,4a,5,6,7,8-hexahydro-1H-pyrazolo[3,4-g]isoquinoline-4a-carboxylate

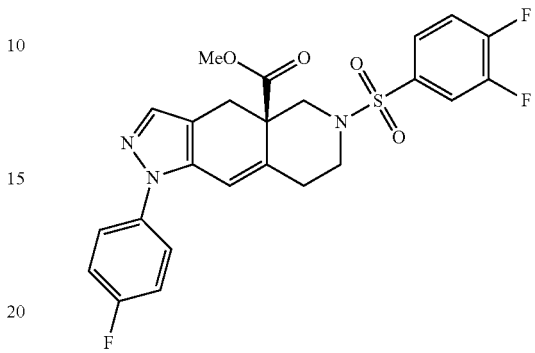

Using HCl (4M solution in dioxane) in place of trifluoroacetic acid/dichloromethane. LCMS (Method F, ES-API): RT 2.48 min, m+H=504.

Intermediate 48. (R)-methyl 6-((3,4-dichlorophenyl)sulfonyl)-1-(3,4-difluorophenyl)-4,4a,5,6,7,8-hexahydro-1H-pyrazolo[3,4-g]isoquinoline-4a-carboxylate

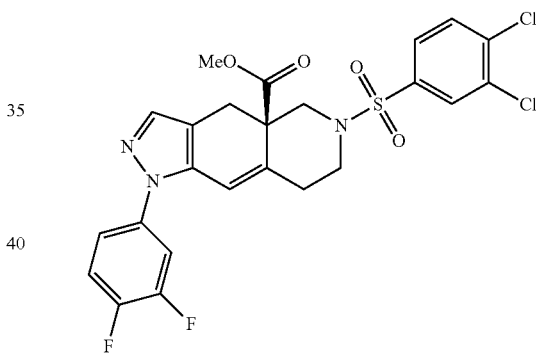

Using HCl (4M solution in dioxane) in place of trifluoroacetic acid/dichloromethane. LCMS (Method F, ES-API): RT 2.78 min, m+H=555.

Intermediate 49. (R)-methyl 6-((4-chloro-3-fluorophenyl)sulfonyl)-1-(4-fluorophenyl)-4,4a,5,6,7,8-hexahydro-1H-pyrazolo[3,4-g]isoquinoline-4a-carboxylate

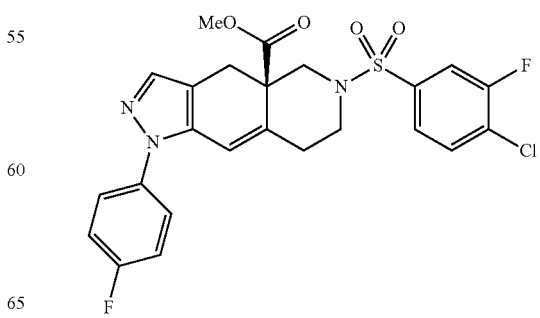

Using HCl (4M solution in dioxane) in place of trifluoroacetic acid/dichloromethane. LCMS (Method F, ES-API): RT 2.59 min, m+H=520.0.

Intermediate 50. (R)-methyl 1-(4-fluorophenyl)-6-((1-methyl-1H-pyrazol-3-yl)sulfonyl)-4,4a,5,6,7,8-hexahydro-1H-pyrazolo[3,4-g]isoquinoline-4a-carboxylate

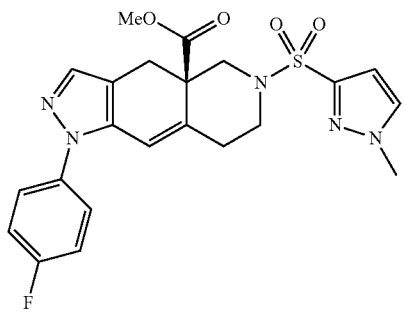 [SMILES: COC(=O)[C@]12Cc3cnn(-c4ccc(F)cc4)c3C=C1CCN(S(=O)(=O)c1ccn(C)n1)C2]

Using HCl (4M solution in dioxane) in place of trifluoroacetic acid/dichloromethane. LCMS (Method F, ES-API): RT 2.00 min, m+H=472.0.

Intermediate 51. (R)-methyl 1-(4-fluorophenyl)-6-((1-methyl-1H-pyrazol-4-yl)sulfonyl)-4,4a,5,6,7,8-hexahydro-1H-pyrazolo[3,4-g]isoquinoline-4a-carboxylate

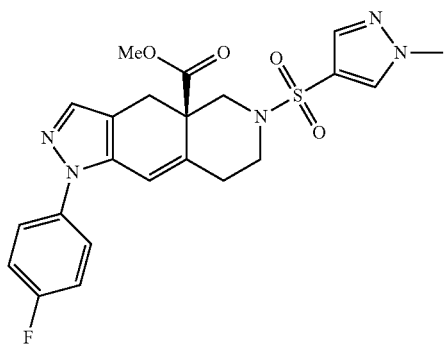 [SMILES: COC(=O)[C@]12Cc3cnn(-c4ccc(F)cc4)c3C=C1CCN(S(=O)(=O)c1cnn(C)c1)C2]

Using HCl (4M solution in dioxane) in place of trifluoroacetic acid/dichloromethane. LCMS (Method F, ES-API): RT 1.99 min, m+H=472.

Intermediate 52. (R)-methyl 6-((1,3-dimethyl-1H-pyrazol-5-yl)sulfonyl)-1-(4-fluorophenyl)-4,4a,5,6,7,8-hexahydro-1H-pyrazolo[3,4-g]isoquinoline-4a-carboxylate

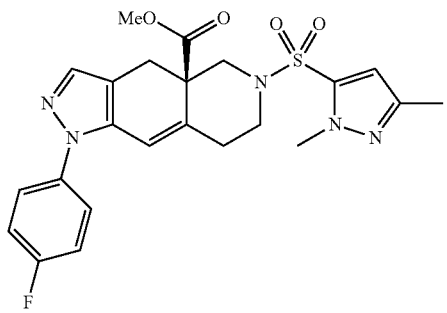 [SMILES: COC(=O)[C@]12Cc3cnn(-c4ccc(F)cc4)c3C=C1CCN(S(=O)(=O)c1cc(C)nn1C)C2]

Using HCl (4M solution in dioxane) in place of trifluoroacetic acid/dichloromethane. LCMS (Method F, ES-API): RT 2.23 min, m+H=486.2.

Intermediate 53. (R)-methyl 1-(4-fluorophenyl)-6-((1-methyl-1H-pyrazol-5-yl)sulfonyl)-4,4a,5,6,7,8-hexahydro-1H-pyrazolo[3,4-g]isoquinoline-4a-carboxylate

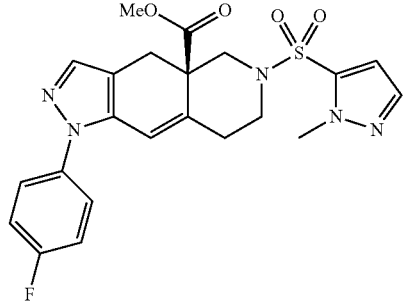 [SMILES: COC(=O)[C@]12Cc3cnn(-c4ccc(F)cc4)c3C=C1CCN(S(=O)(=O)c1ccnn1C)C2]

Using HCl (4M solution in dioxane) in place of trifluoroacetic acid/dichloromethane. LCMS (Method F, ES-API): RT 2.15 min, m+H=472.2.

Intermediate 54. (R)-methyl 6-((1-ethyl-1H-pyrazol-5-yl)sulfonyl)-1-(4-fluorophenyl)-4,4a,5,6,7,8-hexahydro-1H-pyrazolo[3,4-g]isoquinoline-4a-carboxylate

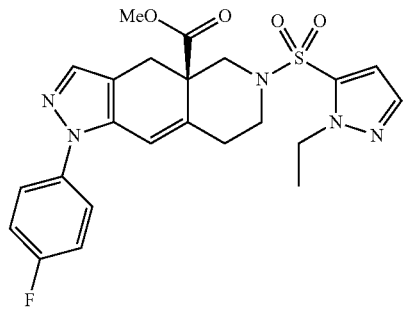 [SMILES: CCn1nccc1S(=O)(=O)N1CCC2=Cc3c(cnn3-c3ccc(F)cc3)C[C@]2(C(=O)OC)C1]

Using HCl (4M solution in dioxane) in place of trifluoroacetic acid/dichloromethane. LCMS (Method F, ES-API): RT 2.26 min, m+H=486.1.

Intermediate 55. (R)-tert-butyl 1-(4-fluorophenyl)-4a-(thiazole-5-carbonyl)-4a,5,7,8-tetrahydro-1H-pyrazolo[3,4-g]isoquinoline-6(4H)-carboxylate

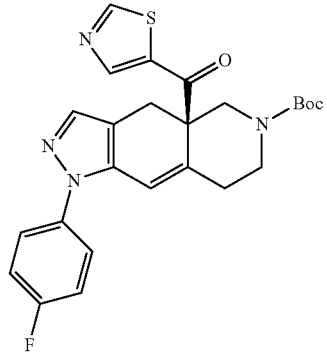 [SMILES: CC(C)(C)OC(=O)N1CCC2=Cc3c(cnn3-c3ccc(F)cc3)C[C@]2(C(=O)c2cncs2)C1]

2-(Trimethylsilyl)thiazole (285 μl, 1.784 mmol) in dry ether (2 mL) was added to butyllithium (2.5 M in Hexanes)

(731 μl, 1.828 mmol) in dry ether (1 mL) at −78° C. The reaction mixture was stirred at −78° C. for 30 minutes. A solution of (R)-6-tert-butyl 4a-methyl 1-(4-fluorophenyl)-4a,5,7,8-tetrahydro-1H-pyrazolo[3,4-g]isoquinoline-4a,6 (4H)-dicarboxylate (250 mg, 0.585 mmol) in dry ether (6 mL) was added dropwise and the reaction mixture was stirred for 0.5 hour at −78° C. Water (10 mL) was added and the reaction mixture was stirred at room temperature for 10 minutes. The aqueous layer was extracted with ethyl acetate (3×15 mL). The combined organic extracts were washed with brine (20 mL), dried over magnesium sulfate, filtered and concentrated in vacuo to give an orange solid. The crude product was purified by chromatography on silica gel (gradient: 0-40% ethyl acetate in isohexane) to afford (R)-tert-butyl 1-(4-fluorophenyl)-4a-(2-(trimethylsilyl)thiazole-5-carbonyl)-4a,5,7,8-tetrahydro-1H-pyrazolo[3,4-g]isoquinoline-6(4H)-carboxylate (88 mg) as a yellow solid. LCMS (Method F, ES-API): RT 2.38 min, m+H=481.2.

Intermediate 56. (R)-(1-(4-fluorophenyl)-6-(m-tolylsulfonyl)-4,4a,5,6,7,8-hexahydro-1H-pyrazolo[3,4-g]isoquinolin-4a-yl)methanol

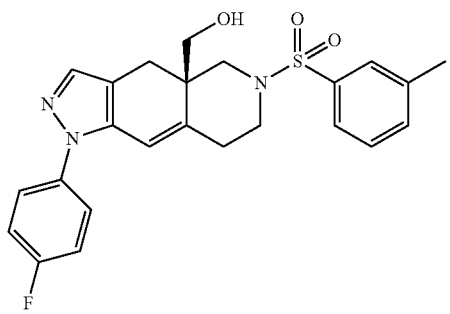 [SMILES: Cc1cccc(S(=O)(=O)N2CCC3=Cc4c(cnn4-c4ccc(F)cc4)C[C@]3(CO)C2)c1]

Superhydride (1M solution in tetrahydrofuran, 43.2 ml, 43.2 mmol) was added slowly to a solution of (R)-methyl 1-(4-fluorophenyl)-6-(m-tolylsulfonyl)-4,4a,5,6,7,8-hexahydro-1H-pyrazolo[3,4-g]isoquinoline-4a-carboxylate (5.2 g, 10.80 mmol) in tetrahydrofuran (100 mL) at 0° C. and stirred for 2 hours. The reaction was quenched with ammonium chloride solution (aqueous, 100 mL) and ethyl acetate (100 mL) was added. The phases were separated and the organic phase was washed with brine (100 mL), dried (sodium sulphate) and solvent removed to give a yellow oil. The crude product was purified by chromatography on silica gel (gradient: 0-80% ethyl acetate in isohexane) to afford (R)-(1-(4-fluorophenyl)-6-(m-tolylsulfonyl)-4,4a,5,6,7,8-hexahydro-1H-pyrazolo[3,4-g]isoquinolin-4a-yl)methanol (4.45 g) as a white solid. LCMS (Method F, ES-API): RT 2.36 min, m+H=454.

The following intermediate 57 was similarly prepared from the appropriate starting materials:

Intermediate 57. (R)-(6-((3,5-difluorophenyl)sulfonyl)-1-(4-fluorophenyl)-4,4a,5,6,7,8-hexahydro-1H-pyrazolo[3,4-g]isoquinolin-4a-yl)methanol

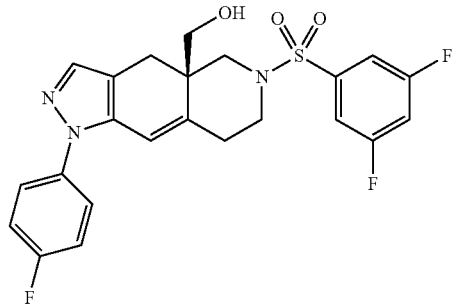 [SMILES: O=S(=O)(c1cc(F)cc(F)c1)N1CCC2=Cc3c(cnn3-c3ccc(F)cc3)C[C@]2(CO)C1]

LCMS (Method F, ES-API): RT 2.40 min, m+H=476.2.

Intermediate 58. (R)-1-(4-fluorophenyl)-6-(m-tolylsulfonyl)-4,4a,5,6,7,8-hexahydro-1H-pyrazolo[3,4-g]isoquinoline-4a-carbaldehyde

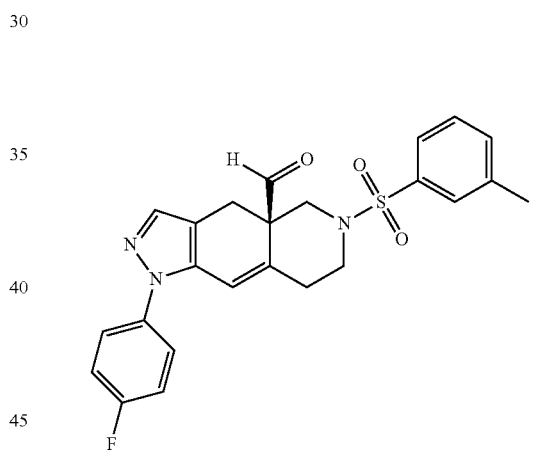

(R)-(1-(4-Fluorophenyl)-6-(m-tolylsulfonyl)-4,4a,5,6,7,8-hexahydro-1H-pyrazolo[3,4-g]isoquinolin-4a-yl)methanol (3.5 g, 7.72 mmol) was dissolved in dichloromethane (80 mL) and Dess-Martin Periodinane (5.24 g, 12.35 mmol) was added. The reaction was stirred at room temperature for 1 hour. A saturated solution of sodium hydrogen carbonate (aqueous, 50 ml) was added and the mixture was stirred for 10 minutes. The phases were separated and solvent removed to give a pale yellow solid. The crude product was purified by chromatography on silica gel (gradient: 0-80% ethyl acetate in isohexane) to afford (R)-1-(4-fluorophenyl)-6-(m-tolyl sulfonyl)-4,4a,5,6,7,8-hexahydro-1H-pyrazolo[3,4-g]isoquinoline-4a-carbaldehyde (2.9 g) as a very pale yellow solid. LCMS (Method F, ES-API): RT 2.46 min, m+H=452.

The following intermediates 59-61 were similarly prepared from the appropriate starting material:

Intermediate 59. (R)-6-((3,5-difluorophenyl)sulfonyl)-1-(4-fluorophenyl)-4,4a,5,6,7,8-hexahydro-1H-pyrazolo[3,4-g]isoquinoline-4a-carbaldehyde

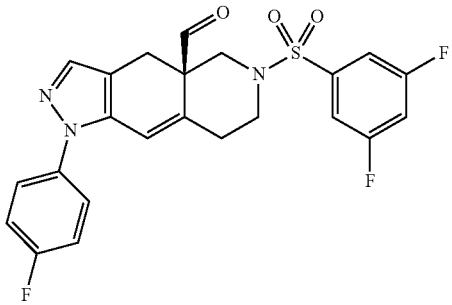 [SMILES: O=C[C@]12Cc3cnn(-c4ccc(F)cc4)c3C=C1CCN(S(=O)(=O)c1cc(F)cc(F)c1)C2]

LCMS (Method F, ES-API): RT 2.54 min, m+H=474.2.

Intermediate 60. (R)-1-(4-fluorophenyl)-6-((3,4,5-trifluorophenyl)sulfonyl)-4,4a,5,6,7,8-hexahydro-1H-pyrazolo[3,4-g]isoquinoline-4a-carbaldehyde

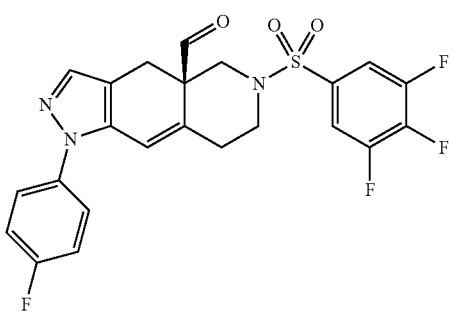 [SMILES: O=C[C@]12Cc3cnn(-c4ccc(F)cc4)c3C=C1CCN(S(=O)(=O)c1cc(F)c(F)c(F)c1)C2]

LCMS (Method F, ES-API): RT 2.85 min, m+H+CH₃OH (sample prepared in CH₃OH, giving methanol hemiacetal)=524.2.

Intermediate 61. (R)-tert-butyl 1-(4-fluorophenyl)-4a-(1-methyl-1H-pyrazole-4-carbonyl)-4a,5,7,8-tetrahydro-1H-pyrazolo[3,4-g]isoquinoline-6(4H)-carboxylate

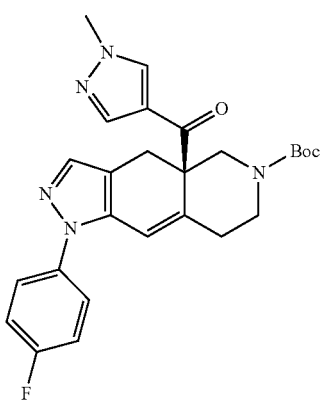 [SMILES: Cn1cc(C(=O)[C@]23Cc4cnn(-c5ccc(F)cc5)c4C=C2CCN(C(=O)OC(C)(C)C)C3)cn1]

LCMS (Method F, ES-API): RT 2.24 min, m+H=478.2.

Intermediate 62. (R)-(1-(4-fluorophenyl)-6-(m-tolylsulfonyl)-4,4a,5,6,7,8-hexahydro-1H-pyrazolo[3,4-g]isoquinolin-4a-yl)(pyrimidin-2-yl)-(R/S)-methanol

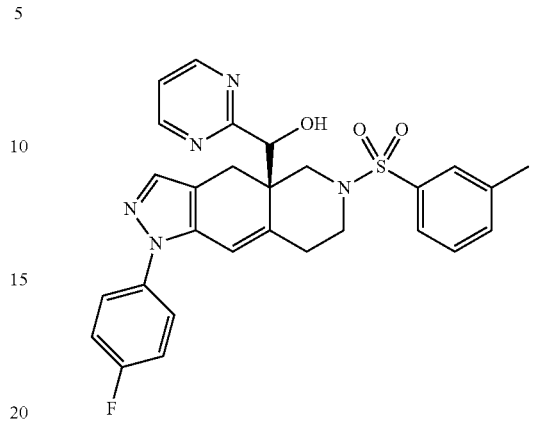

To a stirred solution of 2-(tributylstannyl)pyrimidine (428 µl, 1.351 mmol) in dry tetrahydrofuran (5 mL) was added butyllithium (2.5 M in hexanes) (554 µl, 1.384 mmol) at −78° C. The reaction mixture was stirred at −78° C. for 1.5 hours. A solution of (R)-1-(4-fluorophenyl)-6-(m-tolylsulfonyl)-4,4a,5,6,7,8-hexahydro-1H-pyrazolo[3,4-g]isoquinoline-4a-carbaldehyde (200 mg, 0.443 mmol) in dry tetrahydrofuran (5 mL) was added dropwise and the reaction mixture was stirred for 1.5 hours at −78° C. Water (25 mL) was added and the aqueous layer was extracted with ethyl acetate (2×30 mL). The combined organic layers were washed with brine (30 mL), dried over magnesium sulfate, filtered and concentrated in vacuo. The residue was partitioned between acetonitrile (25 mL) and hexanes (15 mL). The hexane layer was discarded. The acetonitrile layer was concentrated in vacuo to give a pale orange oil. The crude product was purified by chromatography on silica gel (gradient: 0-100% ethyl acetate in isohexane) to afford (R)-(1-(4-fluorophenyl)-6-(m-tolylsulfonyl)-4,4a,5,6,7,8-hexahydro-1H-pyrazolo[3,4-g]isoquinolin-4a-yl)(pyrimidin-2-yl)methanol (75 mg) as a colourless oil. LCMS (Method F, ES-API): RT 2.27 min, m+H=532.2.

Intermediate 63. 2-(benzylthio)-6-(trifluoromethyl)pyridine

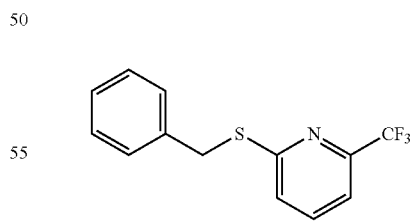

To a suspension of sodium hydride (0.170 g, 4.24 mmol) in tetrahydrofuran (10 mL) was added phenylmethanethiol (0.338 ml, 2.88 mmol) dropwise at 0° C. The reaction mixture was stirred at 0° C. for 15 minutes then 2-fluoro-6-(trifluoromethyl)pyridine (0.365 ml, 3.03 mmol) was added dropwise. The reaction mixture was stirred at 0° C. for 30 minutes. Methanol (1 mL) was added carefully and the reaction mixture was stirred at 0° C. for a further 10 minutes then water (5 mL) and dichloromethane (10 mL) were added. The organic layer was recovered using a phase separator cartridge then concentrated in vacuo to give 2-(benzylthio)-6-(trifluoromethyl)pyridine (538 mg) as a colourless oil. LCMS (Method F, ES-API): RT 2.80 min, m+H=270.1.

Intermediate 64.
6-(trifluoromethyl)pyridine-2-sulfonyl chloride

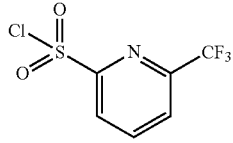

To a suspension of 2-(benzylthio)-6-(trifluoromethyl)pyridine (580 mg, 2.154 mmol) in acetic acid (8 mL) and water (4 mL) was added N-chlorosuccinimide (1438 mg, 10.77 mmol), and the mixture was stirred at room temperature for 1 hour. Water (10 mL) was added and the mixture was extracted with dichloromethane (2×10 mL). The organic extract was washed with saturated aqueous sodium hydrogen carbonate solution (10 mL) and saturated brine (10 mL), dried over magnesium sulfate, filtered and concentrated in vacuo to give 6-(trifluoromethyl)pyridine-2-sulfonyl chloride (436 mg) as a colourless oil. LCMS (quenching with morpholine; Method F, ES-API): RT 1.84 min, (m+H+morpholine-Cl)=297.1.

The following intermediates 65-66 were similarly prepared from appropriate starting materials:

Intermediate 65.
2-(trifluoromethyl)pyridine-4-sulfonyl chloride

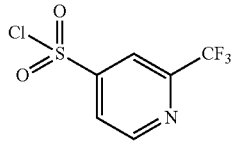

LCMS (quenching with morpholine; Method F, ES-API): RT 2.03 min, (m+H+morpholine-Cl)=297.1.

Intermediate 66.
4-(trifluoromethyl)pyridine-2-sulfonyl chloride

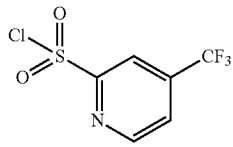

LCMS (quenching with morpholine; Method F, ES-API): RT 1.85 min, (m+H+morpholine-Cl)=297.1.

Intermediate 67.
3-fluoro-4-(trifluoromethyl)benzene-1-sulfonyl chloride

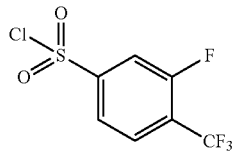

3-Fluoro-4-(trifluoromethyl)aniline (5 g, 27.9 mmol) was dissolved in acetonitrile (10 mL). The solution was cooled to 0° C., and treated with tetrafluoroboric acid (48% aqueous solution, 6.49 ml, 41.9 mmol) and tert-butyl nitrite (4.98 ml, 41.9 mmol). The reaction mixture was maintained at 0° C. for 1 hour. In the meantime, a suspension of copper (I) chloride (4.15 g, 41.9 mmol) in acetonitrile (40 mL) at 0° C. was saturated with sulfur dioxide gas by bubbling the gas through the suspension with vigorous stirring for 30 minutes. When the diazotization reaction was complete after 1 hour, this solution was added dropwise to the suspension of copper (I) chloride, causing vigorous evolution of gas. The reaction mixture was then allowed to warm to room temperature and stirred for 1 hour, after which time it was poured onto 100 mL of an ice/water slurry. Diethyl ether (150 mL) was added, causing a precipitate to form, which was removed by filtration. The filtrate was washed with water (100 mL) and brine (100 mL), dried over magnesium sulfate, filtered, and concentrated in vacuo to give 3-fluoro-4-(trifluoromethyl)benzene-1-sulfonyl chloride (6.62 g) as an orange oil. LCMS (quenching with morpholine; Method F, ES-API): RT 2.25 min, (m+H+morpholine-Cl)=314.1.

Intermediate 68. (R,Z)-2-tert-butyl 8a-methyl 7-(hydroxymethylene)-6-oxo-3,4,6,7,8,8a-hexahydroisoquinolin-2,8a(1H)-dicarboxylate

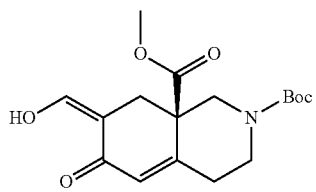 [SMILES: COC(=O)[C@]12C/C(=C/O)C(=O)C=C1CCN(C(=O)OC(C)(C)C)C2]

Lithium hexamethyldisilazide (12.93 ml, 12.93 mmol) was added to diethyl ether (20 mL) at −78° C. (R)-2-tert-butyl 8a-methyl 6-oxo-3,4,6,7,8,8a-hexahydroisoquinolin-2,8a(1H)-dicarboxylate (WO2005087769) (1.0 g, 3.23 mmol) in ether (5 mL) was added followed by the addition of 2,2,2-trifluoroethyl formate (2.51 ml, 25.9 mmol) after 20 minutes. The reaction was stirred at −78° C. for 2 hours then allowed to slowly warm to room temperature. 1M hydrochloric acid (8 mL) was added, followed by water (10 mL) and ethyl acetate (10 mL). The organic phase was separated, washed with brine, dried (magnesium sulfate) and solvent removed to give (R,Z)-2-tert-butyl 8a-methyl 7-(hydroxymethylene)-6-oxo-3,4,6,7,8,8a-hexahydroisoquinoline-2,8a (1H)-dicarboxylate (1.09 g) as a yellow oil. LCMS (Method F, ES-API): RT 1.99 min, m-H=336.

Intermediate 69. (R)-6-tert-butyl 4a-methyl 1-phenyl-4a,5,7,8-tetrahydro-1H-pyrazolo[3,4-g]isoquinoline-4a,6(4H)-dicarboxylate

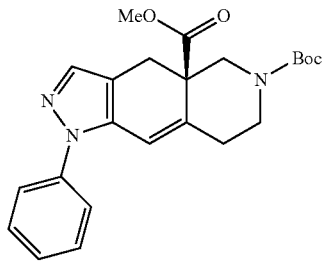 [SMILES: COC(=O)[C@]12Cc3cnn(-c4ccccc4)c3C=C1CCN(C(=O)OC(C)(C)C)C2]

(R,Z)-2-tert-butyl 8a-methyl 7-(hydroxymethylene)-6-oxo-3,4,6,7,8,8a-hexahydroisoquinoline-2,8a(1H)-dicarboxylate (1.09 g, 3.23 mmol) was suspended in acetic acid (20 mL), and sodium acetate trihydrate (0.265 g, 3.23 mmol) and phenylhydrazine (0.318 ml, 3.23 mmol) were added. The reaction mixture was stirred at room temperature for 30 minutes, then water (20 mL) and dichloromethane (20 mL) were added and the phases were separated via a phase separator. The solvent was removed to give an orange oil. The crude product was purified by chromatography on silica gel (gradient: 0-50% ethyl acetate in isohexane) to afford (R)-6-tert-butyl 4a-methyl 1-phenyl-4a,5,7,8-tetrahydro-1H-pyrazolo[3,4-g]isoquinoline-4a,6(4H)-dicarboxylate (694 mg) as a pale yellow solid. LCMS (Method F, ES-API): RT 2.48 min, m+H=410.

The following intermediates 70-73 were similarly prepared from appropriate starting materials:

Intermediate 70. (R)-6-tert-butyl 4a-methyl 1-(pyridin-3-yl)-4a,5,7,8-tetrahydro-1H-pyrazolo[3,4-g]isoquinoline-4a,6(4H)-dicarboxylate

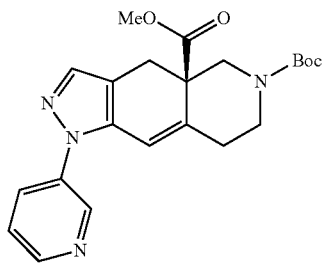 [SMILES: COC(=O)[C@]12Cc3cnn(-c4cccnc4)c3C=C1CCN(C(=O)OC(C)(C)C)C2]

LCMS (Method F, ES-API): RT 2.03 min, m+H=411

Intermediate 71. (R)-6-tert-butyl 4a-methyl 1-(3,4-difluorophenyl)-4a,5,7,8-tetrahydro-1H-pyrazolo[3,4-g]isoquinoline-4a,6(4H)-dicarboxylate

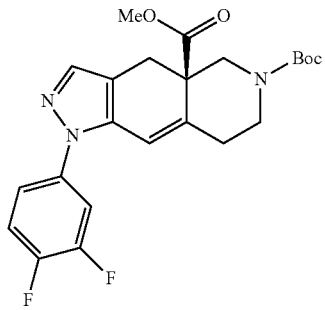 [SMILES: COC(=O)[C@]12Cc3cnn(-c4ccc(F)c(F)c4)c3C=C1CCN(C(=O)OC(C)(C)C)C2]

LCMS (Method F, ES-API): RT 2.58 min, m+H=446.

Intermediate 72. (R)-6-tert-butyl 4a-methyl 1-(4-chlorophenyl)-4a,5,7,8-tetrahydro-1H-pyrazolo[3,4-g]isoquinoline-4a,6(4H)-dicarboxylate

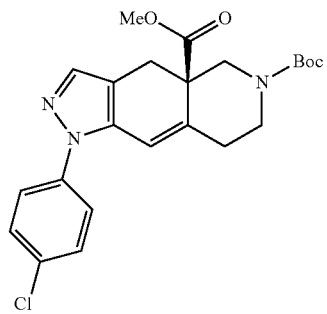 [SMILES: COC(=O)[C@]12Cc3cnn(-c4ccc(Cl)cc4)c3C=C1CCN(C(=O)OC(C)(C)C)C2]

LCMS (Method F, ES-API): RT 2.65 min, m+H=444.2.

Intermediate 73. (R)-6-tert-butyl 4a-methyl 1-(4-(trifluoromethyl)phenyl)-4a,5,7,8-tetrahydro-1H-pyrazolo[3,4-g]isoquinoline-4a,6(4H)-dicarboxylate

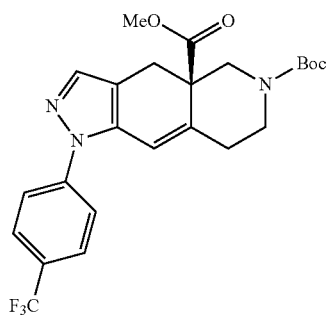 [SMILES: COC(=O)[C@]12Cc3cnn(-c4ccc(C(F)(F)F)cc4)c3C=C1CCN(C(=O)OC(C)(C)C)C2]

LCMS (Method F, ES-API): RT 2.76 min, m+H=478.

Intermediate 74. 4-(benzylthio)-2-(trifluoromethyl)pyridine

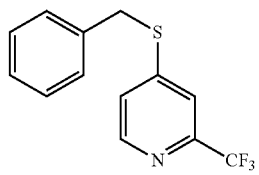 [SMILES: FC(F)(F)c1cc(SCc2ccccc2)ccn1]

4-Chloro-2-(trifluoromethyl)pyridine (141 μl, 1.102 mmol), 1,8-diazabicyclo[5.4.0]undec-7-ene (DBU) (199 μl, 1.322 mmol), and phenylmethanethiol (129 μl, 1.102 mmol) were dissolved in dry dimethylformamide (2 mL). The reaction mixture was heated at 100° C. in a microwave for 30 minutes, then partitioned between ether (25 mL) and water (25 mL). The aqueous layer was extracted with ether (2×25 mL) and the combined organic layers were dried over magnesium sulfate, filtered and concentrated in vacuo to give a pale yellow oil. The crude product was purified by chromatography on silica gel (gradient: 0-30% ethyl acetate in isohexane) to afford 4-(benzylthio)-2-(trifluoromethyl)

pyridine (224 mg) as a colourless oil. LCMS (Method F, ES-API): RT 2.79 min, m+H=270.1.

Intermediate 75. (R)-(1-(4-fluorophenyl)-6-((3,4,5-trifluorophenyl)sulfonyl)-4,4a,5,6,7,8-hexahydro-1H-pyrazolo[3,4-g]isoquinolin-4a-yl)methanol

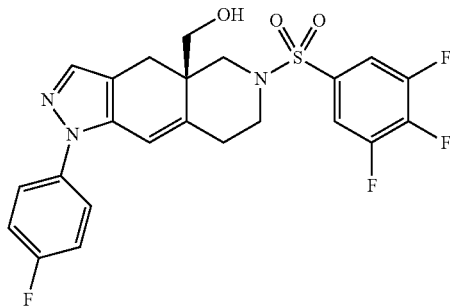

To a solution of (R)-methyl 1-(4-fluorophenyl)-6-((3,4,5-trifluorophenyl)sulfonyl)-4,4a,5,6,7,8-hexahydro-1H-pyrazolo[3,4-g]isoquinoline-4a-carboxylate (1.0 g, 1.918 mmol) in anhydrous dichloromethane (30 mL) at −78° C. under a nitrogen atmosphere was added diisobutyl aluminium hydride (DIBAL-H) (1 M in Heptane) (7.67 ml, 7.67 mmol) dropwise over 10 minutes. The reaction mixture was stirred at −78° C. for 1 hour. Water (10 mL) was then added and the reaction mixture stirred at −78° C. for 5 minutes, then warmed to room temperature over 15 minutes. The solution was partitioned between ethyl acetate (150 mL) and Rochelle's salt (150 mL). The organic layer was washed with Rochelle's salt (150 mL), brine (100 mL), dried over magnesium sulfate, filtered and concentrated in vacuo to give an off white solid. The crude product was purified by chromatography on silica gel (gradient: 0-90% ethyl acetate in isohexane) to afford (R)-(1-(4-fluorophenyl)-6-((3,4,5-trifluorophenyl)sulfonyl)-4,4a,5,6,7,8-hexahydro-1H-pyrazolo[3,4-g]isoquinolin-4a-yl)methanol (680 mg) as a white solid. LCMS (Method F, ES-API): RT 2.58 min, m+H=494.2.

Intermediate 76.
2-(benzylthio)-4-(trifluoromethyl)pyridine

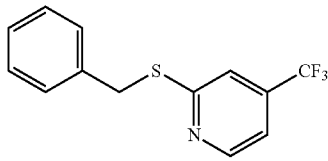 [SMILES: FC(F)(F)c1ccnc(SCc2ccccc2)c1]

To a solution of phenylmethanethiol (356 μl, 3.03 mmol) and 2-fluoro-4-(trifluoromethyl)pyridine (369 μl, 3.03 mmol) in dimethylformamide (5 mL) was added potassium carbonate (628 mg, 4.54 mmol). The reaction mixture was stirred at 60° C. for 2 hours, then cooled to room temperature, water (10 mL) was added, and the mixture was extracted with ethyl acetate (3×15 mL). The combined organic layers were washed with saturated aqueous sodium hydrogen carbonate solution (20 mL), brine (20 mL), dried over magnesium sulfate, filtered and concentrated in vacuo to give a pale yellow oil. The crude product was purified by chromatography on silica gel (gradient: 0-20% ethyl acetate in isohexane) to afford 2-(benzylthio)-4-(trifluoromethyl)pyridine (510 mg) as a colourless oil. LCMS (Method F, ES-API): RT 3.04 min, m+H=270.1.

Intermediate 77.
4-bromo-2-(pyrrolidin-1-yl)pyridine

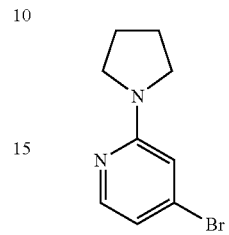

2,4-Dibromopyridine (1.0 g, 4.22 mmol) was dissolved in ethanol (40 mL) and pyrrolidine (1.733 ml, 21.11 mmol) was added. The reaction mixture was stirred at 70° C. for 20 hours. The reaction mixture was cooled to room temperature and the solvent was removed in vacuo to give a pale yellow solid. The crude product was purified by chromatography on silica gel (gradient: 0-80% ethyl acetate in isohexane) to afford 2-bromo-4-(pyrrolidin-1-yl)pyridine (460 mg) as a white solid, and 4-bromo-2-(pyrrolidin-1-yl)pyridine (260 mg) as a white solid. LCMS (Method F, ES-API): RT 0.79 min, m+H=227.1/229.1.

Intermediate 78. (R)-(1-(4-fluorophenyl)-4,4a,5,6,7,8-hexahydro-1H-pyrazolo[3,4-g]isoquinolin-4a-yl)(4-(trifluoromethyl)pyridin-2-yl)methanone

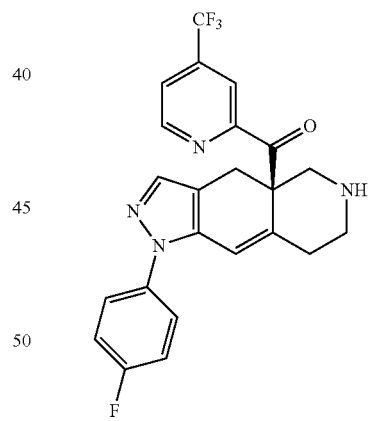

(R)-tert-butyl 1-(4-fluorophenyl)-4a-(4-(trifluoromethyl)picolinoyl)-4a,5,7,8-tetrahydro-1H-pyrazolo[3,4-g]isoquinoline-6(4H)-carboxylate (2 g, 2.65 mmol) was dissolved in a solution of HCl in dioxane (4M) (13.27 ml, 53.1 mmol) and the reaction mixture was stirred at room temperature for 45 minutes. The solvent was removed in vacuo to give an orange gum. This was treated with a mixture of 10% methanol (containing 1% of ammonia)/dichloromethane until complete dissolution of the gum, then the solvent was removed in vacuo to give an orange solid. The crude product was purified by chromatography on silica gel (gradient: 0-10% methanol (containing 1% of ammonia) in dichloromethane) to give (R)-(1-(4-fluorophenyl)-4,4a,5,6,7,8- hexahydro-1H-pyrazolo[3,4-g]isoquinolin-4a-yl)(4-(trifluoromethyl)pyridin-2-yl)methanone (810 mg) as a pale orange solid. LCMS (Method F, ES-API): RT 1.41 min, m+H=443.2.

Intermediate 79.
1-methyl-6-oxo-1,6-dihydropyridine-3-sulfonic acid, ammonium salt

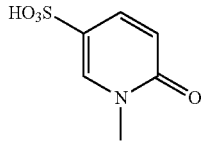

Chlorosulphonic acid (2 ml, 30.1 mmol) was added cautiously dropwise by pipette over 5 minutes to stirred neat 1-methylpyridin-2(1H)-one (8.09 ml, 82 mmol) and the resulting viscous solution was stirred at 50° C. for 40 hours. The cooled solidified reaction mixture was then added cautiously to water (100 ml), giving a clear brown solution. This solution was concentrated in vacuo to 40 ml, then made basic with concentrated ammonia solution, and washed with dichloromethane (6×100 ml). The aqueous phase was then evaporated to give a brown slurry which was triturated in methanol and filtered. The filtrate was evaporated to give 1-methyl-6-oxo-1,6-dihydropyridine-3-sulfonic acid, ammonium salt (3 g) as a brown solid. LCMS (Method F, ES-API): RT 0.46 min, m-H=188.0.

Intermediate 80. (R)-methyl 6-((3,5-difluoro-4-methoxyphenyl)sulfonyl)-1-(4-fluorophenyl)-4,4a,5,6,7,8-hexahydro-1H-pyrazolo[3,4-g]isoquinoline-4a-carboxylate

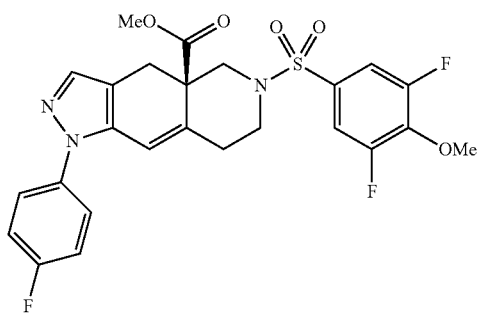 [SMILES: COC(=O)[C@]12Cc3cnn(-c4ccc(F)cc4)c3C=C1CCN(S(=O)(=O)c1cc(F)c(OC)c(F)c1)C2]

To a solution of (R)-methyl 1-(4-fluorophenyl)-6-((3,4,5-trifluorophenyl)sulfonyl)-4,4a,5,6,7,8-hexahydro-1H-pyrazolo[3,4-g]isoquinoline-4a-carboxylate (150 mg, 0.288 mmol) in dimethyl sulphoxide (4 mL) was added sodium methoxide (25% in methanol) (65.8 μl, 0.288 mmol) dropwise. The reaction mixture was stirred at room temperature for 1 hour, then allowed to stand at room temperature overnight. The crude product was purified by column chromatography on silica gel (gradient: 0-50% ethyl acetate in isohexane) to afford (R)-methyl 6-((3,5-difluoro-4-methoxyphenyl)sulfonyl)-1-(4-fluorophenyl)-4,4a,5,6,7, 8-hexahydro-1H-pyrazolo[3,4-g]isoquinoline-4a-carboxylate (150 mg) as a pale yellow solid. LCMS (Method F, ES-API): RT 2.51 min, m+H=534.2.

Intermediate 81. (R)-tert-butyl 1-(4-fluorophenyl)-4a-(R/S)-(hydroxy(1-methyl-1H-pyrazol-4-yl)methyl)-4a,5,7,8-tetrahydro-1H-pyrazolo[3,4-g]isoquinoline-6(4H)-carboxylate

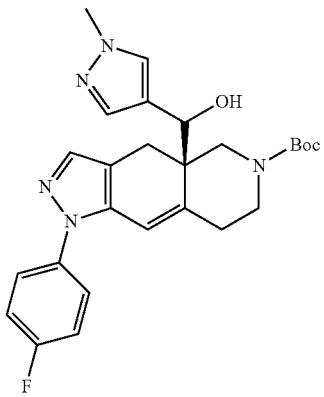 [SMILES: Cn1cc(C(O)[C@]23Cc4cnn(-c5ccc(F)cc5)c4C=C2CCN(C(=O)OC(C)(C)C)C3)cn1]

To a solution of n-butyl lithium (2.5 M in Hexanes) (312 μl, 0.780 mmol) in tetrahydrofuran (2 mL) was added 4-iodo-1-methyl-1H-pyrazole (157 mg, 0.755 mmol) in tetrahydrofuran (1 mL) at −78° C. The mixture was stirred at this temperature for 1 hour, then a solution of (R)-tert-butyl 1-(4-fluorophenyl)-4a-formyl-4a,5,7,8-tetrahydro-1H-pyrazolo[3,4-g]isoquinoline-6(4H)-carboxylate (100 mg, 0.252 mmol) in tetrahydrofuran (1 mL) was added dropwise to the reaction mixture. The mixture was stirred at this temperature for 30 minutes. Water (6 mL) and dichloromethane (8 mL) were added and the phases were separated using a phase separator cartridge. The solvent was removed in vacuo to give an orange oil.

A second reaction was performed with inverse addition of n-butyl lithium. To a solution of 4-iodo-1-methyl-1H-pyrazole (157 mg, 0.755 mmol) in tetrahydrofuran (2 mL) was added n-butyl lithium (2.5 M in Hexanes) (312 μl, 0.780 mmol) at −78° C. The mixture was stirred at this temperature for 1 hour, then a solution of (R)-tert-butyl 1-(4-fluorophenyl)-4a-formyl-4a,5,7,8-tetrahydro-1H-pyrazolo[3,4-g]isoquinoline-6(4H)-carboxylate (100 mg, 0.252 mmol) in tetrahydrofuran (1 mL) was added dropwise to the reaction mixture. The mixture was stirred at this temperature for 30 minutes. Water (6 mL) and dichloromethane (8 mL) were added and the phases were separated using a phase separator cartridge. The solvent was removed in vacuo to give an orange oil, with a similar composition to the previous reaction product according to LC/MS analysis.

Both reaction products were combined and purified by column chromatography on silica gel (gradient: 0-100% ethyl acetate in isohexane) to afford (R)-tert-butyl 1-(4-fluorophenyl)-4a-(hydroxy(1-methyl-1H-pyrazol-4-yl)methyl)-4a,5,7,8-tetrahydro-1H-pyrazolo[3,4-g]isoquinoline-6(4H)-carboxylate (41 mg) as a pale orange gum. LCMS (Method F, ES-API): RT 2.21 min, m+H=480.2.

Intermediate 82. ((R)-tert-butyl 1-(4-fluorophenyl)-4a-(4-(trifluoromethyl)picolinoyl)-4a,5,7,8-tetrahydro-1H-pyrazolo[3,4-g]isoquinoline-6(4H)-carboxylate))

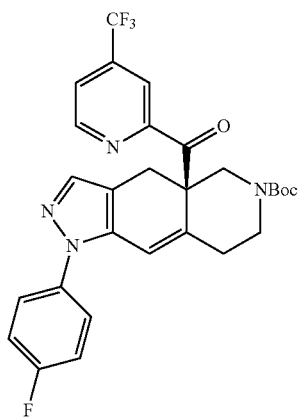 [SMILES: CC(C)(C)OC(=O)N1CCC2=Cc3c(cnn3-c3ccc(F)cc3)C[C@]2(C(=O)c2cc(C(F)(F)F)ccn2)C1]

A solution of 2-bromo-4-(trifluoromethyl)pyridine (2.344 ml, 18.95 mmol) in dry ether (15 mL) was added dropwise over 15 minutes to a solution of isopropylmagnesium chloride (2M, 9.47 ml, 18.95 mmol) in dry ether (30 mL) at 0° C., during which the solution darkened to a brown colour. After stirring at 0° C. for a further 45 minutes a solution of (R)-6-tert-butyl 4a-methyl 1-(4-fluorophenyl)-4a,5,7,8-tetrahydro-1H-pyrazolo[3,4-g]isoquinoline-4a,6(4H)-dicarboxylate (2.7 g, 6.32 mmol) in dry ether:tetrahydrofuran (4:1, 30 mL total) was added dropwise over 20 minutes at 0° C. The resulting dark coloured solution was stirred at 0° C. for 20 minutes, then stirred at room temperature for a further 2 hours. The reaction mixture was diluted with ice/water (20 mL), acidified with 1M HCl (40 mL) and extracted with ethyl acetate (100 mL). The organic phase was washed sequentially with water (50 mL), saturated sodium hydrogen carbonate solution (50 mL) and brine (30 mL), dried (magnesium sulphate), filtered and evaporated in vacuo to give a brown gum. This was dissolved in acetonitrile (50 mL), 1M HCl (10 mL) was added, and the solution stirred for 2 hours at room temperature. Ethyl acetate (150 mL) was added and the organic phase washed sequentially with brine (30 mL), saturated aqueous sodium hydrogen carbonate (50 mL) and further brine (30 mL). The organic phase was then dried (magnesium sulphate), filtered and evaporated in vacuo.

The residual brown gum was purified twice by column chromatography on silica gel (gradients: 0-10% ethyl acetate in dichloromethane, and 0-30% ethyl acetate in isohexane) to give (R)-tert-butyl 1-(4-fluorophenyl)-4a-(4-(trifluoromethyl)picolinoyl)-4a,5,7,8-tetrahydro-1H-pyrazolo[3,4-g]isoquinoline-6(4H)-carboxylate (2.65 g) as a light brown foam. LCMS (Method F, ES-API): RT 2.91 min, m+H=543.

Intermediate 83. ((R)-tert-butyl 1-(4-fluorophenyl)-4a-(thiazole-4-carbonyl)-4a,5,7,8-tetrahydro-1H-pyrazolo[3,4-g]isoquinoline-6(4H)-carboxylate)

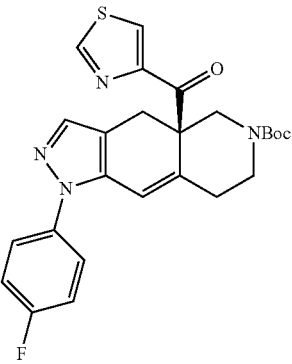 [SMILES: CC(C)(C)OC(=O)N1CCC2=Cc3c(cnn3-c3ccc(F)cc3)C[C@]2(C(=O)c2cscn2)C1]

A suspension of isopropylmagnesium chloride (2M in tetrahydrofuran, 1.755 ml, 3.51 mmol) in dry ether (4.5 mL) at 0° C. was treated dropwise with a solution of 4-bromo-2-(trimethylsilyl)thiazole (0.829 g, 3.51 mmol) in dry ether (2.5 mL) and the resulting suspension stirred at 0° C. for 1 hour. The suspension was then treated dropwise with a solution of (R)-6-tert-butyl 4a-methyl 1-(4-fluorophenyl)-4a,5,7,8-tetrahydro-1H-pyrazolo[3,4-g]isoquinoline-4a,6 (4H)-dicarboxylate (0.5 g, 1.17 mmol) in dry ether:tetrahydrofuran (4:1, 5 mL total volume) and the resulting suspension stirred at 0° C. for 15 minutes. The reaction mixture was then allowed to warm to room temperature, and the solution stirred for a further 3 hours. The reaction mixture was cooled to 0° C., and ice water (50 mL) added dropwise. The aqueous layer was extracted with ethyl acetate (3×50 mL) and the combined organic extracts washed with brine (50 mL) and dried over magnesium sulphate. The solvent was removed to give an orange oil. This was dissolved in acetonitrile (12 mL) and treated dropwise with 1M aqueous HCl (1171 μl, 1.171 mmol) and the resulting solution stirred at room temperature for 1.5 hours. The reaction was diluted with ethyl acetate (150 mL) and washed sequentially with brine (50 mL), saturated aqueous sodium hydrogen carbonate solution (50 mL), and further brine (50 mL). The organic layer was dried over magnesium sulphate and the solvent removed. The crude product was purified by column chromatography on silica gel (gradient: 5-95% ethyl acetate in isohexane) to afford (R)-tert-butyl 1-(4-fluorophenyl)-4a-(thiazole-4-carbonyl)-4a,5,7,8-tetrahydro-1H-pyrazolo[3,4-g]isoquinoline-6(4H)-carboxylate (238 mg) as a pale yellow gum. LCMS (Method F, ES-API): RT 2.55 min, m+H=481.2.

Intermediate 84. 4-(benzylthio)-1H-1,2,3-triazole

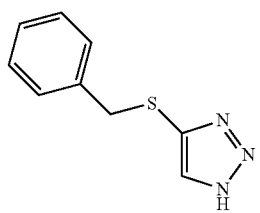 [SMILES: c1ccc(CSc2c[nH]nn2)cc1]

Benzyl bromide (11.79 ml, 99 mmol) was added dropwise to a solution of sodium 1H-1,2,3-triazole-5-thiolate (12.2 g, 99 mmol) in ethanol (100 mL) at 0° C. The reaction mixture was allowed to warm to room temperature and stirred for 20 minutes. The reaction mixture was diluted with ethyl acetate (100 mL) and washed with water (100 mL), brine (100 mL) and dried (sodium sulphate). The solvent was removed to give 4-(benzylthio)-1H-1,2,3-triazole (16.9 g) as a white solid. LCMS (Method F, ES-API): RT 1.66 min, m+H=191.9; 1H NMR (400 MHz, CDCl3): δ 9.72 (1H, v br s), 7.47 (1H, s), 7.30-7.21 (5H, m), 4.12 (2H, s).

Intermediates 85. Methylated Triazole

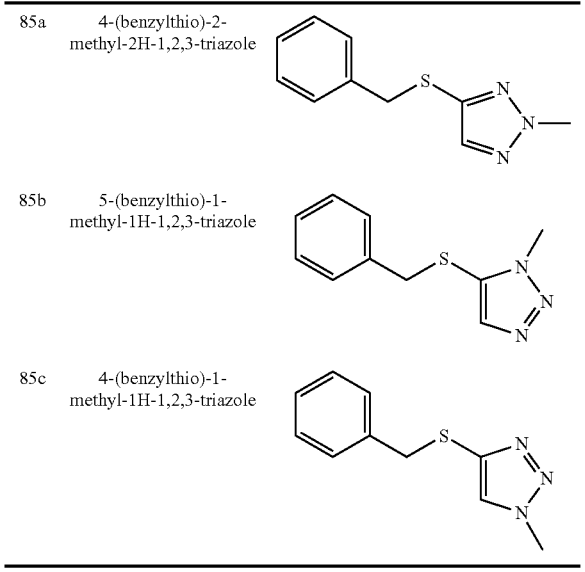

| | | |
|---|---|---|
| 85a | 4-(benzylthio)-2-methyl-2H-1,2,3-triazole | |
| 85b | 5-(benzylthio)-1-methyl-1H-1,2,3-triazole | |
| 85c | 4-(benzylthio)-1-methyl-1H-1,2,3-triazole | |

Iodomethane (2.409 ml, 38.7 mmol) was added dropwise to a mixture of 4-(benzylthio)-1H-1,2,3-triazole (3.7 g, 19.35 mmol) and potassium carbonate (5.88 g, 42.6 mmol) in N,N-dimethylformamide (40 mL) at 0° C. The reaction was then allowed to warm to room temperature and stirred for 1 hour. Water (40 mL) and ethyl acetate (40 mL) were added and the phases separated. The organic phase was washed with water (2×40 mL), brine (40 mL), dried (sodium sulphate) and solvent was removed to give a yellow oil. The crude product was purified by column chromatography on silica gel (gradient: 0-100% ethyl acetate in isohexane) to afford three fractions:

Fraction 1 (1.61 g) as a colourless oil. LCMS (Method F, ES-API): RT 2.05 min, m+H=206; 1H NMR (400 MHz, DMSO-d6): δ 7.68 (1H, s), 7.35-7.19 (5H, m), 4.18 (2H, s), 4.11 (3H, s).

Fraction 2 (816 mg) as a pale yellow oil. LCMS (Method F, ES-API): RT 1.79 min, m+H=206; 1H NMR (400 MHz, DMSO-d6): δ 7.71 (1H, s), 7.36-7.23 (3H, m), 7.22-7.14 (2H, m), 4.09 (2H, s), 3.73 (3H, s).

Fraction 3 (883 mg) as a pale yellow oil. LCMS (Method F, ES-API): RT 1.68 min, m+H=206; 1H NMR (400 MHz, DMSO-d6): δ 8.02 (1H, s), 7.34-7.19 (5H, m), 4.12 (2H, s), 4.00 (3H, s).

The following intermediates 86-88 were similarly prepared from appropriate starting materials:

Intermediates 86. Ethylated Triazole

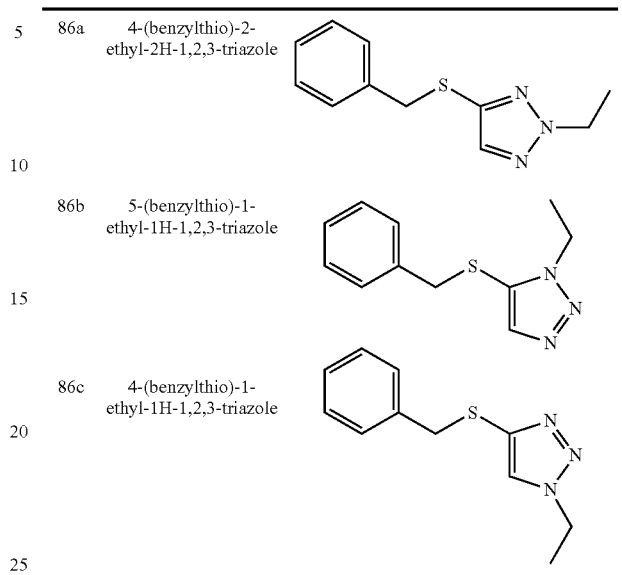

| | | |
|---|---|---|
| 86a | 4-(benzylthio)-2-ethyl-2H-1,2,3-triazole | |
| 86b | 5-(benzylthio)-1-ethyl-1H-1,2,3-triazole | |
| 86c | 4-(benzylthio)-1-ethyl-1H-1,2,3-triazole | |

Fraction 1: LCMS (Method F, ES-API): RT 2.24 min, m+H=220; 1H NMR (400 MHz, DMSO-d6): δ 7.69 (1H, s), 7.32-7.21 (5H, m), 4.39 (2H, q, J=7.3 Hz), 4.18 (2H, s), 1.40 (3H, t, J=7.3 Hz).

Fraction 2: LCMS (Method F, ES-API): RT 1.96 min, m+H=220; 1H NMR (400 MHz, DMSO-d6): δ 7.74 (1H, s), 7.32-7.24 (3H, m), 7.21-7.16 (2H, m), 4.13 (2H, q, J=7.3 Hz), 4.12 (2H, s), 1.23 (3H, t, J=7.3 Hz).

Fraction 3: LCMS (Method F, ES-API): RT 1.85 min, m+H=220; 1H NMR (400 MHz, DMSO-d6): δ 8.07 (1H, s), 7.31-7.19 (5H, m), 4.33 (2H, q, J=7.3 Hz), 4.11 (2H, s), 1.38 (3H, t, J=7.3 Hz).

Intermediates 87. Propylated Triazole

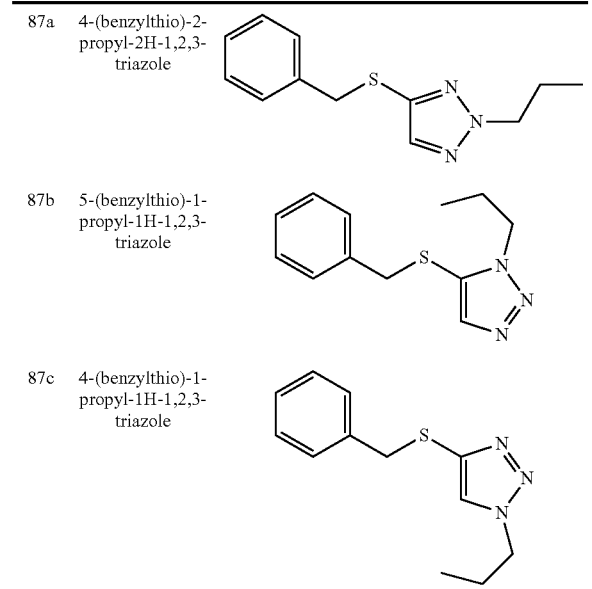

| | | |
|---|---|---|
| 87a | 4-(benzylthio)-2-propyl-2H-1,2,3-triazole | |
| 87b | 5-(benzylthio)-1-propyl-1H-1,2,3-triazole | |
| 87c | 4-(benzylthio)-1-propyl-1H-1,2,3-triazole | |

Fraction 1: LCMS (Method F, ES-API): RT 2.36 min, m+H=234.2; 1H NMR (400 MHz, DMSO-d6): δ 7.69 (1H, s), 7.28-7.27 (4H, m), 7.25-7.20 (1H, m), 4.32 (2H, t, J=7.0 Hz), 4.18 (2H, s), 1.83 (2H, sext, J=7.0 Hz), 0.78 (3H, t, J=7.0 Hz).

Fraction 2: LCMS (Method F, ES-API): RT 2.08 min, m+H=234.2; 1H NMR (400 MHz, DMSO-d6): δ 7.74 (1H, s), 7.38-7.12 (5H, m), 4.13 (2H, s), 4.06 (2H, t, J=7.0 Hz), 1.66 (2H, sext, J=7.0 Hz), 0.74 (3H, t, J=7.0 Hz).

Fraction 3: LCMS (Method F, ES-API): RT 2.01 min, m+H=234.2; 1H NMR (400 MHz, DMSO-d6): δ 8.04 (1H, s), 7.29-7.19 (5H, m), 4.26 (2H, t, J=7.0 Hz), 4.10 (2H, s), 1.77 (2H, sext, J=7.0 Hz), 0.78 (3H, t, J=7.0 Hz).

Intermediates 88. Isopropylated Triazole

| | | |
|---|---|---|
| 88a | 4-(benzylthio)-2-isopropyl-2H-1,2,3-triazole | 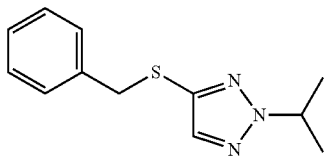 [SMILES: CC(C)n1ncc(SCc2ccccc2)n1] |
| 88b | 5-(benzylthio)-1-isopropyl-1H-1,2,3-triazole | 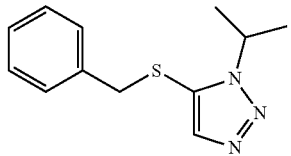 [SMILES: CC(C)n1nncc1SCc1ccccc1] |
| 88c | 4-(benzylthio)-1-isopropyl-1H-1,2,3-triazole | 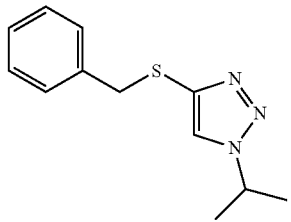 [SMILES: CC(C)n1cc(SCc2ccccc2)nn1] |

Fraction 1: LCMS (Method F, ES-API): RT 2.41 min, m+H=234; 1H NMR (400 MHz, DMSO-d6): δ 7.67 (1H, s), 7.31-7.21 (5H, m), 4.76 (1H, sept, J=6.7 Hz), 4.17 (2H, s), 1.44 (6H, d, J=6.7 Hz).

Fraction 2: LCMS (Method F, ES-API): RT 2.09 min, m+H=234; 1H NMR (400 MHz, DMSO-d6): δ 7.77 (1H, s), 7.32-7.12 (5H, m), 4.60 (1H, sept, J=6.7 Hz), 4.11 (2H, s), 1.29 (6H, d, J=6.7 Hz).

Fraction 3: LCMS (Method F, ES-API): RT 1.99 min, m+H=234; 1H NMR (400 MHz, DMSO-d6): δ 8.10 (1H, s), 7.30-7.18 (5H, m), 4.76 (1H, sept, J=6.7 Hz), 4.10 (2H, s), 1.43 (6H, d, J=6.7 Hz).

Intermediates 89. Preparation of Sulfonyl Chloride

| | | |
|---|---|---|
| 89a | 2-methyl-2H-1,2,3-triazole-4-sulfonyl chloride | 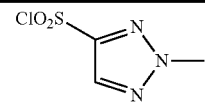 |
| 89b | 1-methyl-1H-1,2,3-triazole-5-sulfonyl chloride | 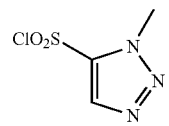 |
| 89c | 1-methyl-1H-1,2,3-triazole-4-sulfonyl chloride | 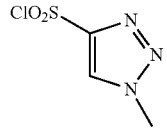 |

Sulfonyl chlorides of Fractions 1, 2 and 3 from Intermediate 85 were prepared according to the following preparations:

Preparation 1, Sulfonyl Chloride of Intermediate 85 Fraction 1: N-chlorosuccinimide (3.38 g, 25.3 mmol) was added to a solution of Intermediate 85 Fraction 1 (1.3 g, 6.33 mmol) in acetic acid (32 mL) and water (16 mL) and stirred at room temperature for 1 hour. Water (40 mL) was added and the mixture was extracted with ethyl acetate (40 mL). The organic phase was washed with saturated aqueous sodium hydrogen carbonate solution (40 mL), brine (40 mL), dried (magnesium sulfate), and solvent removed to give Preparation 1 (1.35 g) as a pale yellow oil. LCMS (Method F, ES-API; quenching into morpholine): RT 1.09 min, m+morpholine-Cl=233.1; 1H NMR (400 MHz, CDCl3): δ 8.11 (1H, s), 4.36 (3H, s).

Preparation 2, Sulfonyl Chloride of Intermediate 85 Fraction 2: Chlorine gas was bubbled through a solution of Intermediate 85 Fraction 2 (200 mg, 0.974 mmol) in dichloromethane (15 mL) and water (3 mL) for 2 minutes at 0° C. then the reaction mixture was stirred at 0° C. for a further 5 minutes. Water (10 mL) was added and the mixture was extracted with dichloromethane (10 mL). The organic phase was dried over magnesium sulfate, filtered and concentrated in vacuo to give Preparation 2 (317 mg) as a colourless oil. LCMS (Method F, ES-API; quenching into morpholine): RT 1.17 min, m+morpholine-Cl=233.1; 1H NMR (400 MHz, CDCl3): δ 8.27 (1H, s), 4.40 (3H, s).

Preparation 3, Sulfonyl Chloride of Intermediate 85 Fraction 3: N-chlorosuccinimide (2.60 g, 19.49 mmol) was added to a solution of Intermediate 85 Fraction 3 (1.0 g, 4.87 mmol) in acetic acid (26 mL) and water (13 mL) and stirred at room temperature for 2 hours. Water (40 mL) was added and the mixture was extracted with ethyl acetate (40 mL). The organic phase was washed with saturated aqueous sodium hydrogen carbonate solution (3×40 mL), brine (40 mL), dried (magnesium sulfate), and solvent removed to give Preparation 3 (810 mg) as a colourless oil. LCMS (Method F, ES-API; quenching into morpholine): RT 0.86 min, m+morpholine-Cl=233.1; 1H NMR (400 MHz, CDCl3): δ 8.22 (1H, s), 4.25 (3H, s).

The following intermediates 90-92 were similarly prepared from appropriate starting materials:

Intermediates 90. Preparation of Sulfonyl Chloride

| | | |
|---|---|---|
| 90a | 2-ethyl-2H-1,2,3-triazole-4-sulfonyl chloride | 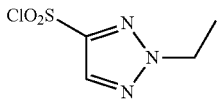 |
| 90b | 1-ethyl-1H-1,2,3-triazole-5-sulfonyl chloride | 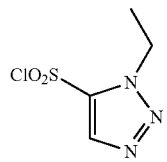 |

| | | |
|---|---|---|
| 90c | 1-ethyl-1H-1,2,3-triazole-4-sulfonyl chloride | 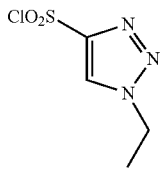 |

Preparation 1, Sulfonyl Chloride of Intermediate 86 Fraction 1: LCMS (Method F, ES-API; quenching into morpholine): RT 1.37 min, m+morpholine-Cl=247; 1H NMR (400 MHz, CDCl3): δ 8.11 (1H, s), 4.62 (2H, q, J=7.4 Hz), 1.66 (3H, t, J=7.4 Hz).

Preparation 2, Sulfonyl Chloride of Intermediate 86 Fraction 2: LCMS (Method F, ES-API; quenching into morpholine): RT 1.37 min, m+morpholine-Cl=247; 1H NMR (400 MHz, CDCl3): δ 8.27 (1H, s), 4.75 (2H, q, J=7.3 Hz), 1.70 (3H, t, J=7.3 Hz).

Preparation 3, Sulfonyl Chloride of Intermediate 86 Fraction 3: LCMS (Method F, ES-API; quenching into morpholine): RT 1.44 min, m+morpholine-Cl=247; 1H NMR (400 MHz, CDCl3): δ 8.23 (1H, s), 4.56 (2H, q, J=7.4 Hz), 1.67 (3H, t, J=7.4 Hz).

Intermediates 91. Preparation of Sulfonyl Chloride

| | | |
|---|---|---|
| 91a | 2-propyl-2H-1,2,3-triazole-4-sulfonyl chloride | 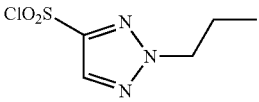 |
| 91b | 1-propyl-1H-1,2,3-triazole-5-sulfonyl chloride | 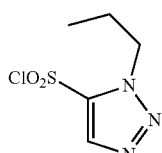 |
| 91c | 1-propyl-1H-1,2,3-triazole-4-sulfonyl chloride | 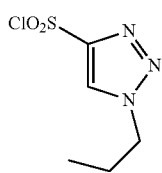 |

Preparation 1, Sulfonyl Chloride of Intermediate 87 Fraction 1: LCMS (Method F, ES-API; quenching into morpholine): RT 1.62 min, m+morpholine-Cl=261.2; 1H NMR (400 MHz, CDCl3): δ 8.11 (1H, s), 4.53 (2H, t, J=7.1 Hz), 2.08 (2H, sext, J=7.1 Hz), 0.98 (3H, t, J=7.1 Hz).

Preparation 2, Sulfonyl Chloride of Intermediate 87 Fraction 2: LCMS (Method F, ES-API; quenching into morpholine): RT 1.58 min, m+morpholine-Cl=261.1; 1H NMR (400 MHz, CDCl3): δ 8.27 (1H, s), 4.68-4.64 (2H, m), 2.12 (2H, sext, J=7.1 Hz), 1.05 (3H, t, J=7.1 Hz).

Preparation 3, Sulfonyl Chloride of Intermediate 87 Fraction 3: LCMS (Method F, ES-API; quenching into morpholine): RT 1.38 min, m+morpholine-Cl=261.2; 1H NMR (400 MHz, CDCl3): δ 8.21 (1H, s), 4.46 (2H, t, J=7.1 Hz), 2.04 (2H, sext, J=7.1 Hz), 1.02 (3H, t, J=7.1 Hz).

Intermediates 92. Preparation of Sulfonyl Chloride

| | | |
|---|---|---|
| 92a | 2-isopropyl-2H-1,2,3-triazole-4-sulfonyl chloride | 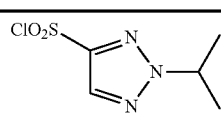 |
| 92b | 1-isopropyl-1H-1,2,3-triazole-5-sulfonyl chloride | 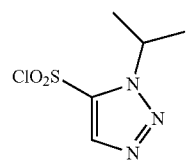 |
| 92c | 1-isopropyl-1H-1,2,3-triazole-4-sulfonyl chloride | 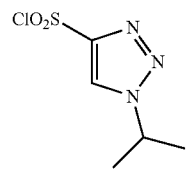 |

Preparation 1, Sulfonyl Chloride of Intermediate 88 Fraction 1: LCMS (Method F, ES-API; quenching into morpholine): RT 1.64 min, m+morpholine-Cl=261; 1H NMR (400 MHz, CDCl3): δ 7.62 (1H, s), 4.76 (1H, sept., J=6.7 Hz), 1.46 (6H, d, J=6.7 Hz).

Preparation 2, Sulfonyl Chloride of Intermediate 88 Fraction 2: LCMS (Method F, ES-API; quenching into morpholine): RT 1.57 min, m+morpholine-Cl=261; 1H NMR (400 MHz, DMSO-d6): δ 7.60 (1H, s), 5.25 (1H, sept., J=6.7 Hz), 1.49 (6H, d, J=6.7 Hz).

Preparation 3, Sulfonyl Chloride of Intermediate 88 Fraction 3: LCMS (Method F, ES-API; quenching into morpholine): RT 1.47 min, m+morpholine-Cl=261; 1H NMR (400 MHz, CDCl3): δ 8.26 (1H, s), 4.95 (1H, sept., J=6.7 Hz), 1.68 (6H, d, J=6.7 Hz).

Intermediate 93. (R)-methyl 1-(4-fluorophenyl)-6-((1-propyl-1H-pyrazol-4-yl)sulfonyl)-4,4a,5,6,7,8-hexahydro-1H-pyrazolo[3,4-g]isoquinoline-4a-carboxylate

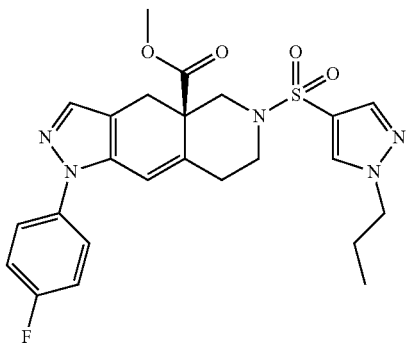 [SMILES: CCCn1cc(S(=O)(=O)N2CCC3=Cc4c(cnn4-c4ccc(F)cc4)C[C@]3(C(=O)OC)C2)cn1]

Made by the method of Intermediate 33, using HCl (4M solution in dioxane) in place of trifluoroacetic acid/dichloromethane. LCMS (Method F, ES-API): RT 2.22 min, m+H=500.

Intermediate 94

| | | |
|---|---|---|
| Isomer A | (R)-methyl 1-(4-fluorophenyl)-6-((2-methyl-2H-1,2,3-triazol-4-yl)sulfonyl)-4,4a,5,6,7,8-hexahydro-1H-pyrazolo[3,4-g]isoquinoline-4a-carboxylate | 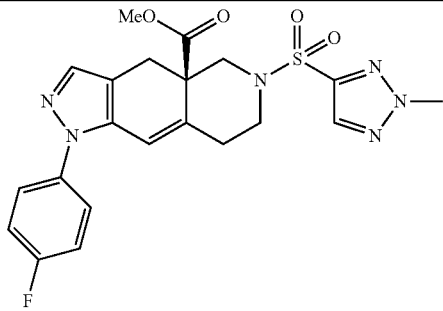 |
| Isomer B | (R)-methyl 1-(4-fluorophenyl)-6-((1-methyl-1H-1,2,3-triazol-5-yl)sulfonyl)-4,4a,5,6,7,8-hexahydro-1H-pyrazolo[3,4-g]isoquinoline-4a-carboxylate | 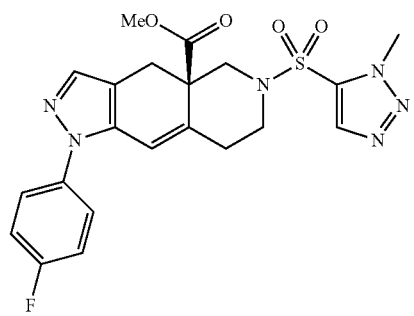 [SMILES: COC(=O)[C@]12Cc3cnn(-c4ccc(F)cc4)c3C=C1CCN(S(=O)(=O)c1cnnn1C)C2] |
| Isomer C | (R)-methyl 1-(4-fluorophenyl)-6-((1-methyl-1H-1,2,3-triazol-4-yl)sulfonyl)-4,4a,5,6,7,8-hexahydro-1H-pyrazolo[3,4-g]isoquinoline-4a-carboxylate | 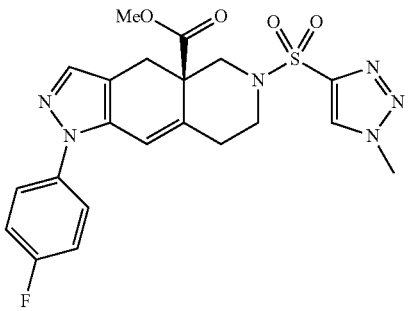 [SMILES: COC(=O)[C@]12Cc3cnn(-c4ccc(F)cc4)c3C=C1CCN(S(=O)(=O)c1cn(C)nn1)C2] |

Made from Preparation 1 of Intermediate 89 by the method of Intermediate 33, using HCl (4M solution in dioxane) in place of trifluoroacetic acid/dichloromethane. LCMS (Method F, ES-API): RT 2.10 min, m+H=473.1.

Intermediate 95

| | | |
|---|---|---|
| Isomer A | (R)-methyl 1-(4-fluorophenyl)-6-((2-propyl-2H-1,2,3-triazol-4-yl)sulfonyl)-4,4a,5,6,7,8-hexahydro-1H-pyrazolo[3,4-g]isoquinoline-4a-carboxylate | 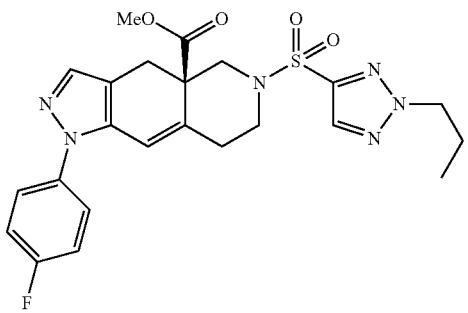 [SMILES: CCCn1ncc(S(=O)(=O)N2CCC3=Cc4c(cnn4-c4ccc(F)cc4)C[C@]3(C(=O)OC)C2)n1] |

-continued

| | | |
|---|---|---|
| Isomer B | (R)-methyl 1-(4-fluorophenyl)-6-((1-propyl-1H-1,2,3-triazol-5-yl)sulfonyl)-4,4a,5,6,7,8-hexahydro-1H-pyrazolo[3,4-g]isoquinoline-4a-carboxylate | |
| Isomer C | (R)-methyl 1-(4-fluorophenyl)-6-((1-propyl-1H-1,2,3-triazol-4-yl)sulfonyl)-4,4a,5,6,7,8-hexahydro-1H-pyrazolo[3,4-g]isoquinoline-4a-carboxylate | |

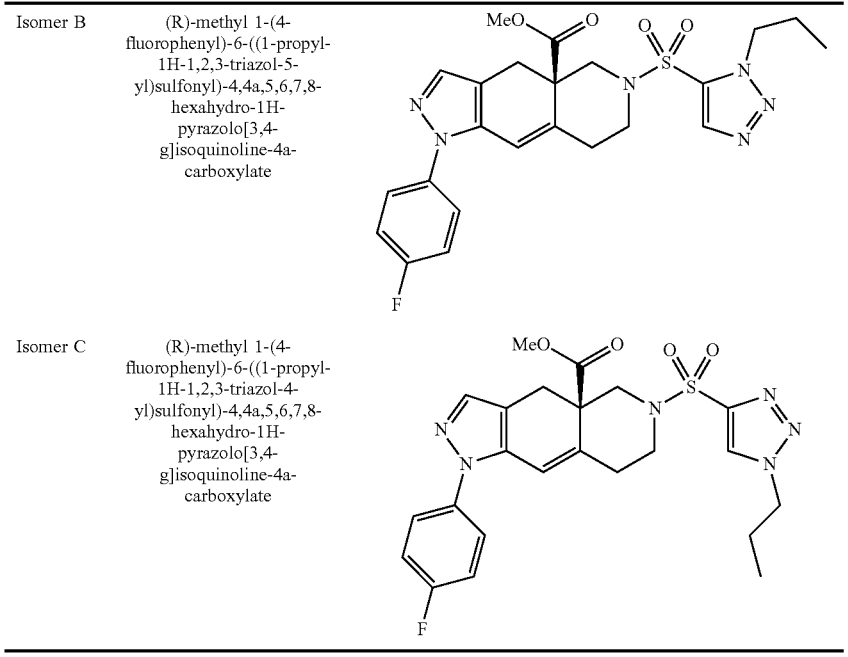

Made from Preparation 1 of Intermediate 91 by the method of Intermediate 33, using HCl (4M solution in dioxane) in place of trifluoroacetic acid/dichloromethane. LCMS (Method F, ES-API): RT 2.40 min, m+H=501.2.

Example 1. (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(pyridin-2-yl)methanone

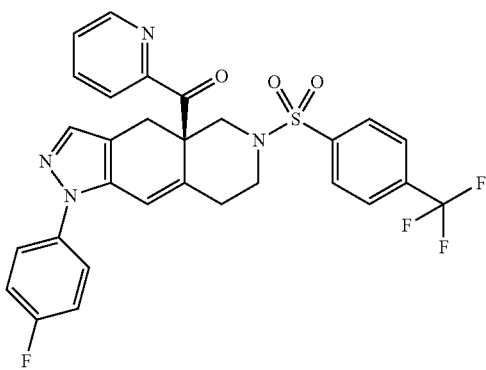 [SMILES: O=C(c1ccccn1)[C@]12Cc3cnn(-c4ccc(F)cc4)c3C=C1CCN(S(=O)(=O)c1ccc(C(F)(F)F)cc1)C2]

A solution of (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(pyridin-2-yl)-(R/S)-methanol (3.1 g, 5.3 mmol) in dry dichloromethane (25 mL) was treated with 1,1,1-triacetoxy-1,1-dihydro-1,2-benziodoxol-3(1H)-one (3.2 g, 7.54 mmol; Dess-Martin periodinane) and the reaction mixture stirred for 1 hour at room temperature. The reaction mixture was cooled and treated with saturated sodium hydrogen carbonate solution (125 mL) followed by dichloromethane (50 mL). The mixture was stirred for 10 minutes and the phases separated. The aqueous phase was extracted with further dichloromethane (×2) and the combined organic phases dried over sodium sulfate. The solids were removed by filtration, the filtrate was concentrated under reduced pressure and the residue purified by column chromatography on silica gel (gradient: 20-30% ethyl acetate in cyclohexane) to afford (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(pyridin-2-yl)methanone as a pale yellow foam (2.20 g). The product was further purified by preparative Hplc (C-18 column eluting with 80% aqueous methanol) to give (R)-(1-(4-fluorophenyl)-6-((4-(trifluoromethyl)phenyl) sulfonyl)-4,4a,5,6,7,8-hexahydro-1H-pyrazolo[3,4-g]isoquinolin-4a-yl)(pyridin-2-yl) methanone as a white solid (1.10 g). LCMS (Method D, ESI): RT 5.61 min, m+H=583.0; 1H NMR (400 MHz, CDCl$_3$): δ 8.62 (ddd, J=4.8, 1.7, 1.0 Hz, 1H); 7.85-7.86 (m, 1H); 7.80-7.81 (m, 3H); 7.70 (d, J=8.3 Hz, 2H); 7.44-7.45 (m, 3H); 7.27 (s, 1H); 7.16 (t, J=8.5 Hz, 2H); 6.49 (d, J=2.2 Hz, 1H); 5.56 (dd, J=12.3, 2.1 Hz, 1H); 4.26 (d, J=16.9 Hz, 1H); 3.86-3.89 (m, 1H); 2.83-2.84 (m, 3H); 2.54-2.56 (m, 2H).

Alternative preparation of Example 1: (R)-tert-butyl 1-(4-fluorophenyl)-4a-picolinoyl-4a,5,7,8-tetrahydro-1H-pyrazolo[3,4-g]isoquinoline-6(4H)-carboxylate (109.5 g) was suspended with stirring in a 4 N HCl/dioxane solution (250 mL) at 20-25° C. After deprotection was complete (1.5 hours) the solution was concentrated to dryness to give 157.1 g of the corresponding HCl salt as an amber oil. The salt was suspended in dichloromethane (1.5 L) and Hunig's base (150 g, 1150 mmol) was added. When the suspension had cleared a solution of 4-(trifluoromethyl)benzenesulfonyl chloride (67.0 g, 275 mmol) in dichloromethane (100 mL) was added. The reaction mixture was allowed to stir overnight at 20-25° C., then was quenched with water (500 mL). The organic layer was washed with 15% aqueous sodium chloride solution (500 mL) and then concentrated. The crude product was purified by column chromatography on silica gel (300 g), eluting with heptane/ethyl acetate (4:1 to 1:1), to give (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(pyridin-2-yl)methanone (78 g) as a pale yellow powder.

The following examples were similarly prepared from the appropriate intermediate:

Example 1A. (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(1-methyl-1H-imidazol-2-yl)methanone

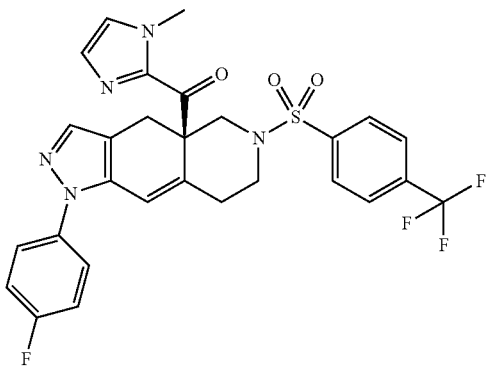 [SMILES: Cn1ccnc1C(=O)[C@]12Cc3cnn(-c4ccc(F)cc4)c3C=C1CCN(S(=O)(=O)c1ccc(C(F)(F)F)cc1)C2]

LCMS (method E), Rt=12.56 min (MH)+586.2; $^1$H NMR (400 MHz, CDCl3): δ 7.82 (d, J=8.2 Hz, 2H); 7.71 (d, J=8.3 Hz, 2H); 7.42-7.43 (m, 2H); 7.31 (s, 1H); 7.14-7.15 (m, 3H); 6.97 (s, 1H); 6.53 (d, J=2.3 Hz, 1H); 5.59 (dd, J=12.5, 2.1 Hz, 1H); 4.41 (d, J=16.7 Hz, 1H); 3.92-3.95 (m, 1H); 3.83 (s, 3H); 2.81-2.82 (m, 3H); 2.57-2.59 (m, 2H).

Example 1B. (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(pyridin-3-yl)methanone

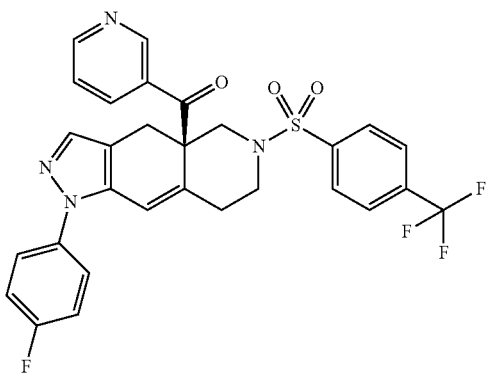 [SMILES: O=C(c1cccnc1)[C@]12Cc3cnn(-c4ccc(F)cc4)c3C=C1CCN(S(=O)(=O)c1ccc(C(F)(F)F)cc1)C2]

LCMS (Method D, ESI): RT 5.17 min, m+H=583.0; 1H NMR (400 MHz, CDCl$_3$): δ 8.91 (d, J=2.2 Hz, 1H); 8.71 (dd, J=4.8, 1.7 Hz, 1H); 8.01 (dt, J=8.0, 2.0 Hz, 1H); 7.94 (d, J=8.2 Hz, 2H); 7.82 (d, J=8.3 Hz, 2H); 7.41-7.42 (m, 3H); 7.35 (dd, J=8.0, 4.8 Hz, 1H); 7.18 (t, J=8.5 Hz, 2H); 6.44 (s, 1H); 4.60 (dd, J=11.4, 1.9 Hz, 1H); 3.89 (dd, J=10.9, 4.9 Hz, 1H); 3.38 (d, J=17.5 Hz, 1H); 2.80 (d, J=17.6 Hz, 1H); 2.55 (d, J=11.4 Hz, 1H); 2.48 (td, J=11.5, 3.4 Hz, 1H); 2.26-2.29 (m, 2H).

Example 1C. (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(thiazol-2-yl)methanone

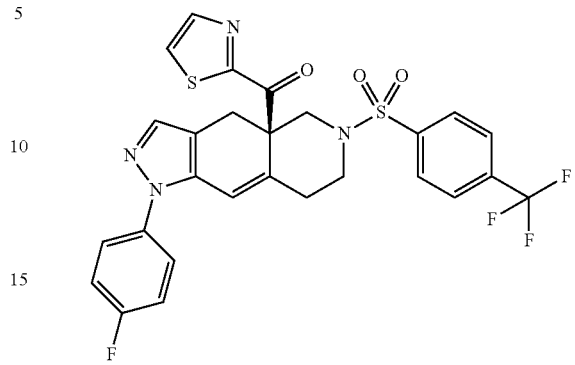

LCMS (Method D, ESI): RT 5.50 min, m+H=589.0; 1H NMR (400 MHz, CDCl$_3$): δ 8.00 (d, J=3.1 Hz, 1H); 7.83 (d, J=8.2 Hz, 2H); 7.68-7.69 (m, 3H); 7.42-7.43 (m, 2H); 7.29 (s, 1H); 7.17 (t, J=8.5 Hz, 2H); 6.54 (d, J=2.3 Hz, 1H); 5.51 (dd, J=12.5, 2.1 Hz, 1H); 4.20 (d, J=16.8 Hz, 1H); 3.91-3.95 (m, 1H); 2.85-2.86 (m, 3H); 2.57-2.59 (m, 2H).

Alternative preparation of Example 1c: (R)-tert-butyl 1-(4-fluorophenyl)-4a-(thiazole-2-carbonyl)-4a,5,7,8-tetrahydro-1H-pyrazolo[3,4-g]isoquinoline-6(4H)-carboxylate (76.1 g) was deprotected using 4 N HCl/dioxane solution (400 mL) at 20-25° C. After reaction was complete (3 h) the solution was concentrated to dryness to provide 91.4 g of the corresponding HCl salt as an amber oil. The salt was suspended in dichloromethane (1.0 L) and Hunig's base (85.0 g, 650 mmol) was added. When the suspension became a clear solution 4-(trifluoromethyl)benzenesulfonyl chloride (37.2 g, 152 mmol) in dichloromethane (100 mL) was added. The mixture was stirred overnight at 20-25° C. The reaction mixture was quenched with water (250 mL) and the organic layer washed with 15% aqueous sodium chloride solution (500 mL) then concentrated. The crude product was purified twice by column chromatography on silica gel (300 g then 800 g), eluting with heptane/ethyl acetate (3:1), to give (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(thiazol-2-yl)methanone (54.2 g) as a pale yellow powder.

Example 1D. (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(5-methyl-1,3,4-oxadiazol-2-yl)methanone

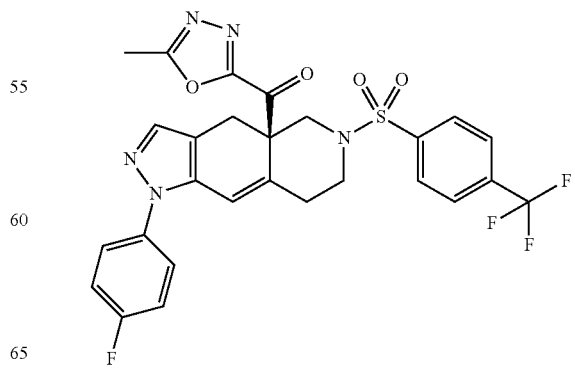

LCMS (Method D, ESI): RT 5.24 min, m+H=588.0; 1H NMR (400 MHz, CDCl₃): δ 7.82-7.84 (m, 4H); 7.40-7.41 (m, 2H); 7.33 (s, 1H); 7.17 (t, J=8.5 Hz, 2H); 6.58 (d, J=2.4 Hz, 1H); 5.27 (dd, J=12.9, 2.1 Hz, 1H); 4.14 (d, J=16.8 Hz, 1H); 3.97 (t, J=7.9 Hz, 1H); 2.85-2.87 (m, 2H); 2.75 (d, J=12.9 Hz, 1H); 2.65 (s, 3H); 2.56-2.58 (m, 2H).

Example 1E. (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(oxazol-4-yl)methanone

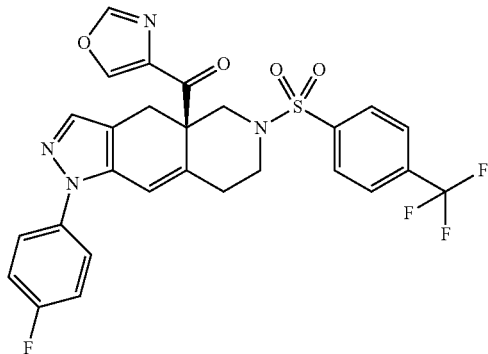

LCMS (Method D, ESI): RT 5.32 min, m+H=573.0; 1H NMR (400 MHz, CDCl₃): δ 7.86 (d, J=8.2 Hz, 2H); 7.76-7.78 (m, 3H); 7.41 (dd, J=8.6, 4.8 Hz, 2H); 7.35 (s, 1H); 7.31 (s, 1H); 7.17 (t, J=8.4 Hz, 2H); 6.54 (s, 1H); 5.38 (d, J=12.6 Hz, 1H); 4.12 (d, J=16.8 Hz, 1H); 3.91-3.94 (m, 1H); 2.82-2.84 (m, 3H); 2.55-2.58 (m, 2H).

Example 1F. (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(oxazol-2-yl)methanone

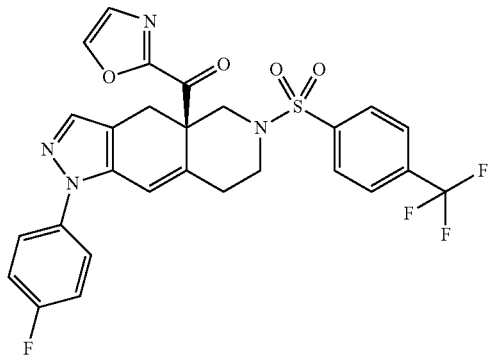 [SMILES: O=C(c1nccs1)[C@]12Cc3cnn(-c4ccc(F)cc4)c3C=C1CCN(S(=O)(=O)c1ccc(C(F)(F)F)cc1)C2]

LCMS (Method D, ESI): RT 5.35 min, m+H=572.9; 1H NMR (400 MHz, CDCl₃): δ 7.86 (d, J=8.2 Hz, 2H); 7.77-7.78 (m, 3H); 7.40-7.41 (m, 2H); 7.35 (d, J=0.7 Hz, 1H); 7.30 (s, 1H); 7.16 (t, J=8.5 Hz, 2H); 6.54 (d, J=2.3 Hz, 1H); 5.38 (dd, J=12.6, 2.1 Hz, 1H); 4.12 (d, J=16.8 Hz, 1H); 3.91-3.94 (m, 1H); 2.82-2.83 (m, 3H); 2.55-2.57 (m, 2H).

Example 1G. (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(furan-2-yl)methanone

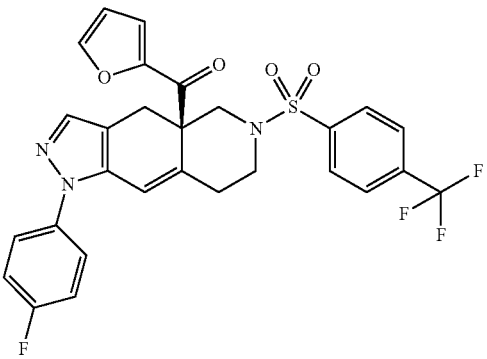 [SMILES: O=C(c1ccco1)[C@]12Cc3cnn(-c4ccc(F)cc4)c3C=C1CCN(S(=O)(=O)c1ccc(C(F)(F)F)cc1)C2]

LCMS (Method D, ESI): RT 5.38 min, m+H=571.9; 1H NMR (400 MHz, CDCl₃): δ 7.86 (d, J=8.2 Hz, 2H); 7.75 (d, J=8.2 Hz, 2H); 7.57 (dd, J=1.7, 0.8 Hz, 1H); 7.41-7.42 (m, 2H); 7.31 (s, 1H); 7.22 (dd, J=3.6, 0.8 Hz, 1H); 7.15-7.16 (m, 2H); 6.51-6.52 (m, 2H); 4.96 (dd, J=12.3, 2.0 Hz, 1H); 3.86 (dd, J=10.8, 5.6 Hz, 1H); 3.63 (d, J=16.9 Hz, 1H); 2.76-2.78 (m, 3H); 2.58-2.60 (m, 1H); 2.47 (d, J=14.8 Hz, 1H).

Example 1H. (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(thiophen-2-yl)methanone

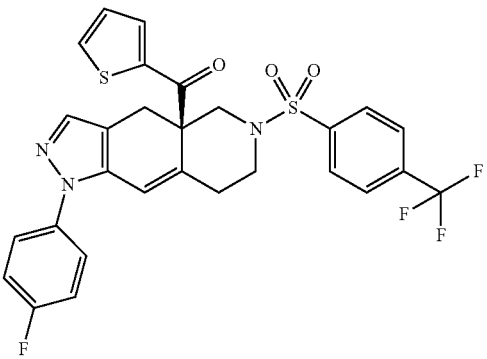 [SMILES: O=C(c1cccs1)[C@]12Cc3cnn(-c4ccc(F)cc4)c3C=C1CCN(S(=O)(=O)c1ccc(C(F)(F)F)cc1)C2]

LCMS (Method D, ESI): RT 5.56 min, m+H=587.9; 1H NMR (400 MHz, CDCl₃): δ 7.92 (d, J=8.2 Hz, 2H); 7.76-7.78 (m, 3H); 7.61 (dd, J=5.0, 1.1 Hz, 1H); 7.45 (dd, J=8.7, 4.7 Hz, 2H); 7.36 (s, 1H); 7.19 (t, J=8.4 Hz, 2H); 7.03 (dd, J=5.0, 3.9 Hz, 1H); 6.51 (s, 1H); 4.64 (d, J=11.5 Hz, 1H); 3.87 (d, J=9.1 Hz, 1H); 3.41 (d, J=17.5 Hz, 1H); 2.82 (d, J=17.5 Hz, 1H); 2.67 (d, J=11.5 Hz, 1H); 2.56-2.60 (m, 1H); 2.47-2.50 (m, 1H); 2.39 (d, J=13.6 Hz, 1H).

Example 1I. (R)-(1-(4-fluorophenyl)-6-(m-tolylsulfonyl)-4,4a,5,6,7,8-hexahydro-1H-pyrazolo[3,4-g]isoquinolin-4a-yl)(oxazol-2-yl)methanone

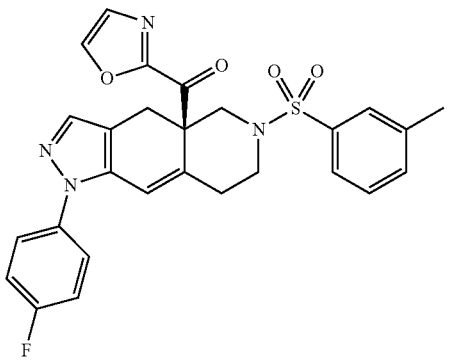 [SMILES: Cc1cccc(S(=O)(=O)N2CCC3=Cc4c(cnn4-c4ccc(F)cc4)C[C@]3(C(=O)c3ncco3)C2)c1]

LCMS (Method F, ES-API): RT 2.53 min, m+H=519.1; 1H NMR (400 MHz, CDCl3): δ 7.82 (1H, d, J=0.6 Hz), 7.55-7.52 (2H, m), 7.44-7.38 (5H, m), 7.31 (1H, s), 7.19-7.13 (2H, m), 6.52 (1H, d, J=2.3 Hz), 5.40 (1H, dd, J=12.5, 2.0 Hz), 4.12 (1H, d, J=16.9 Hz), 3.91-3.85 (1H, m), 2.92-2.82 (2H, m), 2.68 (1H, d, J=12.5 Hz), 2.53-2.42 (5H, m).

Example 1J. (R)-(1-(4-fluorophenyl)-6-(m-tolylsulfonyl)-4,4a,5,6,7,8-hexahydro-1H-pyrazolo[3,4-g]isoquinolin-4a-yl)(pyrimidin-2-yl)methanone

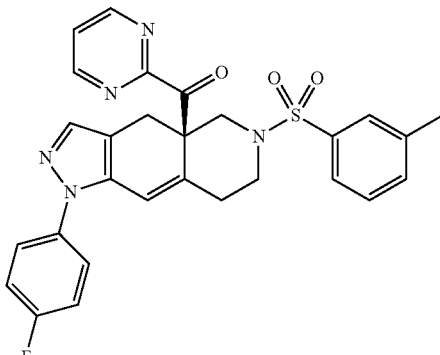

LCMS (Method F, ES-API): RT 2.38 min, m+H=530.2; 1H NMR (400 MHz, CDCl3): δ 8.92 (2H, d, J=4.8 Hz), 7.49-7.36 (7H, m), 7.32 (1H, s), 7-19-7.13 (2H, m), 6.47 (1H, d, J=2.1 Hz), 5.12 (1H, dd, J=12.1, 2.0 Hz), 4.13 (1H, d, J=16.9 Hz), 3.80-3.76 (1H, m), 2.95 (1H, d, J=16.9 Hz), 2.88-2.79 (1H, m), 2.61 (1H, d, J=12.2 Hz), 2.46-2.37 (5H, m).

Example 1K. (R)-(6-((3,5-difluorophenyl)sulfonyl)-1-(4-fluorophenyl)-4,4a,5,6,7,8-hexahydro-1H-pyrazolo[3,4-g]isoquinolin-4a-yl)(4-methoxypyridin-2-yl)methanone

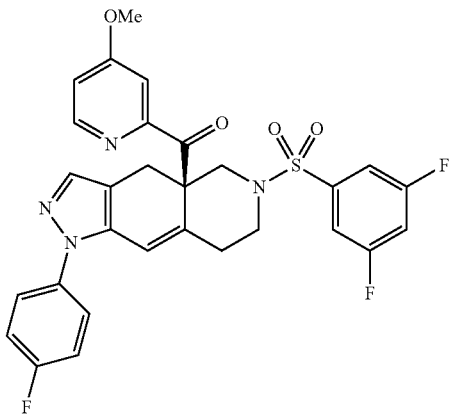 [SMILES: COc1ccnc(C(=O)[C@]23Cc4cnn(-c5ccc(F)cc5)c4C=C2CCN(S(=O)(=O)c2cc(F)cc(F)c2)C3)c1]

LCMS (Method F, ES-API): RT 2.78 min, m+H=581.2; 1H NMR (400 MHz, CDCl3): δ 8.46 (1H, d, J=4.9 Hz), 7.45-7.39 (3H, m), 7.29 (1H, s), 7.21-7.14 (4H, m), 7.00-6.95 (2H, m), 6.49 (1H, s), 5.63-5.60 (1H, m), 4.30 (1H, dd, J=16.9, 2.1 Hz), 3.88-3.83 (4H, m), 2.89-2.78 (3H, m), 2.63-2.57 (1H, m), 2.53-2.49 (1H, m).

Example 1L. (R)-(4-ethylpyridin-2-yl)(1-(4-fluorophenyl)-6-((3,4,5-trifluorophenyl)sulfonyl)-4,4a,5,6,7,8-hexahydro-1H-pyrazolo[3,4-g]isoquinolin-4a-yl)methanone

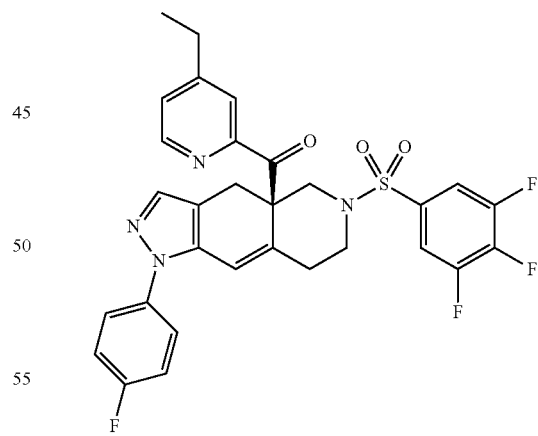

LCMS (Method F, ES-API): RT 3.19 min, m+H=597.2; 1H NMR (400 MHz, CDCl3): δ 8.49 (1H, dd, J=4.9, 0.6 Hz), 7.70 (1H, m), 7.45-7.41 (2H, m), 7.33-7.30 (4H, m), 7.19-7.14 (2H, m), 6.50 (1H, d, J=2.0 Hz), 5.58 (1H, dd, J=12.5, 2.0 Hz), 4.24 (1H, d, J=16.9 Hz), 3.91-3.86 (1H, m), 2.92-2.80 (3H, m), 2.73-2.67 (3H, m), 2.56-2.51 (1H, m), 1.27 (3H, t, J=7.5 Hz).

Example 1M. (R)-(1-(4-fluorophenyl)-6-((3,4,5-trifluorophenyl)sulfonyl)-4,4a,5,6,7,8-hexahydro-1H-pyrazolo[3,4-g]isoquinolin-4a-yl)(4-methoxy-pyridin-2-yl)methanone

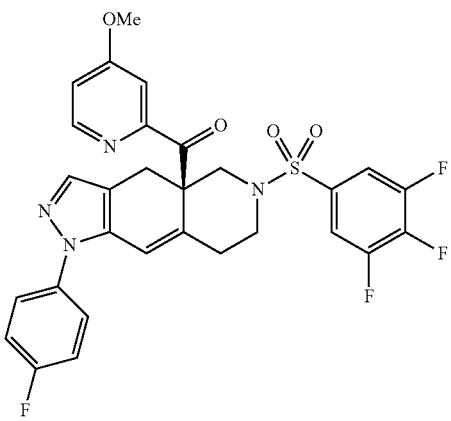 [SMILES: COc1ccnc(C(=O)[C@]23Cc4cnn(-c5ccc(F)cc5)c4C=C2CCN(S(=O)(=O)c2cc(F)c(F)c(F)c2)C3)c1]

LCMS (Method F, ES-API): RT 2.97 min, m+H=599.2; 1H NMR (400 MHz, CDCl3): δ 8.42 (1H, d, J=4.9 Hz), 7.45-7.41 (2H, m), 7.37 (1H, d, J=2.5 Hz), 7.33-7.30 (2H, m), 7.27 (1H, s), 7.19-7.14 (2H, m), 6.97 (1H, dd, J=5.8, 2.5 Hz), 6.50 (1H, d, J=2.0 Hz), 5.58 (1H, dd, J=12.1, 2.0 Hz), 4.28 (1H, d, J=16.9 Hz), 3.91-3.85 (4H, m), 2.91-2.78 (3H, m), 2.70-2.63 (1H, m), 2.55-2.50 (1H, m).

Example 2. (R)-(1-(4-fluorophenyl)-6-((4-fluorophenyl)sulfonyl)-4,4a,5,6,7,8-hexahydro-1H-pyrazolo[3,4-g]isoquinolin-4a-yl)(pyridin-2-yl)methanone

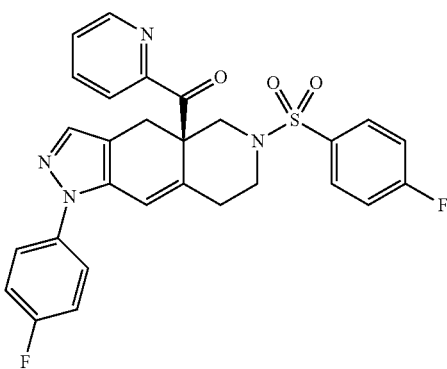 [SMILES: O=C(c1ccccn1)[C@]12Cc3cnn(-c4ccc(F)cc4)c3C=C1CCN(S(=O)(=O)c1ccc(F)cc1)C2]

A solution of (R)-(1-(4-fluorophenyl)-4,4a,5,6,7,8-hexahydro-1H-pyrazolo[3,4-g]isoquinolin-4a-yl)(pyridin-2-yl)methanone in dichloromethane (2.5 ml) (2.7 mL, 0.2 mmol) containing diisopropylethylamine (174 μL, 1 mmol) was added to 4-fluoro-phenyl sulfonyl chloride (48 mg, 0.25 mmol) and diisopropylethylamine (100 μL, 0.57 mmol) and the mixture stirred for 1.25 hours. The reaction mixture was concentrated under reduced pressure and the residue was purified by column chromatography on silica gel (gradient: 20-30% ethyl acetate in cyclohexane) to afford (R)-(1-(4-fluorophenyl)-6-((4-fluorophenyl)sulfonyl)-4,4a,5,6,7,8-hexahydro-1H-pyrazolo[3,4-g]isoquinolin-4a-yl)(pyridin-2-yl)methanone as a white solid (72 mg). LCMS (Method D, ESI): RT 5.32 min, m+H=533.0; 1H NMR (400 MHz, CDCl₃): δ 8.62-8.63 (m, 1H); 7.85-7.86 (m, 2H); 7.69-7.70 (m, 2H); 7.44-7.45 (m, 3H); 7.28 (s, 1H); 7.14 (dt, J=12.9, 8.5 Hz, 4H); 6.48 (d, J=2.2 Hz, 1H); 5.51 (dd, J=12.2, 2.1 Hz, 1H); 4.29 (d, J=16.9 Hz, 1H); 3.82-3.86 (m, 1H); 2.84-2.86 (m, 2H); 2.72 (d, J=12.2 Hz, 1H); 2.46-2.51 (m, 2H).

The following examples were similarly prepared from the appropriate intermediate:

Example 2A. (R)-(6-((3-fluorobenzyl)sulfonyl)-1-(4-fluorophenyl)-4,4a,5,6,7,8-hexahydro-1H-pyrazolo[3,4-g]isoquinolin-4a-yl)(thiazol-2-yl)methanone

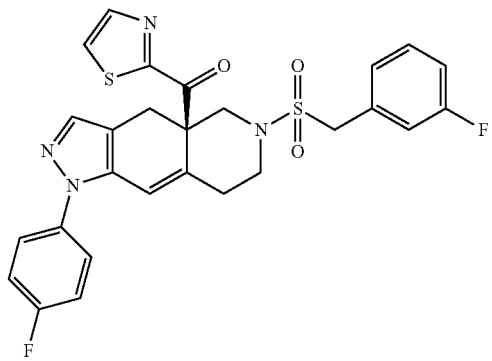 [SMILES: O=C(c1nccs1)[C@]12Cc3cnn(-c4ccc(F)cc4)c3C=C1CCN(S(=O)(=O)Cc1cccc(F)c1)C2]

LCMS (Method F, ES-API): RT 2.48 min, m+H=552.9; 1H NMR (400 MHz, CDCl₃): δ 8.07 (1H, d, J=3.1 Hz), 7.68 (1H, d, J=3.1 Hz), 7.47-7.41 (2H, m), 7.35-7.30 (2H, m), 7.20-7.14 (2H, m), 7.09-7.04 (3H, m), 6.53 (1H, s), 5.43 (1H, dd, J=7.1, 2.0 Hz), 4.23 (1H, d, J=16.8 Hz), 4.08 (1H, d, J=13.8 Hz), 4.02 (1H, d, J=13.8 Hz), 3.61-3.59 (1H, m), 3.07 (1H, d, J=13.1 Hz), 2.85 (1H, d, J=16.8 Hz), 2.73-2.64 (2H, m), 2.45-2.37 (1H, m).

Example 2B. ((4aR)-1-(4-fluorophenyl)-6-((((R/S)-tetrahydrofuran-2-yl)methyl)sulfonyl)-4,4a,5,6,7,8-hexahydro-1H-pyrazolo[3,4-g]isoquinolin-4a-yl)(thiazol-2-yl)methanone

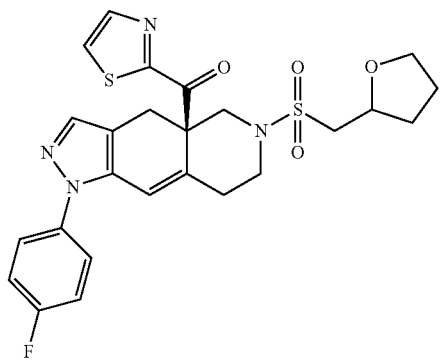 [SMILES: O=C(c1nccs1)[C@]12Cc3cnn(-c4ccc(F)cc4)c3C=C1CCN(S(=O)(=O)CC1CCCO1)C2]

LCMS (Method F, ES-API): RT 2.28 min, m+H=528.9; 1H NMR (400 MHz, CDCl₃): δ 8.07-8.06 (1H, m), 7.66 (1H, d, J=2.9 Hz), 7.48-7.44 (2H, m), 7.33 (1H, s), 7.20-7.14 (2H, m), 6.57 (1H, s), 5.47 (1H, ddd, J=17.5, 13.1, 2.2 Hz), 4.32-4.10 (2H, m), 3.88-3.72 (3H, m), 3.25 (1H, dd, J=43.6, 13.4 Hz), 3.13-2.81 (5H, m), 2.56-2.50 (1H, m), 2.40 (1H, s), 2.13-2.02 (1H, m), 1.91-1.84 (2H, m).

Example 2C. (R)-(1-(4-fluorophenyl)-6-(o-tolylsulfonyl)-4,4a,5,6,7,8-hexahydro-1H-pyrazolo[3,4-g]isoquinolin-4a-yl)(pyridin-2-yl)methanone

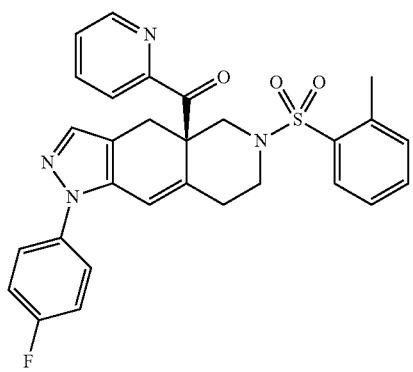 [SMILES: Cc1ccccc1S(=O)(=O)N1CCC2=Cc3c(cnn3-c3ccc(F)cc3)C[C@]2(C(=O)c2ccccn2)C1]

LCMS (Method F, ES-API): RT 2.61 min, m+H=528.8; 1H NMR (400 MHz, CDCl3): δ 8.34 (1H, ddd, J=4.7, 1.8, 0.8 Hz), 7.85 (1H, dd, J=7.6, 1.5 Hz), 7.81-7.79 (1H, m), 7.65 (1H, dt, J=7.6, 1.8 Hz), 7.46-7.41 (2H, m), 7.32 (1H, ddd, J=7.6, 4.8, 1.4 Hz), 7.24-7.14 (5H, m), 6.93-6.91 (1H, m), 6.52 (1H, s), 5.49 (1H, dd, J=12.8, 2.1 Hz), 4.20 (1H, d, J=16.9 Hz), 3.98-3.95 (1H, m), 3.08 (1H, d, J=12.8 Hz), 2.90-2.82 (3H, m), 2.60-2.54 (1H, m), 2.34 (3H, s).

Example 2D. (R)-(6-((4-ethylphenyl)sulfonyl)-1-(4-fluorophenyl)-4,4a,5,6,7,8-hexahydro-1H-pyrazolo[3,4-g]isoquinolin-4a-yl)(pyridin-2-yl)methanone

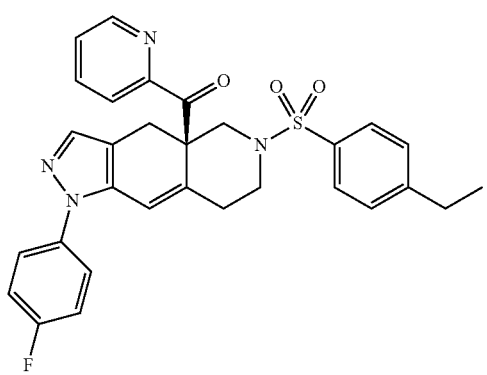 [SMILES: CCc1ccc(S(=O)(=O)N2CCC3=Cc4c(cnn4-c4ccc(F)cc4)C[C@]3(C(=O)c3ccccn3)C2)cc1]

LCMS (Method F, ES-API): RT 2.75 min, m+H=542.8; 1H NMR (400 MHz, CDCl3): δ 8.66 (1H, ddd, J=4.7, 1.7, 0.8 Hz), 7.91-7.89 (1H, m), 7.84 (1H, dt, J=7.5, 1.8 Hz), 7.61-7.58 (2H, m), 7.47 (1H, ddd, J=7.5, 4.7, 1.4 Hz), 7.44-7.40 (2H, m), 7.27-7.22 (3H, m), 7.19-7.13 (2H, m), 6.46 (1H, d, J=2.1 Hz), 5.50 (1H, dd, J=12.4, 2.1 Hz), 4.31 (1H, d, J=16.9 Hz), 3.84-3.79 (1H, m), 2.91-2.77 (2H, m), 2.72-2.65 (3H, m), 2.47-2.38 (2H, m), 1.25 (3H, t, J=7.5 Hz).

Example 2E. (R)-(1-(4-fluorophenyl)-6-(m-tolylsulfonyl)-4,4a,5,6,7,8-hexahydro-1H-pyrazolo[3,4-g]isoquinolin-4a-yl)(pyridin-2-yl)methanone

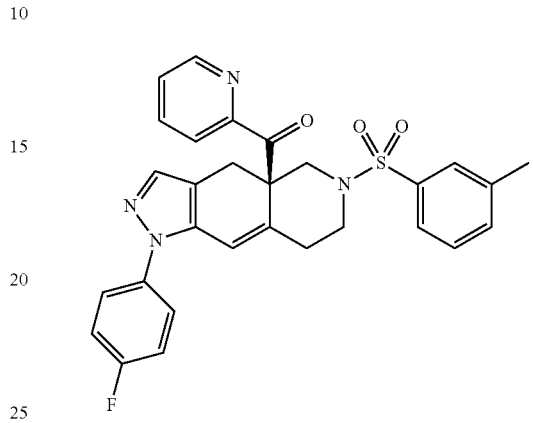

LCMS (Method F, ES-API): RT 2.62 min, m+H=528.8; 1H NMR (400 MHz, CDCl3): δ 8.66 (1H, ddd, J=4.7, 1.7, 0.8 Hz), 7.91-7.89 (1H, m), 7.84 (1H, dt, J=7.4, 1.7 Hz), 7.50-7.40 (5H, m), 7.36-7.34 (2H, m), 7.29 (1H, s), 7.19-7.13 (2H, m), 6.47 (1H, d, J=2.1 Hz), 5.51 (1H, dd, J=12.4, 2.1 Hz), 4.31 (1H, d, J=16.9 Hz), 3.84-3.80 (1H, m), 2.92-2.78 (2H, m), 2.68 (1H, d, J=12.4 Hz), 2.49-2.40 (5H, m).

Example 2F. (R)-(6-((3-chlorophenyl)sulfonyl)-1-(4-fluorophenyl)-4,4a,5,6,7,8-hexahydro-1H-pyrazolo[3,4-g]isoquinolin-4a-yl)(pyridin-2-yl)methanone

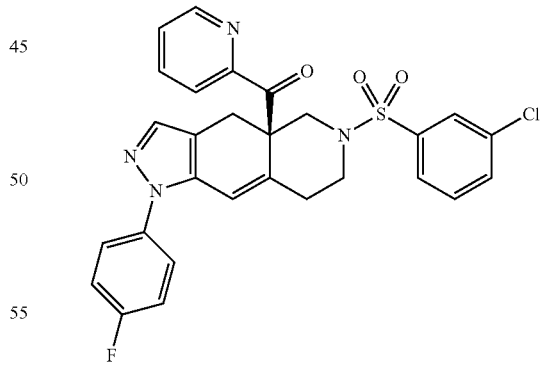

LCMS (Method F, ES-API): RT 2.68 min, m+H=548.8; 1H NMR (400 MHz, CDCl3): δ 8.66 (1H, ddd, J=4.7, 1.7, 0.8 Hz), 7.91-7.88 (1H, m), 7.84 (1H, dt, J=7.5, 1.8 Hz), 7.66-7.65 (1H, m), 7.59-7.56 (1H, m), 7.52-7.47 (2H, m), 7.46-7.41 (3H, m), 7.29 (1H, s), 7.19-7.13 (2H, m), 6.49 (1H, d, J=2.1 Hz), 5.55 (1H, dd, J=12.2, 2.1 Hz), 4.29 (1H, d, J=16.9 Hz), 3.87-3.82 (1H, m), 2.92-2.75 (3H, m), 2.56-2.47 (2H, m).

Example 2G. (R)-(1-(4-fluorophenyl)-6-((3-methoxyphenyl)sulfonyl)-4,4a,5,6,7,8-hexahydro-1H-pyrazolo[3,4-g]isoquinolin-4a-yl)(pyridin-2-yl)methanone

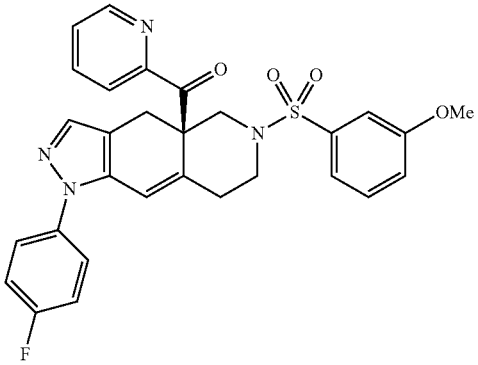 [SMILES: COc1cccc(S(=O)(=O)N2CCC3=Cc4c(cnn4-c4ccc(F)cc4)C[C@]3(C(=O)c3ccccn3)C2)c1]

LCMS (Method F, ES-API): RT 2.60 min, m+H=545.2; 1H NMR (400 MHz, CDCl3): δ 8.65 (1H, ddd, J=4.7, 1.7, 0.8 Hz), 7.91-7.88 (1H, m), 7.83 (1H, dt, J=7.5, 1.8 Hz), 7.49-7.36 (4H, m), 7.29 (2H, m), 7.19-7.13 (3H, m), 7.05 (1H, ddd, J=8.3, 2.5, 0.9 Hz), 6.47 (1H, d, J=2.1 Hz), 5.50 (1H, dd, J=12.2, 2.1 Hz), 4.30 (1H, d, J=16.9 Hz), 3.85-3.80 (4H, m), 2.91-2.78 (2H, m), 2.72 (1H, d, J=12.2 Hz), 2.51-2.44 (2H, m).

Example 2H. (R)-(6-((4-chloro-3-fluorophenyl)sulfonyl)-1-(4-fluorophenyl)-4,4a,5,6,7,8-hexahydro-1H-pyrazolo[3,4-g]isoquinolin-4a-yl)(pyridin-2-yl)methanone

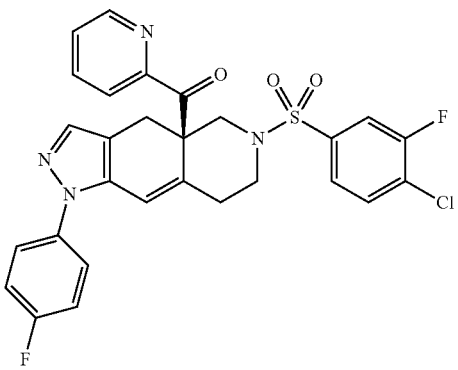 [SMILES: O=C(c1ccccn1)[C@]12Cc3cnn(-c4ccc(F)cc4)c3C=C1CCN(S(=O)(=O)c1ccc(Cl)c(F)c1)C2]

LCMS (Method F, ES-API): RT 2.78 min, m+H=567.1; 1H NMR (400 MHz, CDCl3): δ 8.63-8.61 (1H, m), 7.89-7.82 (2H, m), 7.50-7.41 (6H, m), 7.28 (1H, s), 7.19-7.13 (2H, m), 6.50 (1H, d, J=2.1 Hz), 5.54 (1H, dd, J=12.2, 2.1 Hz), 4.27 (1H, d, J=16.9 Hz), 3.89-3.85 (1H, m), 2.90-2.79 (3H, m), 2.61-2.49 (2H, m).

Example 2I. (R)-(1-(4-fluorophenyl)-6-((4-methoxyphenyl)sulfonyl)-4,4a,5,6,7,8-hexahydro-1H-pyrazolo[3,4-g]isoquinolin-4a-yl)(pyridin-2-yl)methanone

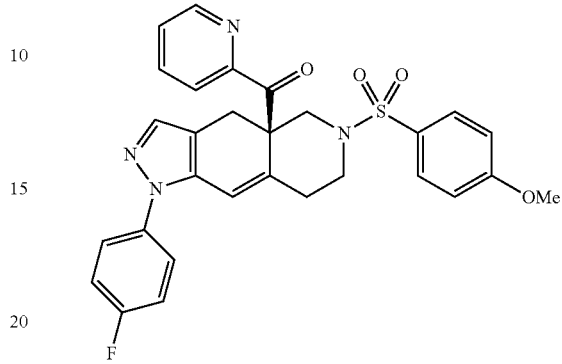

LCMS (Method F, ES-API): RT 2.57 min, m+H=545.2; 1H NMR (400 MHz, CDCl3): δ 8.63 (1H, ddd, J=4.7, 1.7, 0.8 Hz), 7.91-7.88 (1H, m), 7.83 (1H, dt, J=7.6, 1.8 Hz), 7.64-7.60 (2H, m), 7.48-7.40 (3H, m), 7.29 (1H, s), 7.19-7.13 (2H, m), 6.93-6.89 (2H, m), 6.47 (1H, d, J=2.1 Hz), 5.48 (1H, dd, J=12.2, 2.1 Hz), 4.30 (1H, d, J=16.9 Hz), 3.85-3.79 (4H, m), 2.90-2.77 (2H, m), 2.65 (1H, d, J=12.2 Hz), 2.48-2.39 (2H, m).

Example 2J. (R)-(6-((3-fluoro-4-methylphenyl)sulfonyl)-1-(4-fluorophenyl)-4,4a,5,6,7,8-hexahydro-1H-pyrazolo[3,4-g]isoquinolin-4a-yl)(pyridin-2-yl)methanone

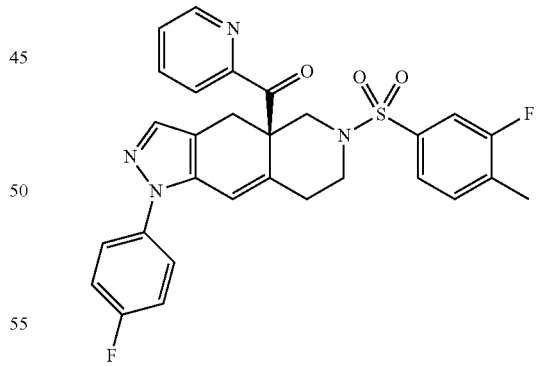

LCMS (Method F, ES-API): RT 2.74 min, m+H=547.2; 1H NMR (400 MHz, CDCl3): δ 8.65 (1H, ddd, J=4.7, 1.7, 0.8 Hz), 7.91-7.88 (1H, m), 7.84 (1H, dt, J=7.6, 1.8 Hz), 7.49-7.40 (3H, m), 7.37 (1H, dd, J=8.1, 2.1 Hz), 7.33-7.26 (3H, m), 7.19-7.13 (2H, m), 6.48 (1H, d, J=2.1 Hz), 5.52 (1H, dd, J=12.2, 2.1 Hz), 4.30 (1H, d, J=16.9 Hz), 3.85-3.80 (1H, m), 2.91-2.77 (2H, m), 2.71 (1H, d, J=12.2 Hz), 2.51-2.44 (2H, m), 2.31 (3H, d, J=1.7 Hz).

Example 2K. (R)-(1-(4-fluorophenyl)-6-(phenylsulfonyl)-4,4a,5,6,7,8-hexahydro-1H-pyrazolo[3,4-g]isoquinolin-4a-yl)(pyridin-2-yl)methanone

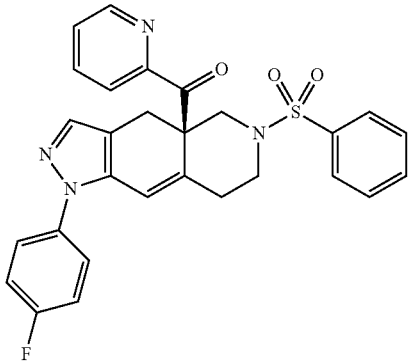

LCMS (Method F, ES-API): RT 2.57 min, m+H=515.2; 1H NMR (400 MHz, CDCl3): δ 8.66 (1H, ddd, J=4.7, 1.7, 0.8 Hz), 7.92-7.89 (1H, m), 7.84 (1H, dt, J=7.6, 1.8 Hz), 7.71-7.68 (2H, m), 7.58-7.53 (1H, m), 7.50-7.40 (5H, m), 7.29 (1H, s), 7.19-7.13 (2H, m), 6.47 (1H, d, J=2.1 Hz), 5.53 (1H, dd, J=12.2, 2.1 Hz), 4.31 (1H, d, J=16.9 Hz), 3.85-3.81 (1H, m), 2.91-2.78 (2H, m), 2.67 (1H, d, J=12.2 Hz), 2.48-2.40 (2H, m).

Example 2L. (R)-(1-(4-fluorophenyl)-6-((2-fluorophenyl)sulfonyl)-4,4a,5,6,7,8-hexahydro-1H-pyrazolo[3,4-g]isoquinolin-4a-yl)(pyridin-2-yl)methanone

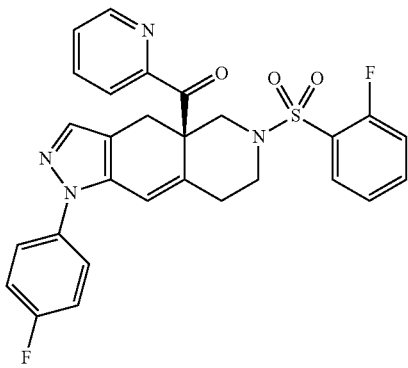

LCMS (Method F, ES-API): RT 2.57 min, m+H=533.2; 1H NMR (400 MHz, CDCl3): δ 8.64 (1H, ddd, J=4.7, 1.7, 0.8 Hz), 7.85-7.82 (1H, m), 7.80 (1H, dt, J=7.6, 1.8 Hz), 7.73-7.68 (1H, m), 7.52-7.41 (4H, m), 7.28 (1H, s), 7.19-7.10 (4H, m), 6.50 (1H, d, J=2.1 Hz), 5.60 (1H, dd, J=12.2, 2.1 Hz), 4.29 (1H, d, J=16.9 Hz), 3.97-3.93 (1H, m), 3.01 (1H, dd, J=12.8. 1.2 Hz), 2.91-2.72 (3H, m), 2.52-2.48 (1H, m).

Example 2M. (R)-(1-(4-fluorophenyl)-6-((1-methyl-1H-pyrazol-4-yl)sulfonyl)-4,4a,5,6,7,8-hexahydro-1H-pyrazolo[3,4-g]isoquinolin-4a-yl)(pyridin-2-yl)methanone

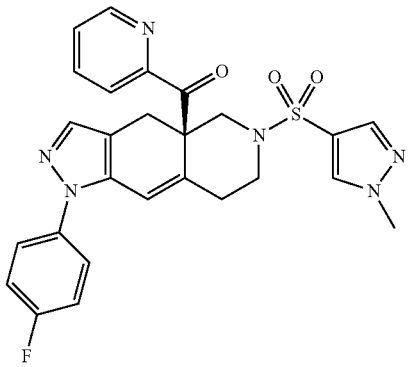 [SMILES: Cn1cc(S(=O)(=O)N2CCC3=Cc4c(cnn4-c4ccc(F)cc4)C[C@]3(C(=O)c3ccccn3)C2)cn1]

LCMS (Method F, ES-API): RT 2.17 min, m+H=519.1; 1H NMR (400 MHz, CDCl3): δ 8.66 (1H, ddd, J=4.7, 1.7, 0.8 Hz), 7.91-7.89 (1H, m), 7.84 (1H, dt, J=7.6, 1.8 Hz), 7.68-7.65 (2H, m), 7.49-7.42 (3H, m), 7.30 (1H, s), 7.20-7.14 (2H, m), 6.49 (1H, d, J=2.1 Hz), 5.46 (1H, dd, J=12.2, 2.1 Hz), 4.31 (1H, d, J=16.9 Hz), 3.91 (3H, s), 3.80-3.76 (1H, m), 2.91 (1H, d, J=16.9 Hz), 2.88-2.79 (1H, m), 2.68 (1H, d, J=12.2 Hz), 2.50-2.41 (2H, m).

Example 2N. (R)-(1-(4-fluorophenyl)-6-((6-(trifluoromethyl)pyridin-3-yl)sulfonyl)-4,4a,5,6,7,8-hexahydro-1H-pyrazolo[3,4-g]isoquinolin-4a-yl)(pyridin-2-yl)methanone

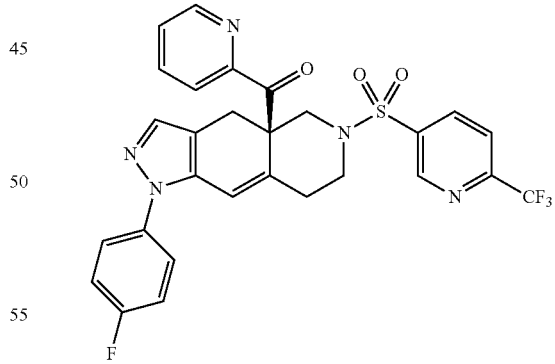

LCMS (Method F, ES-API): RT 2.65 min, m+H=584.1; 1H NMR (400 MHz, CDCl3): δ 8.97 (1H, d, J=2.2 Hz), 8.63-8.61 (1H, m), 8.14 (1H, dd, J=8.3, 2.2 Hz), 7.85-7.82 (2H, m), 7.73 (1H, d, J=8.3 Hz), 7.51-7.46 (1H, m), 7.44-7.40 (2H, m), 7.27 (1H, s), 7.20-7.14 (2H, m), 6.50 (1H, d, J=2.1 Hz), 5.62 (1H, dd, J=12.2, 2.1 Hz), 4.22 (1H, d, J=16.9 Hz), 3.96-3.92 (1H, m), 2.93 (1H, d, J=12.6 Hz), 2.90-2.80 (2H, m), 2.73-2.66 (1H, m), 2.56-2.53 (1H, m).

Example 2O. (R)-(1-(4-fluorophenyl)-6-tosyl-4,4a,5,6,7,8-hexahydro-1H-pyrazolo[3,4-g]isoquinolin-4a-yl)(pyridin-2-yl)methanone

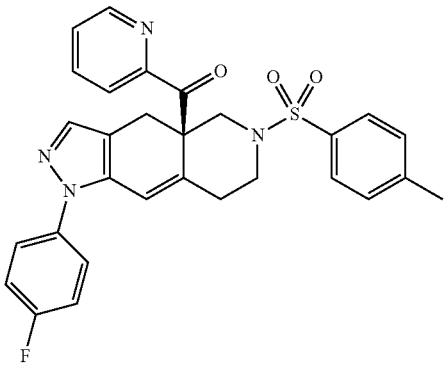 [SMILES: Cc1ccc(S(=O)(=O)N2CCC3=Cc4c(cnn4-c4ccc(F)cc4)C[C@]3(C(=O)c3ccccn3)C2)cc1]

LCMS (Method F, ES-API): RT 2.68 min, m+H=529.2; 1H NMR (400 MHz, CDCl3): δ 8.65 (1H, ddd, J=4.7, 1.7, 0.8 Hz), 7.91-7.88 (1H, m), 7.83 (1H, dt, J=7.6, 1.8 Hz), 7.58-7.56 (2H, m), 7.49-7.40 (3H, m), 7.29 (1H, s), 7.26-7.24 (2H, m), 7.19-7.13 (2H, m), 6.46 (1H, d, J=2.1 Hz), 5.49 (1H, dd, J=12.2, 2.1 Hz), 4.31 (1H, d, J=16.9 Hz), 3.84-3.79 (1H, m), 2.90-2.77 (2H, m), 2.65 (1H, dd, J=12.8. 1.2 Hz), 2.47-2.38 (5H, m).

Example 2P. (R)-(6-((4-fluoro-3-(trifluoromethyl)phenyl)sulfonyl)-1-(4-fluorophenyl)-4,4a,5,6,7,8-hexahydro-1H-pyrazolo[3,4-g]isoquinolin-4a-yl)(pyridin-2-yl)methanone

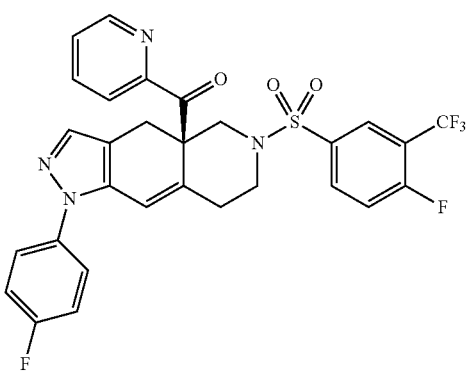 [SMILES: O=C(c1ccccn1)[C@]12Cc3cnn(-c4ccc(F)cc4)c3C=C1CCN(S(=O)(=O)c1ccc(F)c(C(F)(F)F)c1)C2]

LCMS (Method F, ES-API): RT 2.78 min, m+H=601.1; 1H NMR (400 MHz, CDCl3): δ 8.62-8.60 (1H, m), 7.94 (1H, dd, J=6.6, 2.2 Hz), 7.90-7.80 (3H, m), 7.49-7.39 (1H, m), 7.44-7.40 (2H, m), 7.27 (1H, s), 7.26-7.22 (1H, m), 7.20-7.13 (2H, m), 6.50 (1H, d, J=2.1 Hz), 5.55 (1H, dd, J=12.2, 2.1 Hz), 4.24 (1H, d, J=16.9 Hz), 3.91-3.87 (1H, m), 2.90-2.80 (3H, m), 2.65-2.59 (1H, m), 2.55-2.50 (1H, m).

Example 2Q. (R)-4-((1-(4-fluorophenyl)-4a-picolinoyl-4a,5,7,8-tetrahydro-1H-pyrazolo[3,4-g]isoquinolin-6(4H)-yl)sulfonyl)benzonitrile

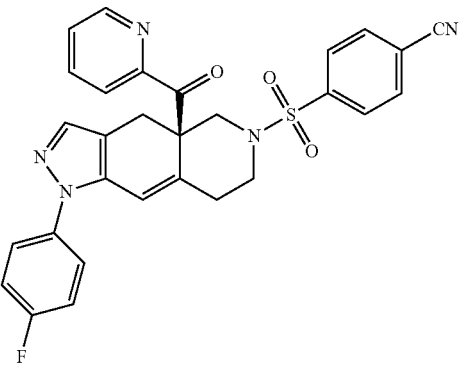 [SMILES: N#Cc1ccc(S(=O)(=O)N2CCC3=Cc4c(cnn4-c4ccc(F)cc4)C[C@]3(C(=O)c3ccccn3)C2)cc1]

LCMS (Method F, ES-API): RT 2.49 min, m+H=540.0; 1H NMR (400 MHz, CDCl3): δ 8.63-8.61 (1H, m), 7.87-7.83 (2H, m), 7.82-7.77 (2H, m), 7.73-7.70 (2H, m), 7.49 (1H, ddd, J=6.2, 4.8, 2.7 Hz), 7.44-7.39 (2H, m), 7.27 (1H, m), 7.18-7.12 (2H, m), 6.49 (1H, d, J=2.0Hz), 5.56 (1H, dd, J=12.3, 2.0 Hz), 4.24 (1H, d, J=16.9 Hz), 3.89-3.85 (1H, m), 2.88-2.79 (3H, m), 2.61-2.49 (2H, m).

Example 2R. (R)-(1-(4-fluorophenyl)-6-((6-methoxypyridin-3-yl)sulfonyl)-4,4a,5,6,7,8-hexahydro-1H-pyrazolo[3,4-g]isoquinolin-4a-yl)(pyridin-2-yl)methanone

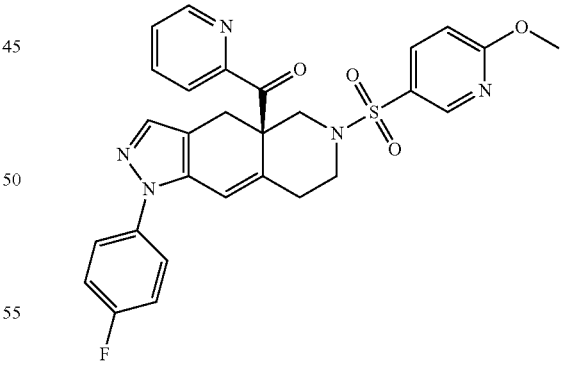

LCMS (Method F, ES-API): RT 2.52 min, m+H=546.0; 1H NMR (400 MHz, CDCl3): δ 8.61 (1H, ddd, J=4.7, 1.7, 0.9 Hz), 8.49 (1H, dd, J=2.5, 0.6 Hz), 7.89-7.79 (2H, m), 7.76 (1H, dd, J=8.8, 2.5 Hz), 7.47-7.41 (3H, m), 7.28 (1H, s), 7.18-7.13 (2H, m), 6.71 (1H, dd, J=8.8, 0.6 Hz), 6.49 (1H, d, J=2.1 Hz), 5.52 (1H, dd, J=12.2, 2.1 Hz), 4.27 (1H, d, J=16.9 Hz), 3.98 (3H, s), 3.90-3.82 (1H, m), 2.90-2.75 (3H, m), 2.58-2.48 (2H, m).

Example 2S. (R)-(1-(4-fluorophenyl)-6-((tetrahydro-2H-pyran-4-yl)sulfonyl)-4,4a,5,6,7,8-hexahydro-1H-pyrazolo[3,4-g]isoquinolin-4a-yl)(pyridin-2-yl)methanone

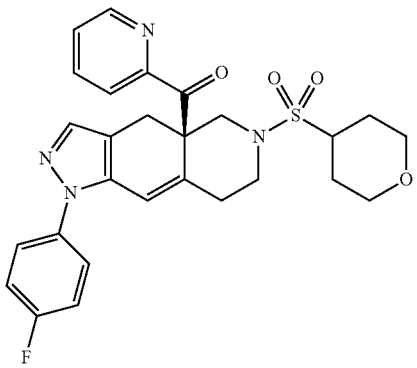 [SMILES: O=C(c1ccccn1)[C@]12Cc3cnn(-c4ccc(F)cc4)c3C=C1CCN(S(=O)(=O)C1CCOCC1)C2]

LCMS (Method F, ES-API): RT 2.21 min, m+H=523.2; 1H NMR (400 MHz, CDCl3): δ 8.69-8.68 (1H, m), 7.90-7.88 (1H, m), 7.84 (1H, dt, J=7.4, 1.8 Hz), 7.52-7.42 (3H, m), 7.29 (1H, s), 7.21-7.15 (2H, m), 6.52 (1H, d, J=2.1 Hz), 5.60 (1H, dd, J=12.2, 2.1 Hz), 4.20 (1H, d, J=16.9 Hz), 4.00-3.83 (4H, m), 3.28 (1H, d, J=12.9 Hz), 3.15 (1H, dt, J=11.9, 2.5 Hz), 3.05-2.98 (2H, m), 2.91 (1H, d, J=16.9 Hz), 2.84-2.74 (1H, m), 2.55-2.51 (1H, m), 1.84-1.65 (4H, m).

Example 2T. (R)-(6-(cyclohexylsulfonyl)-1-(4-fluorophenyl)-4,4a,5,6,7,8-hexahydro-1H-pyrazolo[3,4-g]isoquinolin-4a-yl)(pyridin-2-yl)methanone

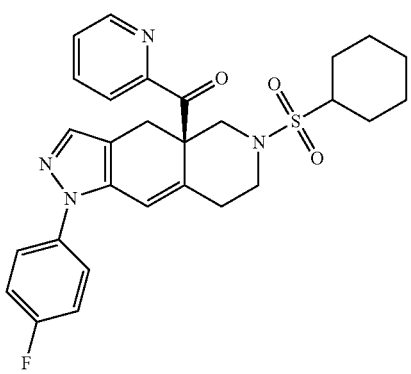 [SMILES: O=C(c1ccccn1)[C@]12Cc3cnn(-c4ccc(F)cc4)c3C=C1CCN(S(=O)(=O)C1CCCCC1)C2]

LCMS (Method F, ES-API): RT 2.65 min, m+H=521.1; 1H NMR (400 MHz, CDCl3): δ 8.68 (1H, ddd, J=4.7, 1.7, 0.9 Hz), 7.90 (1H, dt, J=7.8, 1.2 Hz), 7.84 (1H, td, J=7.5, 1.8 Hz), 7.50-7.43 (3H, m), 7.29 (1H, s), 7.21-7.15 (2H, m), 6.53 (1H, d, J=2.1 Hz), 5.59 (1H, dd, J=13.1, 1.9 Hz), 4.26 (1H, d, J=16.9 Hz), 3.86-3.80 (1H, m), 3.26 (1H, d, J=13.2 Hz), 2.98 (1H, td, J=12.4, 3.2 Hz), 2.92 (1H, d J=16.9 Hz), 2.78 (1H, tdd, J=14.8, 5.8, 2.1 Hz), 2.64 (1H, tt, J=12.3, 3.3 Hz), 2.51 (1H, dt, J=14.7, 2.3 Hz), 2.02-1.95 (1H, m), 1.84-0.85 (9H, m).

Example 2U. (R)-(6-((1-ethyl-1H-pyrazol-5-yl)sulfonyl)-1-(4-fluorophenyl)-4,4a,5,6,7,8-hexahydro-1H-pyrazolo[3,4-g]isoquinolin-4a-yl)(4-(trifluoromethyl)pyridin-2-yl)methanone

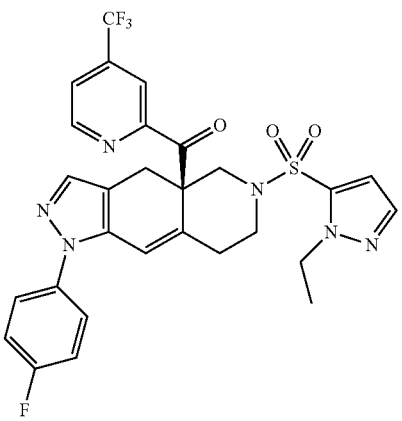 [SMILES: CCn1nccc1S(=O)(=O)N1CCC2=Cc3c(cnn3-c3ccc(F)cc3)C[C@]2(C(=O)c2cc(C(F)(F)F)ccn2)C1]

LCMS (Method F, ES-API): RT 2.67 min, m+H=601.2; 1H NMR (400 MHz, CDCl3): δ 8.81 (1H, d, J=4.9 Hz), 8.13 (1H, m), 7.71-7.69 (1H, m), 7.47-7.42 (2H, m), 7.40 (1H, d, J=2.0 Hz), 7.28 (1H, s), 7.21-7.15 (2H, m), 6.59 (1H, d, J=2.0 Hz), 6.55 (1H, d, J=1.6 Hz), 5.52 (1H, dd, J=12.6, 2.0 Hz), 4.35-4.23 (2H, m), 4.18 (1H, d, J=16.9 Hz), 3.92-3.87 (1H, m), 3.02 (1H, d, J=12.8 Hz), 2.92 (1H, d, J=16.9 Hz), 2.89-2.74 (2H, m), 2.59-2.55 (1H, m), 1.40 (3H, t, J=7.3 Hz).

Example 2V. (R)-(6-((3,5-dimethyl-1H-pyrazol-4-yl)sulfonyl)-1-(4-fluorophenyl)-4,4a,5,6,7,8-hexahydro-1H-pyrazolo[3,4-g]isoquinolin-4a-yl)(4-(trifluoromethyl)pyridin-2-yl)methanone

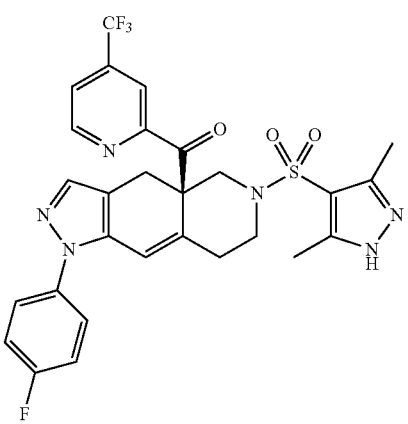 [SMILES: Cc1n[nH]c(C)c1S(=O)(=O)N1CCC2=Cc3c(cnn3-c3ccc(F)cc3)C[C@]2(C(=O)c2cc(C(F)(F)F)ccn2)C1]

LCMS (Method F, ES-API): RT 2.37 min, m+H=601.3; 1H NMR (400 MHz, CDCl3): δ 8.79 (1H, d, J=4.9 Hz), 8.12 (1H, m), 7.67 (1H, dd, J=4.9, 1.0 Hz), 7.47-7.42 (2H, m), 7.27 (1H, s), 7.21-7.15 (2H, m), 6.53 (1H, d, J=2.1 Hz), 5.42 (1H, dd, J=12.3, 2.0 Hz), 4.19 (1H, d, J=16.9 Hz), 3.87-3.83 (1H, m), 2.93 (1H, d, J=16.9 Hz), 2.91 (1H, d, J=12.8 Hz), 2.85-2.80 (1H, m), 2.72-2.76 (1H, m), 2.56-2.52 (1H, m), 2.32 (6H, s).

Example 2W. (R)-(6-((1H-imidazol-4-yl)sulfonyl)-1-(4-fluorophenyl)-4,4a,5,6,7,8-hexahydro-1H-pyrazolo[3,4-g]isoquinolin-4a-yl)(4-(trifluoromethyl)pyridin-2-yl)methanone

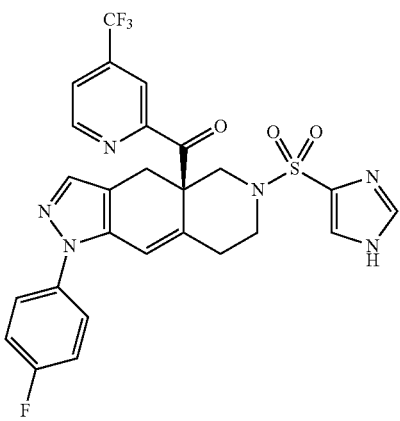 [SMILES: O=C(c1cc(C(F)(F)F)ccn1)[C@]12Cc3cnn(-c4ccc(F)cc4)c3C=C1CCN(S(=O)(=O)c1c[nH]cn1)C2]

LCMS (Method F, ES-API): RT 2.18 min, m+H=573.2; 1H NMR (400 MHz, CDCl3): δ 10.27 (1H, br s), 8.84 (1H, d, J=4.9 Hz), 8.13 (1H, m), 7.67 (1H, dd, J=4.9, 1.0 Hz), 7.64 (1H, s), 7.49 (1H, s), 7.46-7.41 (2H, m), 7.30 (1H, s), 7.20-7.14 (2H, m), 6.51 (1H, d, J=2.0 Hz), 5.55 (1H, dd, J=12.6, 2.0 Hz), 4.22 (1H, d, J=16.9 Hz), 3.88-3.84 (1H, m), 3.01 (1H, d, J=12.7 Hz), 2.94 (1H, d, J=16.9 Hz), 2.86-2.77 (1H, m), 2.71-2.64 (1H, m), 2.50-2.47 (1H, m).

Example 3. (R)-(1-(4-fluorophenyl)-6-((6-morpholinopyridin-3-yl)sulfonyl)-4,4a,5,6,7,8-hexahydro-1H-pyrazolo[3,4-g]isoquinolin-4a-yl)(pyridin-2-yl)methanone

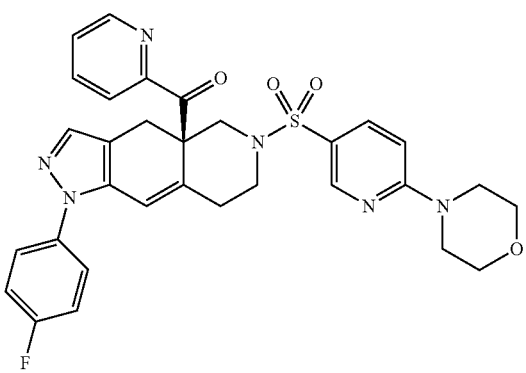 [SMILES: O=C(c1ccccn1)[C@]12Cc3cnn(-c4ccc(F)cc4)c3C=C1CCN(S(=O)(=O)c1ccc(N3CCOCC3)nc1)C2]

A solution of (R)-(6-((6-chloropyridin-3-yl)sulfonyl)-1-(4-fluorophenyl)-4,4a,5,6,7,8-hexahydro-1H-pyrazolo[3,4-g]isoquinolin-4a-yl)(pyridin-2-yl)methanone (80 mg, 0.14 mmol) and morpholine (150 µL, 1.73 mmol) in acetonitrile (2.5 mL) was heated at 100° C. for 70 minutes in a microwave reactor. The reaction mixture was concentrated and the residue purified by column chromatography on silica gel (gradient: 30-60% ethyl acetate in cyclohexane) to afford (R)-(1-(4-fluorophenyl)-6-((6-morpholinopyridin-3-yl)sulfonyl)-4,4a,5,6,7,8-hexahydro-1H-pyrazolo[3,4-g]isoquinolin-4a-yl)(pyridin-2-yl)methanone as a colourless glass (70 mg). LCMS (Method D, ESI): RT 4.94 min, m+H=601.0; 1H NMR (400 MHz, CDCl3): δ 8.63 (ddd, J=4.8, 1.7, 0.9 Hz, 1H); 8.44 (d, J=2.5 Hz, 1H); 7.84-7.85 (m, 2H); 7.66 (dd, J=9.1, 2.5 Hz, 1H); 7.44-7.45 (m, 3H); 7.29 (s, 1H); 7.16 (t, J=8.5 Hz, 2H); 6.49-6.50 (m, 2H); 5.49 (dd, J=12.1, 2.1 Hz, 1H); 4.28 (d, J=16.9 Hz, 1H); 3.80 (t, J=4.8 Hz, 5H); 3.63 (t, J=4.8 Hz, 4H); 2.83-2.85 (m, 2H); 2.71 (d, J=12.1 Hz, 1H); 2.47-2.50 (m, 2H).

Example 4. (R)-(1-(4-fluorophenyl)-6-((6-(pyrrolidin-1-yl)pyridin-3-yl)sulfonyl)-4,4a,5,6,7,8-hexahydro-1H-pyrazolo[3,4-g]isoquinolin-4a-yl)(thiazol-2-yl)methanone

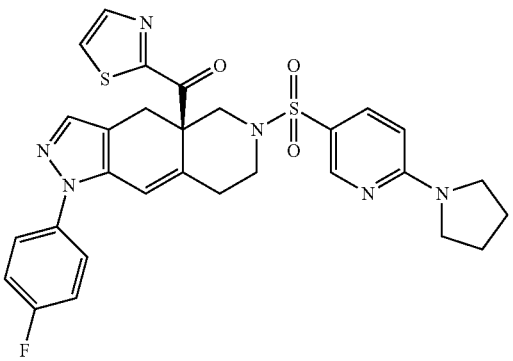 [SMILES: O=C(c1nccs1)[C@]12Cc3cnn(-c4ccc(F)cc4)c3C=C1CCN(S(=O)(=O)c1ccc(N3CCCC3)nc1)C2]

A mixture of (R)-(6-((6-chloropyridin-3-yl)sulfonyl)-1-(4-fluorophenyl)-4,4a,5,6,7,8-hexahydro-1H-pyrazolo[3,4-g]isoquinolin-4a-yl)(thiazol-2-yl)methanone (100 mg, 0.180 mmol) and pyrrolidine (37.5 µL, 0.450 mmol) in acetonitrile (2 mL) was stirred at 40° C. for 0.5 hour. The reaction mixture was cooled to room temperature and concentrated in vacuo to give a yellow oil. The crude product was purified by column chromatography on silica gel (gradient: 0-100% ethyl acetate in isohexane) to give a white solid. This was further purified by preparative HPLC (Gilson, Acidic (0.1% Formic acid), Agilent Prep C-18, 5 µm, 21.2×50 mm column, 30-95% acetonitrile in water) to afford (R)-(1-(4-fluorophenyl)-6-((6-(pyrrolidin-1-yl)pyridin-3-yl)sulfonyl)-4,4a,5,6,7,8-hexahydro-1H-pyrazolo[3,4-g]isoquinolin-4a-yl)(thiazol-2-yl)methanone as a white solid (51 mg). LCMS (Method F, ES-API): RT 2.43 min, m+H=590.9; 1H NMR (400 MHz, CDCl3): δ 8.45 (1H, dd, J=2.0, 0.5 Hz), 8.01 (1H, d, J=3.1 Hz), 7.63-7.59 (2H, m), 7.46-7.41 (2H, m), 7.29 (1H, s), 7.19-7.13 (2H, m), 6.51 (1H, d, J=2.1 Hz), 6.27 (1H, d, J=9.1 Hz), 5.47 (1H, dd, J=12.2, 2.1 Hz), 4.20 (1H, d, J=16.8 Hz), 3.87-3.83 (1H, m), 2.91-2.82 (2H, m), 2.71 (1H, d, J=12.3 Hz), 2.53-2.46 (2H, m), 2.06-2.04 (4H, m), 1.33-1.24 (2H, m), 1.17-1.07 (2H, m).

Example 5. (R)-(1-(4-fluorophenyl)-6-((4-fluorophenyl)sulfonyl)-4,4a,5,6,7,8-hexahydro-1H-pyrazolo[3,4-g]isoquinolin-4a-yl)(thiazol-2-yl)methanone

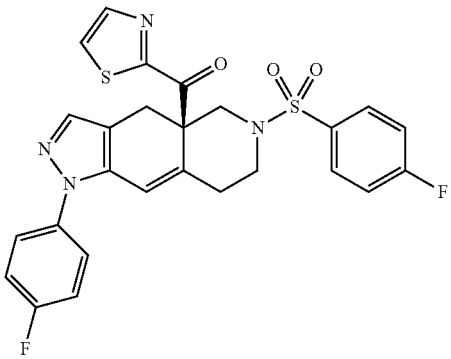 [SMILES: O=C(c1nccs1)[C@]12Cc3cnn(-c4ccc(F)cc4)c3C=C1CCN(S(=O)(=O)c1ccc(F)cc1)C2]

A solution of (R)-tert-butyl 1-(4-fluorophenyl)-4a-(thiazole-2-carbonyl)-4a,5,7,8-tetrahydro-1H-pyrazolo[3,4-g]isoquinoline-6(4H)-carboxylate (0.25 g, 0.520 mmol) in dichloromethane (8 mL) and trifluoroacetic acid (2 mL) was stirred at room temperature for 90 minutes, then evaporated, azeotroping twice with toluene to give a brown oil. This material was re-dissolved in dichloromethane (8 mL), and diisopropylethylamine (0.454 mL, 2.60 mmol) was added, followed by 4-fluorobenzene-1-sulfonyl chloride (0.121 g, 0.624 mmol), and the reaction mixture stirred at room temperature for 48 hours. The reaction mixture was then evaporated in vacuo and the residue purified by column chromatography on silica gel (gradient: 0 to 40% ethyl acetate in isohexane) to give a white solid (204 mg). 80 mg of this sample was purified by preparative HPLC (Varian, Acidic (0.1% Formic acid), Waters X-Select Prep-C18, 5 μm, 19×50 mm column, 25-80% acetonitrile in water) to afford (R)-(1-(4-fluorophenyl)-6-((4-fluorophenyl)sulfonyl)-4,4a,5,6,7,8-hexahydro-1H-pyrazolo[3,4-g]isoquinolin-4a-yl)(thiazol-2-yl)methanone as a pale yellow solid (45 mg). LCMS (Method F, ES-API): RT 2.58 min, m+H=538.9; 1H NMR (400 MHz, CDCl$_3$): δ 8.02 (d, 1H, J=3.1 Hz), 7.75-7.70 (m, 2H), 7.68 (d, 1H, J=3.1 Hz), 7.45-7.40 (m, 2H), 7.29 (s, 1H), 7.20-7.11 (m, 4H), 6.53 (d, 1H, J=2.2 Hz), 5.49 (dd, 1H, J=12.3, 2.0 Hz), 4.20 (d, 1H, J=16.8 Hz), 3.93-3.86 (m, 1H), 2.94-2.83 (m, 2H), 2.74 (d, 1H, J=12.4 Hz), 2.57-2.47 (m, 2H).

The following examples were similarly prepared from the appropriate intermediates:

Example 5A. (R)-(1-(4-fluorophenyl)-6-((3-fluorophenyl)sulfonyl)-4,4a,5,6,7,8-hexahydro-1H-pyrazolo[3,4-g]isoquinolin-4a-yl)(thiazol-2-yl)methanone

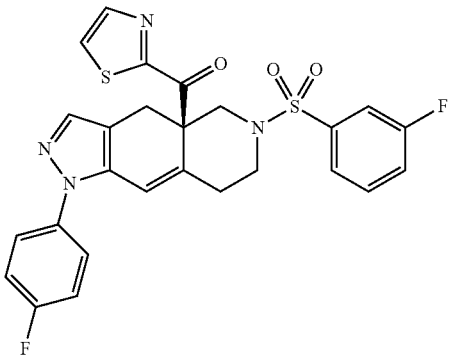 [SMILES: O=C(c1nccs1)[C@]12Cc3cnn(-c4ccc(F)cc4)c3C=C1CCN(S(=O)(=O)c1cccc(F)c1)C2]

LCMS (Method F, ES-API): RT 2.59 min, m+H=539.0; 1H NMR (400 MHz, CDCl$_3$): δ 8.06 (d, 1H, J=3.2 Hz), 7.67 (d, 1H, J=3.1 Hz), 7.53-7.45 (m, 2H), 7.45-7.39 (m, 3H), 7.30 (s, 1H), 7.29-7.23 (m, 1H), 7.19-7.13 (m, 2H), 6.53 (d, 1H, J=2.1 Hz), 5.53 (dd, 1H, J=12.2, 1.7 Hz), 4.22 (d, 1H, J=17.1 Hz), 3.92-3.86 (m, 1H), 2.94-2.81 (m, 2H), 2.76 (d, 1H, J=12.2 Hz), 2.58-2.49 (m, 2H).

Example 5B. (R)-4-(((1-(4-fluorophenyl)-4a-(thiazole-2-carbonyl)-4a,5,7,8-tetrahydro-1H-pyrazolo[3,4-g]isoquinolin-6(4H)-yl)sulfonyl)methyl)benzonitrile

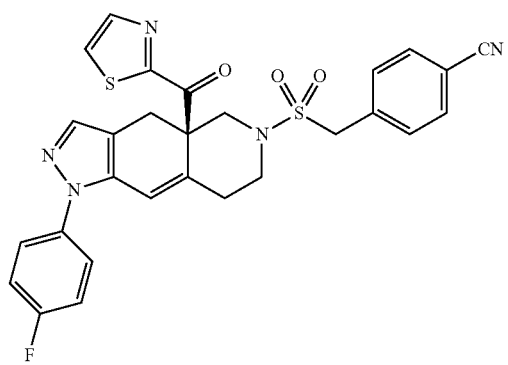 [SMILES: N#Cc1ccc(CS(=O)(=O)N2CCC3=Cc4c(cnn4-c4ccc(F)cc4)C[C@]3(C(=O)c3nccs3)C2)cc1]

LCMS (Method F, ES-API): RT 2.36 min, m+H=560; 1H NMR (400 MHz, CDCl$_3$): δ 8.07 (d, 1H, J=3.1 Hz), 7.66 (d, 1H, J=3.1 Hz) 7.45-7.43 (m, 2H), 7.46-7.41 (m, 5H), 7.32 (s, 1H), 7.20-7.16 (m, 2H), 6.55 (s, 1H), 5.47 (dd, 1H, J=13.5, 2.0 Hz), 4.20 (d, 1H, J=20 Hz), 4.13-4.06 (m, 2H), 3.12 (d, 1H, J=16 Hz), 2.86 (d, 1H, J=20 Hz), 2.70-2.50 (m, 2H), 2.44 (m, 1H).

Example 5C. (R)-(1-(4-fluorophenyl)-6-((3-(trifluoromethyl)phenyl)sulfonyl)-4,4a,5,6,7,8-hexahydro-M-pyrazolo[3,4-g]isoquinolin-4a-yl)(pyridin-2-yl)methanone

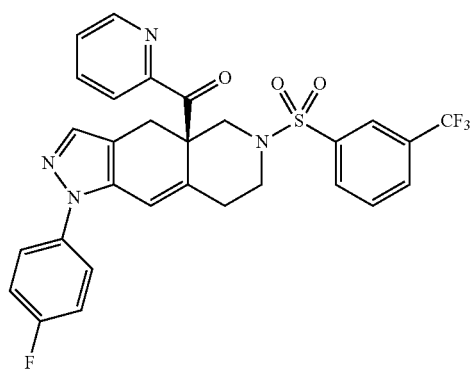 [SMILES: O=C(c1ccccn1)[C@]12Cc3cnn(-c4ccc(F)cc4)c3C=C1CCN(S(=O)(=O)c1cccc(C(F)(F)F)c1)C2]

LCMS (Method F, ES-API): RT 2.73 min, m+H=583.2; 1H NMR (400 MHz, CDCl$_3$): δ0.65-8.64 (1H, m), 7.94 (1H, m), 7.89-7.78 (4H, m), 7.63-7.59 (1H, m), 7.47 (1H, ddd, J=7.3, 4.8, 1.5 Hz), 7.44-7.40 (2H, m), 7.28 (1H, s), 7.19-7.13 (2H, m), 6.48 (1H, d, J=2.2 Hz), 5.56 (1H, dd, J=12.4, 2.2 Hz), 4.26 (1H, d, J=16.9 Hz), 3.89-3.85 (1H, m), 2.91-2.79 (3H, m), 2.58-2.48 (2H, m).

Example 5D. (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(1-methyl-1H-1,2,4-triazol-5-yl)methanone

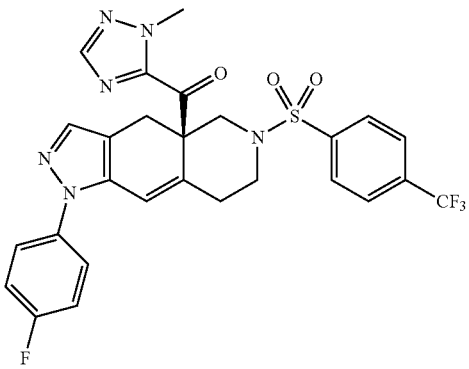 [SMILES: Cn1ncnc1C(=O)[C@]12Cc3cnn(-c4ccc(F)cc4)c3C=C1CCN(S(=O)(=O)c1ccc(C(F)(F)F)cc1)C2]

LCMS (Method F, ES-API): RT 2.60 min, m+H=587.2; 1H NMR (400 MHz, CDCl$_3$): δ 7.99 (1H, d, J=1.3 Hz), 7.83-7.81 (2H, m), 7.78-7.76 (2H, m), 7.44-7.41 (2H, m), 7.33 (1H, s), 7.19-7.15 (2H, m), 6.56 (1H, s), 5.36 (1H, d, J=12.8 Hz), 4.32 (1H, d, J=17.1 Hz), 4.09 (3H, s), 3.96-3.92 (1H, m), 2.89-2.79 (2H, m), 2.71 (1H, d, J=12.8 Hz), 2.57-2.50 (2H, m).

Example 5E. (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(pyrazin-2-yl)methanone

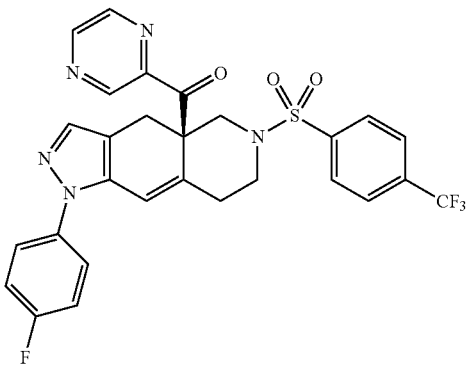 [SMILES: O=C(c1cnccn1)[C@]12Cc3cnn(-c4ccc(F)cc4)c3C=C1CCN(S(=O)(=O)c1ccc(C(F)(F)F)cc1)C2]

LCMS (Method F, ES-API): RT 2.59 min, m+H=583.8; 1H NMR (400 MHz, CDCl$_3$): δ 9.10 (1H, d, J=1.7 Hz), 8.79 (1H, d, J=2.3 Hz), 8.62 (1H, dd, J=2.3, 1.7 Hz), 7.83-7.81 (2H, m), 7.77-7.75 (2H, m), 7.44-7.41 (2H, m), 7.29 (1H, s), 7.20-7.15 (2H, m), 6.51 (1H, d, J=2.1 Hz), 5.39 (1H, dd, J=12.4, 2.3 Hz), 4.12 (1H, d, J=16.9 Hz), 3.90-3.85 (1H, m), 2.92-2.88 (2H, m), 2.72 (1H, d, J=12.4 Hz), 2.52-2.45 (2H, m).

Example 5F. (R)-(1-(4-fluorophenyl)-6-((5-fluoropyridin-3-yl)sulfonyl)-4,4a,5,6,7,8-hexahydro-1H-pyrazolo[3,4-g]isoquinolin-4a-yl)(pyridin-2-yl)methanone LCMS (Method F, ES-API): RT 2.35 min, m+H=534.2; 1H NMR (400 MHz, CDCl3): δ 8.73 (1H, m), 8.67-8.65 (1H, m), 8.60 (1H, d, J=2.8 Hz), 7.89-7.82 (2H, m), 7.65 (1H, ddd, J=7.6, 2.8, 1.8 Hz), 7.49 (1H, ddd, J=6.8, 4.8, 1.8 Hz), 7.45-7.40 (2H, m), 7.29 (1H, s), 7.19-7.13 (2H, m), 6.51 (1H, d, J=2.1 Hz), 5.60 (1H, dd, J=12.4, 2.1 Hz), 4.26 (1H, d, J=16.9 Hz), 3.92-3.88 (1H, m), 2.91-2.79 (3H, m), 2.67-2.61 (1H, m), 2.55-2.50 (1H, m).

Example 5G. (R)-(1-(4-fluorophenyl)-6-((3-fluorophenyl)sulfonyl)-4,4a,5,6,7,8-hexahydro-1H-pyrazolo[3,4-g]isoquinolin-4a-yl)(pyridin-2-yl)methanone LCMS (Method F, ES-API): RT 2.56 min, m+H=532.8; 1H NMR (400 MHz, CDCl3): δ 8.67 (1H, ddd, J=4.7, 1.7, 0.8 Hz), 7.91-7.88 (1H, m), 7.85 (1H, dt, J=7.4, 1.7 Hz), 7.50-7.36 (6H, m), 7.29 (1H, s), 7.27-7.22 (1H, m), 7.19-7.13 (2H, m), 6.48 (1H, d, J=2.1 Hz), 5.55 (1H, dd, J=12.4, 2.1 Hz), 4.30 (1H, d, J=16.9 Hz), 3.86-3.81 (1H, m), 2.91-2.73 (3H, m), 2.54-2.47 (2H, m).

Example 5H. (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(5-methoxypyridin-2-yl)methanone

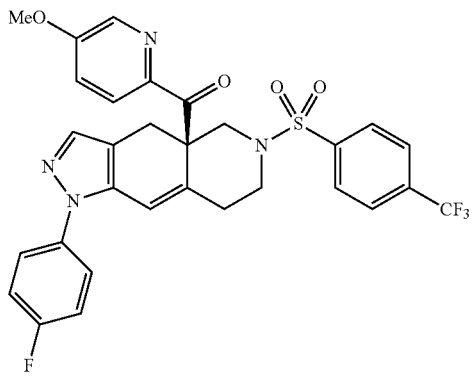 [SMILES: COc1ccc(C(=O)[C@]23Cc4cnn(-c5ccc(F)cc5)c4C=C2CCN(S(=O)(=O)c2ccc(C(F)(F)F)cc2)C3)nc1]

LCMS (Method F, ES-API): RT 2.76 min, m+H=613.2; 1H NMR (400 MHz, CDCl3): δ 8.72 (1H, dd, J=2.5, 0.6 Hz), 8.06 (1H, dd, J=8.8, 2.5 Hz), 7.95-7.93 (2H, m), 7.81-7.79 (2H, m), 7.47-7.42 (2H, m), 7.41 (1H, s), 7.22-7.16 (2H, m), 6.72 (1H, dd, J=8.8, 0.6 Hz), 6.44 (1H, s), 4.59 (1H, dd, J=11.1, 1.7 Hz), 3.96 (3H, s), 3.90-3.86 (1H, m), 3.73 (1H, d, J=17.8 Hz), 2.79 (1H, d, J=17.8 Hz), 2.56 (1H, d, J=11.1 Hz), 2.53-2.46 (1H, m), 2.31-2.20 (2H, m).

Example 5I. (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(thiazol-5-yl)methanone

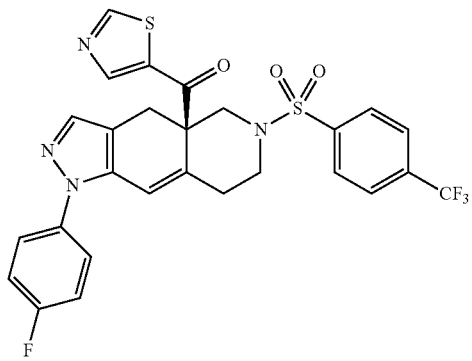 [SMILES: O=C(c1cncs1)[C@]12Cc3cnn(-c4ccc(F)cc4)c3C=C1CCN(S(=O)(=O)c1ccc(C(F)(F)F)cc1)C2]

LCMS (Method F, ES-API): RT 2.56 min, m+H=589.1; 1H NMR (400 MHz, CDCl3): δ 8.95 (1H, d, J=0.5 Hz), 8.48 (1H, d, J=0.5 Hz), 7.94-7.92 (2H, m), 7.81-7.79 (2H, m), 7.47-7.42 (2H, m), 7.37 (1H, s), 7.23-7.17 (2H, m), 6.55 (1H, s), 4.62 (1H, dd, J=11.5, 1.9 Hz), 3.93-3.88 (1H, m), 3.34 (1H, d, J=17.6 Hz), 2.83 (1H, d, J=17.6 Hz), 2.61 (1H, d, J=11.5 Hz), 2.58-2.42 (3H, m).

Example 5J. (R)-(1-(4-fluorophenyl)-6-((5-fluoropyridin-3-yl)sulfonyl)-4,4a,5,6,7,8-hexahydro-1H-pyrazolo[3,4-g]isoquinolin-4a-yl)(thiazol-2-yl)methanone

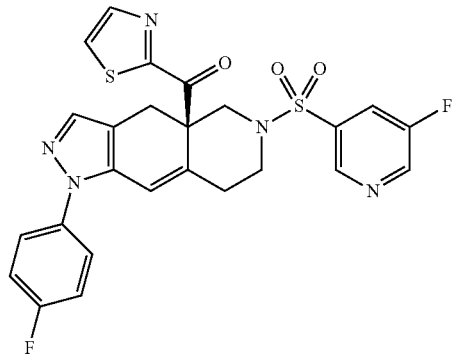 [SMILES: O=C(c1nccs1)[C@]12Cc3cnn(-c4ccc(F)cc4)c3C=C1CCN(S(=O)(=O)c1cncc(F)c1)C2]

LCMS (Method F, ES-API): RT 2.35 min, m+H=540.

Example 6. (R)-(1-(4-fluorophenyl)-6-((4-(pyrrolidin-1-yl)phenyl)sulfonyl)-4,4a,5,6,7,8-hexahydro-1H-pyrazolo[3,4-g]isoquinolin-4a-yl)(thiazol-2-yl)methanone

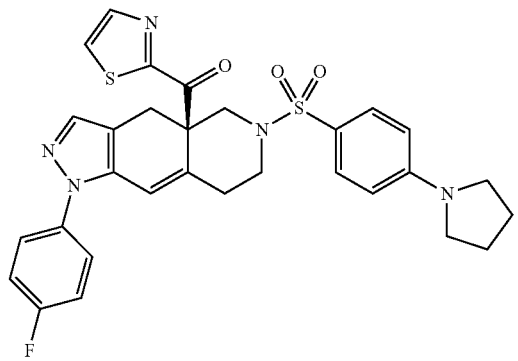 [SMILES: O=C(c1nccs1)[C@]12Cc3cnn(-c4ccc(F)cc4)c3C=C1CCN(S(=O)(=O)c1ccc(N3CCCC3)cc1)C2]

A solution of pyrrolidine (0.046 mL, 0.557 mmol) and (R)-(1-(4-fluorophenyl)-6-((4-fluorophenyl)sulfonyl)-4,4a,5,6,7,8-hexahydro-1H-pyrazolo[3,4-g]isoquinolin-4a-yl)(thiazol-2-yl)methanone (0.1 g, 0.186 mmol) in N-methylpyrrolidine (2 mL) was stirred at 50° C. in a sealed vial for 6 hours, then allowed to stand at room temperature for 72 hours. The reaction mixture was then stirred at 100° C. for an additional 5 hours, cooled to room temperature, and purified directly by preparative HPLC (Varian, Acidic (0.1% Formic acid), Waters X-Select Prep-C18, 5 19×50 mm column, 50-70% acetonitrile in water) to afford (R)-(1-(4-fluorophenyl)-6-((4-(pyrrolidin-1-yl)phenyl)sulfonyl)-4,4a,5,6,7,8-hexahydro-1H-pyrazolo[3,4-g]isoquinolin-4a-yl)(thiazol-2-yl)methanone as a pale yellow solid (58 mg). LCMS (Method F, ES-API): RT 2.81 min, m+H=590.0; 1H NMR (400 MHz, CDCl$_3$): δ 8.02 (d, 1H, J=3.1 Hz), 7.62 (d, 1H, J=3.1 Hz), 7.54-7.50 (m, 2H), 7.45-7.40 (m, 2H), 7.28 (s, 1H), 7.219-7.12 (m, 2H), 6.50-6.45 (m, 3H), 5.46 (dd, 1H, J=12.1, 2.0 Hz), 4.21 (d, 1H, J=16.8 Hz), 3.86-3.80 (m, 1H), 3.35-3.30 (m, 4H), 2.92-2.81 (m, 2H), 2.64 (d, 1H, J=12.2 Hz), 2.52-2.36 (m, 2H), 2.07-2.01 (m, 4H).

The following examples were similarly prepared from the appropriate intermediate:

Example 6A. (R)-(1-(4-fluorophenyl)-6-((3-(pyrrolidin-1-yl)phenyl)sulfonyl)-4,4a,5,6,7,8-hexahydro-1H-pyrazolo[3,4-g]isoquinolin-4a-yl)(thiazol-2-yl)methanone

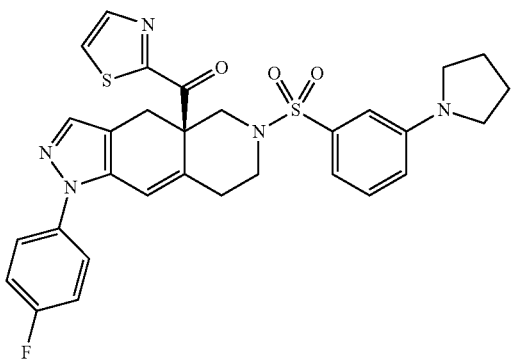 [SMILES: O=C(c1nccs1)[C@]12Cc3cnn(-c4ccc(F)cc4)c3C=C1CCN(S(=O)(=O)c1cccc(N3CCCC3)c1)C2]

LCMS (Method F, ES-API): RT 2.88 min, m+H=590.1; 1H NMR (400 MHz, CDCl$_3$): δ 8.04 (d, 1H, J=2.8 Hz), 7.63 (d, 1H, J=3.2 Hz), 7.45-7.40 (m, 2H), 7.33-7.24 (m, 3H), 7.19-7.10 (m, 2H), 6.99-6.94 (m, 1H), 6.65 (dt, 1H, J=8.0, 2.3 Hz), 6.50 (d, 1H, J=2.4 Hz), 5.46 (dd, 1H, J=12.7, 2.1 Hz), 4.22 (d, 1H, J=16.6 Hz), 3.91-3.81 (m, 1H), 3.33-3.23 (m, 4H), 2.94-2.83 (m, 2H), 2.76 (d, 1H, J=12.4 Hz), 2.54-2.46 (m, 2H), 2.06-2.01 (m, 4H).

Example 7. (R)-(1-(4-fluorophenyl)-6-((5-(piperidin-1-yl)pyridin-3-yl)sulfonyl)-4,4a,5,6,7,8-hexahydro-1H-pyrazolo[3,4-g]isoquinolin-4a-yl)(thiazol-2-yl)methanone

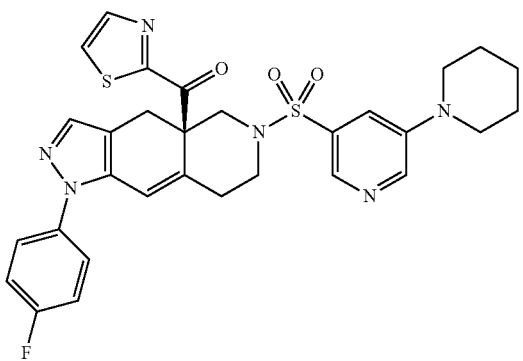 [SMILES: O=C(c1nccs1)[C@]12Cc3cnn(-c4ccc(F)cc4)c3C=C1CCN(S(=O)(=O)c1cncc(N3CCCCC3)c1)C2]

A mixture of (R)-(1-(4-fluorophenyl)-6-((5-fluoropyridin-3-yl)sulfonyl)-4,4a,5,6,7,8-hexahydro-1H-pyrazolo[3,4-g]isoquinolin-4a-yl)(thiazol-2-yl)methanone (100 mg, 0.185 mmol) and piperidine (47 mg, 0.56 mmol) in N-methylpyrrolidine (1 mL) was heated at 100° C. for 6 hours. The mixture was cooled and the reaction mixture was purified by preparative HPLC (Gilson, Acidic (0.1% Formic acid), Waters X-Select Prep-C18, 5 μm, 19×50 mm column, 5-95% acetonitrile in water) to give (R)-(1-(4-fluorophenyl)-6-((5-(piperidin-1-yl)pyridin-3-yl)sulfonyl)-4,4a,5,6,7,8-hexahydro-1H-pyrazolo[3,4-g]isoquinolin-4a-yl)(thiazol-2-yl)methanone as a white solid (35 mg). LCMS (Method F, ES-API): RT 2.64 min, m+H=605; 1H NMR (400 MHz, CDCl$_3$): δ 8.39 (d, 1H, J=3.0 Hz), 8.27 (d, 1H, J=2.0 Hz), 8.05 (d, 1H, J=3.0 Hz), 7.65 (d, 1H, J=3.0 Hz), 7.54-7.41 (m, 2H), 7.31-7.30 (m, 2H). 7.19-7.14 (m, 2H), 6.53 (d, 1H, J=2.0 Hz), 5.51 (dd, 1H, J=12.0, 2.0 Hz), 4.21 (d, 1H, J=17.0 Hz), 3.90-3.86 (m, 1H), 3.27-3.25 (m, 4H), 2.91-2.81 (m, 3H), 2.61-2.52 (m, 2H), 1.75-1.56 (m, 6H).

The following examples were similarly prepared from the appropriate intermediate:

Example 7A. (R)-(1-(4-fluorophenyl)-6-((5-(pyrrolidin-1-yl)pyridin-3-yl)sulfonyl)-4,4a,5,6,7,8-hexahydro-1H-pyrazolo[3,4-g]isoquinolin-4a-yl)(thiazol-2-yl)methanone

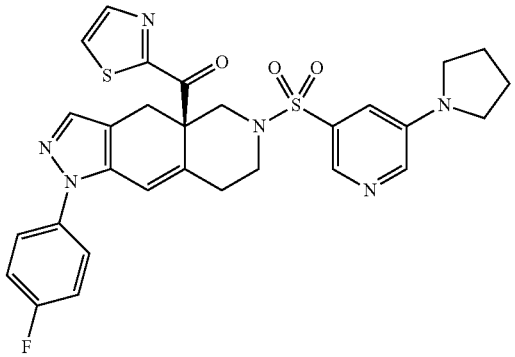 [SMILES: O=C(c1nccs1)[C@]12Cc3cnn(-c4ccc(F)cc4)c3C=C1CCN(S(=O)(=O)c1cncc(N3CCCC3)c1)C2]

LCMS (Method F, ES-API): RT 2.49 min, m+H=591; 1H NMR (400 MHz, CDCl$_3$): δ 8.18 (1H, d, J=2.0 Hz), 8.06 (1H, d, J=3.0 Hz), 8.04 (1H, d, J=3.0 Hz), 7.65 (1H, d, J=3.0 Hz), 7.43 (2H, dd, J=9.0, 5.0 Hz), 7.29 (1H, s), 7.19-7.14 (2H, m), 6.95-6.93 (1H, m), 6.53 (1H, d, J=2.0 Hz), 5.50 (1H, dd, J=12.0, 2.0 Hz), 4.2 (1H, d, J=17.0 Hz), 3.92-3.88 (1H, m), 3.33-3.28 (4H, m), 2.90-2.82 (3H, m), 2.62-2.51 (2H, m), 2.09-2.04 (4H, m).

Example 8. (R)-(1-(4-fluorophenyl)-6-((6-(pyrrolidin-1-yl)pyridin-3-yl)sulfonyl)-4,4a,5,6,7,8-hexahydro-1H-pyrazolo[3,4-g]isoquinolin-4a-yl)(pyridin-2-yl)methanone

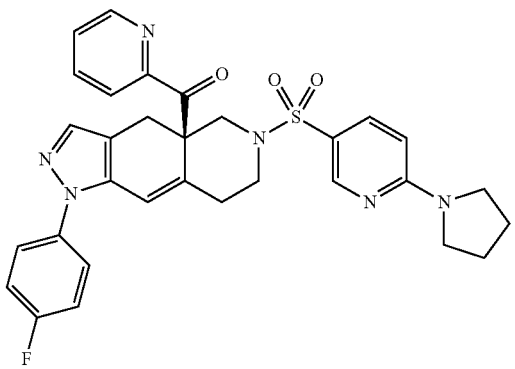 [SMILES: O=C(c1ccccn1)[C@]12Cc3cnn(-c4ccc(F)cc4)c3C=C1CCN(S(=O)(=O)c1ccc(N3CCCC3)nc1)C2]

A solution of (R)-(6-((6-chloropyridin-3-yl)sulfonyl)-1-(4-fluorophenyl)-4,4a,5,6,7,8-hexahydro-1H-pyrazolo[3,4-g]isoquinolin-4a-yl)(pyridin-2-yl)methanone (100 mg, 0.182 mmol) and pyrrolidine (37.9 µl, 0.455 mmol) in acetonitrile (2 mL) was stirred in a sealed vial at 40° C. for 1 hour. The cooled reaction mixture was then purified directly by preparative HPLC (Waters, Acidic (0.1% Formic acid), Waters X-Select Prep-C18, 5 µm, 19×50 mm column, 5-95% acetonitrile in water) to afford (R)-(1-(4-fluorophenyl)-6-((6-(pyrrolidin-1-yl)pyridin-3-yl)sulfonyl)-4,4a,5,6,7,8-hexahydro-1H-pyrazolo[3,4-g]isoquinolin-4a-yl)(pyridin-2-yl)methanone as a white solid (29 mg). LCMS (Method F, ES-API): RT 2.48 min, m+H=585.3; 1H NMR (400 MHz, CDCl$_3$): δ 8.63-8.61 (1H, m), 8.43 (1H, d, J=2.4 Hz), 7.89-7.87 (1H, m), 7.80 (1H, dt, J=7.6, 1.8 Hz), 7.58 (1H, dd, J=9.0, 2.4 Hz), 7.45-7.41 (3H, m), 7.28 (1H, s), 7.19-7.13 (2H, m), 6.47 (1H, d, J=2.1 Hz), 6.22 (1H, d, J=9.0 Hz), 5.46 (1H, dd, J=12.2, 2.1 Hz), 4.27 (1H, d, J=16.9 Hz), 3.83-3.79 (1H, m), 3.52-3.45 (4H, m), 2.90-2.76 (2H, m), 2.68 (1H, d, J=12.3 Hz), 2.51-2.45 (2H, m), 2.06-2.04 (4H, m).

Example 9. ((R)-1-(4-fluorophenyl)-6-((6-((R)-3-fluoropyrrolidin-1-yl)pyridin-3-yl)sulfonyl)-4,4a,5,6,7,8-hexahydro-1H-pyrazolo[3,4-g]isoquinolin-4a-yl)(thiazol-2-yl)methanone

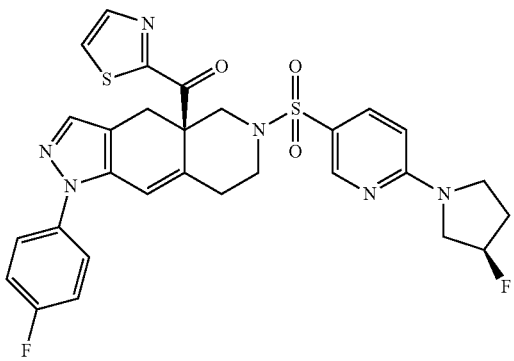 [SMILES: O=C(c1nccs1)[C@]12Cc3cnn(-c4ccc(F)cc4)c3C=C1CCN(S(=O)(=O)c1ccc(N3CC[C@@H](F)C3)nc1)C2]

A mixture of (R)-(6-((6-chloropyridin-3-yl)sulfonyl)-1-(4-fluorophenyl)-4,4a,5,6,7,8-hexahydro-1H-pyrazolo[3,4-g]isoquinolin-4a-yl)(thiazol-2-yl)methanone (92 mg, 0.165 mmol) and (R)-3-fluoropyrrolidine.HCl (41.6 mg, 0.331 mmol) in N,N-dimethylformamide (2 mL) was stirred in a sealed vial at 40° C. for 1 hour, then at 55° C. for a further 2 hours. The cooled reaction mixture was then purified directly by preparative HPLC (Waters, Acidic (0.1% Formic acid), Waters X-Select Prep-C18, 5 µm, 19×50 mm column, 5-95% acetonitrile in water) to afford ((R)-1-(4-fluorophenyl)-6-((6-((R)-3-fluoropyrrolidin-1-yl)pyridin-3-yl)sulfonyl)-4,4a,5,6,7,8-hexahydro-1H-pyrazolo[3,4-g]isoquinolin-4a-yl)(thiazol-2-yl)methanone as a white solid (17 mg). LCMS (Method F, ES-API): RT 2.39 min, m+H=609.2; 1H NMR (400 MHz, CDCl$_3$): δ 8.46 (1H, d, J=2.6 Hz), 7.95 (1H, d, J=3.1 Hz), 7.64 (1H, dd, J=9.0, 2.4 Hz), 7.61 (1H, d, J=3.1 Hz), 7.45-7.40 (2H, m), 7.28 (1H, s), 7.19-7.13 (2H, m), 6.52 (1H, d, J=2.3 Hz), 6.27 (1H, d, J=9.1 Hz), 5.48-5.35 (2H, m), 4.17 (1H, d, J=16.8 Hz), 3.92-3.59 (6H, m), 2.92-2.82 (2H, m), 2.77 (1H, d, J=12.3 Hz), 2.59-2.42 (3H, m).

Example 10. (R)-(1-(4-fluorophenyl)-6-((4-(pyrrolidin-1-yl)phenyl)sulfonyl)-4,4a,5,6,7,8-hexahydro-1H-pyrazolo[3,4-g]isoquinolin-4a-yl)(pyridin-2-yl)methanone

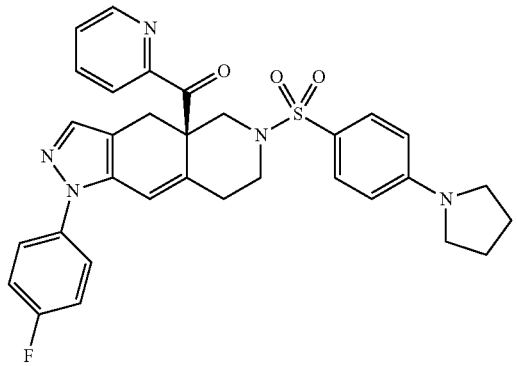 [SMILES: O=C(c1ccccn1)[C@]12Cc3cnn(-c4ccc(F)cc4)c3C=C1CCN(S(=O)(=O)c1ccc(N3CCCC3)cc1)C2]

A solution of pyrrolidine (0.065 mL, 0.783 mmol) and (R)-(1-(4-fluorophenyl)-6-((4-fluorophenyl)sulfonyl)-4,4a,5,6,7,8-hexahydro-1H-pyrazolo[3,4-g]isoquinolin-4a-yl)(pyridin-2-yl)methanone (183 mg, 0.261 mmol) in N-methylpyrrolidine (2 mL) was stirred in a sealed vial at 100° C. for 22 hours. The cooled reaction mixture was then purified directly by preparative HPLC (Waters, Acidic (0.1% Formic acid), Waters X-Select Prep-C18, 5 µm, 19×50 mm column, 5-95% acetonitrile in water) to afford (R)-(1-(4-fluorophenyl)-6-((4-(pyrrolidin-1-yl)phenyl)sulfonyl)-4,4a,5,6,7,8-hexahydro-1H-pyrazolo[3,4-g]isoquinolin-4a-yl)(pyridin-2-yl)methanone as an off-white solid (52 mg). LCMS (Method F, ES-API): RT 2.78 min, m+H=584.3; 1H NMR (400 MHz, CDCl$_3$): δ 8.63-8.62 (1H, m), 7.89 (1H, dt, J=8.0, 1.2 Hz), 7.81 (1H, td, J=7.5, 1.8 Hz), 7.51-7.47 (2H, m), 7.46-7.41 (3H, m), 7.28 (1H, s), 7.18-7.12 (2H, m), 6.48-6.45 (3H, m), 5.41 (1H, dd, J=12.2, 2.1 Hz), 4.31 (1H, d, J=16.9 Hz), 3.80-3.76 (1H, m), 3.33-3.30 (4H, m), 2.88 (1H, d, J=16.9 Hz), 2.85-2.76 (1H, m), 2.61 (1H, d, J=12.1 Hz), 2.45-2.35 (2H, m), 2.07-2.01 (4H, m).

The following examples were similarly prepared from the appropriate intermediate:

Example 10A. (R)-(1-(4-fluorophenyl)-6-((5-(piperidin-1-yl)pyridin-3-yl)sulfonyl)-4,4a,5,6,7,8-hexahydro-1H-pyrazolo[3,4-g]isoquinolin-4a-yl)(pyridin-2-yl)methanone

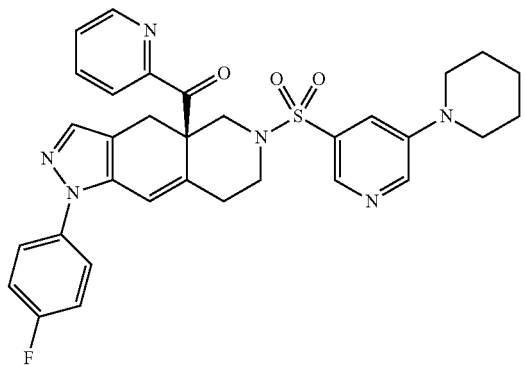 [SMILES: O=C(c1ccccn1)[C@]12Cc3cnn(-c4ccc(F)cc4)c3C=C1CCN(S(=O)(=O)c1cncc(N3CCCCC3)c1)C2]

LCMS (Method F, ES-API): RT 2.56 min, m+H=532.8; 1H NMR (400 MHz, CDCl3): δ 8.65 (1H, ddd, J=4.7, 1.7, 0.8 Hz), 8.36 (1H, d, J=2.8 Hz), 8.25 (1H, d, J=1.7 Hz), 7.90-7.87 (1H, m), 7.83 (1H, dt, J=7.4, 1.7 Hz), 7.49-7.41 (3H, m), 7.29-7.28 (2H, m), 7.19-7.13 (2H, m), 6.49 (1H, d, J=2.1 Hz), 5.52 (1H, dd, J=12.4, 2.1 Hz), 4.28 (1H, d, J=16.9 Hz), 3.86-3.82 (1H, m), 3.25-3.23 (4H, m), 2.92-2.78 (3H, m), 2.59-2.48 (2H, m), 1.74-1.61 (6H, m).

Example 10B. (R)-(1-(4-fluorophenyl)-6-((5-(pyrrolidin-1-yl)pyridin-3-yl)sulfonyl)-4,4a,5,6,7,8-hexahydro-1H-pyrazolo[3,4-g]isoquinolin-4a-yl)(pyridin-2-yl)methanone

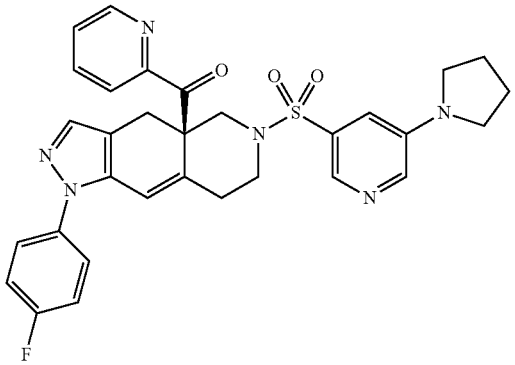 [SMILES: O=C(c1ccccn1)[C@]12Cc3cnn(-c4ccc(F)cc4)c3C=C1CCN(S(=O)(=O)c1cncc(N3CCCC3)c1)C2]

LCMS (Method F, ES-API): RT 2.42 min, m+H=585.3; 1H NMR (400 MHz, CDCl3): δ 8.63 (1H, ddd, J=4.7, 1.8, 0.9 Hz), 8.16 (1H, d, J=1.8 Hz), 8.02 (1H, d, J=3.0 Hz), 7.89-7.86 (1H, m), 7.81 (1H, td, J=7.5, 1.8 Hz), 7.48-7.40 (3H, m), 7.28 (1H, s), 7.19-7.13 (2H, m), 6.91 (1H, dd, J=2.6, 2.1 Hz), 6.48 (1H, d, J=2.1 Hz), 5.50 (1H, dd, J=12.2, 2.1 Hz), 4.27 (1H, d, J=17.0 Hz), 3.87-3.83 (1H, m), 3.32-3.26 (4H, m), 2.91-2.79 (3H, m), 2.59-2.49 (2H, m), 2.08-2.04 (4H, m).

Example 11. (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(thiazol-4-yl)methanone

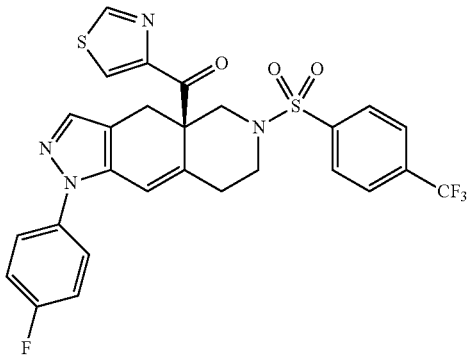 [SMILES: O=C(c1cscn1)[C@]12Cc3cnn(-c4ccc(F)cc4)c3C=C1CCN(S(=O)(=O)c1ccc(C(F)(F)F)cc1)C2]

A solution of (R)-tert-butyl 1-(4-fluorophenyl)-4a-(2-(trimethylsilyl)thiazole-4-carbonyl)-4a,5,7,8-tetrahydro-1H-pyrazolo[3,4-g]isoquinoline-6(4H)-carboxylate (76 mg, 0.103 mmol) in 4 M HCl/dioxane (3 mL) was stirred at room temperature for 1 hour. The solvent was removed in vacuo (azeotroping twice with toluene (~4 mL)) to give a dark orange oil. This was dissolved in dichloromethane (3 mL) and 4-(trifluoromethyl)benzene-1-sulfonyl chloride (30.3 mg, 0.124 mmol) was added followed by diisopropylethylamine (90 μl, 0.516 mmol). The reaction mixture was stirred at room temperature for 0.5 hour. The solvent was removed in vacuo to give a dark orange oil. The crude product was purified by column chromatography on silica gel (gradient: 0-40% ethyl acetate in isohexane) to afford (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(thiazol-4-yl)methanone as a white solid (44 mg). LCMS (Method F, ES-API): RT 2.65 min, m+H=589.2; 1H NMR (400 MHz, CDCl3): δ 8.86 (1H, d, J=2.1 Hz), 8.23 (1H, d, J=2.1 Hz), 7.84-7.82 (2H, m), 7.74-7.72 (2H, m), 7.45-7.40 (2H, m), 7.28 (1H, s), 7.19-7.13 (2H, m), 6.51 (1H, d, J=2.1 Hz), 5.48 (1H, dd, J=12.5, 2.1 Hz), 4.15 (1H, d, J=16.6 Hz), 3.92-3.87 (1H, m), 2.93-2.85 (2H, m), 2.72 (1H, d, J=12.6 Hz), 2.56-2.49 (2H, m).

The following examples were similarly prepared from the appropriate intermediates:

Example 11A. (R)-(6-((4-chlorophenyl)sulfonyl)-1-(4-fluorophenyl)-4,4a,5,6,7,8-hexahydro-1H-pyrazolo[3,4-g]isoquinolin-4a-yl)(pyridin-2-yl)methanone

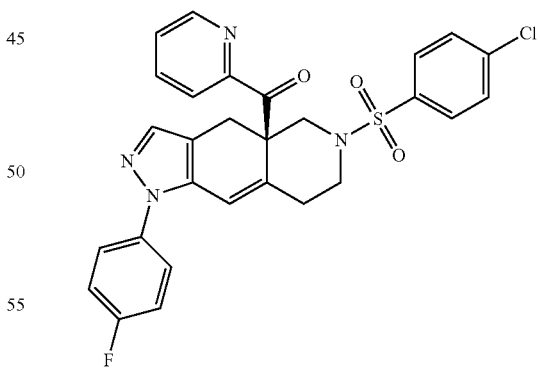

LCMS (Method F, ES-API): RT 2.74 min, m+H=548.9; 1H NMR (400 MHz, CDCl3): δ 8.61 (1H, ddd, J=4.7, 1.7, 0.9 Hz), 7.88-7.81 (2H, m), 7.62-7.58 (2H, m), 7.51-7.37 (5H, m), 7.28 (1H, s), 7.20-7.12 (2H, m), 6.49 (1H, d, J=2.1 Hz), 5.51 (1H, dd, J=12.2, 2.1 Hz), 4.28 (1H, d, J=16.9 Hz), 3.89-3.80 (1H, m), 2.92-2.77 (2H, m), 2.74 (1H, d, J=12.2 Hz), 2.54-2.46 (2H, m).

Example 11B. (R)-(1-(4-fluorophenyl)-6-((4-methoxy-3-methylphenyl)sulfonyl)-4,4a,5,6,7,8-hexahydro-1H-pyrazolo[3,4-g]isoquinolin-4a-yl)(pyridin-2-yl)methanone

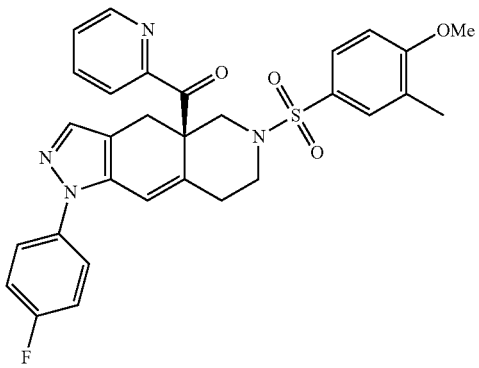 [SMILES: COc1ccc(S(=O)(=O)N2CCC3=Cc4c(cnn4-c4ccc(F)cc4)C[C@]3(C(=O)c3ccccn3)C2)cc1C]

LCMS (Method F, ES-API): RT 2.69 min, m+H=559.0; 1H NMR (400 MHz, CDCl3): δ 8.62 (1H, ddd, J=4.7, 1.7, 0.9 Hz), 7.89-7.86 (1H, m), 7.85-7.79 (1H, m), 7.52 (1H, dd, J=8.6, 2.1 Hz), 7.45-7.41 (4H, m), 7.28 (1H, m), 7.19-7.12 (2H, m), 6.81 (1H, d, J=8.6 Hz), 6.47 (1H, d, J=2.1 Hz), 5.47 (1H, dd, J=12.1, 2.1 Hz), 4.30 (1H, d, J=17.0 Hz), 3.88-3.79 (4H, m), 2.90-2.77 (2H, m), 2.67 (1H, d, J=12.1 Hz), 2.51-2.38 (2H, m), 2.19 (3H, s).

Example 11C. (R)-(6-((3-chloro-4-methoxyphenyl)sulfonyl)-1-(4-fluorophenyl)-4,4a,5,6,7,8-hexahydro-1H-pyrazolo[3,4-g]isoquinolin-4a-yl)(pyridin-2-yl)methanone

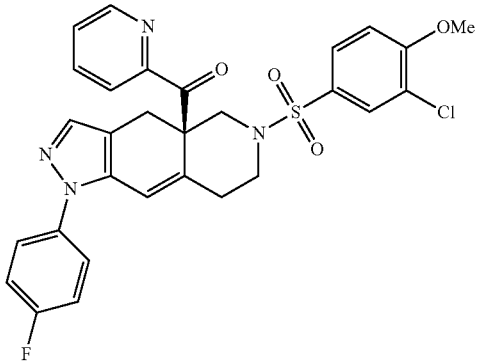 [SMILES: COc1ccc(S(=O)(=O)N2CCC3=Cc4c(cnn4-c4ccc(F)cc4)C[C@]3(C(=O)c3ccccn3)C2)cc1Cl]

LCMS (Method F, ES-API): RT 2.67 min, m+H=578.9; 1H NMR (400 MHz, CDCl3): δ 8.63 (1H, ddd, J=4.7, 1.7, 0.9 Hz), 7.89-7.78 (2H, m), 7.67 (1H, d, J=2.2 Hz), 7.57 (1H, dd, J=8.7, 2.2 Hz), 7.48-7.41 (3H, m), 7.28 (1H, m), 7.18-7.13 (2H, m), 6.91 (1H, d, J=8.7 Hz), 6.48 (1H, d, J=2.1 Hz), 5.50 (1H, dd, J=12.2, 2.1 Hz), 4.28 (1H, d, J=16.9 Hz), 3.94 (3H, m), 3.87-3.79 (1H, m), 2.91-2.78 (2H, m), 2.74 (1H, d, J=12.2 Hz), 2.54-2.47 (2H, m).

Example 11D. (R)-(6-((3-fluoro-4-methoxyphenyl)sulfonyl)-1-(4-fluorophenyl)-4,4a,5,6,7,8-hexahydro-1H-pyrazolo[3,4-g]isoquinolin-4a-yl)(pyridin-2-yl)methanone

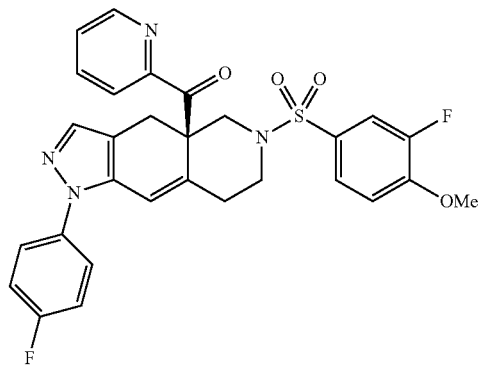 [SMILES: COc1ccc(S(=O)(=O)N2CCC3=Cc4c(cnn4-c4ccc(F)cc4)C[C@]3(C(=O)c3ccccn3)C2)cc1F]

LCMS (Method F, ES-API): RT 2.57 min, m+H=563.2; 1H NMR (400 MHz, CDCl3): δ 8.64 (1H, ddd, J=4.8, 1.7, 0.8 Hz), 7.90-7.87 (1H, m), 7.83 (1H, dt, J=7.5, 1.7 Hz), 7.48-7.41 (4H, m), 7.37 (1H, dd, J=10.3, 2.3 Hz), 7.28 (1H, s), 7.19-7.13 (2H, m), 6.99-6.95 (1H, m), 6.48 (1H, d, J=2.1 Hz), 5.49 (1H, dd, J=12.1, 2.1 Hz), 4.29 (1H, d, J=16.9 Hz), 3.93 (3H, s), 3.85-3.80 (1H, m), 2.91-2.77 (2H, m), 2.72 (1H, d, J=12.2 Hz), 2.53-2.46 (2H, m).

Example 11E. (R)-(6-((2-fluoro-4-methylphenyl)sulfonyl)-1-(4-fluorophenyl)-4,4a,5,6,7,8-hexahydro-1H-pyrazolo[3,4-g]isoquinolin-4a-yl)(pyridin-2-yl)methanone

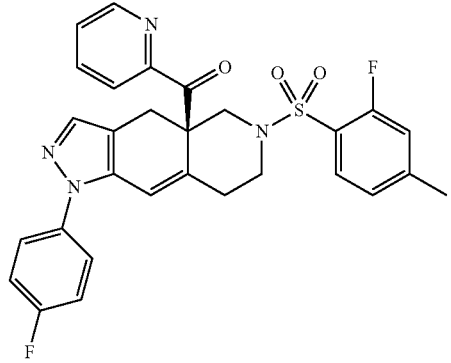 [SMILES: Cc1ccc(S(=O)(=O)N2CCC3=Cc4c(cnn4-c4ccc(F)cc4)C[C@]3(C(=O)c3ccccn3)C2)c(F)c1]

LCMS (Method F, ES-API): RT 2.67 min, m+H=547.2; 1H NMR (400 MHz, CDCl3): δ 8.63 (1H, ddd, J=4.7, 1.6, 1.0 Hz), 7.85-7.82 (1H, m), 7.80 (1H, dt, J=7.3, 1.8 Hz), 7.59-7.55 (1H, m), 7.46-7.41 (3H, m), 7.28 (1H, s), 7.19-7.13 (2H, m), 6.95-6.90 (2H, m), 6.50 (1H, d, J=2.2 Hz), 5.57 (1H, dd, J=12.8, 1.8 Hz), 4.29 (1H, d, J=16.9 Hz), 3.95-3.91 (1H, m), 2.97 (1H, dd, 12.9, 1.1 Hz), 2.91-2.79 (2H, m), 2.74-2.68 (1H, m), 2.51-2.47 (1H, m), 2.37 (3H, s).

Example 11F. (R)-(1-(4-fluorophenyl)-6-(m-tolyl-sulfonyl)-4,4a,5,6,7,8-hexahydro-1H-pyrazolo[3,4-g]isoquinolin-4a-yl)(thiazol-4-yl)methanone

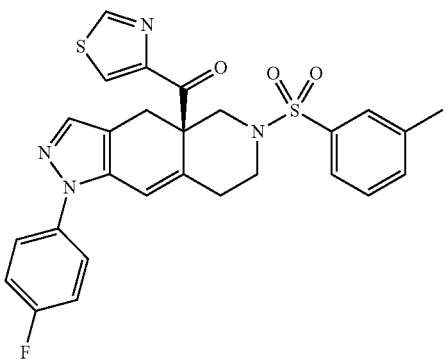 [SMILES: Cc1cccc(S(=O)(=O)N2CCC3=Cc4c(cnn4-c4ccc(F)cc4)C[C@]3(C(=O)c3cscn3)C2)c1]

LCMS (Method F, ES-API): RT 2.57 min, m+H=535.1; 1H NMR (400 MHz, CDCl3): δ 8.88 (1H, d, J=2.4 Hz), 8.25 (1H, d, J=2.4 Hz), 7.52-7.50 (2H, m), 7.45-7.40 (2H, m), 7.37-7.36 (2H, m), 7.28 (1H, s), 7.19-7.13 (2H, m), 6.49 (1H, d, J=2.3 Hz), 5.45 (1H, dd, J=12.1, 2.3 Hz), 4.18 (1H, d, J=16.9 Hz), 3.87-3.83 (1H, m), 2.92-2.82 (2H, m), 2.63 (1H, d, J=12.4 Hz), 2.50-2.39 (5H, m).

Example 11G. (R)-3-((1-(4-fluorophenyl)-4a-picolinoyl-4a,5,7,8-tetrahydro-1H-pyrazolo[3,4-g]isoquinolin-6(4H)-yl)sulfonyl)benzonitrile

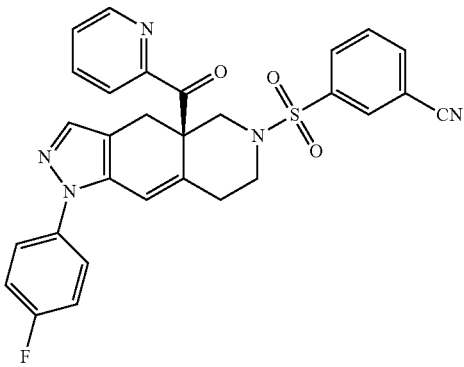 [SMILES: N#Cc1cccc(S(=O)(=O)N2CCC3=Cc4c(cnn4-c4ccc(F)cc4)C[C@]3(C(=O)c3ccccn3)C2)c1]

LCMS (Method F, ES-API): RT 2.48 min, m+H=540.0; 1H NMR (400 MHz, CDCl3): δ 8.68-8.66 (1H, m), 7.93-7.78 (5H, m), 7.60 (1H, td, J=7.8, 0.6 Hz), 7.50 (1H, ddd, J=6.8, 4.8, 2.2 Hz), 7.45-7.39 (2H, m), 7.28 (1H, m), 7.19-7.13 (2H, m), 6.50 (1H, d, J=2.1 Hz), 5.60 (1H, dd, J=12.4, 2.1 Hz), 4.26 (1H, d, J=16.9 Hz), 3.92-3.83 (1H, m), 2.90-2.78 (3H, m), 2.58-2.49 (2H, m).

Example 11H. (R)-(6-((4-(difluoromethoxy)phenyl)sulfonyl)-1-(4-fluorophenyl)-4,4a,5,6,7,8-hexahydro-1H-pyrazolo[3,4-g]isoquinolin-4a-yl)(pyridin-2-yl)methanone

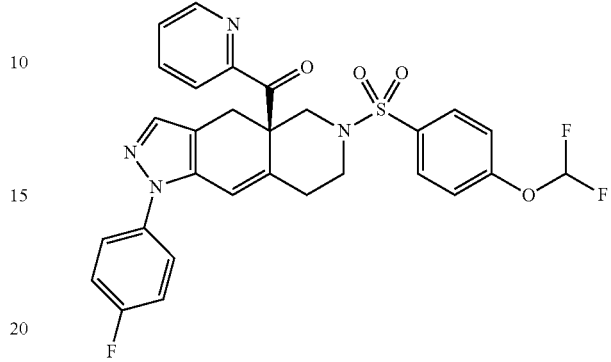

LCMS (Method F, ES-API): RT 2.62 min, m+H=581.2; 1H NMR (400 MHz, CDCl3): δ 8.62 (1H, ddd, J=4.8, 1.7, 0.8 Hz), 7.89-7.87 (1H, m), 7.83 (1H, dt, J=7.5, 1.7 Hz), 7.71-7.68 (2H, m), 7.49-7.40 (3H, m), 7.28 (1H, s), 7.19-7.13 (4H, m), 6.57 (1H, t, J=72.4 Hz), 6.48 (1H, d, J=2.3 Hz), 5.52 (1H, dd, J=12.2, 2.1 Hz), 4.28 (1H, d, J=16.9 Hz), 3.86-3.82 (1H, m), 2.90-2.78 (2H, m), 2.74 (1H, d, J=12.2 Hz), 2.54-2.46 (2H, m).

Example 11I. (R)-(1-(4-fluorophenyl)-6-((3-(trifluoromethoxy)phenyl)sulfonyl)-4,4a,5,6,7,8-hexahydro-1H-pyrazolo[3,4-g]isoquinolin-4a-yl)(pyridin-2-yl)methanone

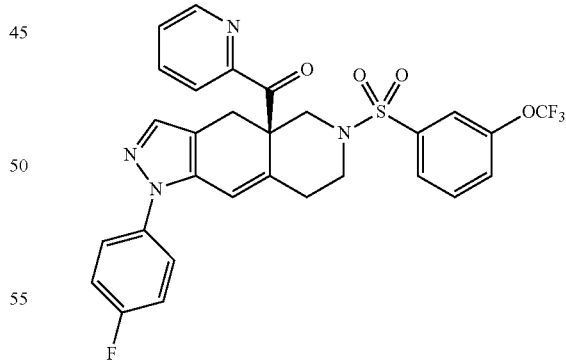

LCMS (Method F, ES-API): RT 2.79 min, m+H=599.2; 1H NMR (400 MHz, CDCl3): δ 8.67 (1H, ddd, J=4.8, 1.7, 0.8 Hz), 7.91-7.88 (1H, m), 7.84 (1H, dt, J=7.5, 1.7 Hz), 7.64-7.62 (1H, m), 7.54-7.47 (3H, m), 7.45-7.38 (3H, m), 7.29 (1H, s), 7.19-7.13 (2H, m), 6.49 (1H, d, J=2.3 Hz), 5.55 (1H, dd, J=12.4, 2.2 Hz), 4.29 (1H, d, J=16.9 Hz), 3.86-3.81 (1H, m), 2.91-2.74 (3H, m), 2.54-2.47 (2H, m).

Example 11J. (R)-(6-((3,5-difluorophenyl)sulfonyl)-1-(4-fluorophenyl)-4,4a,5,6,7,8-hexahydro-1H-pyrazolo[3,4-g]isoquinolin-4a-yl)(pyridin-2-yl)methanone

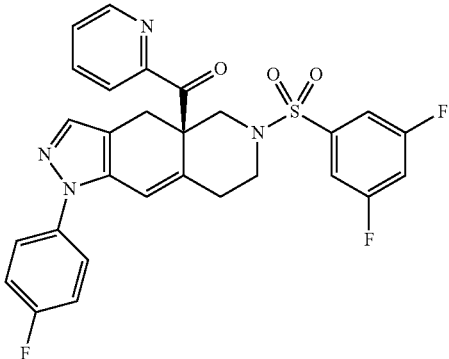 [SMILES: O=C(c1ccccn1)[C@]12Cc3cnn(-c4ccc(F)cc4)c3C=C1CCN(S(=O)(=O)c1cc(F)cc(F)c1)C2]

LCMS (Method F, ES-API): RT 2.67 min, m+H=551.2; 1H NMR (400 MHz, CDCl3): δ 8.67 (1H, ddd, J=4.7, 1.7, 0.8 Hz), 7.88 (1H, ddd, J=7.9, 1.5, 1.0 Hz), 7.84 (1H, dt, J=7.3, 1.7 Hz), 7.48 (1H, ddd, J=7.4, 4.7, 1.5 Hz), 7.46-7.41 (2H, m), 7.29 (1H, s), 7.22-7.13 (4H, m), 6.98 (1H, tt, J=8.5, 2.3 Hz), 6.49 (1H, d, J=2.1 Hz), 5.56 (1H, dd, J=12.3, 2.1 Hz), 4.28 (1H, d, J=16.9 Hz), 3.87-3.82 (1H, m), 2.92-2.78 (3H, m), 2.62-2.55 (1H, m), 2.53-2.48 (1H, m).

Example 11K. (R)-(1-(4-fluorophenyl)-6-tosyl-4,4a,5,6,7,8-hexahydro-1H-pyrazolo[3,4-g]isoquinolin-4a-yl)(thiazol-4-yl)methanone

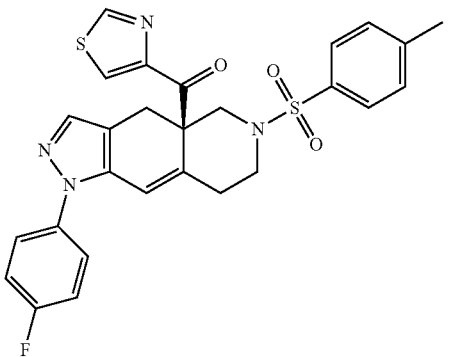 [SMILES: Cc1ccc(S(=O)(=O)N2CCC3=Cc4c(cnn4-c4ccc(F)cc4)C[C@]3(C(=O)c3cscn3)C2)cc1]

LCMS (Method F, ES-API): RT 2.56 min, m+H=535.0; 1H NMR (400 MHz, CDCl3): δ 8.86 (1H, d, J=2.2 Hz), 8.24 (1H, d, J=2.2 Hz), 7.59-7.55 (2H, m), 7.47-7.39 (2H, m), 7.27-7.25 (3H, m), 7.19-7.12 (2H, m), 6.49 (1H, d, J=2.0 Hz), 5.43 (1H, dd, J=12.3, 2.0 Hz), 4.17 (1H, d, J=16.9 Hz), 3.84 (1H, ddt, J=8.5, 4.4, 2.0 Hz), 2.91-2.80 (2H, m), 2.61 (1H, d, J=12.3 Hz), 2.49-2.37 (5H, m).

Example 11L. (R)-(6-((3-(difluoromethoxy)phenyl)sulfonyl)-1-(4-fluorophenyl)-4,4a,5,6,7,8-hexahydro-1H-pyrazolo[3,4-g]isoquinolin-4a-yl)(pyridin-2-yl)methanone

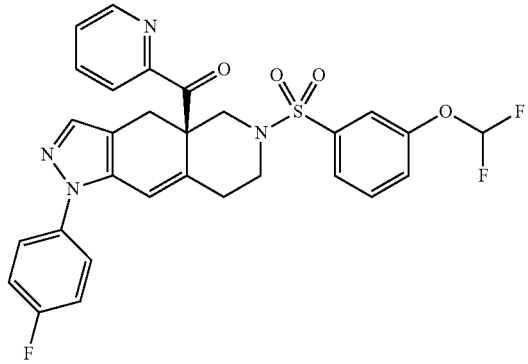 [SMILES: O=C(c1ccccn1)[C@]12Cc3cnn(-c4ccc(F)cc4)c3C=C1CCN(S(=O)(=O)c1cccc(OC(F)F)c1)C2]

LCMS (Method F, ES-API): RT 2.63 min, m+H=581.2; 1H NMR (400 MHz, CDCl3): δ 8.65 (1H, ddd, J=4.8, 1.7, 0.8 Hz), 7.89-7.87 (1H, m), 7.83 (1H, dt, J=7.5, 1.7 Hz), 7.56-7.53 (1H, m), 7.49-7.40 (5H, m), 7.31-7.28 (2H, m), 7.19-7.13 (2H, m), 6.55 (1H, t, J=72.7 Hz), 6.48 (1H, d, J=2.3 Hz), 5.52 (1H, dd, J=12.2, 2.1 Hz), 4.28 (1H, d, J=16.9 Hz), 3.86-3.81 (1H, m), 2.90-2.75 (3H, m), 2.55-2.46 (2H, m).

Example 11M. (R)-(6-((3,4-dimethylphenyl)sulfonyl)-1-(4-fluorophenyl)-4,4a,5,6,7,8-hexahydro-1H-pyrazolo[3,4-g]isoquinolin-4a-yl)(pyridin-2-yl)methanone

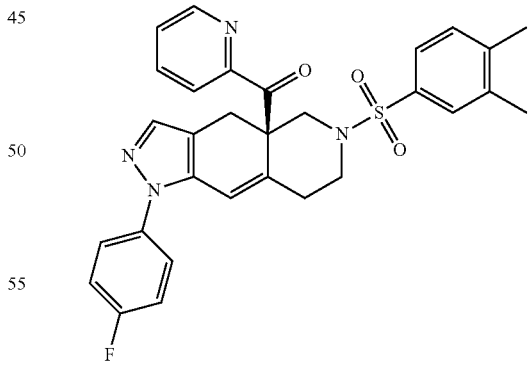

LCMS (Method F, ES-API): RT 2.76 min, m+H=543.0; 1H NMR (400 MHz, CDCl3): δ 8.64 (1H, ddd, J=4.8, 1.7, 0.9 Hz), 7.92-7.80 (2H, m), 7.49-7.39 (5H, m), 7.28 (1H, s), 7.20-7.13 (3H, m), 6.46 (1H, d, J=2.1 Hz), 5.47 (1H, dd, J=12.2, 2.1 Hz), 4.30 (1H, d, J=17.0 Hz), 3.83-3.79 (1H, m), 2.91-2.71 (2H, m), 2.67 (1H, d, J=12.2 Hz), 2.50-2.38 (2H, m), 2.28 (6H, s).

Example 11N. (R)-(6-((3,5-dimethylphenyl)sulfonyl)-1-(4-fluorophenyl)-4,4a,5,6,7,8-hexahydro-1H-pyrazolo[3,4-g]isoquinolin-4a-yl)(pyridin-2-yl)methanone

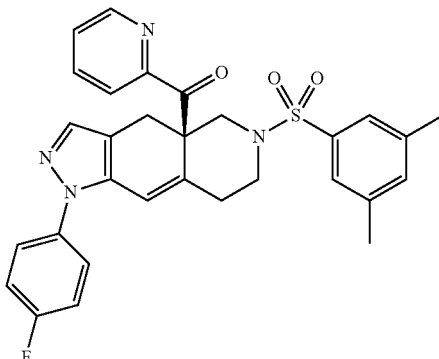

LCMS (Method F, ES-API): RT 2.78 min, m+H=543.0; 1H NMR (400 MHz, CDCl3): δ 8.65 (1H, ddd, J=4.8, 1.7, 0.9 Hz), 7.90-7.88 (1H, m), 7.83 (1H, dt, J=7.5, 1.7 Hz), 7.49-7.40 (3H, m), 7.28 (3H, m), 7.19-7.13 (3H, m), 6.47 (1H, d, J=2.3 Hz), 5.48 (1H, dd, J=12.2, 2.1 Hz), 4.30 (1H, d, J=16.9 Hz), 3.83-3.79 (1H, m), 2.90 (1H, d, J=16.9 Hz), 2.87-2.78 (1H, m), 2.70 (1H, d, J=12.3 Hz), 2.50-2.42 (2H, m), 2.34 (6H, m).

Example 11O. (R)-1-(4-fluorophenyl)-6-((6-methylpyridin-2-yl)sulfonyl)-4,4a,5,6,7,8-hexahydro-1H-pyrazolo[3,4-g]isoquinolin-4a-yl)(pyridin-2-yl)methanone

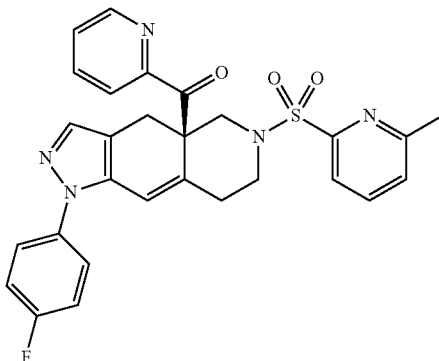

LCMS (Method F, ES-API): RT 2.46 min, m+H=530.1; 1H NMR (400 MHz, CDCl3): δ 8.65 (1H, ddd, J=4.7, 1.6, 1.0 Hz), 7.85-7.78 (2H, m), 7.69-7.65 (1H, m), 7.59-7.57 (1H, m), 7.48-7.42 (3H, m), 7.29 (1H, s), 7.27-7.25 (1H, m), 7.19-7.13 (2H, m), 6.51 (1H, d, J=1.4 Hz), 5.62 (1H, dd, J=12.9, 2.0 Hz), 4.31 (1H, d, J=16.9 Hz), 4.00-3.96 (1H, m), 3.19 (1H, d, J=13.0 Hz), 2.95-2.91 (3H, m), 2.59 (3H, s), 2.50-2.46 (1H, m).

Example 11P. (R)-(6-((3,4-difluorophenyl)sulfonyl)-1-(4-fluorophenyl)-4,4a,5,6,7,8-hexahydro-1H-pyrazolo[3,4-g]isoquinolin-4a-yl)(pyridin-2-yl)methanone

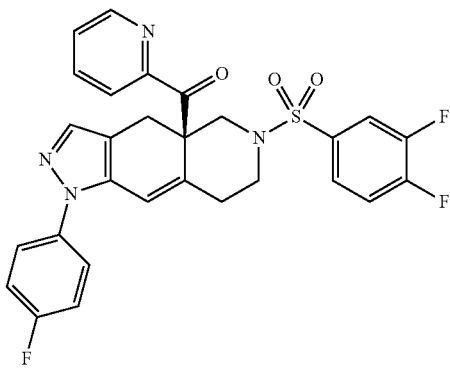 [SMILES: O=C(c1ccccn1)[C@]12Cc3cnn(-c4ccc(F)cc4)c3C=C1CCN(S(=O)(=O)c1ccc(F)c(F)c1)C2]

LCMS (Method F, ES-API): RT 2.65 min, m+H=551.1; 1H NMR (400 MHz, CDCl3): δ 8.63 (1H, ddd, J=4.8, 1.7, 1.0 Hz), 7.88 (1H, ddd, J=7.9, 1.7, 1.0 Hz), 7.84 (1H, dt, J=7.3, 1.7 Hz), 7.52-7.40 (5H, m), 7.28 (1H, s), 7.24-7.22 (1H, m), 7.20-7.13 (2H, m), 6.49 (1H, d, J=2.1 Hz), 5.53 (1H, dd, J=12.2, 2.0 Hz), 4.28 (1H, d, J=16.9 Hz), 3.88-3.83 (1H, m), 2.91-2.78 (3H, m), 2.59-2.48 (2H, m).

Example 11Q. (R)-(1-(4-fluorophenyl)-6-((3,4,5-trifluorophenyl)sulfonyl)-4,4a,5,6,7,8-hexahydro-1H-pyrazolo[3,4-g]isoquinolin-4a-yl)(pyridin-2-yl)methanone

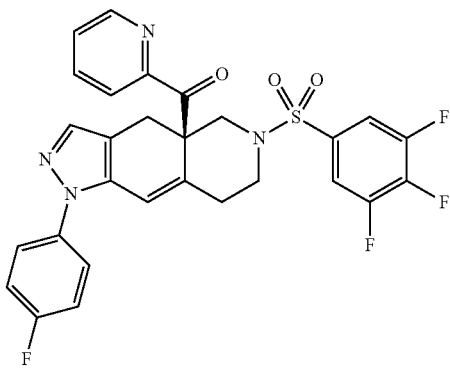 [SMILES: O=C(c1ccccn1)[C@]12Cc3cnn(-c4ccc(F)cc4)c3C=C1CCN(S(=O)(=O)c1cc(F)c(F)c(F)c1)C2]

LCMS (Method F, ES-API): RT 2.72 min, m+H=569.1; 1H NMR (400 MHz, CDCl3): δ 8.63 (1H, ddd, J=4.7, 1.5, 1.1 Hz), 7.89-7.83 (2H, m), 7.49 (1H, ddd, J=6.6, 4.7, 1.7 Hz), 7.46-7.41 (2H, m), 7.34-7.31 (2H, m), 7.28 (1H, s), 7.20-7.14 (2H, m), 6.50 (1H, d, J=2.1 Hz), 5.55 (1H, dd, J=12.2, 2.0 Hz), 4.26 (1H, d, J=16.9 Hz), 3.89-3.84 (1H, m), 2.91-2.79 (3H, m), 2.66-2.60 (1H, m), 2.54-2.51 (1H, m).

Example 11R. (R)-(6-((3-chloro-4-fluorophenyl)sulfonyl)-1-(4-fluorophenyl)-4,4a,5,6,7,8-hexahydro-1H-pyrazolo[3,4-g]isoquinolin-4a-yl)(pyridin-2-yl)methanone

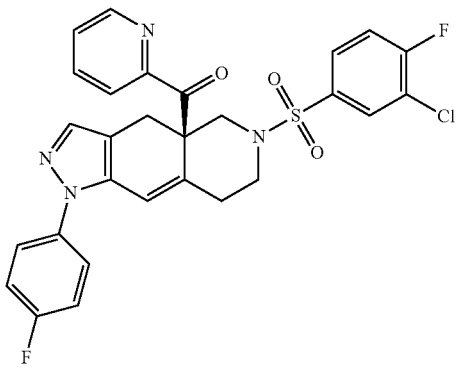 [SMILES: O=C(c1ccccn1)[C@]12Cc3cnn(-c4ccc(F)cc4)c3C=C1CCN(S(=O)(=O)c1ccc(F)c(Cl)c1)C2]

LCMS (Method F, ES-API): RT 2.75 min, m+H=567.0; 1H NMR (400 MHz, CDCl3): δ 8.61 (1H, dt, J=4.7, 1.3 Hz), 7.86-7.79 (2H, m), 7.73 (1H, dd, J=6.7, 2.3 Hz), 7.57 (1H, ddd, J=8.6, 4.3, 2.3 Hz), 7.47-7.40 (3H, m), 7.27 (1H, s), 7.18-7.13 (3H, m), 6.48 (1H, d, J=2.0 Hz), 5.50 (1H, br. dd, J=12.5, 1.4 Hz), 4.24 (1H, d, J=16.9 Hz), 3.86 (1H, dtd, J=8.5, 3.9, 1.9 Hz), 2.91-2.79 (3H, m), 2.61 (1H, td, J=11.6, 3.4 Hz), 2.55-2.46 (1H, m).

Example 11S. (R)-3-((1-(4-fluorophenyl)-4a-(4-methylpicolinoyl)-4a,5,7,8-tetrahydro-1H-pyrazolo[3,4-g]isoquinolin-6(4H)-yl)sulfonyl)benzonitrile

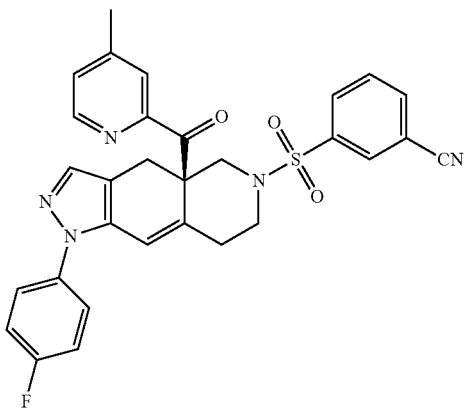 [SMILES: Cc1ccnc(C(=O)[C@]23Cc4cnn(-c5ccc(F)cc5)c4C=C2CCN(S(=O)(=O)c2cccc(C#N)c2)C3)c1]

LCMS (Method F, ES-API): RT 2.57 min, m+H=554.0; 1H NMR (400 MHz, CDCl3): δ 8.50 (1H, br. d, J=4.9 Hz), 7.93-7.91 (2H, m), 7.79 (1H, dt, J=7.8, 1.3 Hz), 7.69-7.68 (1H, m), 7.63-7.58 (1H, m), 7.44-7.41 (2H, m), 7.30 (1H, ddd, J=4.9, 1.7, 0.7 Hz), 7.27 (1H, s), 7.19-7.13 (2H, m), 6.49 (1H, d, J=2.0 Hz), 5.64 (1H, dd, J=12.4, 2.0 Hz), 4.25 (1H, d, J=16.9 Hz), 3.89 (1H, ddt, J=8.5, 3.9, 2.0 Hz), 2.85-2.79 (3H, m), 2.63-2.50 (2H, m), 2.41 (3H, s).

Example 11T. (R)-(1-(4-fluorophenyl)-6-((1-methyl-1H-pyrazol-4-yl)sulfonyl)-4,4a,5,6,7,8-hexahydro-1H-pyrazolo[3,4-g]isoquinolin-4a-yl)(4-methylpyridin-2-yl)methanone

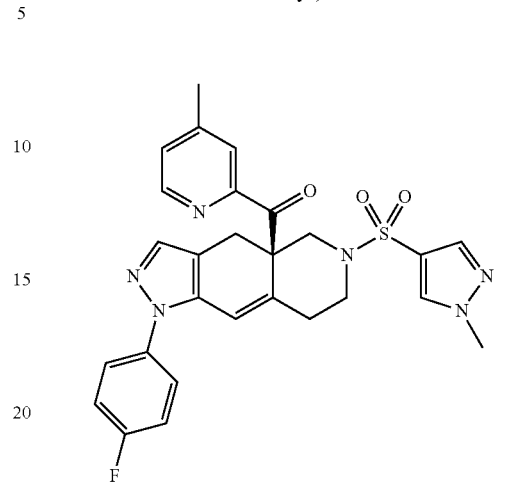

LCMS (Method F, ES-API): RT 2.25 min, m+H=533.2; 1H NMR (400 MHz, CDCl3): δ 8.49 (1H, dd, J=5.0, 0.5 Hz), 7.71 (1H, m), 7.67-7.65 (2H, m), 7.46-7.41 (2H, m), 7.29-7.26 (2H, m), 7.19-7.13 (2H, m), 6.48 (1H, d, J=2.1 Hz), 5.47 (1H, dd, J=12.1, 2.1 Hz), 4.29 (1H, d, J=16.9 Hz), 3.91 (3H, s), 3.80-3.75 (1H, m), 2.92-2.78 (2H, m), 2.68 (1H, d, J=12.0 Hz), 2.50-2.42 (2H, m), 2.40 (3H, s).

Example 11U. (R)-(6-((3,4-difluorophenyl)sulfonyl)-1-(4-fluorophenyl)-4,4a,5,6,7,8-hexahydro-1H-pyrazolo[3,4-g]isoquinolin-4a-yl)(4-methylpyridin-2-yl)methanone

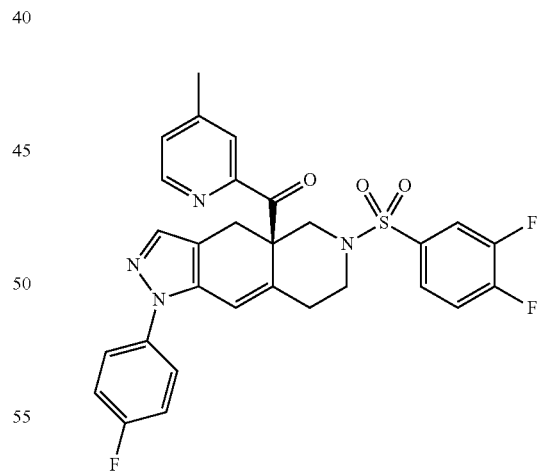

LCMS (Method F, ES-API): RT 2.74 min, m+H=565.2; 1H NMR (400 MHz, CDCl3): δ 8.46 (1H, dd, J=5.0, 0.5 Hz), 7.68 (1H, m), 7.50-7.40 (4H, m), 7.29-7.26 (2H, m), 7.24-7.13 (3H, m), 6.48 (1H, d, J=2.1 Hz), 5.55 (1H, dd, J=12.4, 2.1 Hz), 4.27 (1H, d, J=16.9 Hz), 3.89-3.84 (1H, m), 2.88-2.78 (3H, m), 2.62-2.56 (1H, m), 2.53-2.48 (1H, m), 2.40 (3H, s).

Example 11V. (R)-(1-(4-fluorophenyl)-6-((1-methyl-1H-imidazol-4-yl)sulfonyl)-4,4a,5,6,7,8-hexahydro-1H-pyrazolo[3,4-g]isoquinolin-4a-yl)(4-methylpyridin-2-yl)methanone

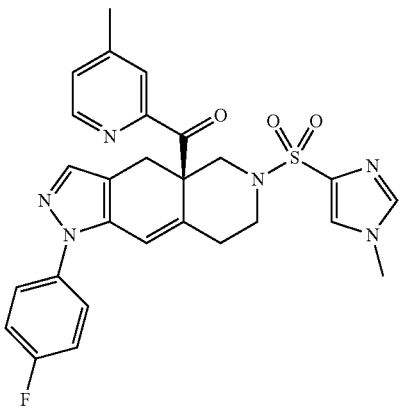 [SMILES: Cc1ccnc(C(=O)[C@]23Cc4cnn(-c5ccc(F)cc5)c4C=C2CCN(S(=O)(=O)c2cn(C)cn2)C3)c1]

LCMS (Method F, ES-API): RT 2.13 min, m+H=533.2; 1H NMR (400 MHz, CDCl3): δ 8.50 (1H, dd, J=4.8, 0.5 Hz), 7.71-7.70 (1H, m), 7.47-7.42 (3H, m), 7.35 (1H, d, J=1.4 Hz), 7.29 (1H, s), 7.26-7.25 (1H, m), 7.19-7.13 (2H, m), 6.48 (1H, d, J=2.1 Hz), 5.56 (1H, dd, J=12.5, 2.1 Hz), 4.32 (1H, d, J=16.9 Hz), 3.90-3.85 (1H, m), 3.72 (3H, s), 2.96 (1H, d, J=12.5 Hz), 2.91 (1H, d, J=16.9 Hz), 2.87-2.78 (1H, m), 2.74-2.68 (1H, m), 2.49-2.44 (1H, m), 2.39 (3H, s).

Example 11W. (R)-(6-((3,5-difluorophenyl)sulfonyl)-1-(4-fluorophenyl)-4,4a,5,6,7,8-hexahydro-1H-pyrazolo[3,4-g]isoquinolin-4a-yl)(4-methylpyridin-2-yl)methanone

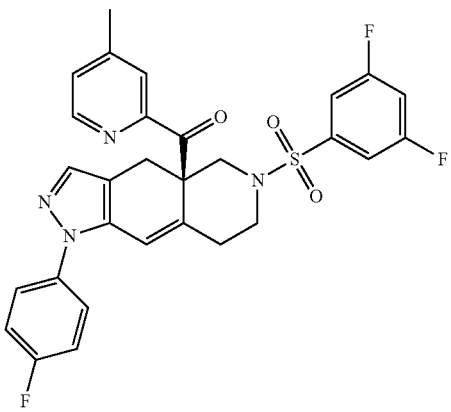 [SMILES: Cc1ccnc(C(=O)[C@]23Cc4cnn(-c5ccc(F)cc5)c4C=C2CCN(S(=O)(=O)c2cc(F)cc(F)c2)C3)c1]

LCMS (Method F, ES-API): RT 2.76 min, m+H=565.0; 1H NMR (400 MHz, CDCl3): δ 8.51 (1H, br. d, J=4.9 Hz), 7.72-7.69 (1H, m), 7.46-7.41 (2H, m), 7.32-7.27 (2H, m), 7.20-7.13 (4H, m), 6.97 (1H, tt, J=8.5, 2.3 Hz), 6.49 (1H, d, J=2.1 Hz), 5.61 (1H, dd, J=12.3, 2.1 Hz), 4.29 (1H, d, J=16.9 Hz), 3.85 (1H, ddt, J=8.4, 3.9, 2.1 Hz), 2.90-2.77 (3H, m), 2.63-2.57 (1H, m), 2.50 (1H, br. dt, J=14.9, 2.0 Hz), 2.41 (3H, s).

Example 11X. (R)-(1-(4-fluorophenyl)-6-((3,4,5-trifluorophenyl)sulfonyl)-4,4a,5,6,7,8-hexahydro-1H-pyrazolo[3,4-g]isoquinolin-4a-yl)(4-methylpyridin-2-yl)methanone

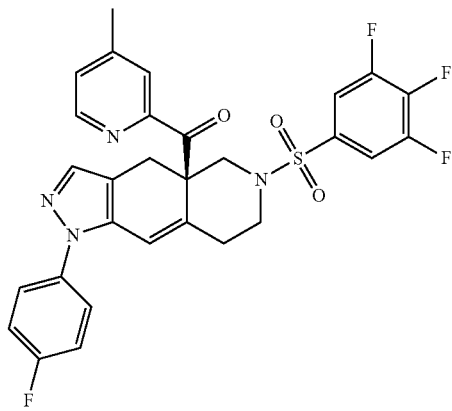 [SMILES: Cc1ccnc(C(=O)[C@]23Cc4cnn(-c5ccc(F)cc5)c4C=C2CCN(S(=O)(=O)c2cc(F)c(F)c(F)c2)C3)c1]

LCMS (Method F, ES-API): RT 2.82 min, m+H=583.0; 1H NMR (400 MHz, CDCl3): δ 8.48-8.47 (1H, m), 7.69-7.68 (1H, m), 7.47-7.39 (2H, m), 7.36-7.29 (3H, m), 7.27 (1H, s), 7.20-7.13 (2H, m), 6.50 (1H, d, J=2.1 Hz), 5.58 (1H, dd, J=12.5, 2.1 Hz), 4.26 (1H, d, J=16.9 Hz), 3.88 (1H, dtd, J=7.9, 4.0, 2.1 Hz), 2.91-2.76 (3H, m), 2.72-2.62 (1H, m), 2.56-2.50 (1H, m), 2.41 (3H, s).

Example 11Y. (R)-(1-(4-fluorophenyl)-6-((3-(methylsulfonyl)phenyl)sulfonyl)-4,4a,5,6,7,8-hexahydro-1H-pyrazolo[3,4-g]isoquinolin-4a-yl)(pyridin-2-yl)methanone

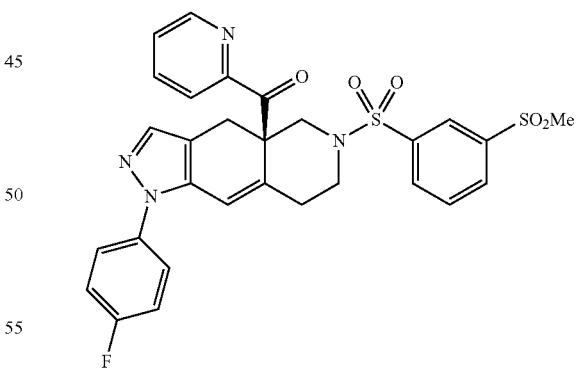

LCMS (Method F, ES-API): RT 2.32 min, m+H=593.2; 1H NMR (400 MHz, CDCl3): δ 8.65 (1H, ddd, J=4.7, 1.7, 0.8 Hz), 8.27-8.26 (1H, m), 8.09 (1H, ddd, J=7.9, 1.7, 1.2 Hz), 7.96 (1H, ddd, J=7.9, 1.7, 1.2 Hz), 7.87-7.80 (2H, m), 7.70-7.66 (1H, m), 7.48 (1H, ddd, J=6.6, 4.7, 1.7 Hz), 7.45-7.40 (2H, m), 7.28 (1H, s), 7.19-7.13 (2H, m), 6.48 (1H, d, J=2.1 Hz), 5.56 (1H, dd, J=12.3, 2.1 Hz), 4.23 (1H, d, J=16.9 Hz), 3.91-3.87 (1H, m), 3.08 (3H, s), 2.91-2.79 (3H, m), 2.62-2.48 (2H, m).

Example 11Z. (R)-3-((1-(4-fluorophenyl)-4a-picolinoyl-4a,5,7,8-tetrahydro-1H-pyrazolo[3,4-g]isoquinolin-6(4H)-yl)sulfonyl)benzoic acid

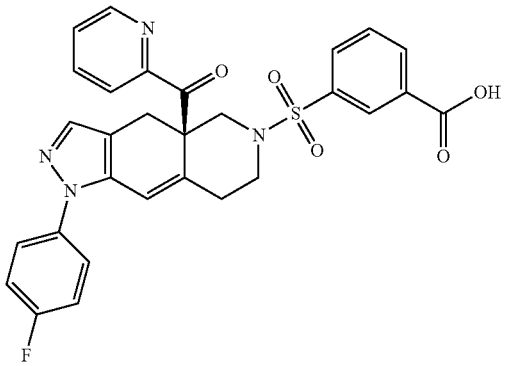 [SMILES: O=C(O)c1cccc(S(=O)(=O)N2CCC3=Cc4c(cnn4-c4ccc(F)cc4)C[C@]3(C(=O)c3ccccn3)C2)c1]

LCMS (Method F, ES-API): RT 2.38 min, m+H=559.

Example 11AA. (R)-(1-(4-fluorophenyl)-6-((3-(methoxymethyl)phenyl)sulfonyl)-4,4a,5,6,7,8-hexahydro-1H-pyrazolo[3,4-g]isoquinolin-4a-yl)(pyridin-2-yl)methanone

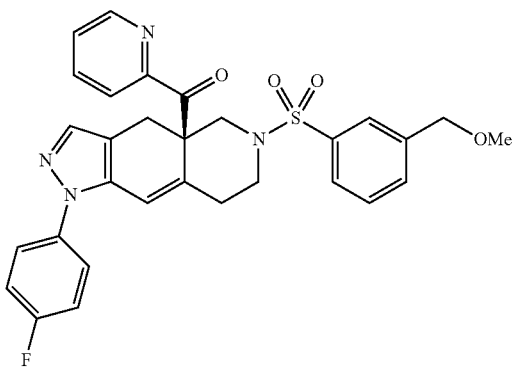 [SMILES: COCc1cccc(S(=O)(=O)N2CCC3=Cc4c(cnn4-c4ccc(F)cc4)C[C@]3(C(=O)c3ccccn3)C2)c1]

LCMS (Method F, ES-API): RT 2.54 min, m+H=559.3; 1H NMR (400 MHz, CDCl3): δ 8.67 (1H, ddd, J=4.7, 1.4, 0.8 Hz), 7.91-7.89 (1H, m), 7.83 (1H, dt, J=7.5, 1.5 Hz), 7.65 (1H, m), 7.62-7.59 (1H, m), 7.54-7.52 (1H, m), 7.49-7.40 (4H, m), 7.29 (1H, s), 7.18-7.13 (2H, m), 6.46 (1H, d, J=2.1 Hz), 5.50 (1H, dd, J=12.4, 2.1 Hz), 4.48 (2H, s), 4.30 (1H, d, J=16.9 Hz), 3.84-3.79 (1H, m), 3.42 (3H, s), 2.91-2.77 (2H, m), 2.69 (1H, d, J=12.1 Hz), 2.47-2.41 (2H, m).

Example 11AB. (R)-(1-(4-fluorophenyl)-6-((4-methyl-3,4-dihydro-2H-pyrido[3,2-b][1,4]oxazin-7-yl)sulfonyl)-4,4a,5,6,7,8-hexahydro-1H-pyrazolo[3,4-g]isoquinolin-4a-yl)(pyridin-2-yl)methanone

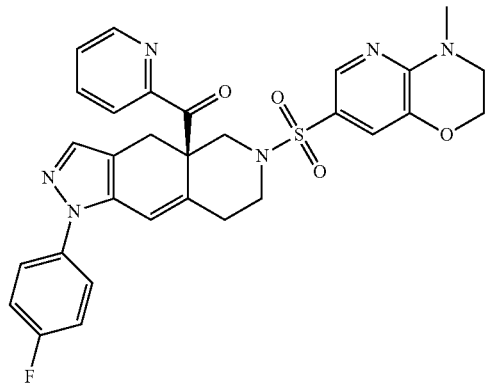 [SMILES: CN1CCOc2cc(S(=O)(=O)N3CCC4=Cc5c(cnn5-c5ccc(F)cc5)C[C@]4(C(=O)c4ccccn4)C3)cnc21]

LCMS (Method F, ES-API): RT 2.40 min, m+H=587.0; 1H NMR (400 MHz, CDCl3): δ 8.65 (1H, ddd, J=4.7, 1.7, 0.9 Hz), 8.06 (1H, d, J=2.1 Hz), 7.89 (1H, dt, J=7.8, 1.2 Hz), 7.82 (1H, td, J=7.8, 1.8 Hz), 7.47-7.41 (3H, m), 7.29 (1H, s), 7.19-7.13 (2H, m), 7.04 (1H, d, J=2.1 Hz), 6.48 (1H, d, J=2.1 Hz), 5.47 (1H, dd, J=12.2, 2.1 Hz), 4.30 (1H, d, J=17.0 Hz), 4.25-4.20 (2H, m), 3.82-3.77 (1H, m), 3.54-3.52 (2H, m), 3.19 (3H, s), 2.90 (1H, d, J=11.5 Hz), 2.85-2.75 (1H, m), 2.70 (1H, d, J=12.2 Hz), 2.52-2.45 (2H, m).

Example 11AC. (R)-(1-(4-fluorophenyl)-6-((2,3,4-trifluorophenyl)sulfonyl)-4,4a,5,6,7,8-hexahydro-1H-pyrazolo[3,4-g]isoquinolin-4a-yl)(pyridin-2-yl)methanone

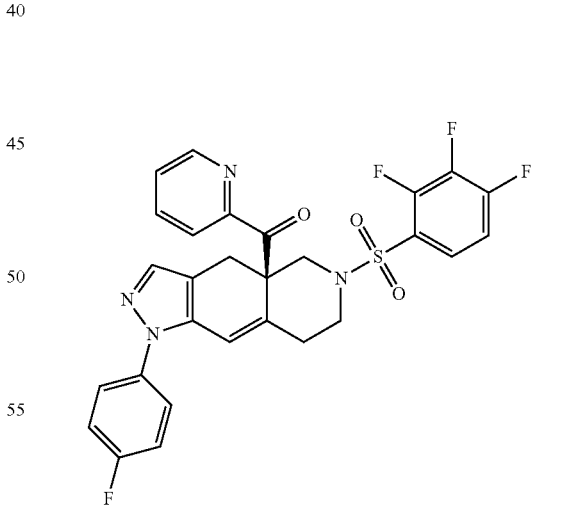

LCMS (Method F, ES-API): RT 2.69 min, m+H=569.0; 1H NMR (400 MHz, CDCl3): δ 8.62-8.59 (1H, m), 7.86-7.78 (2H, m), 7.49-7.40 (4H, m), 7.27 (1H, s), 7.19-7.13 (2H, m), 6.97-6.91 (1H, m), 6.52 (1H, s), 5.57 (1H, dd, J=12.8, 1.8 Hz), 4.24 (1H, d, J=16.9 Hz), 4.02-3.95 (1H, m), 3.09 (1H, d, J=12.3 Hz), 2.87-2.80 (3H, m), 2.57-2.49 (1H, m).

Example 11AD. (R)-(1-(4-fluorophenyl)-6-((6-(trifluoromethyl)pyridin-2-yl)sulfonyl)-4,4a,5,6,7,8-hexahydro-1H-pyrazolo[3,4-g]isoquinolin-4a-yl)(pyridin-2-yl)methanone

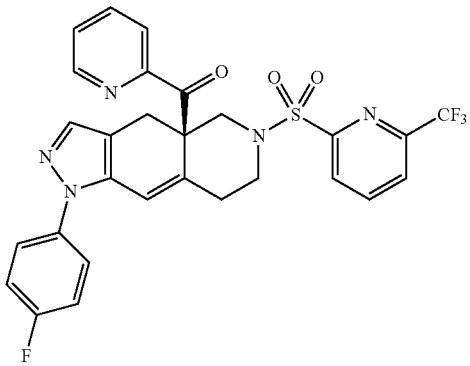 [SMILES: O=C(c1ccccn1)[C@]12Cc3cnn(-c4ccc(F)cc4)c3C=C1CCN(S(=O)(=O)c1cccc(C(F)(F)F)n1)C2]

LCMS (Method F, ES-API): RT 2.66 min, m+H=584.2; 1H NMR (400 MHz, CDCl3): δ 8.66-8.64 (1H, m), 8.07-8.03 (1H, m), 7.97 (1H, d, J=7.6 Hz), 7.85-7.79 (3H, m), 7.48-7.43 (3H, m), 7.30 (1H, s), 7.21-7.15 (2H, m), 6.54 (1H, d, J=2.1 Hz), 5.64 (1H, dd, J=13.2, 2.0 Hz), 4.30 (1H, d, J=16.9 Hz), 4.06-4.01 (1H, m), 3.32 (1H, d, J=13.0 Hz), 3.07 (1H, dd, J=12.6, 3.5 Hz), 2.91 (1H, d, J=16.9 Hz), 2.89-2.80 (1H, m), 2.54-2.50 (1H, m).

Example 11AE. (R)-(1-(4-fluorophenyl)-6-((6-(trifluoromethyl)pyridin-2-yl)sulfonyl)-4,4a,5,6,7,8-hexahydro-1H-pyrazolo[3,4-g]isoquinolin-4a-yl)(4-methylpyridin-2-yl)methanone

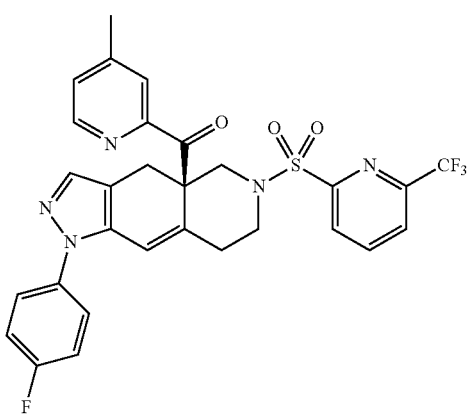 [SMILES: Cc1ccnc(C(=O)[C@]23Cc4cnn(-c5ccc(F)cc5)c4C=C2CCN(S(=O)(=O)c2cccc(C(F)(F)F)n2)C3)c1]

LCMS (Method F, ES-API): RT 2.77 min, m+H=598.2; 1H NMR (400 MHz, CDCl3): δ 8.49 (1H, d, J=4.9 Hz), 8.07-8.03 (1H, m), 7.98 (1H, d, J=7.7 Hz), 7.82 (1H, dd, 7.7, 1.1 Hz), 7.65 (1H, s), 7.48-7.43 (2H, m), 7.29 (1H, s), 7.27-7.26 (1H, m), 7.20-7.14 (2H, m), 6.53 (1H, d, J=2.0 Hz), 5.67 (1H, dd, J=12.8, 1.7 Hz), 4.29 (1H, d, J=16.9 Hz), 4.06-4.02 (1H, m), 3.31 (1H, d, J=13.0 Hz), 3.08 (1H, dd, J=12.6, 3.5 Hz), 2.92-2.80 (2H, m), 2.55-2.50 (1H, m), 2.39 (3H, s).

Example 11AF. (R)-(6-((3,4-dichlorophenyl)sulfonyl)-1-(4-fluorophenyl)-4,4a,5,6,7,8-hexahydro-1H-pyrazolo[3,4-g]isoquinolin-4a-yl)(pyridin-2-yl)methanone

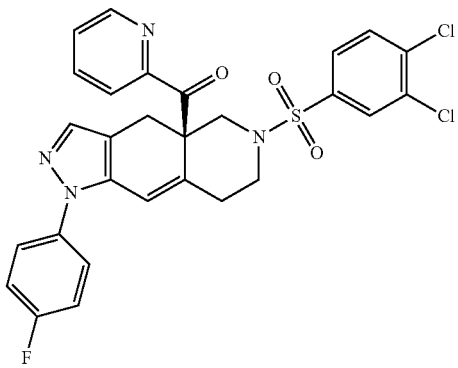 [SMILES: O=C(c1ccccn1)[C@]12Cc3cnn(-c4ccc(F)cc4)c3C=C1CCN(S(=O)(=O)c1ccc(Cl)c(Cl)c1)C2]

LCMS (Method F, ES-API): RT 2.88 min, m+H=582.9; 1H NMR (400 MHz, CDCl3): δ 8.61 (1H, ddd, J=4.7, 1.7, 1.0 Hz), 7.89-7.81 (2H, m), 7.74 (1H, dd, J=1.7, 0.5 Hz), 7.49-7.38 (5H, m), 7.28 (1H, s), 7.20-7.12 (2H, m), 6.50 (1H, d, J=2.0 Hz), 5.54 (1H, dd, J=12.4, 2.0 Hz), 4.26 (1H, d, J=16.9 Hz), 3.88 (1H, ddt, J=8.4, 3.9, 2.0 Hz), 2.93-2.79 (3H, m), 2.65-2.50 (2H, m).

Example 11AG. (R)-(1-(4-fluorophenyl)-6-((3-(trifluoromethyl)phenyl)sulfonyl)-4,4a,5,6,7,8-hexahydro-1H-pyrazolo[3,4-g]isoquinolin-4a-yl)(4-methylpyridin-2-yl)methanone

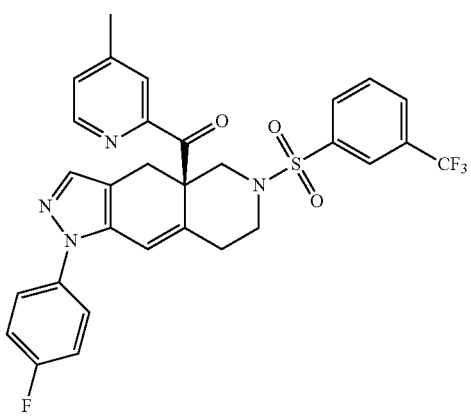 [SMILES: Cc1ccnc(C(=O)[C@]23Cc4cnn(-c5ccc(F)cc5)c4C=C2CCN(S(=O)(=O)c2cccc(C(F)(F)F)c2)C3)c1]

LCMS (Method F, ES-API): RT 2.83 min, m+H=597.0; 1H NMR (400 MHz, CDCl3): δ 8.49 (1H, dd, J=4.9, 0.38 Hz), 8.00-7.88 (2H, m), 7.80-7.78 (1H, m), 7.71-7.68 (1H, m), 7.61 (1H, t, J=7.8 Hz), 7.46-7.39 (2H, m), 7.29-7.27 (2H, m), 7.19-7.13 (2H, m), 6.48 (1H, d, J=2.0 Hz), 5.61 (1H, dd, J=12.3, 2.0 Hz), 4.27 (1H, d, J=16.9 Hz), 3.91-3.81 (1H, m), 2.92-2.78 (3H, m), 2.62-2.49 (2H, m), 2.40 (3H, s).

Example 11AH. (R)-(6-((1-ethyl-1H-pyrazol-4-yl)sulfonyl)-1-(4-fluorophenyl)-4,4a,5,6,7,8-hexahydro-1H-pyrazolo[3,4-g]isoquinolin-4a-yl)(4-methylpyridin-2-yl)methanone

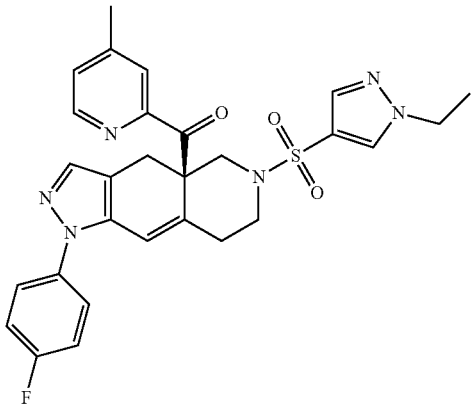 [SMILES: CCn1cc(S(=O)(=O)N2CCC3=Cc4c(cnn4-c4ccc(F)cc4)C[C@]3(C(=O)c3cc(C)ccn3)C2)cn1]

LCMS (Method F, ES-API): RT 2.39 min, m+H=547.0; 1H NMR (400 MHz, CDCl3): δ 8.51 (1H, d, J=4.9 Hz), 7.71 (2H, s), 7.66 (1H, d, J=0.6 Hz), 7.47-7.40 (2H, m), 7.30-7.27 (2H, m), 7.20-7.13 (2H, m), 6.48 (1H, d, J=2.0 Hz), 5.49 (1H, dd, J=12.0, 2.0 Hz), 4.30 (1H, d, J=16.9 Hz), 4.17 (2H, q, J=7.3 Hz), 3.82-3.71 (1H, m), 2.94-2.79 (2H, m), 2.69 (1H, d, J=12.0 Hz), 2.52-2.41 (2H, m), 2.40 (3H, s), 1.50 (3H, t, J=7.3 Hz).

Example 11AI. (R)-(6-((1,5-dimethyl-1H-pyrazol-4-yl)sulfonyl)-1-(4-fluorophenyl)-4,4a,5,6,7,8-hexahydro-1H-pyrazolo[3,4-g]isoquinolin-4a-yl)(4-methylpyridin-2-yl)methanone

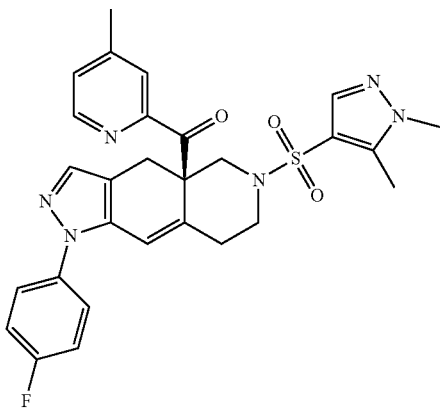 [SMILES: Cc1ccnc(C(=O)[C@]23Cc4cnn(-c5ccc(F)cc5)c4C=C2CCN(S(=O)(=O)c2cnn(C)c2C)C3)c1]

LCMS (Method F, ES-API): RT 2.33 min, m+H=547.0; 1H NMR (400 MHz, CDCl3): δ 8.46 (1H, d, J=4.9 Hz), 7.71-7.68 (1H, m), 7.61 (1H, s), 7.46-7.41 (2H, m), 7.27-7.25 (2H, m), 7.20-7.13 (2H, m), 6.49 (1H, d, J=2.0 Hz), 5.52 (1H, dd, J=12.1, 2.0 Hz), 4.24 (1H, d, J=16.9 Hz), 3.84-3.80 (1H, m), 3.69 (3H, m), 2.90-2.77 (3H, m), 2.61-2.48 (2H, m), 2.40 (3H, s), 2.34 (3H, s).

Example 11AJ. (R)-(1-(4-fluorophenyl)-6-((1-methyl-1H-pyrazol-5-yl)sulfonyl)-4,4a,5,6,7,8-hexahydro-1H-pyrazolo[3,4-g]isoquinolin-4a-yl)(4-methylpyridin-2-yl)methanone

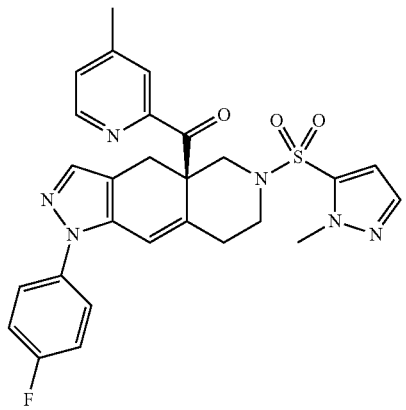 [SMILES: Cc1ccnc(C(=O)[C@]23Cc4cnn(-c5ccc(F)cc5)c4C=C2CCN(S(=O)(=O)c2ccnn2C)C3)c1]

LCMS (Method F, ES-API): RT 2.49 min, m+H=533.2; 1H NMR (400 MHz, CDCl3): δ 8.43 (1H, d, J=5.0 Hz), 7.68 (1H, m), 7.47-7.41 (2H, m), 7.32 (1H, d, J=2.0 Hz), 7.27-7.25 (2H, m), 7.20-7.14 (2H, m), 6.64 (1H, d, J=2.0 Hz), 6.52 (1H, br s), 5.59 (1H, dd, J=12.4, 2.2 Hz), 4.27 (1H, d, J=16.9 Hz), 3.92-3.89 (4H, m), 3.03 (1H, d, J=12.5 Hz), 2.90-2.76 (3H, m), 2.59-2.55 (1H, m), 2.40 (3H, s).

Example 11AK. (R)-(1-(4-fluorophenyl)-6-((1-methyl-1H-pyrazol-3-yl)sulfonyl)-4,4a,5,6,7,8-hexahydro-1H-pyrazolo[3,4-g]isoquinolin-4a-yl)(4-methylpyridin-2-yl)methanone

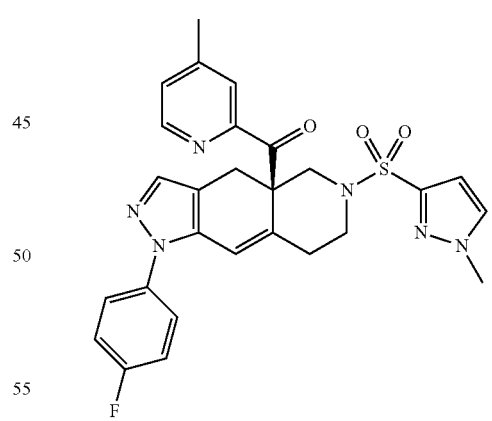

LCMS (Method F, ES-API): RT 2.36 min, m+H=533.2; 1H NMR (400 MHz, CDCl3): δ 8.51 (1H, dd, J=5.0, 0.5 Hz), 7.71 (1H, m), 7.47-7.42 (2H, m), 7.38 (1H, d, J=2.2 Hz), 7.30 (1H, s), 7.27-7.25 (1H, m), 7.19-7.13 (2H, m), 6.58 (1H, d, J=2.2 Hz), 6.49 (1H, d, J=2.1 Hz), 5.55 (1H, dd, J=12.4, 2.0 Hz), 4.33 (1H, d, J=16.9 Hz), 3.95 (3H, s), 3.88-3.83 (1H, m), 2.92 (1H, d, J=16.9 Hz), 2.91 (1H, d, J=12.4 Hz), 2.88-2.79 (1H, m), 2.68-2.61 (1H, m), 2.49-2.44 (1H, m), 2.39 (3H, s).

Example 11AL. (R)-(6-((4-fluoro-3-methylphenyl)sulfonyl)-1-(4-fluorophenyl)-4,4a,5,6,7,8-hexahydro-1H-pyrazolo[3,4-g]isoquinolin-4a-yl)(4-methylpyridin-2-yl)methanone

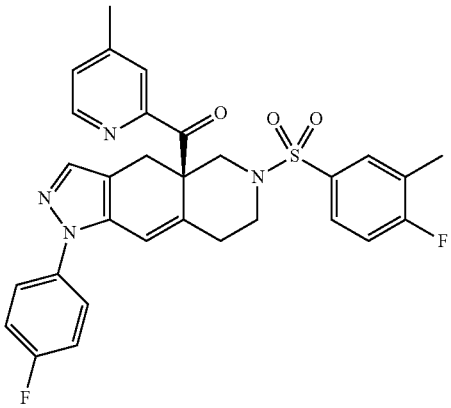 [SMILES: Cc1ccnc(C(=O)[C@]23Cc4cnn(-c5ccc(F)cc5)c4C=C2CCN(S(=O)(=O)c2ccc(F)c(C)c2)C3)c1]

LCMS (Method F, ES-API): RT 2.90 min, m+H=561.2; 1H NMR (400 MHz, CDCl3): δ 8.50 (1H, dd, J=5.0, 0.4 Hz), 7.69-7.68 (1H, m), 7.53-7.49 (2H, m), 7.45-7.40 (2H, m), 7.28-7.26 (2H, m), 7.19-7.13 (2H, m), 7.05-7.00 (1H, m), 6.47 (1H, d, J=2.1 Hz), 5.52 (1H, dd, J=12.4, 2.3 Hz), 4.28 (1H, d, J=16.9 Hz), 3.86-3.81 (1H, m), 2.89-2.78 (2H, m), 2.74 (1H, d, J=12.3 Hz), 2.54-2.46 (2H, m), 2.40 (3H, s), 2.28 (3H, d, J=1.7 Hz).

Example 11AM. (R)-(1-(4-fluorophenyl)-6-((4-methyl-3,4-dihydro-2H-pyrido[3,2-b][1,4]oxazin-7-yl)sulfonyl)-4,4a,5,6,7,8-hexahydro-1H-pyrazolo[3,4-g]isoquinolin-4a-yl)(4-methylpyridin-2-yl)methanone

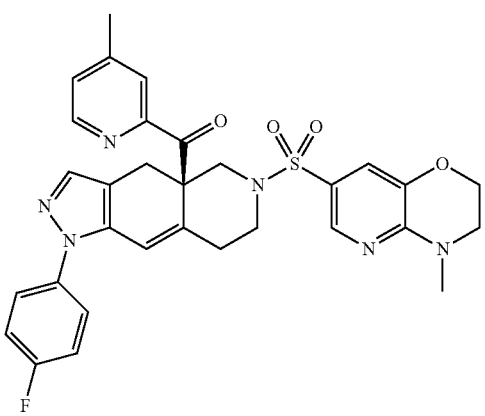 [SMILES: Cc1ccnc(C(=O)[C@]23Cc4cnn(-c5ccc(F)cc5)c4C=C2CCN(S(=O)(=O)c2cnc4c(c2)OCCN4C)C3)c1]

LCMS (Method F, ES-API): RT 2.58 min, m+H=601.3; 1H NMR (400 MHz, CDCl3): δ 8.49 (1H, d, J=4.9 Hz), 8.06 (1H, d, J=2.0 Hz), 7.71 (1H, m), 7.46-7.41 (2H, m), 7.28 (1H, s), 7.25 (1H, m), 7.19-7.12 (2H, m), 7.04 (1H, d, J=2.0 Hz), 6.46 (1H, d, J=2.1 Hz), 5.50 (1H, dd, J=12.3, 2.1 Hz), 4.29 (1H, d, J=16.9 Hz), 4.22-4.20 (2H, m), 3.80-3.76 (1H, m), 3.54-3.52 (2H, m), 3.19 (3H, s), 2.88 (1H, d, J=16.9 Hz), 2.84-2.75 (1H, m), 2.69 (1H, d, J=12.3 Hz), 2.52-2.44 (2H, m), 2.40 (3H, s).

Example 11AN. (R)-(6-((2,3-dihydrobenzofuran-5-yl)sulfonyl)-1-(4-fluorophenyl)-4,4a,5,6,7,8-hexahydro-1H-pyrazolo[3,4-g]isoquinolin-4a-yl)(4-methylpyridin-2-yl)methanone

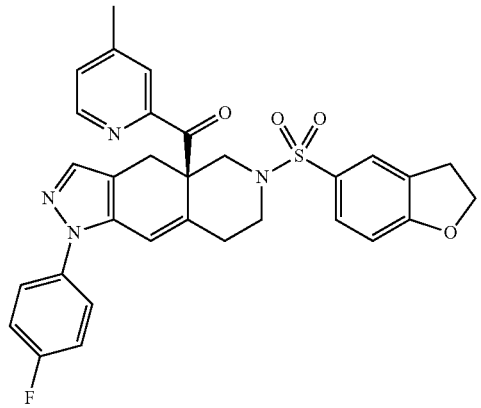 [SMILES: Cc1ccnc(C(=O)[C@]23Cc4cnn(-c5ccc(F)cc5)c4C=C2CCN(S(=O)(=O)c2ccc4c(c2)CCO4)C3)c1]

LCMS (Method F, ES-API): RT 2.73 min, m+H=571.2; 1H NMR (400 MHz, CDCl3): δ 8.47 (1H, d, J=4.9 Hz), 7.71-7.70 (1H, m), 7.49-7.41 (4H, m), 7.27-7.26 (2H, m), 7.19-7.13 (2H, m), 6.78-6.75 (1H, m), 6.47 (1H, d, J=2.0 Hz), 5.51 (1H, dd, J=12.3, 2.1 Hz), 4.67-4.63 (2H, m), 4.30 (1H, d, J=16.9 Hz), 3.84-3.79 (1H, m), 3.24-3.20 (2H, m), 2.90-2.78 (2H, m), 2.67 (1H, d, J=12.3 Hz), 2.48-2.40 (5H, m).

Example 11AO. (R)-5-((1-(4-fluorophenyl)-4a-(4-methylpicolinoyl)-4a,5,7,8-tetrahydro-1H-pyrazolo[3,4-g]isoquinolin-6(4H)-yl)sulfonyl)-1-methylindolin-2-one LCMS (Method F, ES-API): RT 2.44 min, m+H=598.3; 1H NMR (400 MHz, CDCl3): δ 8.44 (1H, d, J=4.9 Hz), 7.70-7.68 (2H, m), 7.52 (1H, d, J=0.9 Hz), 7.45-7.40 (2H, m), 7.26 (1H, s), 7.24-7.23 (1H, m), 7.19-7.13 (2H, m), 6.82 (1H, d, J=8.3 Hz), 6.47 (1H, d, J=2.0 Hz), 5.53 (1H, dd, J=12.3, 2.0 Hz), 4.25 (1H, d, J=16.9 Hz), 3.88-3.84 (1H, m), 3.53, 3.47 (2H, AB system, J=22.4 Hz), 3.22 (3H, s), 2.89-2.79 (2H, m), 2.72 (1H, d, J=12.3 Hz), 2.53-2.46 (2H, m), 2.39 (3H, s).

Example 11AP. (R)-(1-(4-fluorophenyl)-6-((3-(methylsulfonyl)phenyl)sulfonyl)-4,4a,5,6,7,8-hexahydro-1H-pyrazolo[3,4-g]isoquinolin-4a-yl)(4-methylpyridin-2-yl)methanone

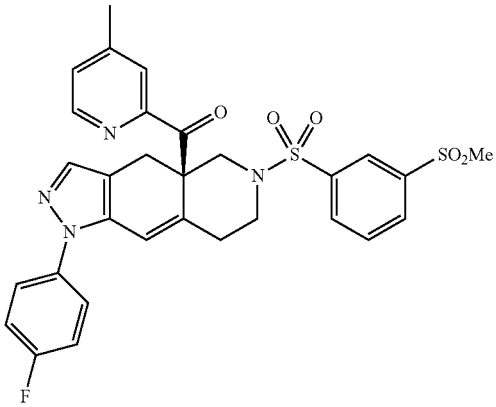 [SMILES: Cc1ccnc(C(=O)[C@]23Cc4cnn(-c5ccc(F)cc5)c4C=C2CCN(S(=O)(=O)c2cccc(S(C)(=O)=O)c2)C3)c1]

LCMS (Method F, ES-API): RT 2.52 min, m+H=607.2; 1H NMR (400 MHz, CDCl3): δ 8.49 (1H, d, J=4.9 Hz), 8.26-8.25 (1H, m), 8.09 (1H, ddd, J=7.9, 1.7, 1.2 Hz), 7.97 (1H, ddd, J=7.9, 1.7, 1.2 Hz), 7.69-7.66 (1H, m), 7.45-7.40 (2H, m), 7.29-7.26 (2H, m), 7.19-7.13 (2H, m), 6.48 (1H, d, J=2.1 Hz), 5.60 (1H, dd, J=12.3, 2.1 Hz), 4.23 (1H, d, J=16.9 Hz), 3.92-3.87 (1H, m), 3.08 (3H, s), 2.88-2.79 (3H, m), 2.63-2.49 (2H, m), 2.40 (3H, s).

Example 11AQ. (R)-(6-((1,3-dimethyl-1H-pyrazol-4-yl)sulfonyl)-1-(4-fluorophenyl)-4,4a,5,6,7,8-hexahydro-1H-pyrazolo[3,4-g]isoquinolin-4a-yl)(4-methylpyridin-2-yl)methanone

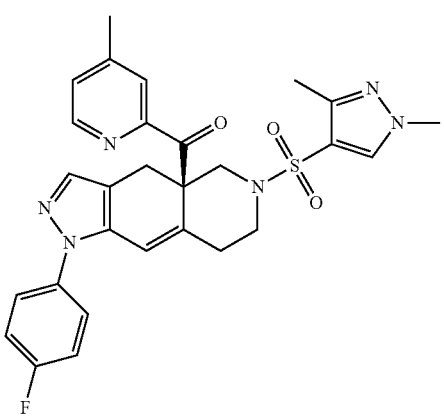 [SMILES: Cc1ccnc(C(=O)[C@]23Cc4cnn(-c5ccc(F)cc5)c4C=C2CCN(S(=O)(=O)c2cn(C)nc2C)C3)c1]

LCMS (Method F, ES-API): RT 2.33 min, m+H=547.0; 1H NMR (400 MHz, CDCl3): δ 8.44 (1H, d, J=4.9 Hz), 7.71-7.69 (1H, m), 7.59 (1H, m), 7.46-7.41 (2H, m), 7.28-7.26 (2H, m), 7.20-7.13 (2H, m), 6.50 (1H, d, J=2.0 Hz), 5.49 (1H, dd, J=12.1, 2.0 Hz), 4.28 (1H, d, J=16.9 Hz), 3.85-3.76 (4H, m), 2.92-2.78 (3H, m), 2.63-2.48 (2H, m), 2.40 (3H, s), 2.27 (3H, s).

Example 11AR. (R)-(6-((2,3-dihydrobenzo[b][1,4]dioxin-6-yl)sulfonyl)-1-(4-fluorophenyl)-4,4a,5,6,7,8-hexahydro-1H-pyrazolo[3,4-g]isoquinolin-4a-yl)(4-methylpyridin-2-yl)methanone

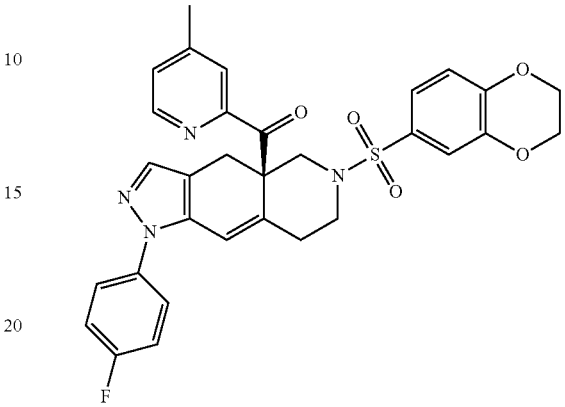

LCMS (Method F, ES-API): RT 2.60 min, m+H=587.0; 1H NMR (400 MHz, CDCl3): δ 8.50 (1H, d, J=4.9 Hz), 7.71 (1H, s), 7.45-7.41 (2H, m), 7.28-7.26 (2H, m), 7.22-7.13 (4H, m), 6.89 (1H, d, J=8.5 Hz), 6.46 (1H, d, J=1.9 Hz), 5.49 (1H, dd, J=12.2, 1.9 Hz), 4.31-4.25 (5H, m), 3.81-3.73 (1H, m), 2.92-2.77 (2H, m), 2.68 (1H, d, J=12.2 Hz), 2.50-2.39 (5H, m).

Example 11AS. (R)-(6-((3-fluoro-4-(trifluoromethyl)phenyl)sulfonyl)-1-(4-fluorophenyl)-4,4a,5,6,7,8-hexahydro-1H-pyrazolo[3,4-g]isoquinolin-4a-yl)(4-methylpyridin-2-yl)methanone

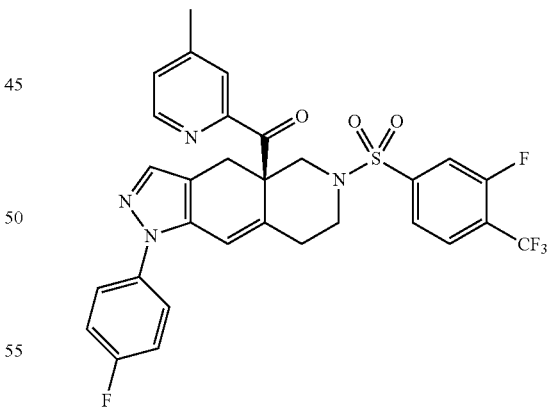

LCMS (Method F, ES-API): RT 3.03 min, m+H=615.2; 1H NMR (400 MHz, CDCl3): δ 8.47 (1H, dd, J=4.9, 0.3 Hz), 7.69-7.65 (2H, m), 7.58-7.56 (1H, m), 7.48 (1H, br d, J=9.4 Hz), 7.45-7.40 (2H, m), 7.28 (1H, ddd, J=4.9, 1.6, 0.7 Hz), 7.26 (1H, s), 7.19-7.13 (2H, m), 6.49 (1H, d, J=2.0 Hz), 5.64 (1H, dd, J=12.5, 2.0 Hz), 4.23 (1H, d, J=16.9 Hz), 3.92-3.88 (1H, m), 2.91-2.80 (3H, m), 2.69-2.63 (1H, m), 2.55-2.50 (1H, m), 2.39 (3H, s).

Example 11AT. (R)-(6-((3-fluoro-4-(trifluoromethyl)phenyl)sulfonyl)-1-(4-fluorophenyl)-4,4a,5,6,7,8-hexahydro-1H-pyrazolo[3,4-g]isoquinolin-4a-yl)(pyridin-2-yl)methanone

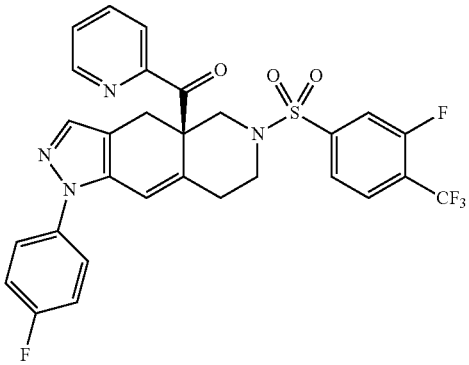 [SMILES: O=C(c1ccccn1)[C@]12Cc3cnn(-c4ccc(F)cc4)c3C=C1CCN(S(=O)(=O)c1ccc(C(F)(F)F)c(F)c1)C2]

LCMS (Method F, ES-API): RT 2.93 min, m+H=601.2; 1H NMR (400 MHz, CDCl3): δ 8.64 (1H, ddd, J=4.9, 1.5, 1.1 Hz), 7.87-7.81 (2H, m), 7.71-7.67 (1H, m), 7.57 (1H, br d, J=8.2 Hz), 7.51-7.47 (2H, m), 7.45-7.40 (2H, m), 7.28 (1H, s), 7.19-7.13 (2H, m), 6.50 (1H, d, J=2.0 Hz), 5.59 (1H, dd, J=12.4, 2.0 Hz), 4.25 (1H, d, J=16.9 Hz), 3.92-3.87 (1H, m), 2.91-2.80 (3H, m), 2.67-2.61 (1H, m), 2.55-2.51 (1H, m).

Example 11AU. (R)-3-((4a-(4-ethylpicolinoyl)-1-(4-fluorophenyl)-4a,5,7,8-tetrahydro-1H-pyrazolo[3,4-g]isoquinolin-6(4H)-yl)sulfonyl)benzonitrile

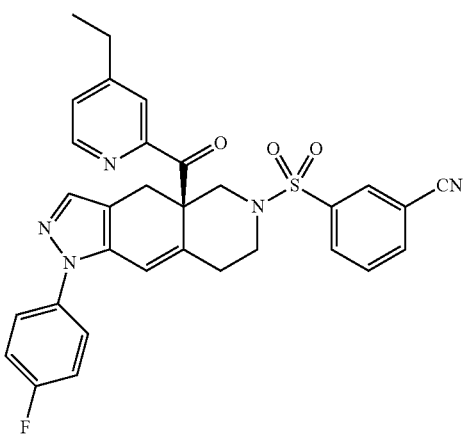 [SMILES: CCc1ccnc(C(=O)[C@]23Cc4cnn(-c5ccc(F)cc5)c4C=C2CCN(S(=O)(=O)c2cccc(C#N)c2)C3)c1]

LCMS (Method F, ES-API): RT 2.79 min, m+H=568.2; 1H NMR (400 MHz, CDCl3): δ 8.53 (1H, dd, J=4.9, 0.5 Hz), 7.95 (1H, m), 7.91 (1H, ddd, J=7.9, 1.9, 1.2 Hz), 7.78 (1H, ddd, J=7.9, 1.2, 0.3 Hz), 7.71-7.70 (1H, m), 7.59 (1H, dt, J=7.9, 0.5 Hz), 7.45-7.40 (2H, m), 7.33-7.32 (1H, m), 7.27 (1H, s), 7.19-7.13 (2H, m), 6.49 (1H, d, J=2.0 Hz), 5.64 (1H, dd, J=12.3, 2.0 Hz), 4.25 (1H, d, J=16.9 Hz), 3.91-3.86 (1H, m), 2.88-2.80 (3H, m), 2.71 (2H, q, J=7.7 Hz), 2.63-2.50 (2H, m), 1.27 (3H, t, J=7.7 Hz).

Example 11AV. (R)-(4-ethylpyridin-2-yl)(1-(4-fluorophenyl)-6-((6-(trifluoromethyl)pyridin-2-yl)sulfonyl)-4,4a,5,6,7,8-hexahydro-1H-pyrazolo[3,4-g]isoquinolin-4a-yl)methanone

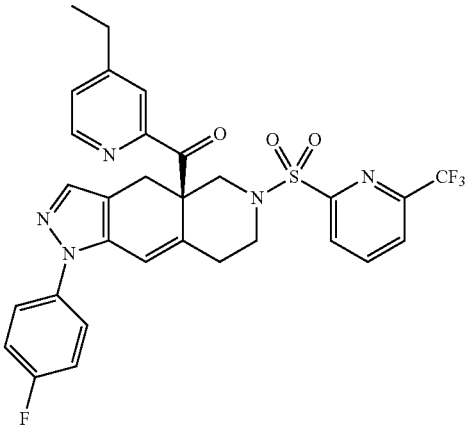 [SMILES: CCc1ccnc(C(=O)[C@]23Cc4cnn(-c5ccc(F)cc5)c4C=C2CCN(S(=O)(=O)c2cccc(C(F)(F)F)n2)C3)c1]

LCMS (Method F, ES-API): RT 2.93 min, m+H=612.2; 1H NMR (400 MHz, CDCl3): δ 8.51 (1H, dd, J=4.9, 0.5 Hz), 8.06-8.02 (1H, m), 7.99-7.97 (1H, m), 7.81 (1H, dd, J=7.9, 1.2 Hz), 7.67 (1H, m), 7.48-7.43 (2H, m), 7.29 (1H, s), 7.28-7.27 (1H, m), 7.20-7.14 (2H, m), 6.53 (1H, d, J=2.0 Hz), 5.67 (1H, dd, J=12.3, 2.0 Hz), 4.28 (1H, d, J=16.9 Hz), 4.06-4.02 (1H, m), 3.31 (1H, d, J=13.0 Hz), 3.12-3.05 (1H, m), 2.91-2.81 (2H, m), 2.69 (2H, q, J=7.7 Hz), 2.54-2.50 (1H, m), 1.26 (3H, t, J=7.7 Hz).

Example 11AW. (R)-3-((1-(4-fluorophenyl)-4a-(4-methylpicolinoyl)-4a,5,7,8-tetrahydro-1H-pyrazolo[3,4-g]isoquinolin-6(4H)-yl)sulfonyl)benzoic acid

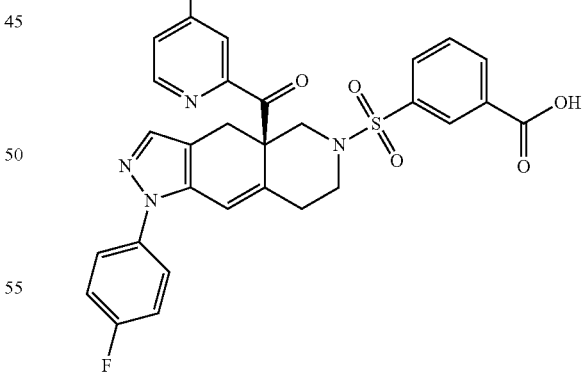

LCMS (Method F, ES-API): RT 2.47 min, m+H=573.0; 1H NMR (400 MHz, CDCl3): δ 8.55 (1H, d, J=5.0 Hz), 8.17 (1H, dt, J=7.9, 1.2 Hz), 8.07 (1H, t, J=1.7 Hz), 7.88 (1H, dt, J=8.2, 1.2 Hz), 7.70 (1H, t, J=7.9 Hz), 7.60 (1H, m), 7.51-7.45 (3H, m), 7.41-7.35 (3H, m), 6.63 (1H, s), 5.39 (1H, d, J=12.2 Hz), 4.13 (1H, d, J=17.0 Hz), 3.77-3.71 (1H, m), 2.92-2.84 (2H, m), 2.69-2.44 (3H, m), 2.38 (3H, s).

Example 11AX. (R)-(6-((3,5-dimethylisoxazol-4-yl)sulfonyl)-1-(4-fluorophenyl)-4,4a,5,6,7,8-hexahydro-1H-pyrazolo[3,4-g]isoquinolin-4a-yl)(4-methylpyridin-2-yl)methanone

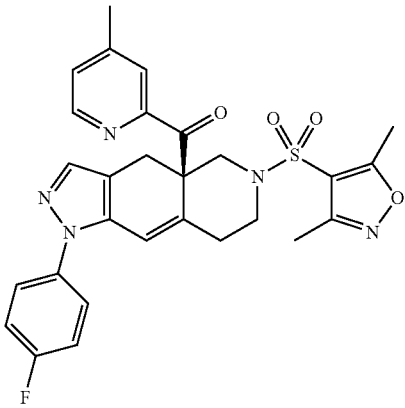 [SMILES: Cc1ccnc(C(=O)[C@]23Cc4cnn(-c5ccc(F)cc5)c4C=C2CCN(S(=O)(=O)c2c(C)noc2C)C3)c1]

LCMS (Method F, ES-API): RT 2.79 min, m+H=548.2; 1H NMR (400 MHz, CDCl3): δ 8.38 (1H, d, J=4.9 Hz), 7.65-7.64 (1H, m), 7.46-7.41 (2H, m), 7.28-7.26 (1H, m), 7.25 (1H, s), 7.20-7.14 (2H, m), 6.52 (1H, s), 5.49 (1H, dd, J=12.6, 2.1 Hz), 4.24 (1H, d, J=16.9 Hz), 3.95-3.92 (1H, m), 3.04 (1H, d, J=12.6 Hz), 2.90-2.79 (3H, m), 2.62-2.55 (1H, m), 2.53 (3H, s), 2.39 (3H, s), 2.21 (3H, s).

Example 11AY. (R)-(6-((1-ethyl-1H-pyrazol-4-yl)sulfonyl)-1-(4-fluorophenyl)-4,4a,5,6,7,8-hexahydro-1H-pyrazolo[3,4-g]isoquinolin-4a-yl)(pyridin-2-yl)methanone

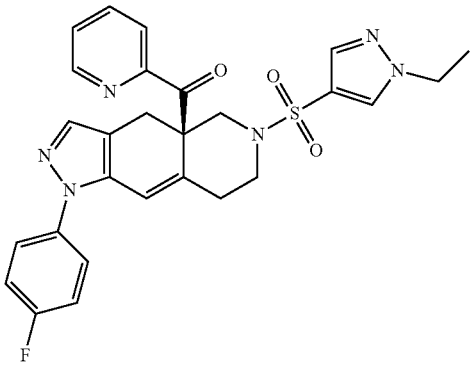 [SMILES: CCn1cc(S(=O)(=O)N2CCC3=Cc4c(cnn4-c4ccc(F)cc4)C[C@]3(C(=O)c3ccccn3)C2)cn1]

LCMS (Method F, ES-API): RT 2.28 min, m+H=533.0; 1H NMR (400 MHz, CDCl3): δ 8.66 (1H, ddd, J=4.7, 1.7, 0.9 Hz), 7.92-7.87 (1H, m), 7.83 (1H, td, J=7.5, 1.7 Hz), 7.71 (1H, s), 7.66 (1H, s), 7.48-7.41 (3H, m), 7.30 (1H, s), 7.21-7.13 (2H, m), 6.49 (1H, d, J=2.0 Hz), 5.46 (1H, dd, J=12.0, 2.0 Hz), 4.31 (1H, d, J=16.9 Hz), 4.17 (2H, q, J=7.3 Hz), 3.80-3.75 (1H, m), 2.95-2.77 (2H, m), 2.69 (1H, d, J=12.0 Hz), 2.52-2.40 (2H, m), 1.50 (3H, t, J=7.3 Hz).

Example 11AZ. (R)-(1-phenyl-6-((3-(trifluoromethyl)phenyl)sulfonyl)-4,4a,5,6,7,8-hexahydro-1H-pyrazolo[3,4-g]isoquinolin-4a-yl)(pyridin-2-yl)methanone

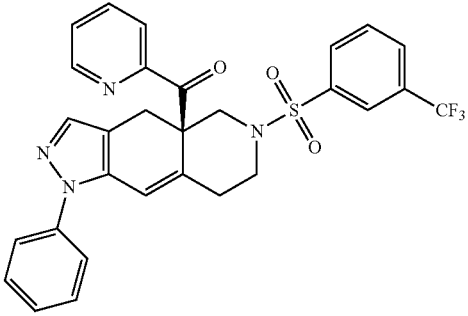 [SMILES: O=C(c1ccccn1)[C@]12Cc3cnn(-c4ccccc4)c3C=C1CCN(S(=O)(=O)c1cccc(C(F)(F)F)c1)C2]

LCMS (Method F, ES-API): RT 2.72 min, m+H=565.0; 1H NMR (400 MHz, CDCl3): δ 8.64 (1H, ddd, J=4.7, 1.7, 0.9 Hz), 7.94-7.78 (5H, m), 7.61 (1H, t, J=7.8 Hz), 7.50-7.45 (5H, m), 7.39-7.33 (1H, m), 7.29 (1H, s), 6.56 (1H, d, J=2.1 Hz), 5.56 (1H, dd, J=12.3, 2.1 Hz), 4.25 (1H, d, J=16.9 Hz), 3.90-3.84 (1H, m), 2.92-2.78 (3H, m), 2.58-2.48 (2H, m).

Example 11BA. (R)-(6-((1,3-dimethyl-1H-pyrazol-5-yl)sulfonyl)-1-(4-fluorophenyl)-4,4a,5,6,7,8-hexahydro-1H-pyrazolo[3,4-g]isoquinolin-4a-yl)(4-methylpyridin-2-yl)methanone

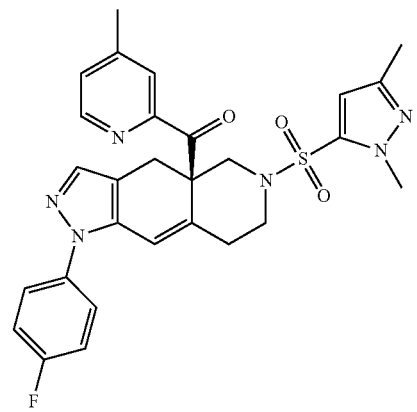 [SMILES: Cc1ccnc(C(=O)[C@]23Cc4cnn(-c5ccc(F)cc5)c4C=C2CCN(S(=O)(=O)c2cc(C)nn2C)C3)c1]

LCMS (Method F, ES-API): RT 2.54 min, m+H=547.1; 1H NMR (400 MHz, CDCl3): δ 8.42 (1H, d, J=4.9 Hz), 7.70-7.68 (1H, m), 7.48-7.41 (2H, m), 7.26-7.24 (2H, m), 7.21-7.14 (2H, m), 6.52 (1H, d, J=1.9 Hz), 6.40 (1H, d, J=0.39 Hz), 5.58 (1H, dd, J=12.5, 1.9 Hz), 4.28 (1H, d, J=16.8 Hz), 3.94-3.87 (1H, m), 3.84 (3H, s), 3.02 (1H, d, J=12.5 Hz), 2.91-2.75 (3H, m), 2.60-2.53 (1H, m), 2.39 (3H, s), 2.17 (3H, s).

Example 11BB. (R)-(1-(4-fluorophenyl)-6-((2-(trifluoromethyl)pyridin-4-yl)sulfonyl)-4,4a,5,6,7,8-hexahydro-1H-pyrazolo[3,4-g]isoquinolin-4a-yl)(4-methylpyridin-2-yl)methanone

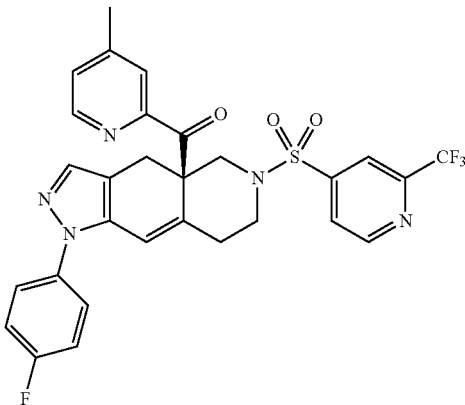 [SMILES: Cc1ccnc(C(=O)[C@]23Cc4cnn(-c5ccc(F)cc5)c4C=C2CCN(S(=O)(=O)c2ccnc(C(F)(F)F)c2)C3)c1]

LCMS (Method F, ES-API): RT 2.99 min, m+H=598.2; 1H NMR (400 MHz, CDCl3): δ 8.83 (1H, d, J=5.0 Hz), 8.46 (1H, dd, J=5.0, 0.4 Hz), 7.86 (1H, m), 7.71 (1H, dd, J=5.0, 1.3 Hz), 7.63-7.62 (1H, m), 7.45-7.40 (2H, m), 7.29-7.26 (2H, m), 7.19-7.13 (2H, m), 6.50 (1H, d, J=2.0 Hz), 5.64 (1H, dd, J=12.6, 2.0 Hz), 4.20 (1H, d, J=16.9 Hz), 3.95-3.90 (1H, m), 2.97 (1H, d, J=12.6 Hz), 2.88-2.80 (2H, m), 2.77-2.70 (1H, m), 2.57-2.53 (1H, m), 2.39 (3H, s).

Example 11BC. (R)-(1-(4-fluorophenyl)-6-((4-(trifluoromethyl)pyridin-2-yl)sulfonyl)-4,4a,5,6,7,8-hexahydro-1H-pyrazolo[3,4-g]isoquinolin-4a-yl)(4-methylpyridin-2-yl)methanone

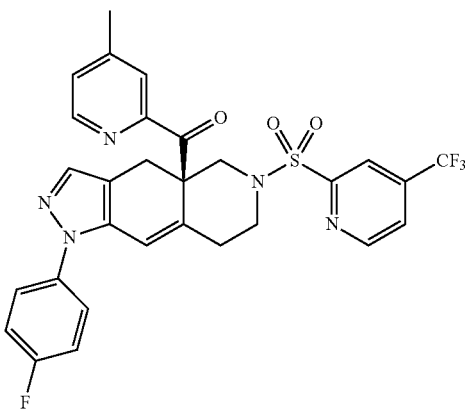 [SMILES: Cc1ccnc(C(=O)[C@]23Cc4cnn(-c5ccc(F)cc5)c4C=C2CCN(S(=O)(=O)c2cc(C(F)(F)F)ccn2)C3)c1]

LCMS (Method F, ES-API): RT 3.13 min, m+H=598.2; 1H NMR (400 MHz, CDCl3): δ 8.82 (1H, d, J=4.9 Hz), 8.50 (1H, dd, J=4.9, 0.9 Hz), 7.98 (1H, m), 7.65-7.62 (2H, m), 7.47-7.42 (2H, m), 7.27-7.26 (2H, m), 7.20-7.14 (2H, m), 6.51 (1H, d, J=2.0 Hz), 5.78 (1H, dd, J=12.9, 2.0 Hz), 4.25 (1H, d, J=16.9 Hz), 4.07-4.02 (1H, m), 3.28 (1H, d, J=12.9 Hz), 3.02-2.96 (1H, m), 2.92-2.83 (2H, m), 2.54-2.49 (1H, m), 2.38 (3H, s).

Example 11BD. (R)-(1-(4-fluorophenyl)-6-((5-methyl-1H-pyrazol-4-yl)sulfonyl)-4,4a,5,6,7,8-hexahydro-1H-pyrazolo[3,4-g]isoquinolin-4a-yl)(4-methylpyridin-2-yl)methanone LCMS (Method F, ES-API): RT 2.54 min, m+H=533.2; 1H NMR (400 MHz, CDCl3): δ 8.45 (1H, d, J=4.9 Hz), 7.74 (1H, s), 7.71-7.70 (1H, m), 7.46-7.41 (2H, m), 7.28 (1H, s) 7.26-7.25 (2H, m), 7.20-7.14 (2H, m), 6.49 (1H, d, J=2.0 Hz), 5.52 (1H, dd, J=12.0, 2.0 Hz), 4.27 (1H, d, J=16.9 Hz), 3.84-3.81 (1H, m), 2.91-2.78 (3H, m), 2.60-2.49 (2H, m), 2.39 (6H, s).

Example 11BE. (R)-(1-(4-fluorophenyl)-6-((2-(trifluoromethyl)pyridin-4-yl)sulfonyl)-4,4a,5,6,7,8-hexahydro-1H-pyrazolo[3,4-g]isoquinolin-4a-yl)(pyridin-2-yl)methanone LCMS (Method F, ES-API): RT 3.07 min, m+H=584.2; 1H NMR (400 MHz, CDCl3): δ 8.86 (1H, d, J=5.0 Hz), 8.64 (1H, dt, J=5.0, 1.6 Hz), 7.87 (1H, m), 7.85-7.83 (2H, m), 7.72 (1H, dd, J=5.0, 1.3 Hz), 7.52-7.46 (1H, m), 7.45-7.40 (2H, m), 7.28 (1H, s), 7.20-7.14 (2H, m), 6.51 (1H, d, J=2.0 Hz), 5.61 (1H, dd, J=12.5, 2.1 Hz), 4.22 (1H, d, J=16.9 Hz), 3.94-3.90 (1H, m), 2.94 (1H, d, J=12.5 Hz), 2.90-2.80 (2H, m), 2.73-2.66 (1H, m), 2.57-2.53 (1H, m).

Example 11BF. (R)-(6-((4-chloro-3-(trifluoromethyl)phenyl)sulfonyl)-1-(4-fluorophenyl)-4,4a,5,6,7,8-hexahydro-1H-pyrazolo[3,4-g]isoquinolin-4a-yl)(pyridin-2-yl)methanone

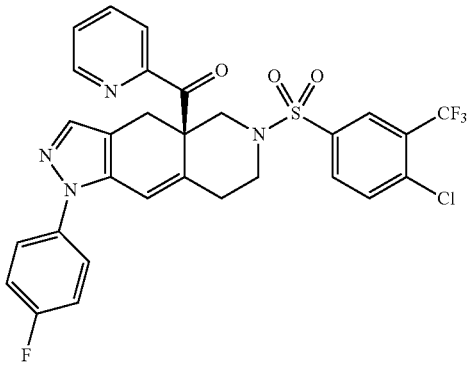 [SMILES: O=C(c1ccccn1)[C@]12Cc3cnn(-c4ccc(F)cc4)c3C=C1CCN(S(=O)(=O)c1ccc(Cl)c(C(F)(F)F)c1)C2]

LCMS (Method F, ES-API): RT 3.39 min, m+H 616.8; 1H NMR (400 MHz, CDCl3): δ 8.60-8.58 (1H, m), 7.97 (1H, d, J=2.1 Hz), 7.85-7.80 (2H, m), 7.76 (1H, dd, J=8.4, 2.1 Hz), 7.52 (1H, d, J=8.5 Hz), 7.48-7.40 (3H, m), 7.27 (1H, m), 7.19-7.13 (2H, m), 6.50 (1H, d, J=2.1 Hz), 5.54 (1H, dd, J=12.6, 2.0 Hz), 4.22 (1H, d, J=16.9 Hz), 3.93-3.88 (1H, m), 2.90-2.80 (3H, m), 2.68-2.61 (1H, m), 2.56-2.51 (1H, m).

Example 11BG. (R)-(6-((3-chloro-4-methylphenyl)sulfonyl)-1-(4-fluorophenyl)-4,4a,5,6,7,8-hexahydro-1H-pyrazolo[3,4-g]isoquinolin-4a-yl)(pyridin-2-yl)methanone

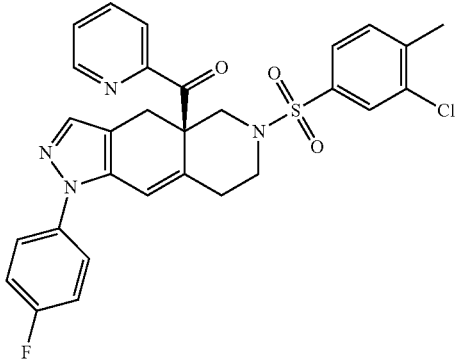 [SMILES: Cc1ccc(S(=O)(=O)N2CCC3=Cc4c(cnn4-c4ccc(F)cc4)C[C@]3(C(=O)c3ccccn3)C2)cc1Cl]

LCMS (Method F, ES-API): RT 2.81 min, m+H 563.0; 1H NMR (400 MHz, CDCl3): δ 8.64 (1H, ddd, J=4.7, 1.8, 0.9 Hz), 7.91-7.87 (1H, m), 7.83 (1H, td, J=7.4, 1.7 Hz), 7.64 (1H, d, J=1.8 Hz), 7.50-7.40 (4H, m), 7.31 (1H, s), 7.29 (1H, s), 7.20-7.12 (2H, m), 6.48 (1H, d, J=2.1 Hz), 5.52 (1H, dd, J=12.2, 2.1 Hz), 4.29 (1H, d, J=16.9 Hz), 3.86-3.82 (1H, m), 2.92-2.70 (3H, m), 2.54-2.47 (2H, m), 2.40 (3H, s).

Example 11BH. (R)-(6-((3,4-difluorophenyl)sulfonyl)-1-(4-fluorophenyl)-4,4a,5,6,7,8-hexahydro-1H-pyrazolo[3,4-g]isoquinolin-4a-yl)(2-(pyrrolidin-1-yl)pyridin-4-yl)methanone

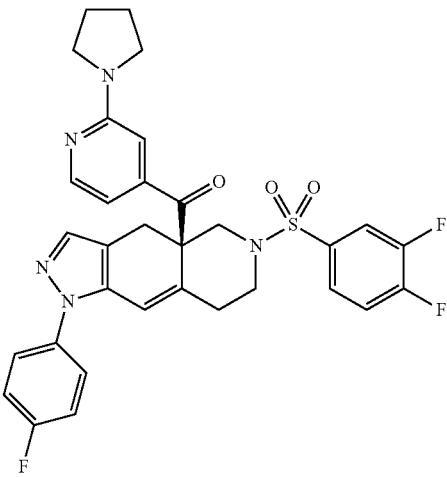 [SMILES: O=C(c1ccnc(N2CCCC2)c1)[C@]12Cc3cnn(-c4ccc(F)cc4)c3C=C1CCN(S(=O)(=O)c1ccc(F)c(F)c1)C2]

LCMS (Method F, ES-API): RT 2.11 min, m+H=619.9; 1H NMR (400 MHz, CDCl3): δ 8.14 (1H, d, J=5.0 Hz), 7.69-7.59 (2H, m), 7.46 (1H, s), 7.40-7.35 (3H, m), 7.21-7.15 (2H, m), 6.50 (1H, dd, J=5.2, 1.2 Hz), 6.39 (2H, d, J=14.0 Hz), 4.56 (1H, dd, J=11.4, 1.6 Hz), 3.88-3.87 (1H, m), 3.36-3.30 (5H, m), 2.70 (1H, d, J=16.9 Hz), 2.48-2.36 (4H, m), 1.97-1.89 (4H, m).

Example 11BI. (R)-(1-(4-fluorophenyl)-6-((1-methyl-1H-pyrazol-3-yl)sulfonyl)-4,4a,5,6,7,8-hexahydro-1H-pyrazolo[3,4-g]isoquinolin-4a-yl)(4-(trifluoromethyl)pyridin-2-yl)methanone

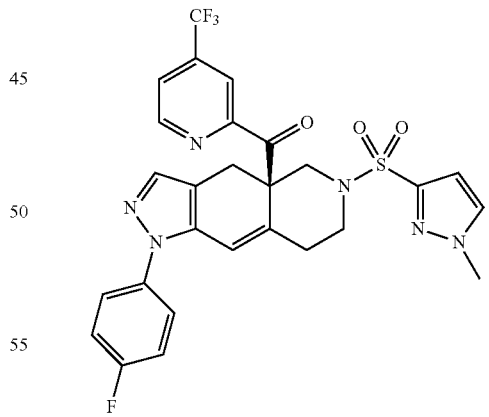

LCMS (Method F, ES-API): RT 2.42 min, m+H=587.0; 1H NMR (400 MHz, CDCl3): δ 8.89 (1H, d, J=5.0 Hz), 8.14 (1H, m), 7.70-7.68 (1H, m), 7.47-7.42 (2H, m), 7.39 (1H, d, J=2.3 Hz), 7.31 (1H, s), 7.21-7.15 (2H, m), 6.57 (1H, d, J=2.2 Hz), 6.52 (1H, d, J=2.1 Hz), 5.56 (1H, dd, J=12.6, 2.1 Hz), 4.24 (1H, d, J=16.9 Hz), 3.96 (3H, s), 3.89-3.85 (1H, m), 2.96 (1H, d, J=16.9 Hz), 2.93 (1H, d, J=12.4 Hz), 2.88-2.79 (1H, m), 2.68-2.61 (1H, m), 2.51-2.47 (1H, m).

Example 11BJ. (R)-(1-(4-fluorophenyl)-6-((1-methyl-1H-pyrazol-3-yl)sulfonyl)-4,4a,5,6,7,8-hexahydro-1H-pyrazolo[3,4-g]isoquinolin-4a-yl)(pyridin-2-yl)methanone

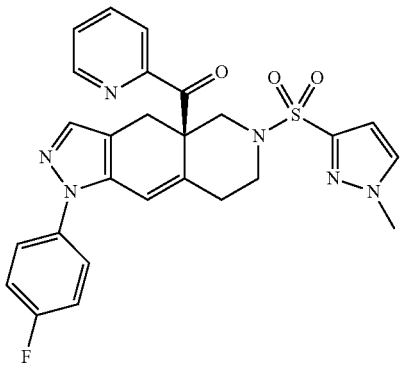 [SMILES: Cn1ccc(S(=O)(=O)N2CCC3=Cc4c(cnn4-c4ccc(F)cc4)C[C@]3(C(=O)c3ccccn3)C2)n1]

LCMS (Method F, ES-API): RT 2.15 min, m+H=519.0; 1H NMR (400 MHz, CDCl3): δ 8.67 (1H, ddd, J=4.7, 1.7, 0.9 Hz), 7.91-7.88 (1H, m), 7.85-7.81 (1H, m), 7.48-7.42 (3H, m), 7.38 (1H, d, J=2.2 Hz), 7.31 (1H, s), 7.20-7.14 (2H, m), 6.58 (1H, d, J=2.2 Hz), 6.50 (1H, d, J=2.1 Hz), 5.54 (1H, dd, J=12.5, 2.0 Hz), 4.34 (1H, d, J=16.9 Hz), 3.95 (3H, s), 3.88-3.84 (1H, m), 2.94 (1H, d, J=16.9 Hz), 2.91 (1H, d, J=12.4 Hz), 2.88-2.79 (1H, m), 2.67-2.60 (1H, m), 2.50-2.45 (1H, m).

Example 11BK. (R)-(1-(4-fluorophenyl)-6-((5-methyl-1H-pyrazol-4-yl)sulfonyl)-4,4a,5,6,7,8-hexahydro-1H-pyrazolo[3,4-g]isoquinolin-4a-yl)(4-(trifluoromethyl)pyridin-2-yl)methanone

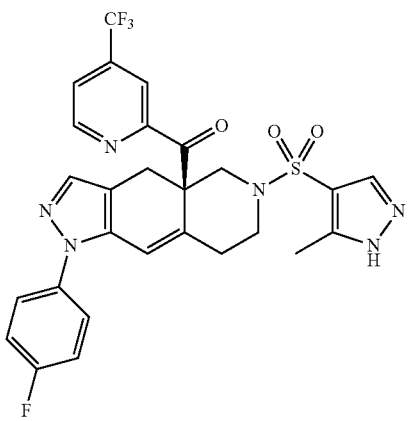

LCMS (Method F, ES-API): RT 2.36 min, m+H=587.0; 1H NMR (400 MHz, CDCl3): δ 8.83 (1H, d, J=4.9 Hz), 8.14-8.13 (1H, m), 7.73 (1H, s), 7.68 (1H, dd, J=4.9, 1.1 Hz), 7.46-7.41 (2H, m), 7.29 (1H, s), 7.20-7.14 (2H, m), 6.51 (1H, d, J=2.1 Hz), 5.45 (1H, dd, J=12.3, 2.0 Hz), 4.19 (1H, d, J=16.9 Hz), 3.85-3.80 (1H, m), 2.93 (1H, d, J=16.9 Hz), 2.86-2.78 (2H, m), 2.59-2.50 (2H, m), 2.38 (3H, s).

Example 11BL. (R)-3-((1-(4-fluorophenyl)-4a-(4-(trifluoromethyl)picolinoyl)-4a,5,7,8-tetrahydro-1H-pyrazolo[3,4-g]isoquinolin-6(4H)-yl)sulfonyl)benzonitrile

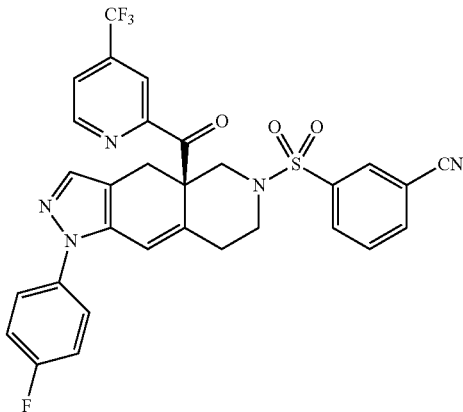 [SMILES: N#Cc1cccc(S(=O)(=O)N2CCC3=Cc4c(cnn4-c4ccc(F)cc4)C[C@]3(C(=O)c3cc(C(F)(F)F)ccn3)C2)c1]

LCMS (Method F, ES-API): RT 2.68 min, m+H=608.0; 1H NMR (400 MHz, CDCl3): δ 8.90 (1H, d, J=5.0 Hz), 8.13 (1H, m), 7.98 (1H, m), 7.91-7.89 (1H, m), 7.84-7.81 (1H, m), 7.74 (1H, dd, J=5.0, 0.9 Hz), 7.65-7.61 (1H, m), 7.45-7.40 (2H, m), 7.29 (1H, s), 7.20-7.14 (2H, m), 6.51 (1H, d, J=2.0 Hz), 5.53 (1H, dd, J=12.3, 2.0 Hz), 4.18 (1H, d, J=16.9 Hz), 3.91-3.87 (1H, m), 2.90 (1H, d, J=16.9 Hz), 2.88-2.77 (2H, m), 2.58-2.51 (2H, m).

Example 11BM. (R)-(1-(4-fluorophenyl)-6-((1-methyl-1H-pyrazol-5-yl)sulfonyl)-4,4a,5,6,7,8-hexahydro-1H-pyrazolo[3,4-g]isoquinolin-4a-yl)(4-(trifluoromethyl)pyridin-2-yl)methanone

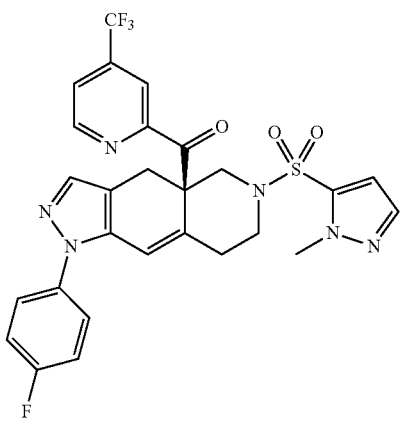 [SMILES: Cn1nccc1S(=O)(=O)N1CCC2=Cc3c(cnn3-c3ccc(F)cc3)C[C@]2(C(=O)c2cc(C(F)(F)F)ccn2)C1]

LCMS (Method F, ES-API): RT 2.55 min, m+H=587.0; 1H NMR (400 MHz, CDCl3): δ 8.81 (1H, d, J=4.9 Hz), 8.12 (1H, m), 7.70-7.69 (1H, m), 7.47-7.41 (2H, m), 7.35 (1H, d, J=2.1 Hz), 7.28 (1H, s), 7.21-7.15 (2H, m), 6.62 (1H, d, J=2.1 Hz), 6.54 (1H, d, J=2.0 Hz), 5.50 (1H, dd, J=12.4, 2.0 Hz), 4.18 (1H, d, J=16.9 Hz), 3.95 (3H, s), 3.94-3.90 (1H, m), 3.02 (1H, d, J=12.6 Hz), 2.92 (1H, d, J=16.9 Hz), 2.86-2.74 (2H, m), 2.60-2.55 (1H, m).

Example 11BN. (R)-(6-((1,5-dimethyl-1H-pyrazol-4-yl)sulfonyl)-1-(4-fluorophenyl)-4,4a,5,6,7,8-hexahydro-1H-pyrazolo[3,4-g]isoquinolin-4a-yl)(4-(trifluoromethyl)pyridin-2-yl)methanone

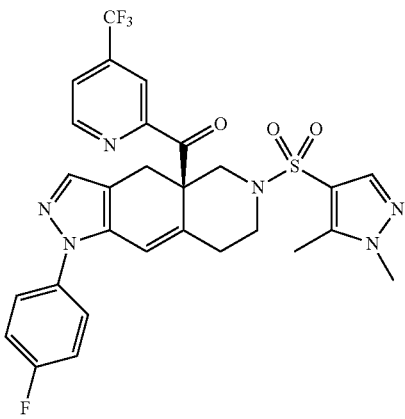

LCMS (Method F, ES-API): RT 2.44 min, m+H=601.2; 1H NMR (400 MHz, CDCl3): δ 8.84 (1H, d, J=4.9 Hz), 8.13 (1H, br s), 7.69 (1H, dd, J=4.9, 1.0 Hz), 7.61 (1H, s), 7.47-7.41 (2H, m), 7.28 (1H, s), 7.20-7.14 (2H, m), 6.51 (1H, d, J=2.0 Hz), 5.46 (1H, dd, J=12.3, 1.9 Hz), 4.16 (1H, d, J=16.9 Hz), 3.85-3.79 (1H, m), 3.71 (3H, s), 2.92 (1H, d, J=16.9 Hz), 2.87-2.76 (2H, m), 2.58-2.50 (2H, m), 2.34 (3H, s).

Example 11BO. (R)-(6-((1H-pyrazol-4-yl)sulfonyl)-1-(4-fluorophenyl)-4,4a,5,6,7,8-hexahydro-1H-pyrazolo[3,4-g]isoquinolin-4a-yl)(4-(trifluoromethyl)pyridin-2-yl)methanone

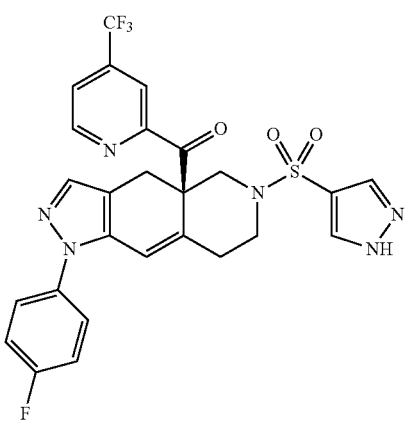

LCMS (Method F, ES-API): RT 2.28 min, m+H=573.2; 1H NMR (400 MHz, CDCl3): δ 11.0 (1H, br s), 8.86 (1H, d, J=4.9 Hz), 8.15 (1H, m), 7.83 (2H, s), 7.71-7.69 (1H, m), 7.46-7.41 (2H, m), 7.31 (1H, s), 7.20-7.14 (2H, m), 6.50 (1H, d, J=2.0 Hz), 5.44 (1H, dd, J=12.1, 2.0 Hz), 4.20 (1H, d, J=16.9 Hz), 3.82-3.78 (1H, m), 2.92 (1H, d, J=16.9 Hz), 2.87-2.78 (1H, m), 2.67 (1H, d, J=12.2 Hz), 2.52-2.40 (2H, m).

Example 11BP. (R)-(1-(4-fluorophenyl)-6-((1-methyl-3-(trifluoromethyl)-1H-pyrazol-4-yl)sulfonyl)-4,4a,5,6,7,8-hexahydro-1H-pyrazolo[3,4-g]isoquinolin-4a-yl)(pyridin-2-yl)methanone

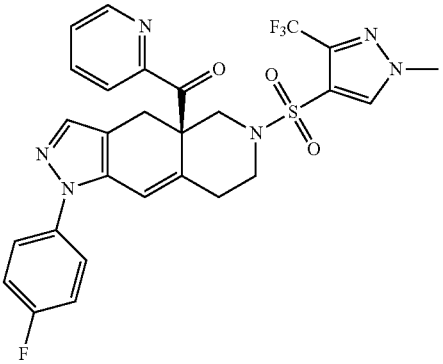 [SMILES: Cn1cc(S(=O)(=O)N2CCC3=Cc4c(cnn4-c4ccc(F)cc4)C[C@]3(C(=O)c3ccccn3)C2)c(C(F)(F)F)n1]

LCMS (Method F, ES-API): RT 2.47 min, m+H 587.0; 1H NMR (400 MHz, CDCl3): δ 8.61 (1H, ddd, J=4.8, 1.7, 0.9 Hz), 7.90-7.80 (2H, m), 7.74 (1H, s), 7.48-7.42 (3H, m), 7.28 (1H, s), 7.21-7.14 (2H, m), 6.51 (1H, d, J=2.0 Hz), 5.50 (1H, dd, J=12.6, 2.0 Hz), 4.26 (1H, d, J=16.8 Hz), 3.92 (3H, s), 3.89-3.85 (1H, m), 2.98 (1H, d, J=12.6 Hz), 2.90 (1H, d, J=16.8 Hz), 2.86-2.68 (2H, m), 2.56-2.46 (1H, m).

Example 11BQ. (R)-(1-(4-fluorophenyl)-6-((3,4,5-trifluorophenyl)sulfonyl)-4,4a,5,6,7,8-hexahydro-1H-pyrazolo[3,4-g]isoquinolin-4a-yl)(4-(trifluoromethyl)pyridin-2-yl)methanone

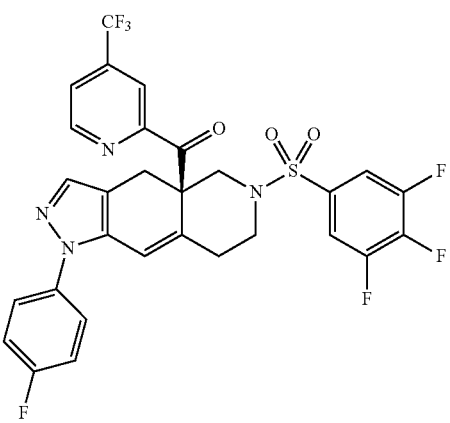 [SMILES: O=C(c1cc(C(F)(F)F)ccn1)[C@]12Cc3cnn(-c4ccc(F)cc4)c3C=C1CCN(S(=O)(=O)c1cc(F)c(F)c(F)c1)C2]

LCMS (Method F, ES-API): RT 2.85 min, m+H=637.2; 1H NMR (400 MHz, CDCl3): δ 8.87 (1H, d, J=4.9 Hz), 8.14 (1H, br s), 7.72 (1H, dd, J=4.9, 1.0 Hz), 7.46-7.41 (2H, m), 7.37-7.31 (2H, m), 7.29 (1H, s), 7.20-7.15 (2H, m), 6.52 (1H, d, J=2.1 Hz), 5.50 (1H, dd, J=12.3, 2.1 Hz), 4.17 (1H, d, J=16.9 Hz), 3.88-3.83 (1H, m), 2.91 (1H, d, J=16.9 Hz), 2.88-2.78 (2H, m), 2.61-2.51 (2H, m).

Example 11BR. (R)-(1-(4-chlorophenyl)-6-((1-methyl-1H-pyrazol-3-yl)sulfonyl)-4,4a,5,6,7,8-hexahydro-1H-pyrazolo[3,4-g]isoquinolin-4a-yl)(4-(trifluoromethyl)pyridin-2-yl)methanone

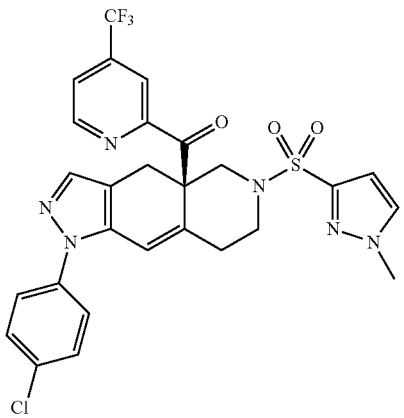 [SMILES: Cn1ccc(S(=O)(=O)N2CCC3=Cc4c(cnn4-c4ccc(Cl)cc4)C[C@]3(C(=O)c3cc(C(F)(F)F)ccn3)C2)n1]

LCMS (Method F, ES-API): RT 2.60 min, m+H=603.2; 1H NMR (400 MHz, CDCl3): δ 8.88 (1H, d, J=4.9 Hz), 8.14 (1H, br s), 7.68 (1H, dd, J=4.9, 1.0 Hz), 7.47-7.41 (4H, m), 7.38 (1H, d, J=2.3 Hz), 7.32 (1H, s), 6.56 (1H, d, J=2.3 Hz), 6.55 (1H, d, J=2.0 Hz), 5.55 (1H, dd, J=12.5, 2.0 Hz), 4.23 (1H, d, J=16.9 Hz), 3.96 (3H, s), 3.89-3.85 (1H, m), 2.95 (1H, d, J=16.9 Hz), 2.94 (1H, d, J=12.5 Hz), 2.89-2.80 (1H, m), 2.69-2.63 (1H, m), 2.51-2.47 (1H, m).

Example 11BS. (R)-(6-((1H-pyrazol-4-yl)sulfonyl)-1-(4-fluorophenyl)-4,4a,5,6,7,8-hexahydro-1H-pyrazolo[3,4-g]isoquinolin-4a-yl)(pyridin-2-yl)methanone

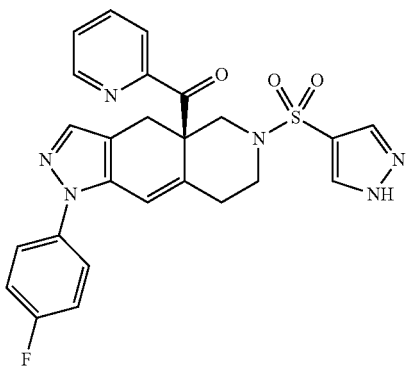

LCMS (Method F, ES-API): RT 2.25 min, m+H=505.0; 1H NMR (400 MHz, CDCl3): δ 11.12 (1H, br. s), 8.65 (1H, ddd, J=4.7, 1.6, 1.0 Hz), 8.36 (1H, d, J=0.6 Hz), 7.88-7.81 (2H, m), 7.78 (1H, d, J=0.6 Hz), 7.51-7.39 (3H, m), 7.31 (1H, s), 7.20-7.13 (2H, m), 6.50 (1H, d, J=2.0 Hz), 5.50 (1H, dd, J=12.1, 2.0 Hz), 4.24 (1H, d, J=17.0 Hz), 3.86-3.78 (1H, m), 2.91 (1H, d, J=17.0 Hz), 2.86-2.74 (2H, m), 2.64-2.45 (2H, m).

Example 11BT. (R)-(6-((1-methyl-1H-pyrazol-3-yl)sulfonyl)-1-(4-(trifluoromethyl)phenyl)-4,4a,5,6,7,8-hexahydro-1H-pyrazolo[3,4-g]isoquinolin-4a-yl)(pyridin-2-yl)methanone LCMS (Method F, ES-API): RT 2.48 min, m+H=569.0; 1H NMR (400 MHz, CDCl3): δ 8.67 (1H, ddd, J=4.8, 1.8, 0.9 Hz), 7.89 (1H, dt, J=7.9, 1.4 Hz), 7.83 (1H, td, J=7.6, 1.8 Hz), 7.74 (2H, d, J=8.4 Hz), 7.63 (2H, d, J=8.4 Hz), 7.46 (1H, ddd, J=7.6, 4.8, 1.4 Hz), 7.38 (1H, d, J=2.3 Hz), 7.37 (1H, s), 6.59 (1H, br. d, J=2.3 Hz), 6.58 (1H, br. d, J=2.3 Hz), 5.53 (1H, dd, J=12.5, 2.0 Hz), 4.37 (1H, d, J=17.1 Hz), 3.96 (3H, s), 3.87 (1H, ddt, J=8.5, 4.1, 2.0 Hz), 2.98-2.80 (3H, m), 2.66 (1H, ddd, J=12.6, 11.1, 3.5 Hz), 2.53-2.44 (1H, m).

Example 11BU. (R)-(6-((3,4-difluorophenyl)sulfonyl)-1-(4-fluorophenyl)-4,4a,5,6,7,8-hexahydro-1H-pyrazolo[3,4-g]isoquinolin-4a-yl)(thiazol-4-yl)methanone

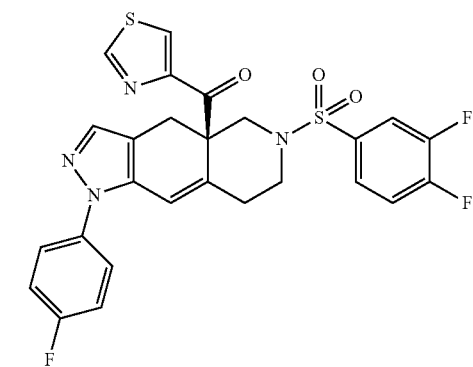 [SMILES: O=C(c1cscn1)[C@]12Cc3cnn(-c4ccc(F)cc4)c3C=C1CCN(S(=O)(=O)c1ccc(F)c(F)c1)C2]

LCMS (Method F, ES-API): RT 2.76 min, m+H=556.9; 1H NMR (400 MHz, CDCl3): δ 8.87 (1H, d, J=2.2 Hz), 8.24 (1H, d, J=2.2 Hz), 7.56-7.46 (2H, m), 7.46-7.39 (2H, m), 7.29-7.23 (2H, m), 7.19-7.12 (2H, m), 6.52 (1H, d, J=2.1 Hz), 5.45 (1H, dd, J=12.4, 2.1 Hz), 4.15 (1H, d, J=17.0 Hz), 3.89-3.84 (1H, m), 2.92-2.80 (2H, m), 2.73 (1H, d, J=12.5 Hz), 2.57-2.50 (2H, m).

Example 11BV. (R)-(6-((1,2-dimethyl-1H-imidazol-4-yl)sulfonyl)-1-(4-fluorophenyl)-4,4a,5,6,7,8-hexahydro-1H-pyrazolo[3,4-g]isoquinolin-4a-yl)(4-(trifluoromethyl)pyridin-2-yl)methanone

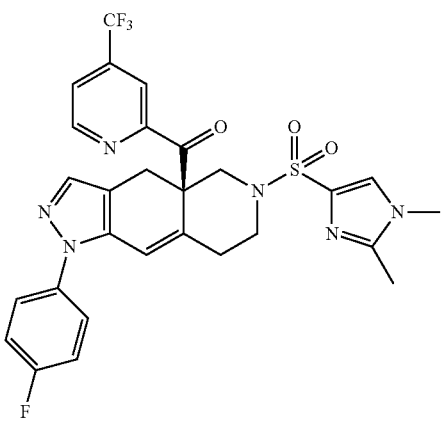 [SMILES: Cc1nc(S(=O)(=O)N2CCC3=Cc4c(cnn4-c4ccc(F)cc4)C[C@]3(C(=O)c3cc(C(F)(F)F)ccn3)C2)cn1C]

LCMS (Method F, ES-API): RT 2.28 min, m+H=601.1; 1H NMR (400 MHz, CDCl3): δ 8.87 (1H, d, J=5.0 Hz), 8.15-8.11 (1H, m), 7.70-7.65 (1H, m), 7.49-7.40 (2H, m), 7.30 (1H, s), 7.21-7.14 (2H, m), 6.51 (1H, d, J=2.1 Hz), 5.54 (1H, dd, J=12.6, 2.1 Hz), 4.23 (1H, d, J=17.2 Hz), 3.83 (1H, ddt, J=8.5, 4.0, 2.1 Hz), 3.58 (3H, s), 2.99 (1H, d, J=12.6 Hz), 2.97 (1H, d, J=17.2 Hz), 2.82 (1H, tdd, J=14.8, 5.9, 2.4 Hz), 2.70-2.61 (1H, m), 2.47-2.43 (1H, m), 2.37 (3H, s).

Example 11BW. (R)-(6-((1,2-dimethyl-1H-imidazol-5-yl)sulfonyl)-1-(4-fluorophenyl)-4,4a,5,6,7,8-hexahydro-1H-pyrazolo[3,4-g]isoquinolin-4a-yl)(4-(trifluoromethyl)pyridin-2-yl)methanone

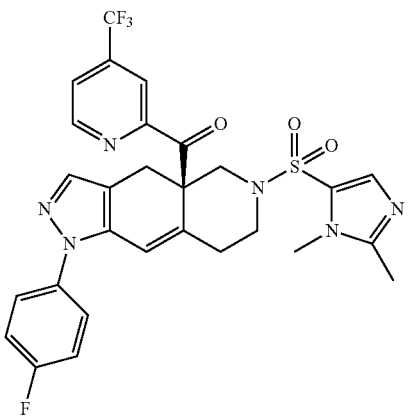 [SMILES: Cc1ncc(S(=O)(=O)N2CCC3=Cc4c(cnn4-c4ccc(F)cc4)C[C@]3(C(=O)c3cc(C(F)(F)F)ccn3)C2)n1C]

LCMS (Method F, ES-API): RT 2.20 min, m+H=601.0; 1H NMR (400 MHz, CDCl3): δ 8.76 (1H, d, J=5.0 Hz), 8.04 (1H, s), 7.72-7.65 (1H, m), 7.45-7.41 (3H, m), 7.24 (1H, s), 7.22-7.13 (2H, m), 6.55 (1H, s), 5.60 (1H, dd, J=12.9, 2.0 Hz), 4.08 (1H, d, J=16.9 Hz), 4.01-3.96 (1H, m), 3.40 (3H, s), 3.12 (1H, d, J=13.0 Hz), 2.96-2.82 (3H, m), 2.69-2.59 (1H, m), 2.12 (3H, s).

Example 11BX. (R)-1-(4-fluorophenyl)-6-((1-methyl-1H-imidazol-2-yl)sulfonyl)-4,4a,5,6,7,8-hexahydro-1H-pyrazolo[3,4-g]isoquinolin-4a-yl)(4-(trifluoromethyl)pyridin-2-yl)methanone

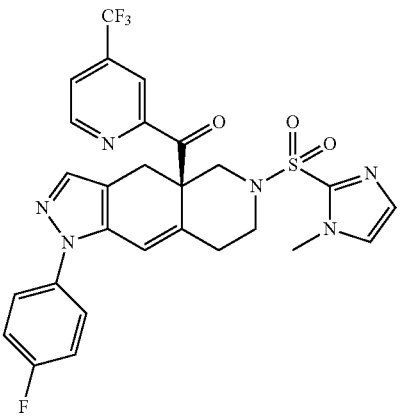 [SMILES: Cn1ccnc1S(=O)(=O)N1CCC2=Cc3c(cnn3-c3ccc(F)cc3)C[C@]2(C(=O)c2cc(C(F)(F)F)ccn2)C1]

LCMS (Method F, ES-API): RT 2.49 min, m+H=587.0; 1H NMR (400 MHz, CDCl3): δ 8.83 (1H, d, J=5.0 Hz), 8.15-8.13 (1H, m), 7.70-7.64 (1H, m), 7.51-7.42 (2H, m), 7.30 (1H, s), 7.23-7.14 (2H, m), 7.00 (1H, d, J=1.1 Hz), 6.90 (1H, d, J=1.1 Hz), 6.57 (1H, d, J=2.1 Hz), 5.60 (1H, dd, J=13.0, 2.1 Hz), 4.24 (1H, d, J=17.0 Hz), 3.93 (1H, ddt, J=9.2, 4.2, 2.1 Hz), 3.80 (3H, s), 3.57 (1H, d, J=13.1 Hz), 3.28-3.15 (1H, m), 3.01 (1H, d, J=17.0 Hz), 2.87 (1H, dddd, J=15.1, 12.6, 6.1, 2.4 Hz), 2.58-2.51 (1H, m).

Example 11BY. (R)-(6-((1-ethyl-1H-imidazol-4-yl)sulfonyl)-1-(4-fluorophenyl)-4,4a,5,6,7,8-hexahydro-1H-pyrazolo[3,4-g]isoquinolin-4a-yl)(4-(trifluoromethyl)pyridin-2-yl)methanone

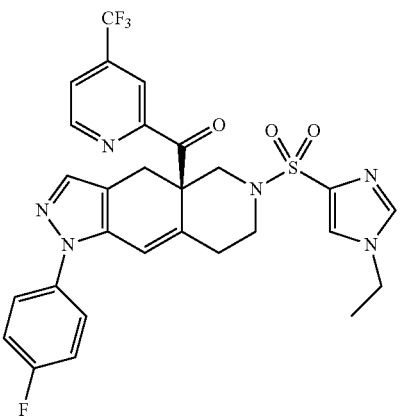 [SMILES: CCn1cnc(S(=O)(=O)N2CCC3=Cc4c(cnn4-c4ccc(F)cc4)C[C@]3(C(=O)c3cc(C(F)(F)F)ccn3)C2)c1]

LCMS (Method F, ES-API): RT 2.34 min, m+H=601.1; 1H NMR (400 MHz, CDCl3): δ 8.87 (1H, d, J=4.9 Hz), 8.14 (1H, m), 7.67 (1H, dd, J=4.9, 1.0 Hz), 7.49 (1H, d, J=1.4 Hz), 7.47-7.42 (2H, m), 7.40 (1H, d, J=1.4 Hz), 7.30 (1H, s), 7.20-7.14 (2H, m), 6.51 (1H, d, J=2.1 Hz), 5.58 (1H, dd, J=12.4, 2.1 Hz), 4.24 (1H, d, J=16.9 Hz), 4.02 (2H, q, J=7.4 Hz), 3.88-3.83 (1H, m), 3.03 (1H, d, J=12.4 Hz), 2.96 (1H, d, J=16.9 Hz), 2.87-2.78 (1H, m), 2.72-2.65 (1H, m), 2.50-2.46 (1H, m), 1.49 (3H, t, J=7.4 Hz).

Example 11BZ. (R)-(6-((1-ethyl-1H-pyrazol-4-yl)sulfonyl)-1-(4-fluorophenyl)-4,4a,5,6,7,8-hexahydro-1H-pyrazolo[3,4-g]isoquinolin-4a-yl)(thiazol-4-yl)methanone

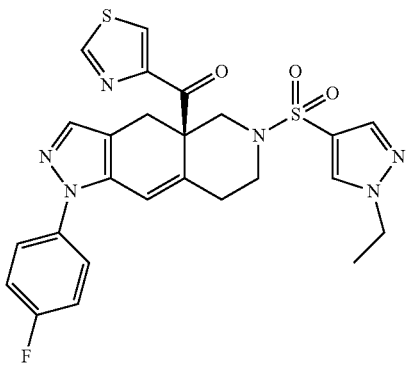 [SMILES: CCn1cc(S(=O)(=O)N2CCC3=Cc4c(cnn4-c4ccc(F)cc4)C[C@]3(C(=O)c3cscn3)C2)cn1]

LCMS (Method F, ES-API): RT 2.34 min, m+H=539.0; 1H NMR (400 MHz, CDCl3): δ 8.89 (1H, d, J=2.2 Hz), 8.26 (1H, d, J=2.2 Hz), 7.73 (1H, s), 7.67 (1H, d, J=0.7 Hz), 7.48-7.39 (2H, m), 7.30 (1H, s), 7.21-7.12 (2H, m), 6.52 (1H, d, J=2.2 Hz), 5.42 (1H, dd, J=12.1, 2.2 Hz), 4.25-4.13 (3H, m), 3.80 (1H, ddt, J=10.5, 6.4, 2.0 Hz), 2.94-2.81 (2H, m), 2.63 (1H, d, J=12.1 Hz), 2.55-2.38 (2H, m), 1.52 (3H, t, J=7.3 Hz).

Example 11CA. (R)-1-(4-fluorophenyl)-6-((1-propyl-1H-pyrazol-4-yl)sulfonyl)-4,4a,5,6,7,8-hexahydro-1H-pyrazolo[3,4-g]isoquinolin-4a-yl)(pyridin-2-yl)methanone

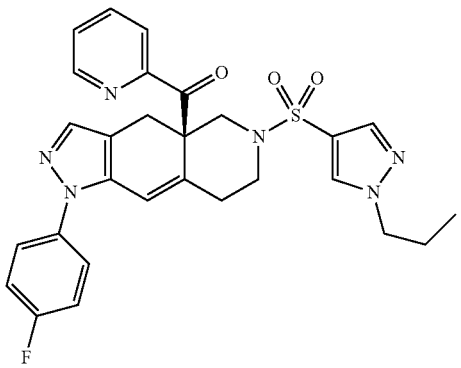 [SMILES: CCCn1cc(S(=O)(=O)N2CCC3=Cc4c(cnn4-c4ccc(F)cc4)C[C@]3(C(=O)c3ccccn3)C2)cn1]

LCMS (Method F, ES-API): RT 2.36 min, m+H=547.2; 1H NMR (400 MHz, CDCl3): δ 8.66 (1H, dq, J=4.8, 0.8 Hz), 7.90 (1H, dt, J=8.0, 1.2 Hz), 7.84 (1H, td, J=7.6, 1.6 Hz), 7.68 (2H, dd, J=14.0, 0.8), 7.49-7.42 (3H, m), 7.30 (1H, s), 7.19-7.14 (2H, m), 6.49 (1H, d, J=2.0 Hz), 5.46 (1H, dd, J=12.0, 2.0 Hz), 4.32 (1H, d, J=16.8 Hz), 4.07 (2H, t, J=7.0 Hz), 3.79-3.75 (1H, m), 2.91 (1H, d, J=16.8 Hz), 2.88-2.80 (1H, m), 2.67 (1H, d, J=12.0 Hz), 2.50-2.39 (2H, m), 1.89 (2H, sex, J=7.6 Hz), 0.91 (3H, t, J=7.6 Hz).

Example 11CB. (R)-(1-(4-fluorophenyl)-6-((1-(2-methoxyethyl)-1H-pyrazol-4-yl)sulfonyl)-4,4a,5,6,7,8-hexahydro-1H-pyrazolo[3,4-g]isoquinolin-4a-yl)(pyridin-2-yl)methanone

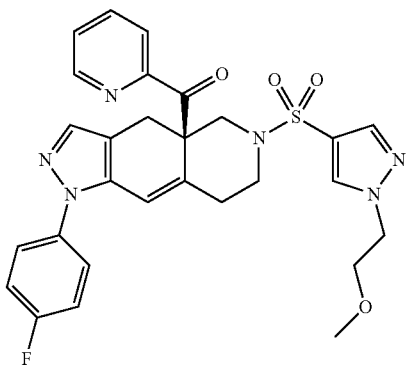 [SMILES: COCCn1cc(S(=O)(=O)N2CCC3=Cc4c(cnn4-c4ccc(F)cc4)C[C@]3(C(=O)c3ccccn3)C2)cn1]

LCMS (Method F, ES-API): RT 2.19 min, m+H=563.3; 1H NMR (400 MHz, CDCl3): δ 8.67 (1H, d, J=4.9, 1.7, 0.9 Hz), 7.92-7.89 (1H, m), 7.84 (1H, dt, J=7.5, 1.7 Hz), 7.81 (1H, s), 7.66 (1H, d, J=0.5 Hz), 7.49-7.42 (3H, m), 7.31 (1H, s), 7.19-7.13 (2H, m), 6.49 (1H, d, J=2.1 Hz), 5.46 (1H, dd, J=12.1, 2.1 Hz), 4.32 (1H, d, J=16.9 Hz), 4.28 (2H, dd, J=4.9 Hz), 3.79-3.75 (1H, m), 3.71 (2H, dd, J=4.9 Hz), 3.32 (3H, s), 2.91 (1H, d, J=16.9 Hz), 2.88-2.78 (1H, m), 2.66 (1H, d, J=12.0 Hz), 2.51-2.39 (2H, m).

Example 11CC. (R)-(6-((3,4-dichlorophenyl)sulfonyl)-1-(4-fluorophenyl)-4,4a,5,6,7,8-hexahydro-1H-pyrazolo[3,4-g]isoquinolin-4a-yl)(1-methyl-1H-pyrazol-4-yl)methanone

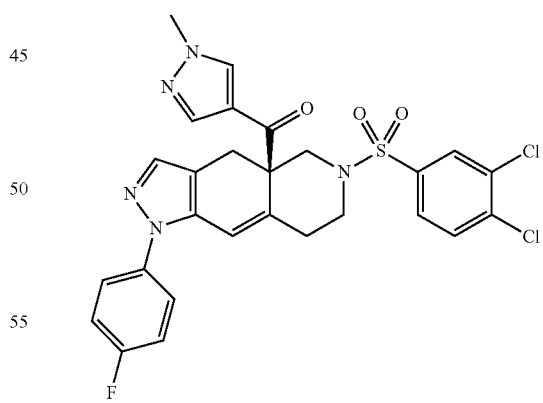

LCMS (Method F, ES-API): RT 2.52 min, m+H=586.1; 1H NMR (400 MHz, CDCl3): δ 7.88 (1H, s), 7.87 (1H, d, J=1.8 Hz), 7.84 (1H, d, J=0.5 Hz), 7.63-7.58 (2H, m), 7.46-7.41 (2H, m), 7.35 (1H, s), 7.22-7.16 (2H, m), 6.50 (1H, s), 4.55 (1H, dd, J=11.4, 1.7 Hz), 3.89 (3H, s), 3.89-3.82 (1H, m), 3.29 (1H, d, J=17.2 Hz), 2.76 (1H, d, J=17.2 Hz), 2.62-2.45 (3H, m), 2.42-2.37 (1H, m).

Example 11CD. (R)-(1-(4-fluorophenyl)-6-((1-isopropyl-1H-pyrazol-4-yl)sulfonyl)-4,4a,5,6,7,8-hexahydro-1H-pyrazolo[3,4-g]isoquinolin-4a-yl)(pyridin-2-yl)methanone

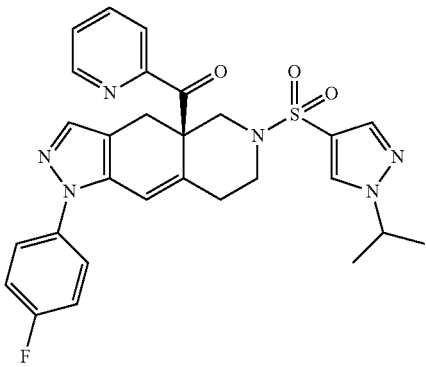 [SMILES: CC(C)n1cc(S(=O)(=O)N2CCC3=Cc4c(cnn4-c4ccc(F)cc4)C[C@]3(C(=O)c3ccccn3)C2)cn1]

LCMS (Method F, ES-API): RT 2.41 min, m+H=547.1; 1H NMR (400 MHz, CDCl3): δ 8.67 (1H, ddd, J=4.8, 1.8, 0.9 Hz), 7.90 (1H, ddd, J=7.9, 1.3, 0.9 Hz), 7.84 (1H, td, J=7.5, 1.8 Hz), 7.73 (1H, s), 7.66 (1H, d, J=0.7 Hz), 7.52-7.41 (3H, m), 7.30 (1H, s), 7.21-7.12 (2H, m), 6.50 (1H, d, J=2.1 Hz), 5.47 (1H, dd, J=12.0, 2.1 Hz), 4.49 (1H, hept, J=6.9 Hz), 4.32 (1H, d, J=17.0 Hz), 3.80-3.74 (1H, m), 2.93 (1H, d, J=17.0 Hz), 2.88-2.79 (1H, m), 2.68 (1H, d, J=12.0 Hz), 2.58-2.39 (2H, m), 1.52 (6H, d, J=6.9 Hz).

Examples 110E, 11CF and 11CG

| | | |
|---|---|---|
| 11CE | (R)-(1-(4-fluorophenyl)-6-((2-methyl-2H-1,2,3-triazol-4-yl)sulfonyl)-4,4a,5,6,7,8-hexahydro-1H-pyrazolo[3,4-g]isoquinolin-4a-yl)(4-(trifluoromethyl)pyridin-2-yl)methanone | 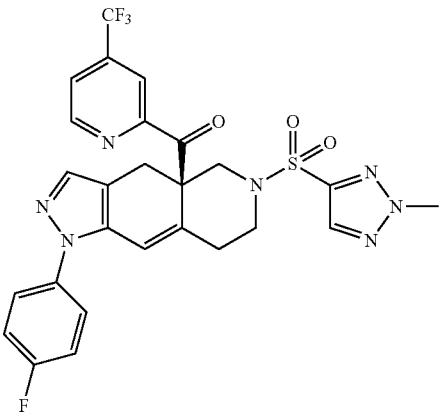 [SMILES: Cn1ncc(S(=O)(=O)N2CCC3=Cc4c(cnn4-c4ccc(F)cc4)C[C@]3(C(=O)c3cc(C(F)(F)F)ccn3)C2)n1] |
| 11CF | (R)-(1-(4-fluorophenyl)-6-((1-methyl-1H-1,2,3-triazol-5-yl)sulfonyl)-4,4a,5,6,7,8-hexahydro-1H-pyrazolo[3,4-g]isoquinolin-4a-yl)(4-(trifluoromethyl)pyridin-2-yl)methanone | 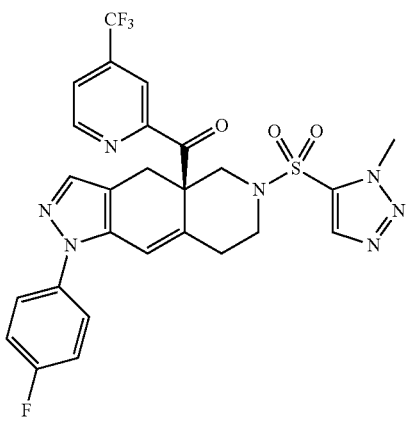 [SMILES: Cn1nncc1S(=O)(=O)N1CCC2=Cc3c(cnn3-c3ccc(F)cc3)C[C@]2(C(=O)c2cc(C(F)(F)F)ccn2)C1] |

| | | |
|---|---|---|
| 11CG | (R)-(1-(4-fluorophenyl)-6-((1-methyl-1H-1,2,3-triazol-4-yl)sulfonyl)-4,4a,5,6,7,8-hexahydro-1H-pyrazolo[3,4-g]isoquinolin-4a-yl)(4-(trifluoromethyl)pyridin-2-yl)methanone | 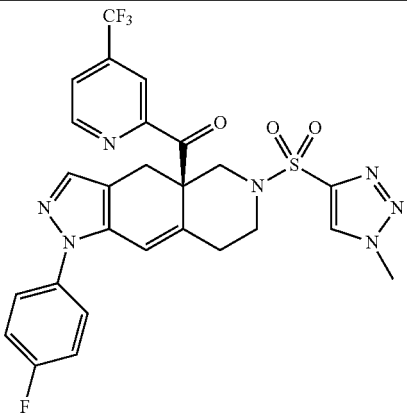 |

Prepared from Preparation 1 of Intermediate 89. LCMS (Method F, ES-API): RT 2.55 min, m+H=588.0; 1H NMR (400 MHz, CDCl3): δ 8.89 (1H, dt, J=5.0, 0.8 Hz), 8.15-8.13 (1H, m), 7.81 (1H, s), 7.70 (1H, ddd, J=5.1, 1.7, 0.8 Hz), 7.48-7.42 (2H, m), 7.30 (1H, s), 7.22-7.13 (2H, m), 6.54 (1H, d, J=2.2 Hz), 5.59 (1H, dd, J=12.7, 2.2 Hz), 4.25 (3H, s), 4.22 (1H, d, J=17.0 Hz), 3.90 (1H, ddt, J=10.6, 6.0, 2.0 Hz), 2.99 (1H, d, J=12.7 Hz), 2.95 (1H, d, J=17.0 Hz), 2.84 (1H, tdd, J=12.7, 5.9, 3.0 Hz), 2.74-2.67 (1H, m), 2.52 (1H, br. dt, J=14.6, 2.7 Hz).

Prepared from Preparation 2 of Intermediate 89. LCMS (Method F, ES-API): RT 2.50 min, m+H=588.2; 1H NMR (400 MHz, CDCl3): δ 8.80 (1H, d, J=4.9 Hz), 8.11 (1H, m), 7.91 (1H, s), 7.73-7.71 (1H, m), 7.47-7.41 (2H, m), 7.28 (1H, s), 7.21-7.16 (2H, m), 6.56 (1H, s), 5.51 (1H, dd, J=12.7, 2.1 Hz), 4.13 (1H, d, J=16.9 Hz), 4.11 (3H, s), 4.01-3.93 (1H, m), 3.09 (1H, d, J=12.7 Hz), 2.92 (1H, d, J=16.9 Hz), 2.87-2.81 (2H, m), 2.65-2.60 (1H, m).

Prepared from Preparation 3 of Intermediate 89. LCMS (Method F, ES-API): RT 2.41 min, m+H=588.2; 1H NMR (400 MHz, CDCl3): δ 8.87 (1H, d, J=4.9 Hz), 8.15 (1H, m), 7.89 (1H, s), 7.70-7.69 (1H, m), 7.48-7.43 (2H, m), 7.31 (1H, s), 7.21-7.15 (2H, m), 6.54 (1H, s), 5.61 (1H, dd, J=12.5, 2.0 Hz), 4.23 (1H, d, J=16.9 Hz), 4.15 (3H, s), 3.95-3.87 (1H, m), 3.14 (1H, d, J=12.5 Hz), 2.96 (1H, d, J=16.9 Hz), 2.88-2.78 (2H, m), 2.57-2.48 (1H, m).

Examples 11CH, 11CI and 11CJ

| | | |
|---|---|---|
| 11CH | (R)-(6-((2-ethyl-2H-1,2,3-triazol-4-yl)sulfonyl)-1-(4-fluorophenyl)-4,4a,5,6,7,8-hexahydro-1H-pyrazolo[3,4-g]isoquinolin-4a-yl)(pyridin-2-yl)methanone | 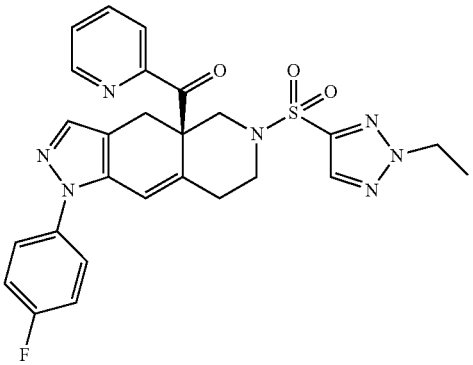 [SMILES: CCn1ncc(S(=O)(=O)N2CCC3=Cc4c(cnn4-c4ccc(F)cc4)C[C@]3(C(=O)c3ccccn3)C2)n1] |
| 11CI | (R)-(6-((1-ethyl-1H-1,2,3-triazol-5-yl)sulfonyl)-1-(4-fluorophenyl)-4,4a,5,6,7,8-hexahydro-1H-pyrazolo[3,4-g]isoquinolin-4a-yl)(pyridin-2-yl)methanone | 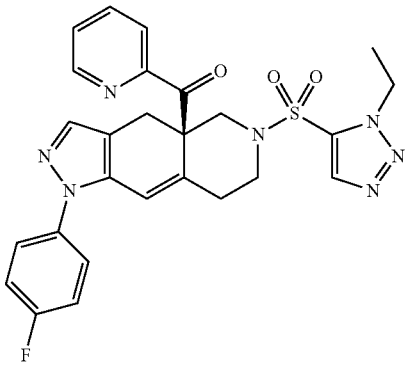 [SMILES: CCn1nncc1S(=O)(=O)N1CCC2=Cc3c(cnn3-c3ccc(F)cc3)C[C@]2(C(=O)c2ccccn2)C1] |

| | | |
|---|---|---|
| 11CJ | (R)-(6-((1-ethyl-1H-1,2,3-triazol-4-yl)sulfonyl)-1-(4-fluorophenyl)-4,4a,5,6,7,8-hexahydro-1H-pyrazolo[3,4-g]isoquinolin-4a-yl)(pyridin-2-yl)methanone | 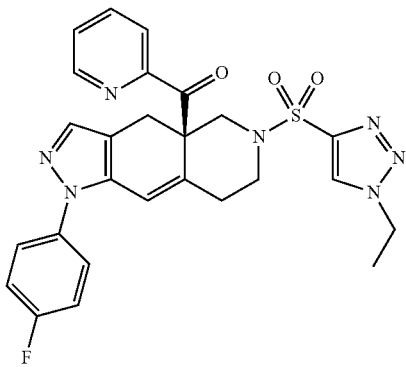 [SMILES: CCn1cc(S(=O)(=O)N2CCC3=Cc4c(cnn4-c4ccc(F)cc4)C[C@]3(C(=O)c3ccccn3)C2)nn1] |

Prepared from Preparation 1 of Intermediate 90. LCMS (Method F, ES-API): RT 2.44 min, m+H=534.0; 1H NMR (400 MHz, CDCl3): δ 8.68 (1H, ddd, J=4.8, 1.7, 0.9 Hz), 7.88 (1H, ddd, J=7.9, 1.7, 0.9 Hz), 7.84 (1H, td, J=7.4, 1.7 Hz), 7.80 (1H, s), 7.51-7.40 (3H, m), 7.31 (1H, s), 7.22-7.12 (2H, m), 6.51 (1H, d, J=2.1 Hz), 5.61 (1H, dd, J=12.7, 2.1 Hz), 4.51 (2H, q, J=7.3 Hz), 4.32 (1H, d, J=17.0 Hz), 3.90 (1H, ddt, J=11.0, 6.0, 2.0 Hz), 3.00-2.90 (2H, m), 2.84 (1H, tdd, J=12.7, 6.0, 3.0 Hz), 2.70 (1H, ddd, J=12.7, 11.0, 3.3 Hz), 2.50 (1H, dt, J=14.3, 3.0 Hz), 1.59 (3H, t, J=7.3 Hz).

Prepared from Preparation 2 of Intermediate 90. LCMS (Method F, ES-API): RT 2.42 min, m+H=534.1; 1H NMR (400 MHz, CDCl3): δ 8.61-8.55 (1H, m), 7.88 (1H, s), 7.86-7.79 (2H, m), 7.52-7.40 (3H, m), 7.27 (1H, br. s), 7.22-7.13 (2H, m), 6.54 (1H, br. s), 5.62 (1H, dd, J=12.6, 2.0 Hz), 4.50-4.36 (2H, m), 4.21 (1H, d, J=16.9 Hz), 3.98-3.89 (1H, m), 3.13 (1H, d, J=12.7 Hz), 2.96-2.76 (3H, m), 2.64-2.56 (1H, m), 1.51 (3H, t, J=7.3 Hz).

Prepared from Preparation 3 of Intermediate 90. LCMS (Method F, ES-API): RT 2.32 min, m+H=534.1; 1H NMR (400 MHz, CDCl3): δ 8.66 (1H, ddd, J=4.8, 1.8, 0.9 Hz), 7.92-7.87 (2H, m), 7.83 (1H, td, J=7.7, 1.8 Hz), 7.49-7.40 (3H, m), 7.30 (1H, s), 7.21-7.12 (2H, m), 6.51 (1H, br. s), 5.59 (1H, dd, J=12.6, 2.1 Hz), 4.45 (2H, q, J=7.4 Hz), 4.31 (1H, d, J=16.9 Hz), 3.98-3.87 (1H, m), 3.14 (1H, d, J=12.6 Hz), 2.94 (1H, d, J=16.9 Hz), 2.87-2.78 (2H, m), 2.56-2.44 (1H, m), 1.59 (3H, t, J=7.4 Hz).

Examples 11CK, 11CL and 11CM

| | | |
|---|---|---|
| 11CK | (R)-(6-((2-ethyl-2H-1,2,3-triazol-4-yl)sulfonyl)-1-(4-fluorophenyl)-4,4a,5,6,7,8-hexahydro-1H-pyrazolo[3,4-g]isoquinolin-4a-yl)(4-(trifluoromethyl)pyridin-2-yl)methanone | 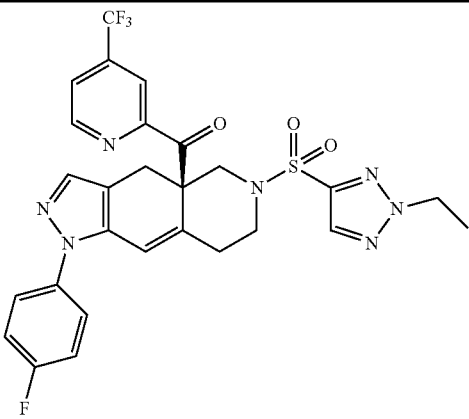 |
| 11CL | (R)-(6-((1-ethyl-1H-1,2,3-triazol-5-yl)sulfonyl)-1-(4-fluorophenyl)-4,4a,5,6,7,8-hexahydro-1H-pyrazolo[3,4-g]isoquinolin-4a-yl)(4-(trifluoromethyl)pyridin-2-yl)methanone | 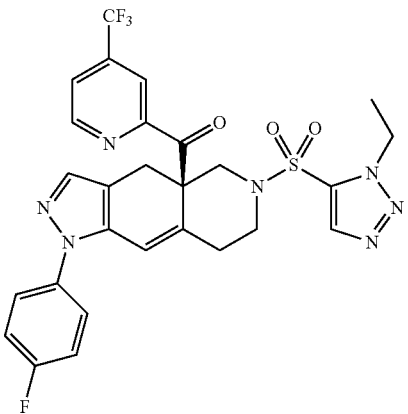 [SMILES: CCn1nncc1S(=O)(=O)N1CCC2=Cc3c(cnn3-c3ccc(F)cc3)C[C@]2(C(=O)c2cc(C(F)(F)F)ccn2)C1] |

| | | |
|---|---|---|
| 11CM | (R)-(6-((1-ethyl-1H-1,2,3-triazol-4-yl)sulfonyl)-1-(4-fluorophenyl)-4,4a,5,6,7,8-hexahydro-1H-pyrazolo[3,4-g]isoquinolin-4a-yl)(4-(trifluoromethyl)pyridin-2-yl)methanone | 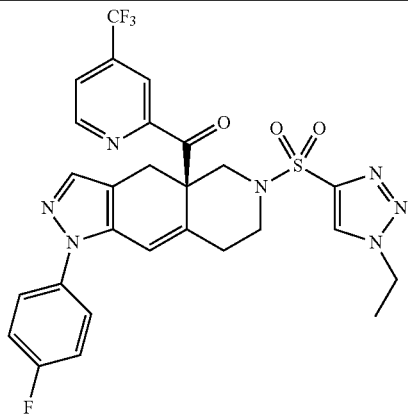 |

Prepared from Preparation 1 of Intermediate 90. LCMS (Method F, ES-API): RT 2.67 min, m+H=602.0; 1H NMR (400 MHz, CDCl3): δ 8.89 (1H, d, J=5.1 Hz), 8.16-8.12 (1H, m), 7.81 (1H, s), 7.71 (1H, ddd, J=5.0, 1.8, 0.7 Hz), 7.49-7.40 (2H, m), 7.30 (1H, s), 7.23-7.15 (2H, m), 6.54 (1H, d, J=2.1 Hz), 5.59 (1H, dd, J=12.7, 2.1 Hz), 4.51 (2H, q, J=7.3 Hz), 4.22 (1H, d, J=17.0 Hz), 3.95-3.84 (1H, m), 2.97 (1H, d, J=12.7 Hz), 2.95 (1H, d, J=17.0 Hz), 2.89-2.78 (1H, m), 2.73-2.66 (1H, m), 2.58-2.47 (1H, m), 1.59 (3H, t, J=7.3 Hz).

Prepared from Preparation 2 of Intermediate 90. LCMS (Method F, ES-API): RT 2.62 min, m+H=602.1; 1H NMR (400 MHz, CDCl3): δ 8.81 (1H, d, J=5.1 Hz), 8.12-8.11 (1H, m), 7.89 (1H, s), 7.72 (1H, ddd, J=5.1, 1.8, 0.7 Hz), 7.48-7.39 (2H, m), 7.28 (1H, s), 7.24-7.13 (2H, m), 6.57 (1H, br. s), 5.54 (1H, dd, J=12.8, 2.1 Hz), 4.53-4.40 (2H, m), 4.14 (1H, d, J=16.9 Hz), 4.01-3.90 (1H, m), 3.11 (1H, d, J=12.8 Hz), 2.92 (1H, d, J=16.9 Hz), 2.86-2.79 (2H, m), 2.68-2.55 (1H, m), 1.52 (3H, t, J=7.2 Hz).

Prepared from Preparation 3 of Intermediate 90. LCMS (Method F, ES-API): RT 2.53 min, m+H=602.1; 1H NMR (400 MHz, CDCl3): δ 8.88 (1H, br. d, J=5.1 Hz), 8.15-8.14 (1H, m), 7.91 (1H, s), 7.69 (1H, ddd, J=5.1, 1.8, 0.8 Hz), 7.49-7.41 (2H, m), 7.31 (1H, s), 7.23-7.13 (2H, m), 6.54 (1H, br. s), 5.62 (1H, dd, J=12.8, 2.1 Hz), 4.46 (2H, q, J=7.4 Hz), 4.23 (1H, d, J=17.0 Hz), 3.94-3.88 (1H, m), 3.17 (1H, d, J=12.8 Hz), 2.97 (1H, d, J=17.0 Hz), 2.89-2.80 (2H, m), 2.57-2.46 (1H, m), 1.60 (3H, t, J=7.4 Hz).

Examples 11CN, 11CO and 11CP

| | | |
|---|---|---|
| 11CN | (R)-1-(4-fluorophenyl)-6-((2-propyl-2H-1,2,3-triazol-4-yl)sulfonyl)-4,4a,5,6,7,8-hexahydro-1H-pyrazolo[3,4-g]isoquinolin-4a-yl)(pyridin-2-yl)methanone | 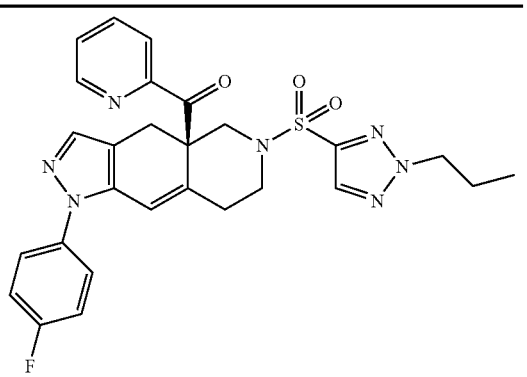 |
| 11CO | (R)-(1-(4-fluorophenyl)-6-((1-propyl-1H-1,2,3-triazol-5-yl)sulfonyl)-4,4a,5,6,7,8-hexahydro-1H-pyrazolo[3,4-g]isoquinolin-4a-yl)(pyridin-2-yl)methanone | 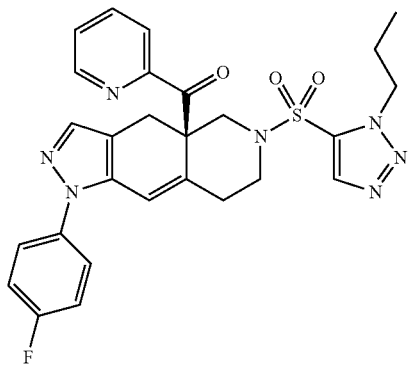 [SMILES: CCCn1nncc1S(=O)(=O)N1CCC2=Cc3c(cnn3-c3ccc(F)cc3)C[C@]2(C(=O)c2ccccn2)C1] |

| | | |
|---|---|---|
| 11CP | (R)-(1-(4-fluorophenyl)-6-((1-propyl-1H-1,2,3-triazol-4-yl)sulfonyl)-4,4a,5,6,7,8-hexahydro-1H-pyrazolo[3,4-g]isoquinolin-4a-yl)(pyridin-2-yl)methanone | 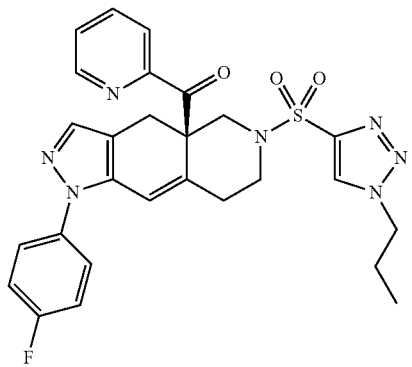 [SMILES: CCCn1cc(S(=O)(=O)N2CCC3=Cc4c(cnn4-c4ccc(F)cc4)C[C@]3(C(=O)c3ccccn3)C2)nn1] |

Prepared from Preparation 1 of Intermediate 91. LCMS (Method F, ES-API): RT 2.54 min, m+H=548.2; 1H NMR (400 MHz, CDCl3): δ 8.68 (1H, ddd, J=4.9, 1.6, 0.9 Hz), 7.88 (1H, ddd, J=7.9, 1.4, 0.9 Hz), 7.83 (1H, dt, J=7.4, 1.6 Hz), 7.80 (1H, s), 7.49-7.42 (3H, m), 7.30 (1H, s), 7.20-7.14 (2H, m), 6.51 (1H, d, J=2.1 Hz), 5.60 (1H, dd, J=12.5, 2.0 Hz), 4.42 (2H, t, J=7.1 Hz), 4.32 (1H, d, J=16.9 Hz), 3.92-3.87 (1H, m), 2.95 (1H, d, J=12.5 Hz), 2.92 (1H, d, J=16.9 Hz), 2.89-2.80 (1H, m), 2.71-2.64 (1H, m), 2.52-2.47 (1H, m), 2.00 (2H, sext, J=7.1 Hz), 0.93 (3H, t, J=7.1 Hz).

Prepared from Preparation 2 of Intermediate 91. LCMS (Method F, ES-API): RT 2.47 min, m+H=548.2; 1H NMR (400 MHz, CDCl3): δ 8.59 (1H, ddd, J=4.9, 1.6, 0.9 Hz), 7.88 (1H, s), 7.87-7.81 (2H, m), 7.48 (1H, ddd, J=6.8, 4.9, 2.1 Hz), 7.46-7.41 (2H, m), 7.27 (1H, s), 7.20-7.14 (2H, m), 6.54 (1H, br s), 5.61 (1H, dd, J=12.7, 2.0 Hz), 4.40-4.29 (2H, m), 4.22 (1H, d, J=16.9 Hz), 3.97-3.89 (1H, m), 3.12 (1H, d, J=12.7 Hz), 2.91-2.81 (3H, m), 2.64-2.56 (1H, m), 1.92 (2H, dsext, J=7.1, 0.7 Hz), 0.93 (3H, t, J=7.1 Hz).

Prepared from Preparation 3 of Intermediate 91. LCMS (Method F, ES-API): RT 2.37 min, m+H=548.2; 1H NMR (400 MHz, CDCl3): δ 8.66 (1H, ddd, J=4.7, 1.6, 0.9 Hz), 7.91-7.88 (2H, m), 7.83 (1H, dt, J=7.5, 1.6 Hz), 7.48-7.42 (3H, m), 7.30 (1H, s), 7.19-7.14 (2H, m), 6.51 (1H, s), 5.60 (1H, dd, J=12.5, 2.0 Hz), 4.35 (2H, t, J=7.1 Hz), 4.32 (1H, d, J=16.9 Hz), 3.97-3.88 (1H, m), 3.12 (1H, d, J=12.5 Hz), 2.94 (1H, d, J=16.9 Hz), 2.88-2.79 (2H, m), 2.55-2.46 (1H, m), 1.96 (2H, sext, J=7.1 Hz), 0.97 (3H, t, J=7.1 Hz).

Examples 11CQ, 11CR and 11CS

| | | |
|---|---|---|
| 11CQ | (R)-(1-(4-fluorophenyl)-6-((2-propyl-2H-1,2,3-triazol-4-yl)sulfonyl)-4,4a,5,6,7,8-hexahydro-1H-pyrazolo[3,4-g]isoquinolin-4a-yl)(thiazol-4-yl)methanone | 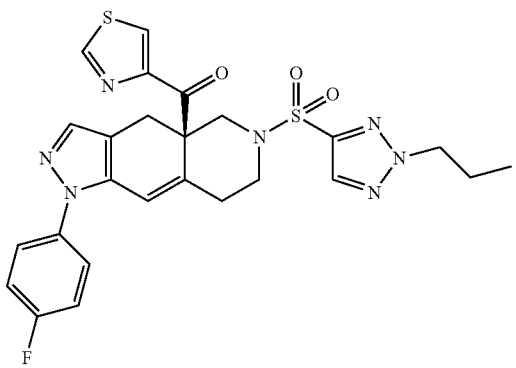 [SMILES: CCCn1ncc(S(=O)(=O)N2CCC3=Cc4c(cnn4-c4ccc(F)cc4)C[C@]3(C(=O)c3cscn3)C2)n1] |
| 11CR | (R)-(1-(4-fluorophenyl)-6-((1-propyl-1H-1,2,3-triazol-5-yl)sulfonyl)-4,4a,5,6,7,8-hexahydro-1H-pyrazolo[3,4-g]isoquinolin-4a-yl)(thiazol-4-yl)methanone | 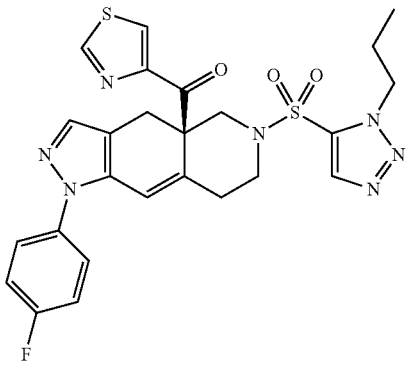 [SMILES: CCCn1nncc1S(=O)(=O)N1CCC2=Cc3c(cnn3-c3ccc(F)cc3)C[C@]2(C(=O)c2cscn2)C1] |

| | | |
|---|---|---|
| 11CS | (R)-(1-(4-fluorophenyl)-6-((1-propyl-1H-1,2,3-triazol-4-yl)sulfonyl)-4,4a,5,6,7,8-hexahydro-1H-pyrazolo[3,4-g]isoquinolin-4a-yl)(thiazol-4-yl)methanone | 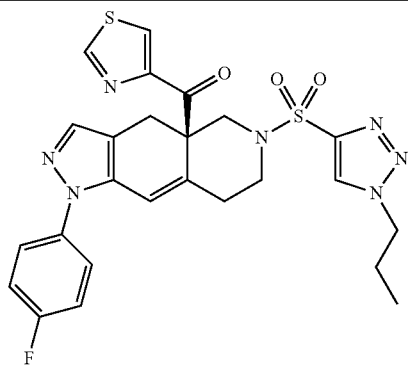 |

Prepared from Preparation 1 of Intermediate 91. LCMS (Method F, ES-API): RT 2.45 min, m+H=554.2; 1H NMR (400 MHz, CDCl3): δ 8.90 (1H, d, J=2.1 Hz), 8.25 (1H, d, J=2.1 Hz), 7.82 (1H, s), 7.47-7.42 (2H, m), 7.30 (1H, s), 7.20-7.14 (2H, m), 6.54 (1H, d, J=2.1 Hz), 5.55 (1H, dd, J=12.7, 2.0 Hz), 4.43 (2H, t, J=7.1 Hz), 4.21 (1H, d, J=16.9 Hz), 3.95-3.90 (1H, m), 2.93-2.85 (3H, m), 2.69-2.63 (1H, m), 2.53-2.49 (1H, m), 2.01 (2H, sext, J=7.1 Hz), 0.94 (3H, t, J=7.1 Hz).

Prepared from Preparation 2 of Intermediate 91. LCMS (Method F, ES-API): RT 2.38 min, m+H=554.2; 1H NMR (400 MHz, CDCl3): δ 8.81 (1H, d, J=2.2 Hz), 8.22 (1H, d, J=2.2 Hz), 7.89 (1H, s), 7.47-7.42 (2H, m), 7.28 (1H, s), 7.21-7.15 (2H, m), 6.57 (1H, br s), 5.48 (1H, dd, J=12.8, 2.0 Hz), 4.39-4.28 (2H, m), 4.12 (1H, d, J=16.9 Hz), 4.01-3.93 (1H, m), 3.06 (1H, d, J=12.8 Hz), 2.92-2.83 (3H, m), 2.66-2.57 (1H, m), 1.93 (2H, dsext, J=7.1, 0.6 Hz), 0.94 (3H, t, J=7.1 Hz).

Prepared from Preparation 3 of Intermediate 91. LCMS (Method F, ES-API): RT 2.29 min, m+H=554.2; 1H NMR (400 MHz, CDCl3): δ: 8.88 (1H, d, J=2.1 Hz), 8.26 (1H, d, J=2.1 Hz), 7.90 (1H, s), 7.48-7.42 (2H, m), 7.30 (1H, s), 7.20-7.14 (2H, m), 6.54 (1H, d, J=1.4 Hz), 5.55 (1H, dd, J=12.7, 2.0 Hz), 4.37 (2H, t, J=7.1 Hz), 4.21 (1H, d, J=16.9 Hz), 3.96-3.91 (1H, m), 3.06 (1H, d, J=12.7 Hz), 2.94-2.80 (3H, m), 2.57-2.48 (1H, m), 1.97 (2H, sext, J=7.1 Hz), 0.98 (3H, t, J=7.1 Hz).

Examples 11CT, 11CU and 11CV

| | | |
|---|---|---|
| 11CT | (R)-(1-(4-fluorophenyl)-6-((2-isopropyl-2H-1,2,3-triazol-4-yl)sulfonyl)-4,4a,5,6,7,8-hexahydro-1H-pyrazolo[3,4-g]isoquinolin-4a-yl)(pyridin-2-yl)methanone | 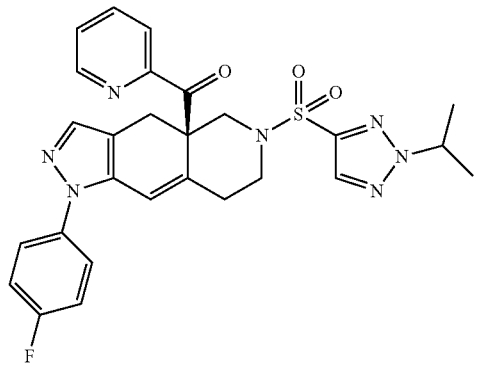 [SMILES: CC(C)n1ncc(S(=O)(=O)N2CCC3=Cc4c(cnn4-c4ccc(F)cc4)C[C@]3(C(=O)c3ccccn3)C2)n1] |
| 11CU | (R)-(1-(4-fluorophenyl)-6-((1-isopropyl-1H-1,2,3-triazol-5-yl)sulfonyl)-4,4a,5,6,7,8-hexahydro-1H-pyrazolo[3,4-g]isoquinolin-4a-yl)(pyridin-2-yl)methanone | 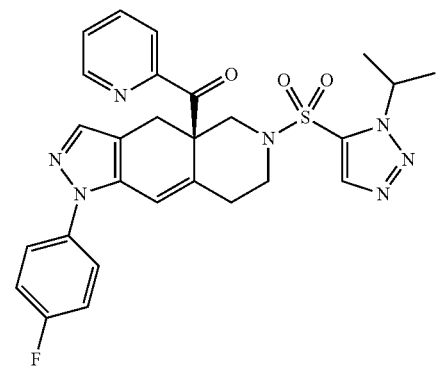 [SMILES: CC(C)n1nncc1S(=O)(=O)N1CCC2=Cc3c(cnn3-c3ccc(F)cc3)C[C@]2(C(=O)c2ccccn2)C1] |

| | |
|---|---|
| 11CV | (R)-(1-(4-fluorophenyl)-6-((1-isopropyl-1H-1,2,3-triazol-4-yl)sulfonyl)-4,4a,5,6,7,8-hexahydro-1H-pyrazolo[3,4-g]isoquinolin-4a-yl)(pyridin-2-yl)methanone |

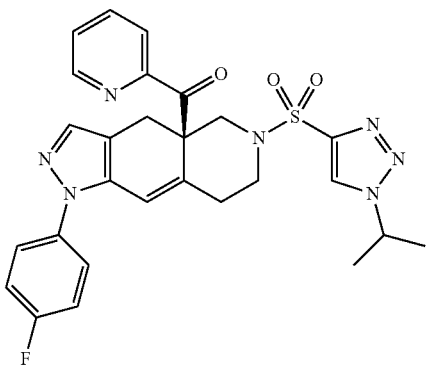 [SMILES: CC(C)n1cc(S(=O)(=O)N2CCC3=Cc4c(cnn4-c4ccc(F)cc4)C[C@]3(C(=O)c3ccccn3)C2)nn1]

Prepared from Preparation 1 of Intermediate 92. LCMS (Method F, ES-API): RT 2.56 min, m+H=548; 1H NMR (400 MHz, CDCl3): δ 8.68 (ddd, J=4.7, 1.8, 1.0 Hz, 1H), 7.92-7.81 (m, 2H), 7.79 (s, 1H), 7.52-7.39 (m, 3H), 7.30 (d, J=0.8 Hz, 1H), 7.22-7.11 (m, 2H), 6.52 (d, J=2.2 Hz, 1H), 5.61 (dd, J=12.7, 2.0 Hz, 1H), 4.86 (hept, J=6.7 Hz, 1H), 4.33 (d, J=17.0 Hz, 1H), 3.91 (ddt, J=10.8, 6.1, 2.1 Hz, 1H), 3.00-2.78 (m, 3H), 2.69 (ddd, J=12.6, 11.0, 3.3 Hz, 1H), 2.50 (dt, J=14.8, 2.7 Hz, 1H), 1.6 (d, J=6.6 Hz, 6H).

Prepared from Preparation 2 of Intermediate 92. LCMS (Method F, ES-API): RT 2.49 min, m+H=548; 1H NMR (400 MHz, CDCl3): δ 8.64-8.59 (m, 1H), 7.86 (s, 1H), 7.85-7.82 (m, 2H), 7.54-7.47 (m, 1H), 7.46-7.41 (m, 2H), 7.29-7.27 (m, 1H), 7.21-7.13 (m, 2H), 6.55 (d, J=1.5 Hz, 1H), 5.67 (dd, J=12.7, 2.1 Hz, 1H), 4.95 (hept, J=6.7 Hz, 1H), 4.21 (d, J=16.8 Hz, 1H), 3.96-3.84 (m, 1H), 3.14 (d, J=12.7 Hz, 1H), 2.95-2.84 (m, 3H), 2.61 (m, 1H), 1.56 (d, J=6.7 Hz, 3H), 1.53 (d, J=6.7 Hz, 3H).

Prepared from Preparation 3 of Intermediate 92. LCMS (Method F, ES-API): RT 2.43 min, m+H=548.1; 1H NMR (400 MHz, CDCl3): δ 8.67 (1H, ddd, J=4.8, 1.8, 0.9 Hz), 7.91-7.86 (2H, m), 7.83 (1H, td, J=7.7, 1.8 Hz), 7.50-7.41 (3H, m), 7.31 (1H, s), 7.21-7.13 (2H, m), 6.52 (1H, br. s), 5.61 (1H, dd, J=12.6, 2.1 Hz), 4.86 (1H, hept, J=6.7 Hz), 4.32 (1H, d, J=16.9 Hz), 3.97-3.89 (1H, m), 3.15 (1H, d, J=12.6 Hz), 2.94 (1H, d, J=16.9 Hz), 2.91-2.78 (2H, m), 2.58-2.44 (1H, m), 1.61 (3H, d, J=6.7 Hz), 1.60 (3H, d, J=6.7 Hz).

Example 11CW. (R)-(6-((1-ethyl-1H-pyrazol-5-yl)sulfonyl)-1-(4-fluorophenyl)-4,4a,5,6,7,8-hexahydro-1H-pyrazolo[3,4-g]isoquinolin-4a-yl)(thiazol-4-yl)methanone

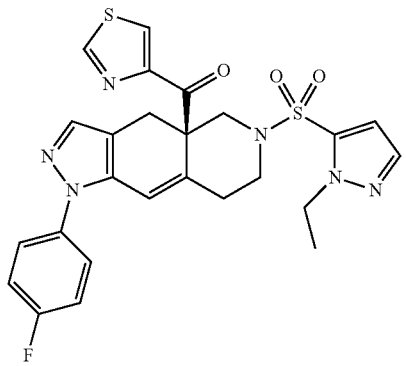 [SMILES: CCn1nccc1S(=O)(=O)N1CCC2=Cc3c(cnn3-c3ccc(F)cc3)C[C@]2(C(=O)c2cscn2)C1]

LCMS (Method F, ES-API): RT 2.32 min, m+H=539.2; 1H NMR (400 MHz, CDCl3): δ 8.81 (1H, d, J=2.1 Hz), 8.22 (1H, d, J=2.2 Hz), 7.47-7.42 (2H, m), 7.39 (1H, d, J=2.0 Hz), 7.28 (1H, s), 7.20-7.14 (2H, m), 6.63 (1H, d, J=2.0 Hz), 6.55 (1H, d, J=2.1 Hz), 5.46 (1H, dd, J=12.7, 2.0 Hz), 4.34-4.17 (2H, m), 4.16 (1H, d, J=16.9 Hz), 3.94-3.89 (1H, m), 2.98 (1H, d, J=12.9 Hz), 2.92-2.75 (3H, m), 2.60-2.56 (1H, m), 1.41 (3H, t, J=7.2 Hz).

Example 11CX. (R)-(1-(4-fluorophenyl)-6-((1-propyl-1H-pyrazol-4-yl)sulfonyl)-4,4a,5,6,7,8-hexahydro-1H-pyrazolo[3,4-g]isoquinolin-4a-yl)(4-(trifluoromethyl)pyridin-2-yl)methanone

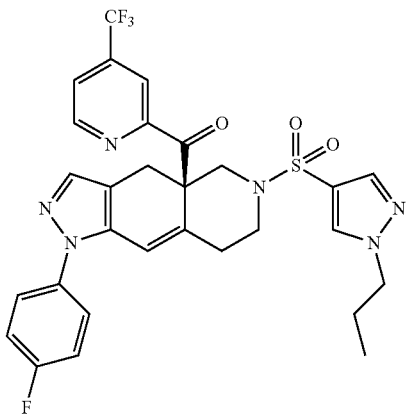 [SMILES: CCCn1cc(S(=O)(=O)N2CCC3=Cc4c(cnn4-c4ccc(F)cc4)C[C@]3(C(=O)c3cc(C(F)(F)F)ccn3)C2)cn1]

LCMS (Method F, ES-API): RT 2.58 min, m+H=615.2; 1H NMR (400 MHz, CDCl3): δ 8.88 (1H, d, J=5.0 Hz), 8.17-8.13 (1H, m), 7.73-7.66 (3H, m), 7.47-7.40 (2H, m), 7.30 (1H, s), 7.22-7.12 (2H, m), 6.51 (1H, d, J=2.1 Hz), 5.45 (1H, dd, J=12.1, 2.1 Hz), 4.21 (1H, d, J=17.0 Hz), 4.09 (2H, t, J=11.3 Hz), 3.78 (1H, ddd, J=10.6, 5.3, 3.1 Hz), 2.93 (1H, d, J=17.0 Hz), 2.83 (1H, dddd, J=14.9, 12.5, 6.0, 2.4 Hz), 2.65 (1H, d, J=12.1 Hz), 2.50 (1H, br. d, J=15.6 Hz), 2.41 (1H, ddd, J=12.8, 10.8, 3.5 Hz), 1.90 (2H, sextet, J=7.4 Hz), 0.91 (3H, t, J=7.4 Hz).

Example 11CY. (R)-(1-(4-fluorophenyl)-6-((1-methyl-1H-pyrazol-4-yl)sulfonyl)-4,4a,5,6,7,8-hexahydro-1H-pyrazolo[3,4-g]isoquinolin-4a-yl)(thiazol-4-yl)methanone

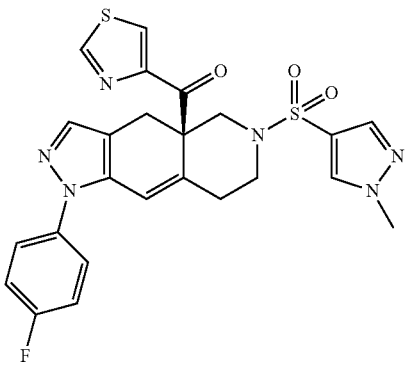 [SMILES: Cn1cc(S(=O)(=O)N2CCC3=Cc4c(cnn4-c4ccc(F)cc4)C[C@]3(C(=O)c3cscn3)C2)cn1]

LCMS (Method F, ES-API): RT 2.02 min, m+H=525.2; 1H NMR (400 MHz, CDCl3): δ 8.88 (1H, d, J=2.2 Hz), 8.26 (1H, d, J=2.2 Hz), 7.69 (1H, s), 7.66 (1H, d, J=0.6 Hz), 7.47-7.40 (2H, m), 7.30 (1H, s), 7.21-7.12 (2H, m), 6.52 (1H, d, J=2.2 Hz), 5.41 (1H, dd, J=12.2, 2.2 Hz), 4.18 (1H, d, J=16.9 Hz), 3.93 (s, 3H), 3.80 (1H, ddt, J=8.5, 4.4, 1.9 Hz), 2.94-2.80 (2H, m), 2.63 (1H, d, J=12.2 Hz), 2.56-2.38 (2H, m).

Example 11CZ. (R)-(1-(4-fluorophenyl)-6-((1-propyl-1H-pyrazol-4-yl)sulfonyl)-4,4a,5,6,7,8-hexahydro-1H-pyrazolo[3,4-g]isoquinolin-4a-yl)(thiazol-4-yl)methanone

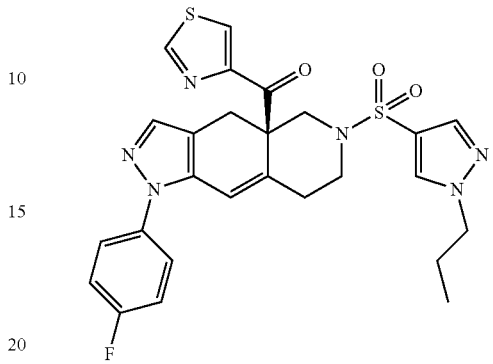

LCMS (Method F, ES-API): RT 2.31 min, m+H=553.2; 1H NMR (400 MHz, CDCl3): δ 8.90 (1H, d, J=1.6 Hz), 8.27 (1H, d, J=2.0 Hz), 7.72 (1H, s), 7.68 (1H, d, J=0.5 Hz), 7.46-7.42 (2H, m), 7.30 (1H, s), 7.20-7.15 (2H, m), 6.52 (1H, d, J=2.0 Hz), 5.43 (1H, dd, J=12.4, 2.0 Hz), 4.19 (1H, d, J=16.8 Hz), 4.09 (2H, t, J=7.1 Hz), 3.82-3.78 (1H, m), 2.94-2.81 (2H, m), 2.61 (1H, d, J=12.4 Hz), 2.53-2.48 (1H, m), 2.44-2.37 (1H, m), 1.91 (2H, sext., J=7.2 Hz), 0.92 (3H, t, J=7.2 Hz).

Example 11DA

| Isomer A | (R)-(1-(4-fluorophenyl)-6-((2-methyl-2H-1,2,3-triazol-4-yl)sulfonyl)-4,4a,5,6,7,8-hexahydro-1H-pyrazolo[3,4-g]isoquinolin-4a-yl)(thiazol-4-yl)methanone | 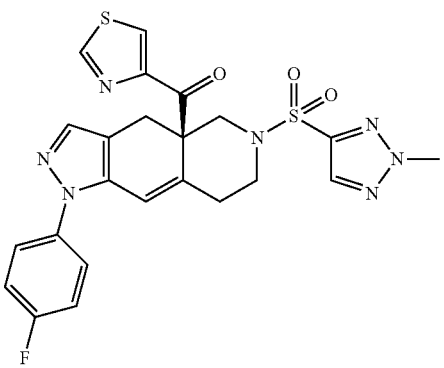 [SMILES: Cn1ncc(S(=O)(=O)N2CCC3=Cc4c(cnn4-c4ccc(F)cc4)C[C@]3(C(=O)c3cscn3)C2)n1] |
| --- | --- | --- |
| Isomer B | (R)-(1-(4-fluorophenyl)-6-((1-methyl-1H-1,2,3-triazol-5-yl)sulfonyl)-4,4a,5,6,7,8-hexahydro-1H-pyrazolo[3,4-g]isoquinolin-4a-yl)(thiazol-4-yl)methanone | 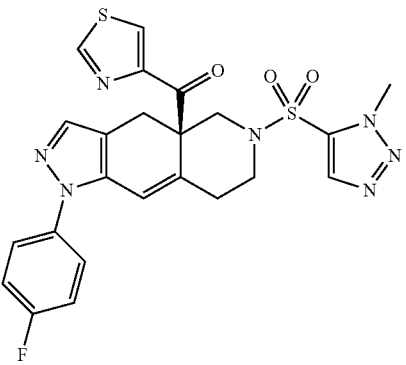 [SMILES: Cn1nncc1S(=O)(=O)N1CCC2=Cc3c(cnn3-c3ccc(F)cc3)C[C@]2(C(=O)c2cscn2)C1] |

| Isomer C | (R)-(1-(4-fluorophenyl)-6-((1-methyl-1H-1,2,3-traizol-4-yl)sulfonyl)-4,4a,5,6,7,8-hexahydro-1H-pyrazolo[3,4-g]isoquinolin-4a-yl)(thiazol-4-yl)methanone | 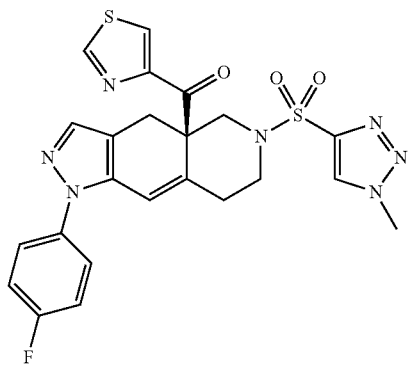 [SMILES: Cn1cc(S(=O)(=O)N2CCC3=Cc4c(cnn4-c4ccc(F)cc4)C[C@]3(C(=O)c3cscn3)C2)nn1] |

Prepared from Preparation 1 of Intermediate 89. LCMS (Method F, ES-API): RT 2.16 min, m+H=526.2; 1H NMR (400 MHz, CDCl3): δ 8.90 (1H, d, J=2.2 Hz), 8.25 (1H, d, J=2.2 Hz), 7.82 (1H, s), 7.47-7.42 (2H, m), 7.30 (1H, s), 7.20-7.14 (2H, m), 6.54 (1H, d, J=2.1 Hz), 5.55 (1H, dd, J=12.7, 2.1 Hz), 4.25 (3H, s), 4.20 (1H, d, J=16.9 Hz), 3.96-3.90 (1H, m), 2.93-2.85 (3H, m), 2.73-2.66 (1H, m), 2.54-2.49 (1H, m).

Example 11DB

| Isomer A | (R)-(1-(4-fluorophenyl)-6-((2-methyl-2H-1,2,3-triazol-4-yl)sulfonyl)-4,4a,5,6,7,8-hexahydro-1H-pyrazolo[3,4-g]isoquinolin-4a-yl)(pyridin-2-yl)methanone | 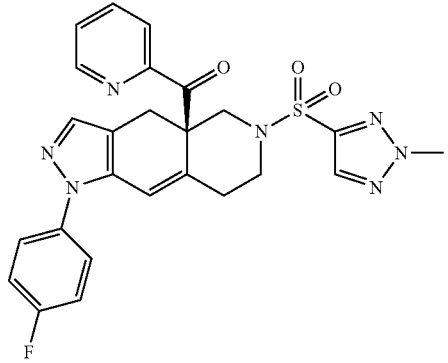 [SMILES: Cn1ncc(S(=O)(=O)N2CCC3=Cc4c(cnn4-c4ccc(F)cc4)C[C@]3(C(=O)c3ccccn3)C2)n1] |

| Isomer B | (R)-(1-(4-fluorophenyl)-6-((1-methyl-1H-1,2,3-triazol-5-yl)sulfonyl)-4,4a,5,6,7,8-hexahydro-1H-pyrazolo[3,4-g]isoquinolin-4a-yl)(pyridin-2-yl)methanone | 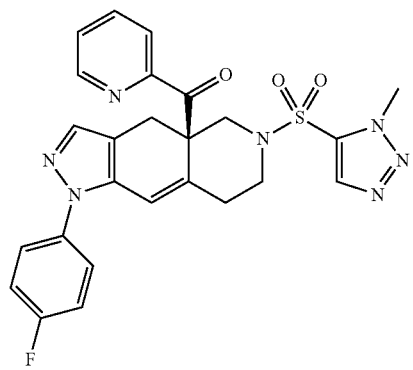 [SMILES: Cn1nncc1S(=O)(=O)N1CCC2=Cc3c(cnn3-c3ccc(F)cc3)C[C@]2(C(=O)c2ccccn2)C1] |

| Isomer C | (R)-(1-(4-fluorophenyl)-6-((1-methyl-1H-1,2,3-triazol-4-yl)sulfonyl)-4,4a,5,6,7,8-hexahydro-1H-pyrazolo[3,4-g]isoquinolin-4a-yl)(pyridin-2-yl)methanone | 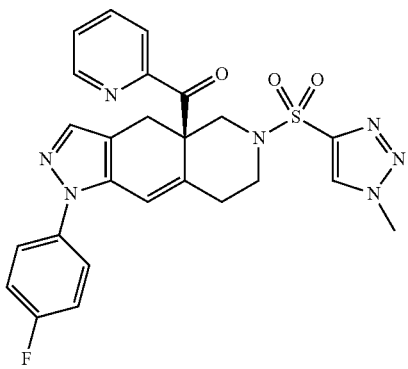 [SMILES: Cn1cc(S(=O)(=O)N2CCC3=Cc4c(cnn4-c4ccc(F)cc4)C[C@]3(C(=O)c3ccccn3)C2)nn1] |

Prepared from Preparation 1 of Intermediate 89. LCMS (Method F, ES-API): RT 2.26 min, m+H=520.0; 1H NMR (400 MHz, CDCl3): δ 8.67 (1H, ddd, J=4.9, 1.6, 1.0 Hz), 7.88 (1H, ddd, J=8.0, 1.6, 1.0 Hz), 7.83 (1H, dt, J=7.4, 1.6 Hz), 7.80 (1H, s), 7.49-7.42 (3H, m), 7.30 (1H, s), 7.20-7.14 (2H, m), 6.51 (1H, d, J=2.1 Hz), 5.60 (1H, dd, J=12.4, 2.0 Hz), 4.31 (1H, d, J=16.9 Hz), 4.24 (3H, s), 3.92-3.87 (1H, m), 2.98 (1H, d, J=12.6 Hz), 2.93 (1H, d, J=16.9 Hz), 2.89-2.80 (1H, m), 2.74-2.68 (1H, m), 2.53-2.48 (1H, m).

Example 11DC

| Isomer A | (R)-(1-(4-fluorophenyl)-6-((2-propyl-2H-1,2,3-triazol-4-yl)sulfonyl)-4,4a,5,6,7,8-hexahydro-1H-pyrazolo[3,4-g]isoquinolin-4a-yl)(4-(trifluoromethyl)pyridin-2-yl)methanone | 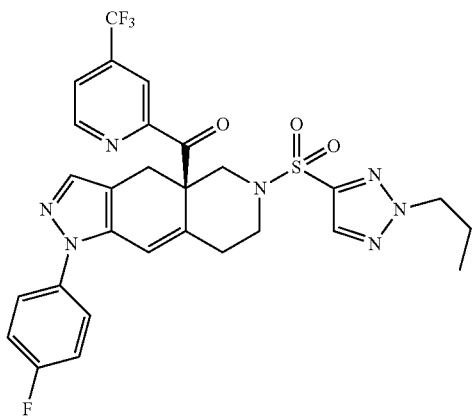 [SMILES: CCCn1ncc(S(=O)(=O)N2CCC3=Cc4c(cnn4-c4ccc(F)cc4)C[C@]3(C(=O)c3cc(C(F)(F)F)ccn3)C2)n1] |
| Isomer B | (R)-(1-(4-fluorophenyl)-6-((1-propyl-1H-1,2,3-triazol-5-yl)sulfonyl)-4,4a,5,6,7,8-hexahydro-1H-pyrazolo[3,4-g]isoquinolin-4a-yl)(4-(trifluoromethyl)pyridin-2-yl)methanone | 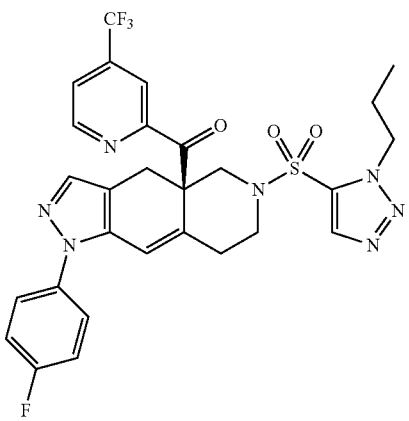 [SMILES: CCCn1nncc1S(=O)(=O)N1CCC2=Cc3c(cnn3-c3ccc(F)cc3)C[C@]2(C(=O)c2cc(C(F)(F)F)ccn2)C1] |

| | | |
|---|---|---|
| Isomer C | (R)-(1-(4-fluorophenyl)-6-((1-propyl-1H-1,2,3-triazol-4-yl)sulfonyl)-4,4a,5,6,7,8-hexahydro-1H-pyrazolo[3,4-g]isoquinolin-4a-yl)(4-(trifluoromethyl)pyridin-2-yl)methanone | 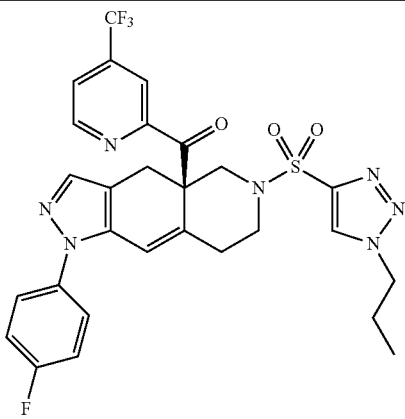 |

Prepared from Preparation 1 of Intermediate 91. LCMS (Method F, ES-API): RT 2.75 min, m+H=616.2; 1H NMR (400 MHz, CDCl3): δ 8.89 (1H, d, J=4.9 Hz), 8.14 (1H, m), 7.82 (1H, s), 7.71-7.70 (1H, m), 7.47-7.42 (2H, m), 7.30 (1H, s), 7.21-7.15 (2H, m), 6.53 (1H, d, J=2.1 Hz), 5.58 (1H, dd, J=12.5, 2.0 Hz), 4.42 (2H, t, J=7.1 Hz), 4.22 (1H, d, J=16.9 Hz), 3.92-3.87 (1H, m), 2.96 (1H, br s), 2.93-2.92 (1H, m), 2.88-2.79 (1H, m), 2.70-2.64 (1H, m), 2.54-2.50 (1H, m), 2.01 (2H, sext, J=7.1 Hz), 0.93 (3H, t, J=7.1 Hz).

Example 12. (R)-(1-(4-fluorophenyl)-6-((3-(trifluoromethyl)phenyl)sulfonyl)-4,4a,5,6,7,8-hexahydro-1H-pyrazolo[3,4-g]isoquinolin-4a-yl)(thiazol-2-yl) methanone

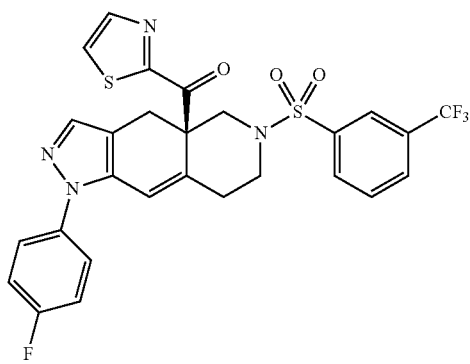 [SMILES: O=C(c1nccs1)[C@]12Cc3cnn(-c4ccc(F)cc4)c3C=C1CCN(S(=O)(=O)c1cccc(C(F)(F)F)c1)C2]

2-Bromothiazole (187 mg, 1.139 mmol) in dry ether (2 mL) was added to butyllithium (1.6M in hexanes) (729 µl, 1.167 mmol) in dry ether (4 mL) at −78° C. The reaction mixture was stirred at −78° C. for 45 minutes. A solution of (R)-methyl 1-(4-fluorophenyl)-6-((3-(trifluoromethyl)phenyl)sulfonyl)-4,4a,5,6,7,8-hexahydro-1H-pyrazolo[3,4-g]isoquinoline-4a-carboxylate (200 mg, 0.373 mmol) in dry ether (4 mL) was added dropwise and the reaction mixture was stirred for 30 minutes at −78° C. Water (20 mL) was added and the reaction mixture was stirred at room temperature for 10 minutes. The aqueous layer was extracted with ethyl acetate (3×30 mL). The combined organic extracts were washed with brine (30 mL), dried (magnesium sulfate), and solvent removed to give a yellow oil. The crude product was purified first by chromatography on silica gel (gradient: 0 to 40% isohexane in ethyl acetate) followed by preparative HPLC (Waters, Acidic (0.1% Formic acid), Waters X-Select Prep-C18, 5 µm, 19×50 mm column, 40-65% acetonitrile in water) to afford (R)-(1-(4-fluorophenyl)-6-((3-(trifluoromethyl)phenyl)sulfonyl)-4,4a,5,6,7,8-hexahydro-1H-pyrazolo[3,4-g]isoquinolin-4a-yl)(thiazol-2-yl)methanone (127 mg) as a pale yellow solid. LCMS (Method F, ES-API): RT 2.73 min, m+H=589.0; 1H NMR (400 MHz, CDCl3): δ 8.04 (1H, d, J=3.1 Hz), 7.97 (1H, s), 7.90 (1H, d, J=7.9 Hz), 7.81 (1H, d, J=7.9 Hz), 7.70-7.59 (2H, m), 7.46-7.39 (2H, m), 7.30 (1H, s), 7.13-7.19 (2H, m), 6.53 (1H, d, J=2.2 Hz), 5.54 (1H, dd, J=12.4, 2.0 Hz), 4.21 (1H, d, J=16.8 Hz), 3.93-3.89 (1H, m), 2.95-2.84 (2H, m), 2.80 (1H, d, J=12.5 Hz), 2.61-2.52 (2H, m).

The following examples were similarly prepared from the appropriate intermediates:

Example 12A. (R)-(1-(4-fluorophenyl)-6-(m-tolylsulfonyl)-4,4a,5,6,7,8-hexahydro-1H-pyrazolo[3,4-g] isoquinolin-4a-yl)(thiazol-2-yl)methanone

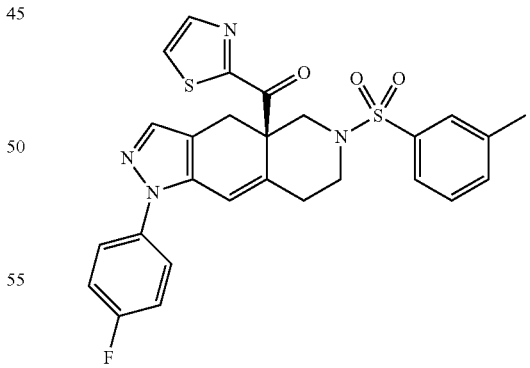

LCMS (Method F, ES-API): RT 2.65 min, m+H=535.0; 1H NMR (400 MHz, CDCl3): δ 8.05 (1H, d, J=3.1 Hz), 7.66 (1H, d, J=3.1 Hz), 7.54-7.47 (2H, m), 7.44-7.40 (2H, m), 7.36-7.34 (2H, m), 7.29 (1H, s), 7.19-7.13 (2H, m), 6.51 (1H, d, J=2.3 Hz), 5.52 (1H, dd, J=12.3, 2.1 Hz), 4.22 (1H, d, J=16.8 Hz), 3.89-3.84 (1H, m), 2.93-2.84 (2H, m), 2.71 (1H, d, J=12.3 Hz), 2.56-2.43 (2H, m), 2.41 (3H, s).

Example 12B. (R)-(1-(4-fluorophenyl)-6-((3-methoxyphenyl)sulfonyl)-4,4a,5,6,7,8-hexahydro-1H-pyrazolo[3,4-g]isoquinolin-4a-yl)(thiazol-2-yl)methanone

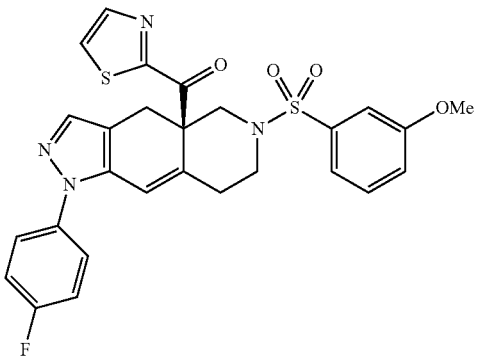 [SMILES: COc1cccc(S(=O)(=O)N2CCC3=Cc4c(cnn4-c4ccc(F)cc4)C[C@]3(C(=O)c3nccs3)C2)c1]

LCMS (Method F, ES-API): RT 2.57 min, m+H=551.0; 1H NMR (400 MHz, CDCl3): δ 8.04 (1H, d, J=3.1 Hz), 7.66 (1H, d, J=3.1 Hz), 7.44-7.35 (3H, m), 7.31-7.27 (2H, m), 7.21-7.14 (3H, m), 7.07 (1H, ddd, J=8.2, 2.6, 1.0 Hz), 6.52 (1H, d, J=2.1 Hz), 5.50 (1H, dd, J=12.4, 2.1 Hz), 4.22 (1H, d, J=16.8 Hz), 3.89-3.83 (4H, m), 2.93-2.82 (2H, m), 2.74 (1H, d, J=12.4 Hz), 2.53-2.47 (2H, m).

Example 12C. (R)-(6-((3-fluoro-4-methylphenyl)sulfonyl)-1-(4-fluorophenyl)-4,4a,5,6,7,8-hexahydro-1H-pyrazolo[3,4-g]isoquinolin-4a-yl)(thiazol-2-yl)methanone

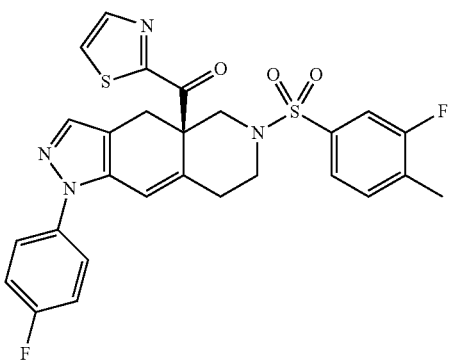 [SMILES: Cc1ccc(S(=O)(=O)N2CCC3=Cc4c(cnn4-c4ccc(F)cc4)C[C@]3(C(=O)c3nccs3)C2)cc1F]

LCMS (Method F, ES-API): RT 2.70 min, m+H=552.9; 1H NMR (400 MHz, CDCl3): δ 8.04 (1H, d, J=3.1 Hz), 7.67 (1H, d, J=3.1 Hz), 7.43-7.38 (3H, m), 7.34-7.26 (3H, m), 7.19-7.13 (2H, m), 6.52 (1H, d, J=2.2 Hz), 5.50 (1H, dd, J=12.4, 2.2 Hz), 4.21 (1H, d, J=16.8 Hz), 3.87 (1H, ddt, J=8.5, 4.3, 1.9 Hz), 2.93-2.83 (2H, m), 2.74 (1H, d, J=12.4 Hz), 2.54-2.48 (2H, m), 2.32 (3H, d, J=1.8 Hz).

Example 12D. (R)-(1-(4-fluorophenyl)-6-(phenylsulfonyl)-4,4a,5,6,7,8-hexahydro-1H-pyrazolo[3,4-g]isoquinolin-4a-yl)(thiazol-2-yl)methanone

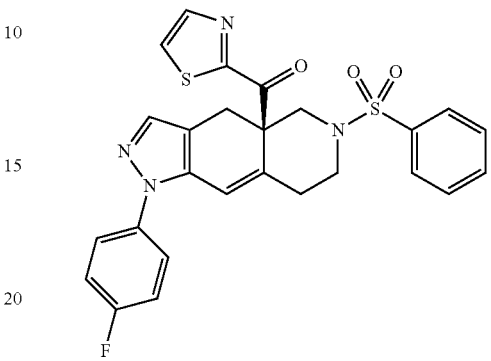

LCMS (Method F, ES-API): RT 2.54 min, m+H=521.2; 1H NMR (400 MHz, CDCl3): δ 8.05 (1H, d, J=3.1 Hz), 7.74-7.71 (2H, m), 7.67 (1H, d, J=3.1 Hz), 7.59-7.55 (1H, m), 7.51-7.47 (2H, m), 7.45-7.40 (2H, m), 7.29 (1H, s), 7.19-7.13 (2H, m), 6.51 (1H, d, J=2.5 Hz), 5.53 (1H, dd, J=12.3, 2.2 Hz), 4.22 (1H, d, J=16.7 Hz), 3.91-3.85 (1H, m), 2.93-2.84 (2H, m), 2.70 (1H, d, J=12.4 Hz), 2.53-2.43 (2H, m).

Example 12E. (R)-(6-((3-chlorophenyl)sulfonyl)-1-(4-fluorophenyl)-4,4a,5,6,7,8-hexahydro-1H-pyrazolo[3,4-g]isoquinolin-4a-yl)(thiazol-2-yl)methanone

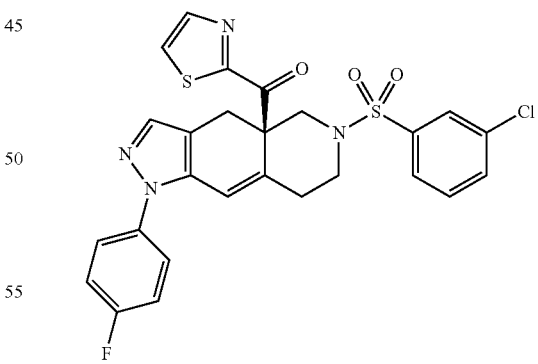

LCMS (Method F, ES-API): RT 2.71 min, m+H=555.2; 1H NMR (400 MHz, CDCl3): δ 8.05 (1H, d, J=3.2 Hz), 7.69-7.67 (2H, m), 7.61-7.58 (1H, m), 7.54-7.51 (1H, m), 7.45-7.40 (3H, m), 7.30 (1H, s), 7.20-7.14 (2H, m), 6.53 (1H, d, J=2.5 Hz), 5.52 (1H, dd, J=12.6, 1.5 Hz), 4.21 (1H, d, J=16.8 Hz), 3.91-3.87 (1H, m), 2.93-2.83 (2H, m), 2.78 (1H, d, J=12.4 Hz), 2.58-2.52 (2H, m).

Example 12F. (R)-(1-(4-fluorophenyl)-6-(m-tolyl-sulfonyl)-4,4a,5,6,7,8-hexahydro-1H-pyrazolo[3,4-g]isoquinolin-4a-yl)(5-methylpyridin-2-yl)methanone

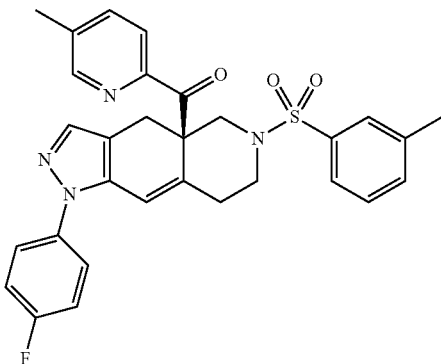 [SMILES: Cc1ccc(C(=O)[C@]23Cc4cnn(-c5ccc(F)cc5)c4C=C2CCN(S(=O)(=O)c2cccc(C)c2)C3)nc1]

LCMS (Method F, ES-API): RT 2.77 min, m+H=543.2; 1H NMR (400 MHz, CDCl3): δ 8.46 (1H, m), 7.82 (1H, d, J=8.0 Hz), 7.61 (1H, ddd, J=8.0, 2.3, 0.9 Hz), 7.51-7.48 (2H, m), 7.45-7.40 (2H, m), 7.35-7.33 (2H, m), 7.27 (1H, s), 7.18-7.12 (2H, m), 6.46 (1H, d, J=2.1 Hz), 5.57 (1H, dd, J=12.2, 2.1 Hz), 4.29 (1H, d, J=16.9 Hz), 3.84-3.79 (1H, m), 2.90-2.78 (2H, m), 2.70 (1H, d, J=12.0 Hz), 2.48-2.39 (8H, m).

Example 12G. (R)-(1-(4-fluorophenyl)-6-(m-tolyl-sulfonyl)-4,4a,5,6,7,8-hexahydro-1H-pyrazolo[3,4-g]isoquinolin-4a-yl)(4-methylpyridin-2-yl)methanone

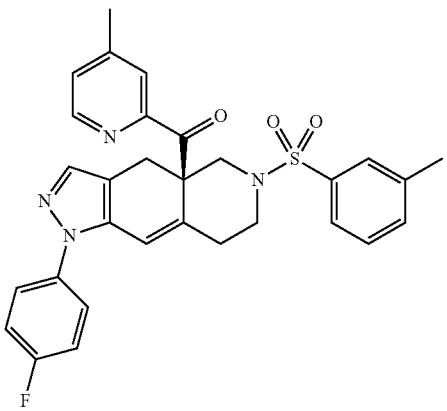 [SMILES: Cc1cccc(S(=O)(=O)N2CCC3=Cc4c(cnn4-c4ccc(F)cc4)C[C@]3(C(=O)c3cc(C)ccn3)C2)c1]

LCMS (Method F, ES-API): RT 2.75 min, m+H=543.2; 1H NMR (400 MHz, CDCl3): δ 8.50 (1H, dd, J=3.9, 0.4 Hz), 7.71 (1H, m), 7.51-7.48 (2H, m), 7.45-7.40 (2H, m), 7.35-7.33 (2H, m), 7.28-7.26 (2H, m), 7.18-7.12 (2H, m), 6.46 (1H, d, J=2.1 Hz), 5.53 (1H, dd, J=12.2, 2.1 Hz), 4.30 (1H, d, J=16.9 Hz), 3.84-3.80 (1H, m), 2.90-2.77 (2H, m), 2.69 (1H, d, J=12.3 Hz), 2.48-2.42 (2H, m), 2.40 (3H, s), 2.39 (3H, s).

Example 12H. (R)-(1-(4-fluorophenyl)-6-(m-tolyl-sulfonyl)-4,4a,5,6,7,8-hexahydro-1H-pyrazolo[3,4-g]isoquinolin-4a-yl)(6-methylpyridin-2-yl)methanone

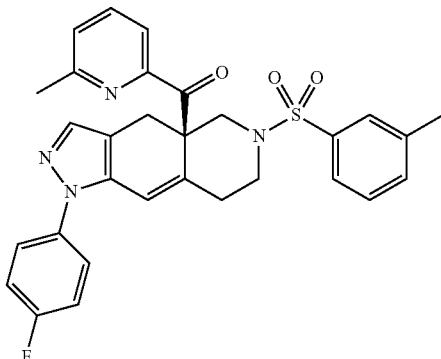

LCMS (Method F, ES-API): RT 2.77 min, m+H=543.0; 1H NMR (400 MHz, CDCl3): δ 7.72-7.68 (2H, m), 7.42-7.36 (4H, m), 7.34-7.30 (4H, m), 7.18-7.13 (2H, m), 6.45 (1H, d, J=2.0 Hz), 5.55 (1H, dd, J=12.2, 2.0 Hz), 4.19 (1H, d, J=17.0 Hz), 3.84-3.80 (1H, m), 2.87 (1H, d, J=17.0 Hz), 2.83-2.73 (1H, m), 2.71 (1H, d, J=12.2 Hz), 2.62 (3H, s), 2.54-2.42 (2H, m), 2.39 (3H, s).

Example 12I. (R)-(6-((4-fluoro-3-(trifluoromethyl)phenyl)sulfonyl)-1-(4-fluorophenyl)-4,4a,5,6,7,8-hexahydro-1H-pyrazolo[3,4-g]isoquinolin-4a-yl)(thiazol-2-yl)methanone

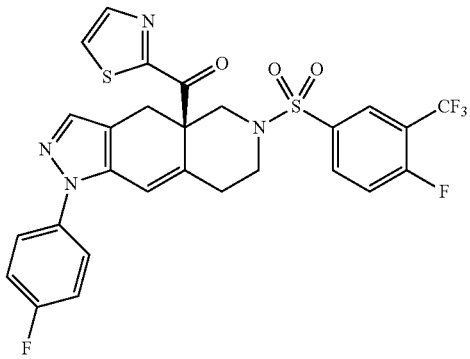 [SMILES: O=C(c1nccs1)[C@]12Cc3cnn(-c4ccc(F)cc4)c3C=C1CCN(S(=O)(=O)c1ccc(F)c(C(F)(F)F)c1)C2]

LCMS (Method F, ES-API): RT 2.77 min, m+H=606.9; 1H NMR (400 MHz, CDCl3): δ 8.00 (1H, d, J=3.0 Hz), 7.98 (1H, dd, J=6.4, 2.3 Hz), 7.90 (1H, ddd, J=8.5, 4.3, 2.3 Hz), 7.68 (1H, d, J=3.1 Hz), 7.47-7.40 (2H, m), 7.29 (1H, s), 7.27-7.25 (1H, m), 7.20-7.14 (2H, m), 6.55 (1H, d, J=2.1 Hz), 5.49 (1H, dd, J=12.5, 2.1 Hz), 4.18 (1H, d, J=16.8 Hz), 3.94 (1H, ddd, J=8.9, 5.1, 2.1 Hz), 2.93-2.84 (3H, m), 2.66-2.55 (2H, m).

Example 12J. (R)-(1-(4-fluorophenyl)-6-((3,4,5-trifluorophenyl)sulfonyl)-4,4a,5,6,7,8-hexahydro-1H-pyrazolo[3,4-g]isoquinolin-4a-yl)(thiazol-2-yl)methanone

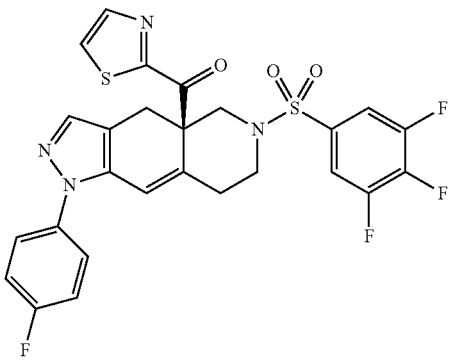 [SMILES: O=C(c1nccs1)[C@]12Cc3cnn(-c4ccc(F)cc4)c3C=C1CCN(S(=O)(=O)c1cc(F)c(F)c(F)c1)C2]

LCMS (Method F, ES-API): RT 2.75 min, m+H=575.1; 1H NMR (400 MHz, CDCl3): δ 8.04 (1H, d, J=3.0 Hz), 7.70 (1H, d, J=3.0 Hz), 7.47-7.41 (2H, m), 7.37-7.34 (2H, m), 7.30 (1H, s), 7.20-7.14 (2H, m), 6.55 (1H, d, J=2.1 Hz), 5.49 (1H, dd, J=12.5, 2.0 Hz), 4.20 (1H, d, J=16.8 Hz), 3.93-3.88 (1H, m), 2.92-2.83 (3H, m), 2.67-2.55 (2H, m).

Example 12K. (R)-(6-((3-fluoro-4-(trifluoromethyl)phenyl)sulfonyl)-1-(4-fluorophenyl)-4,4a,5,6,7,8-hexahydro-1H-pyrazolo[3,4-g]isoquinolin-4a-yl)(thiazol-2-yl)methanone

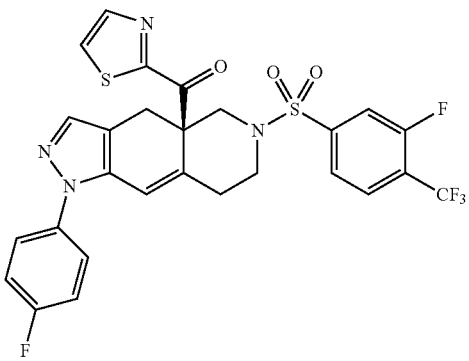 [SMILES: O=C(c1nccs1)[C@]12Cc3cnn(-c4ccc(F)cc4)c3C=C1CCN(S(=O)(=O)c1ccc(C(F)(F)F)c(F)c1)C2]

LCMS (Method F, ES-API): RT 2.94 min, m+H=607.1; 1H NMR (400 MHz, CDCl3): δ 8.02 (1H, d, J=3.0 Hz), 7.73-7.69 (1H, m), 7.68 (1H, d, J=3.0 Hz), 7.59 (1H, br d, J=8.2 Hz), 7.53 (1H, br d, J=9.4 Hz), 7.45-7.40 (2H, m), 7.30 (1H, s), 7.20-7.14 (2H, m), 6.55 (1H, d, J=2.2 Hz), 5.52 (1H, dd, J=12.4, 2.0 Hz), 4.20 (1H, d, J=16.9 Hz), 3.96-3.92 (1H, m), 2.93-2.84 (3H, m), 2.67-2.62 (1H, m), 2.59-2.55 (1H, m).

Example 12L. (R)-(1-(4-fluorophenyl)-6-((3-(trifluoromethyl)phenyl)sulfonyl)-4,4a,5,6,7,8-hexahydro-1H-pyrazolo[3,4-g]isoquinolin-4a-yl)(5-methylthiazol-2-yl)methanone

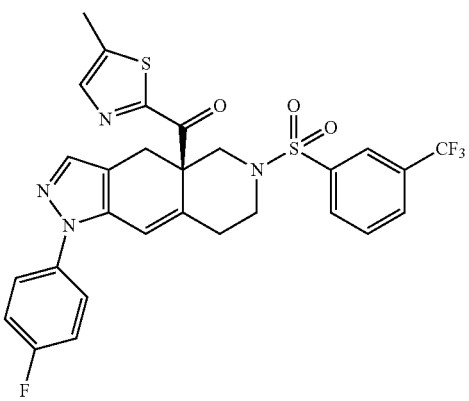 [SMILES: Cc1cnc(C(=O)[C@]23Cc4cnn(-c5ccc(F)cc5)c4C=C2CCN(S(=O)(=O)c2cccc(C(F)(F)F)c2)C3)s1]

LCMS (Method F, ES-API): RT 2.83 min, m+H=603; 1H NMR (400 MHz, CDCl3): δ 7.98 (1H, s), 7.91 (1H, br. d, J=7.9 Hz), 7.84-7.80 (1H, m), 7.68-7.61 (2H, m), 7.46-7.39 (2H, m), 7.29 (1H, s), 7.20-7.12 (2H, m), 6.51 (1H, d, J=2.1 Hz), 5.54 (1H, dd, J=12.4, 2.1 Hz), 4.17 (1H, d, J=16.7 Hz), 3.93-3.89 (1H, m), 2.95-2.77 (3H, m), 2.60-2.49 (5H, m).

Example 12M. (R)-(1-(4-fluorophenyl)-6-((3-(trifluoromethyl)phenyl)sulfonyl)-4,4a,5,6,7,8-hexahydro-1H-pyrazolo[3,4-g]isoquinolin-4a-yl)(4-methylthiazol-2-yl)methanone

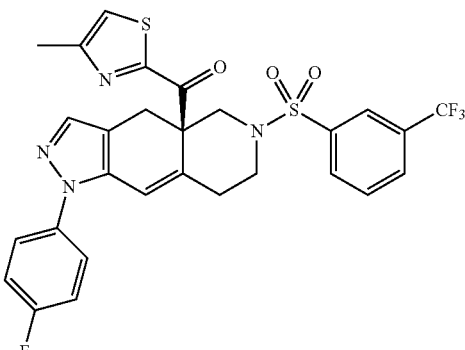

LCMS (Method F, ES-API): RT 2.80 min, m+H=603.0; 1H NMR (400 MHz, CDCl3): δ 7.96 (1H, s), 7.88 (1H, d, J=7.9 Hz), 7.80 (1H, d, J=7.9 Hz), 7.62 (1H, t, J=7.9 Hz), 7.42 (2H, ddt, J=8.1, 5.6, 2.8 Hz), 7.30 (1H, s), 7.21 (1H, d, J=0.9 Hz), 7.20-7.12 (2H, m), 6.52 (1H, d, J=2.2 Hz), 5.56 (1H, dd, J=12.4, 2.2 Hz), 4.18 (1H, d, J=16.8 Hz), 3.95-3.88 (1H, m), 2.91-2.80 (3H, m), 2.63-2.50 (5H, m).

Example 12N. (R)-(6-((3,4-dichlorophenyl)sulfonyl)-1-(4-fluorophenyl)-4,4a,5,6,7,8-hexahydro-1H-pyrazolo[3,4-g]isoquinolin-4a-yl)(thiazol-2-yl)methanone

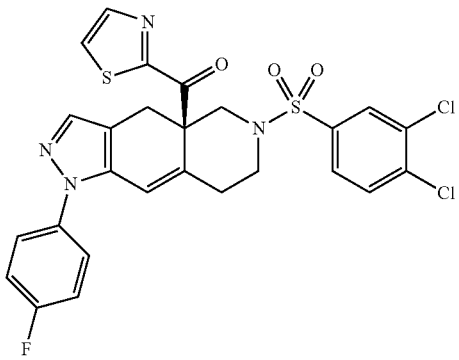 [SMILES: O=C(c1nccs1)[C@]12Cc3cnn(-c4ccc(F)cc4)c3C=C1CCN(S(=O)(=O)c1ccc(Cl)c(Cl)c1)C2]

LCMS (Method F, ES-API): RT 3.34 min, m+H=589.1; 1H NMR (400 MHz, CDCl3): δ 8.00 (1H, d, J=3.0 Hz), 7.77 (1H, dd, J=1.8, 0.9 Hz), 7.67 (1H, d, J=3.0 Hz), 7.54-7.48 (2H, m), 7.45-7.40 (2H, m), 7.29 (1H, s), 7.20-7.14 (2H, m), 6.54 (1H, d, J=2.1 Hz), 5.46 (1H, dd, J=12.6, 2.0 Hz), 4.18 (1H, d, J=16.9 Hz), 3.94-3.90 (1H, m), 2.92-2.84 (3H, m), 2.66-2.54 (2H, m).

Example 12O. (R)-(6-((3,4-dichlorophenyl)sulfonyl)-1-(4-fluorophenyl)-4,4a,5,6,7,8-hexahydro-1H-pyrazolo[3,4-g]isoquinolin-4a-yl)(5-methylthiazol-2-yl)methanone

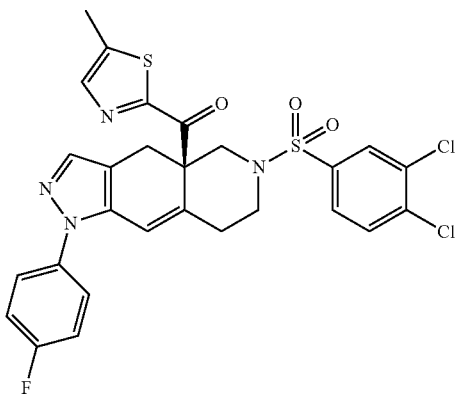 [SMILES: Cc1cnc(C(=O)[C@]23Cc4cnn(-c5ccc(F)cc5)c4C=C2CCN(S(=O)(=O)c2ccc(Cl)c(Cl)c2)C3)s1]

LCMS (Method F, ES-API): RT 2.92 min, m+H=603.9; 1H NMR (400 MHz, CDCl3): δ 7.77 (1H, d, J=1.9 Hz), 7.60 (1H, d, J=1.0 Hz), 7.56-7.48 (2H, m), 7.45-7.40 (2H, m), 7.28 (1H, s), 7.21-7.13 (2H, m), 6.53 (1H, d, J=2.1 Hz), 5.45 (1H, dd, J=12.5, 2.1 Hz), 4.13 (1H, d, J=16.6 Hz), 3.94 (1H, ddt, J=8.5, 3.9, 2.0 Hz), 2.93-2.84 (3H, m), 2.68-2.61 (1H, m), 2.57 (3H, d, J=1.0 Hz), 2.58-2.52 (1H, m).

Example 12P. (R)-(6-((3,4-difluorophenyl)sulfonyl)-1-(4-fluorophenyl)-4,4a,5,6,7,8-hexahydro-1H-pyrazolo[3,4-g]isoquinolin-4a-yl)(thiazol-2-yl)methanone

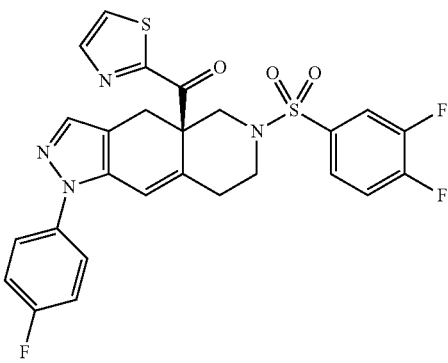 [SMILES: O=C(c1nccs1)[C@]12Cc3cnn(-c4ccc(F)cc4)c3C=C1CCN(S(=O)(=O)c1ccc(F)c(F)c1)C2]

LCMS (Method F, ES-API): RT 2.62 min, m+H=556.9; 1H NMR (400 MHz, CDCl3): δ 8.02 (1H, d, J=3.1 Hz), 7.68 (1H, d, J=3.1 Hz), 7.55-7.47 (2H, m), 7.45-7.40 (2H, m), 7.29 (1H, s), 7.27-7.21 (1H, m), 7.20-7.13 (2H, m), 6.54 (1H, d, J=2.2 Hz), 5.47 (1H, dd, J=12.4, 2.0 Hz), 4.19 (1H, d, J=16.8 Hz), 3.93-3.86 (1H, m), 2.93-2.79 (3H, m), 2.63-2.52 (2H, m).

Example 12Q. (R)-(6-((3,4-difluorophenyl)sulfonyl)-1-(4-fluorophenyl)-4,4a,5,6,7,8-hexahydro-1H-pyrazolo[3,4-g]isoquinolin-4a-yl)(5-methylthiazol-2-yl)methanone

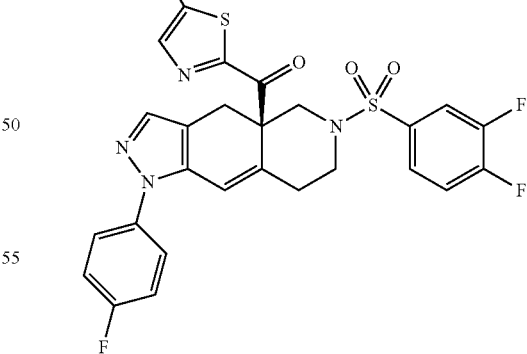

LCMS (Method F, ES-API): RT 2.67 min, m+H=571.1; 1H NMR (400 MHz, CDCl3): δ 7.63 (1H, m), 7.54-7.49 (2H, m), 7.45-7.40 (2H, m), 7.29 (1H, s), 7.27-7.21 (1H, m), 7.19-7.13 (2H, m), 6.52 (1H, d, J=2.0 Hz), 5.44 (1H, dd, J=12.4, 2.0 Hz), 4.15 (1H, d, J=16.9 Hz), 3.93-3.89 (1H, m), 2.91-2.80 (3H, m), 2.64-2.52 (5H, m).

Example 12R. (R)-(6-((4-chloro-3-fluorophenyl)sulfonyl)-1-(4-fluorophenyl)-4,4a,5,6,7,8-hexahydro-1H-pyrazolo[3,4-g]isoquinolin-4a-yl)(5-methylthiazol-2-yl)methanone

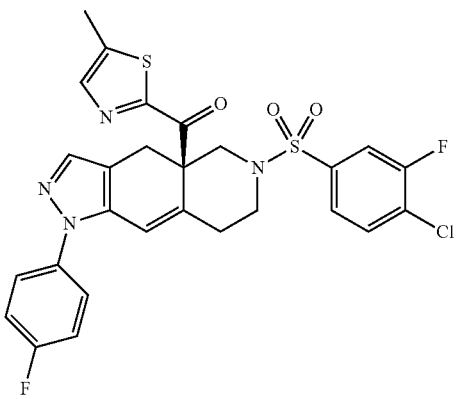 [SMILES: Cc1cnc(C(=O)[C@]23Cc4cnn(-c5ccc(F)cc5)c4C=C2CCN(S(=O)(=O)c2ccc(Cl)c(F)c2)C3)s1]

Using tetrahydrofuran as the reaction solvent in place of diethyl ether. LCMS (Method F, ES-API): RT 2.78 min, m+H=587.1; 1H NMR (400 MHz, CDCl3): δ 7.62 (1H, m), 7.50-7.40 (5H, m), 7.28 (1H, s), 7.19-7.13 (2H, m), 6.52 (1H, d, J=2.0 Hz), 5.45 (1H, dd, J=12.4, 2.0 Hz), 4.14 (1H, d, J=16.9 Hz), 3.94-3.90 (1H, m), 2.91-2.82 (3H, m), 2.67-2.53 (5H, m).

Example 12S. (R)-1-(4-fluorophenyl)-6-((1-methyl-1H-pyrazol-3-yl)sulfonyl)-4,4a,5,6,7,8-hexahydro-1H-pyrazolo[3,4-g]isoquinolin-4a-yl)(5-methylthiazol-2-yl)methanone

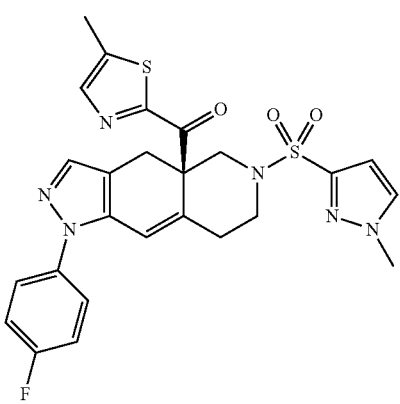 [SMILES: Cc1cnc(C(=O)[C@]23Cc4cnn(-c5ccc(F)cc5)c4C=C2CCN(S(=O)(=O)c2ccn(C)n2)C3)s1]

LCMS (Method F, ES-API): RT 2.27 min, m+H=539.2; 1H NMR (400 MHz, CDCl3): δ 7.71 (1H, m), 7.46-7.41 (2H, m), 7.39 (1H, d, J=2.3 Hz), 7.30 (1H, s), 7.19-7.13 (2H, m), 6.60 (1H, d, J=2.3 Hz), 6.52 (1H, d, J=2.0 Hz), 5.59 (1H, dd, J=12.5, 1.9 Hz), 4.22 (1H, d, J=16.9 Hz), 3.96 (3H, s), 3.92-3.88 (1H, m), 2.94-2.86 (3H, m), 2.69-2.62 (1H, m), 2.55 (3H, d, J=0.9 Hz), 2.52-2.48 (1H, m).

Example 12T. (R)-(1-(4-fluorophenyl)-6-((1-methyl-1H-pyrazol-4-yl)sulfonyl)-4,4a,5,6,7,8-hexahydro-1H-pyrazolo[3,4-g]isoquinolin-4a-yl)(5-methylthiazol-2-yl)methanone

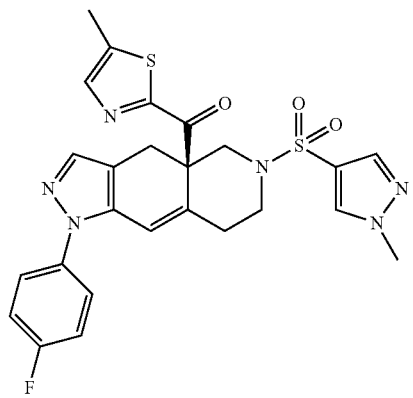 [SMILES: Cc1cnc(C(=O)[C@]23Cc4cnn(-c5ccc(F)cc5)c4C=C2CCN(S(=O)(=O)c2cnn(C)c2)C3)s1]

LCMS (Method F, ES-API): RT 2.25 min, m+H=539.0; 1H NMR (400 MHz, CDCl3): δ 7.72-7.65 (3H, m), 7.43 (2H, ddt, J=8.2, 5.6, 2.8 Hz), 7.30 (1H, s), 7.20-7.13 (2H, m), 6.51 (1H, d, J=2.0 Hz), 5.48 (1H, dd, J=12.1, 2.0 Hz), 4.19 (1H, d, J=16.7 Hz), 3.93 (3H, s), 3.84-3.79 (1H, m), 2.95-2.83 (2H, m), 2.68 (1H, d, J=12.1 Hz), 2.56-2.43 (5H, m).

Example 12U. (R)-(6-((1,3-dimethyl-1H-pyrazol-5-yl)sulfonyl)-1-(4-fluorophenyl)-4,4a,5,6,7,8-hexahydro-1H-pyrazolo[3,4-g]isoquinolin-4a-yl)(5-methylthiazol-2-yl)methanone

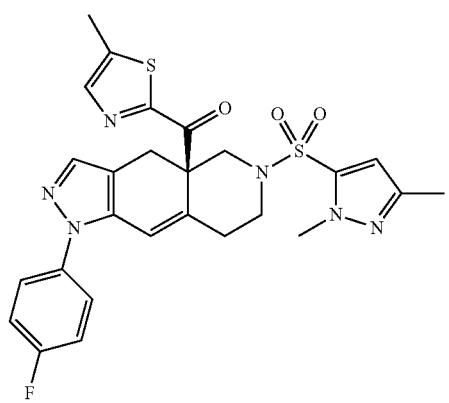 [SMILES: Cc1cc(S(=O)(=O)N2CCC3=Cc4c(cnn4-c4ccc(F)cc4)C[C@]3(C(=O)c3ncc(C)s3)C2)n(C)n1]

Using tetrahydrofuran as the reaction solvent in place of diethyl ether. LCMS (Method F, ES-API): RT 2.46 min, m+H=553.2; 1H NMR (400 MHz, CDCl3): δ 7.61-7.60 (1H, m), 7.46-7.41 (2H, m), 7.29 (1H, s), 7.20-7.14 (2H, m), 6.55 (1H, d, J=2.0 Hz), 6.46 (1H, s), 5.42 (1H, dd, J=12.5, 2.0 Hz), 4.20 (1H, d, J=16.9 Hz), 3.96-3.92 (1H, m), 3.84 (3H, s), 3.01 (1H, d, J=12.7 Hz), 2.92-2.76 (3H, m), 2.61-2.56 (4H, m), 2.20 (3H, s).

Example 12V. (R)-(1-(4-fluorophenyl)-6-((1-methyl-1H-pyrazol-5-yl)sulfonyl)-4,4a,5,6,7,8-hexahydro-1H-pyrazolo[3,4-g]isoquinolin-4a-yl)(5-methylthiazol-2-yl)methanone

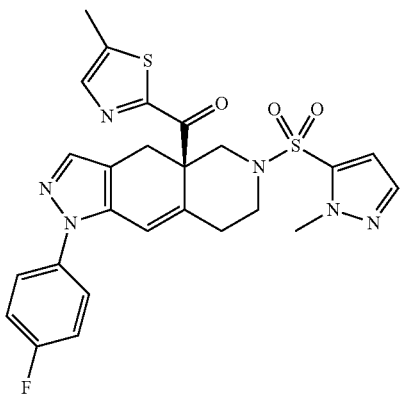 [SMILES: Cc1cnc(C(=O)[C@]23Cc4cnn(-c5ccc(F)cc5)c4C=C2CCN(S(=O)(=O)c2ccnn2C)C3)s1]

LCMS (Method F, ES-API): RT 2.40 min, m+H=539.2; 1H NMR (400 MHz, CDCl3): δ 7.61 (1H, m), 7.46-7.41 (2H, m), 7.35 (1H, d, J=2.0 Hz), 7.29 (1H, s), 7.20-7.14 (2H, m), 6.68 (1H, d, J=2.0 Hz), 6.55 (1H, d, J=1.9 Hz), 5.45 (1H, dd, J=12.5, 2.0 Hz), 4.20 (1H, d, J=16.9 Hz), 3.97-3.93 (4H, m), 3.02 (1H, d, J=12.7 Hz), 2.92-2.76 (3H, m), 2.61-2.55 (4H, m).

Example 12W. (R)-(6-((1-ethyl-1H-pyrazol-5-yl)sulfonyl)-1-(4-fluorophenyl)-4,4a,5,6,7,8-hexahydro-1H-pyrazolo[3,4-g]isoquinolin-4a-yl)(thiazol-2-yl)methanone

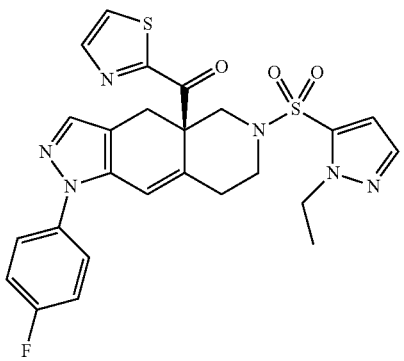 [SMILES: CCn1nccc1S(=O)(=O)N1CCC2=Cc3c(cnn3-c3ccc(F)cc3)C[C@]2(C(=O)c2nccs2)C1]

LCMS (Method F, ES-API): RT 2.40 min, m+H=539.1; 1H NMR (400 MHz, CDCl3): δ 7.98 (1H, d, J=3.1 Hz), 7.65 (1H, d, J=3.1 Hz), 7.47-7.41 (2H, m), 7.39 (1H, d, J=2.0 Hz), 7.30 (1H, s), 7.20-7.14 (2H, m), 6.64 (1H, d, J=2.0 Hz), 6.57 (1H, d, J=1.8 Hz), 5.48 (1H, dd, J=12.7, 2.1 Hz), 4.33-4.16 (3H, m), 3.96-3.91 (1H, m), 3.04 (1H, d, J=12.7 Hz), 2.92-2.77 (3H, m), 2.62-2.58 (1H, m), 1.40 (3H, t, J=7.2 Hz).

Example 12X. (R)-(6-((1-ethyl-1H-pyrazol-4-yl)sulfonyl)-1-(4-fluorophenyl)-4,4a,5,6,7,8-hexahydro-1H-pyrazolo[3,4-g]isoquinolin-4a-yl)(thiazol-2-yl)methanone

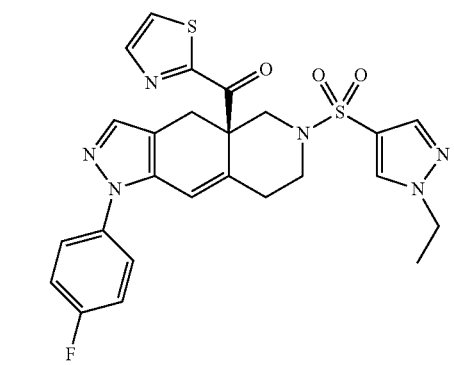 [SMILES: CCn1cc(S(=O)(=O)N2CCC3=Cc4c(cnn4-c4ccc(F)cc4)C[C@]3(C(=O)c3nccs3)C2)cn1]

LCMS (Method F, ES-API): RT 2.24 min, m+H=539.1; 1H NMR (400 MHz, CDCl3): δ 8.06 (1H, d, J=3.1 Hz), 7.73 (1H, s), 7.68-7.67 (2H, m), 7.46-7.41 (2H, m), 7.31 (1H, s), 7.20-7.14 (2H, m), 6.53 (1H, d, J=2.2 Hz), 5.49 (1H, dd, J=12.2, 2.0 Hz), 4.23 (1H, d, J=16.9 Hz), 4.19 (2H, q, J=7.3 Hz), 3.85-3.80 (1H, m), 2.95-2.86 (2H, m), 2.70 (1H, d, J=12.2 Hz), 2.55-2.44 (2H, m), 1.52 (3H, t, J=7.3 Hz).

Example 12Y. (R)-(1-(4-fluorophenyl)-6-((1-propyl-1H-pyrazol-4-yl)sulfonyl)-4,4a,5,6,7,8-hexahydro-1H-pyrazolo[3,4-g]isoquinolin-4a-yl)(thiazol-2-yl)methanone

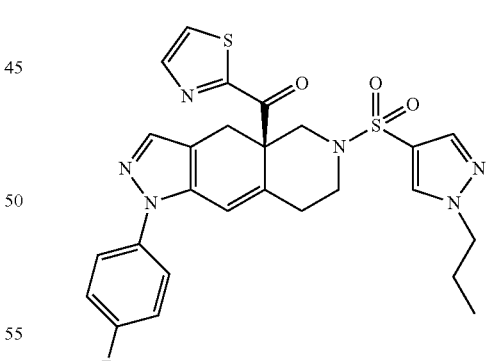

LCMS (Method F, ES-API): RT 2.45 min, m+H=553; 1H NMR (400 MHz, CDCl3): δ 8.07 (d, J=3.1 Hz, 1H), 7.72 (d, J=0.7 Hz, 1H), 7.70-7.65 (m, 2H), 7.49-7.39 (m, 2H), 7.31 (s, 1H), 7.22-7.11 (m, 2H), 6.54 (d, J=2.3 Hz, 1H), 5.50 (dd, J=12.1, 2.1 Hz, 1H), 4.23 (d, J=16.8 Hz, 1H), 4.09 (t, J=7.1 Hz, 2H), 3.87-3.78 (m, 1H), 2.97-2.84 (m, 2H), 2.68 (d, J=12.2 Hz, 1H), 2.57-2.39 (m, 2H), 1.91 (sext., J=7.3 Hz, 2H), 0.92 (t, J=7.4 Hz, 3H).

Example 12Z

| Isomer A | (R)-(1-(4-fluorophenyl)-6-((2-methyl-2H-1,2,3-triazol-4-yl)sulfonyl)-4,4a,5,6,7,8-hexahydro-1H-pyrazolo[3,4-g]isoquinolin-4a-yl)(thiazol-2-yl)methanone | 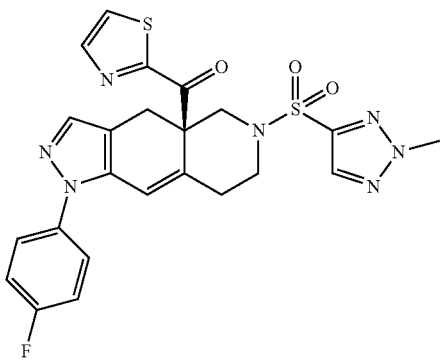 [SMILES: Cn1ncc(S(=O)(=O)N2CCC3=Cc4c(cnn4-c4ccc(F)cc4)C[C@]3(C(=O)c3nccs3)C2)n1] |
|---|---|---|
| Isomer B | (R)-(1-(4-fluorophenyl)-6-((1-methyl-1H-1,2,3-triazol-5-yl)sulfonyl)-4,4a,5,6,7,8-hexahydro-1H-pyrazolo[3,4-g]isoquinolin-4a-yl)(thiazol-2-yl)methanone | 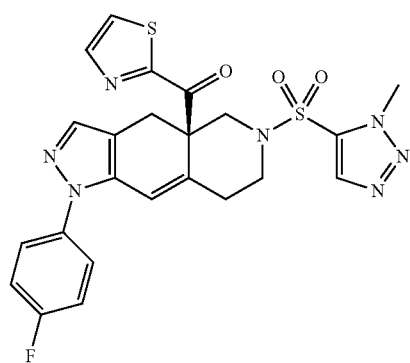 [SMILES: Cn1nncc1S(=O)(=O)N1CCC2=Cc3c(cnn3-c3ccc(F)cc3)C[C@]2(C(=O)c2nccs2)C1] |
| Isomer C | (R)-(1-(4-fluorophenyl)-6-((1-methyl-1H-1,2,3-triazol-4-yl)sulfonyl)-4,4a,5,6,7,8-hexahydro-1H-pyrazolo[3,4-g]isoquinolin-4a-yl)(thiazol-2-yl)methanone | 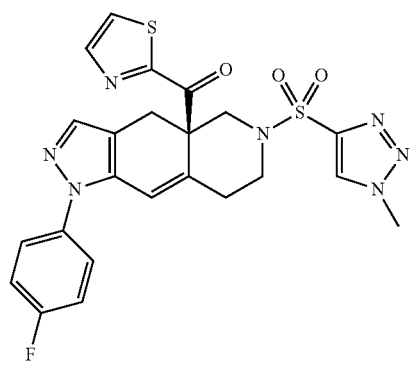 [SMILES: Cn1cc(S(=O)(=O)N2CCC3=Cc4c(cnn4-c4ccc(F)cc4)C[C@]3(C(=O)c3nccs3)C2)nn1] |

Prepared from Intermediate 94. LCMS (Method F, ES-API): RT 2.26 min, m+H=526.1; 1H NMR (400 MHz, CDCl3): δ 8.07 (1H, d, J=3.1 Hz), 7.81 (1H, s), 7.67 (1H, d, J=3.1 Hz), 7.47-7.42 (2H, m), 7.31 (1H, s), 7.20-7.14 (2H, m), 6.56 (1H, d, J=2.1 Hz), 5.63 (1H, dd, J=12.6, 2.1 Hz), 4.25 (3H, s), 4.24 (1H, d, J=16.9 Hz), 3.97-3.93 (1H, m), 2.99 (1H, d, J=12.7 Hz), 2.99-2.86 (2H, m), 2.77-2.70 (1H, m), 2.57-2.52 (1H, m).

Example 12AA

| Isomer A | (R)-(1-(4-fluorophenyl)-6-((2-propyl-2H-1,2,3-triazol-4-yl)sulfonyl)-4,4a,5,6,7,8-hexahydro-1H-pyrazolo[3,4-g]isoquinolin-4a-yl)(thiazol-2-yl)methanone | 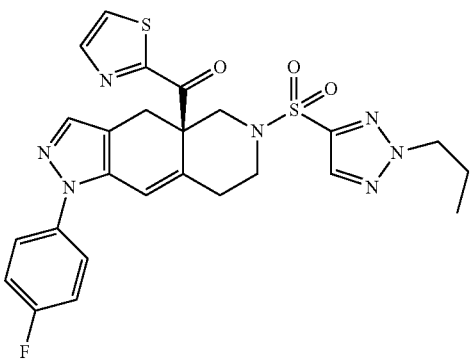 [SMILES: CCCn1ncc(S(=O)(=O)N2CCC3=Cc4c(cnn4-c4ccc(F)cc4)C[C@]3(C(=O)c3nccs3)C2)n1] |
|---|---|---|
| Isomer B | (R)-(1-(4-fluorophenyl)-6-((1-propyl-1H-1,2,3-triazol-5-yl)sulfonyl)-4,4a,5,6,7,8-hexahydro-1H-pyrazolo[3,4-g]isoquinolin-4a-yl)(thiazol-2-yl)methanone | 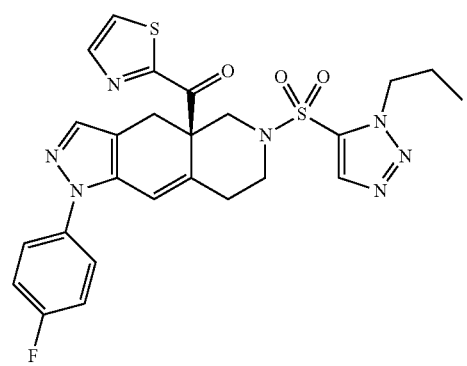 [SMILES: CCCn1nncc1S(=O)(=O)N1CCC2=Cc3c(cnn3-c3ccc(F)cc3)C[C@]2(C(=O)c2nccs2)C1] |
| Isomer C | (R)-(1-(4-fluorophenyl)-6-((1-propyl-1H-1,2,3-triazol-4-yl)sulfonyl)-4,4a,5,6,7,8-hexahydro-1H-pyrazolo[3,4-g]isoquinolin-4a-yl)(thiazol-2-yl)methanone | 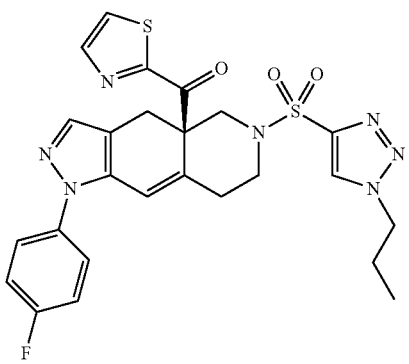 [SMILES: CCCn1cc(S(=O)(=O)N2CCC3=Cc4c(cnn4-c4ccc(F)cc4)C[C@]3(C(=O)c3nccs3)C2)nn1] |

Prepared from Intermediate 95. LCMS (Method F, ES-API): RT 2.54 min, m+H=554.2; 1H NMR (400 MHz, CDCl3): δ 8.08 (1H, d, J=3.1 Hz), 7.82 (1H, s), 7.68 (1H, d, J=3.1 Hz), 7.47-7.42 (2H, m), 7.31 (1H, s), 7.20-7.14 (2H, m), 6.55 (1H, d, J=2.2 Hz), 5.64 (1H, dd, J=12.6, 2.0 Hz), 4.43 (2H, t, J=7.1 Hz), 4.25 (1H, d, J=16.9 Hz), 3.97-3.92 (1H, m), 2.96 (1H, d, J=12.9 Hz), 2.94-2.86 (2H, m), 2.74-2.67 (1H, m), 2.56-2.52 (1H, m), 2.01 (2H, sext, J=7.1 Hz), 0.94 (3H, t, J=7.1 Hz).

Example 13. (R)-(1-(4-fluorophenyl)-6-tosyl-4,4a,5,6,7,8-hexahydro-1H-pyrazolo[3,4-g]isoquinolin-4a-yl)(1-methyl-1H-imidazol-2-yl)methanone

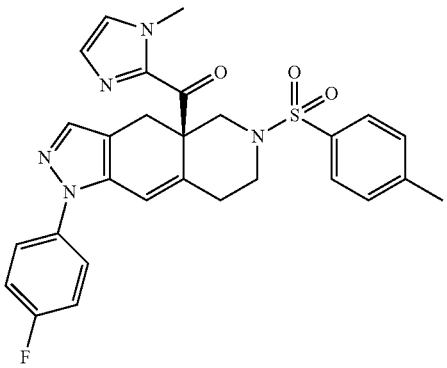 [SMILES: Cc1ccc(S(=O)(=O)N2CCC3=Cc4c(cnn4-c4ccc(F)cc4)C[C@]3(C(=O)c3nccn3C)C2)cc1]

1-Methyl-1H-imidazole (104 mg, 1.267 mmol) in dry ether (5 mL) was added to butyllithium (2.5M in hexanes) (519 µl, 1.298 mmol) in dry ether (2 mL) at −78° C. The reaction mixture was stirred at −78° C. for 45 minutes. A solution of (R)-methyl 1-(4-fluorophenyl)-6-tosyl-4,4a,5,6,7,8-hexahydro-1H-pyrazolo[3,4-g]isoquinoline-4a-carboxylate (200 mg, 0.415 mmol) in dry ether (5 mL) was added dropwise and the reaction mixture was stirred for 45 minutes at −78° C., then allowed to warm to room temperature over 2 hours. Water (20 mL) was added and the reaction mixture was stirred at room temperature for 10 minutes. The aqueous phase was extracted with ethyl acetate (3×20 mL), the combined organic phases were washed with brine (20 mL), dried (magnesium sulfate), and solvent removed to give a yellow oil. The crude product was purified by chromatography on silica gel (gradient: 0-60% ethyl acetate in isohexane) to afford (R)-(1-(4-fluorophenyl)-6-tosyl-4,4a,5,6,7,8-hexahydro-1H-pyrazolo[3,4-g]isoquinolin-4a-yl)(1-methyl-1H-imidazol-2-yl)methanone (22 mg) as a pale yellow solid. LCMS (Method F, ES-API): RT 2.52 min, m+H=532.0; 1H NMR (400 MHz, CDCl3): δ 7.61-7.58 (2H, m), 7.46-7.40 (2H, m), 7.31 (1H, s), 7.29-7.27 (2H, m), 7.18 (1H, d, J=0.9 Hz), 7.17-7.12 (2H, m), 6.99 (1H, br. s), 6.50 (1H, d, J=2.2 Hz), 5.53 (1H, dd, J=12.2, 2.2 Hz), 4.45 (1H, d, J=16.7 Hz), 3.88-3.84 (4H, m), 2.92-2.78 (2H, m), 2.60 (1H, d, J=12.2 Hz), 2.50-2.37 (5H, m).

The following examples were similarly prepared from the appropriate starting materials:

Example 13A. (R)-(1-(4-fluorophenyl)-6-(m-tolylsulfonyl)-4,4a,5,6,7,8-hexahydro-1H-pyrazolo[3,4-g]isoquinolin-4a-yl)(1-methyl-1H-imidazol-2-yl)methanone

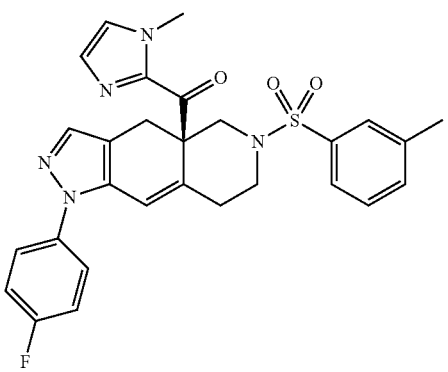 [SMILES: Cc1cccc(S(=O)(=O)N2CCC3=Cc4c(cnn4-c4ccc(F)cc4)C[C@]3(C(=O)c3nccn3C)C2)c1]

LCMS (Method F, ES-API): RT 2.52 min, m+H=532.2; 1H NMR (400 MHz, CDCl3): δ 7.52-7.49 (2H, m), 7.46-7.36 (4H, m), 7.32 (1H, s), 7.20 (1H, d, J=0.9 Hz), 7.18-7.12 (2H, m), 7.00 (1H, d, J=0.4 Hz), 6.51 (1H, d, J=2.2 Hz), 5.55 (1H, dd, J=12.2, 2.1 Hz), 4.46 (1H, d, J=16.7 Hz), 3.89-3.85 (4H, m), 2.91-2.80 (2H, m), 2.62 (1H, d, J=12.4 Hz), 2.51-2.40 (5H, m).

Example 14. (R)-3-((1-(4-fluorophenyl)-4a-picolinoyl-4a,5,7,8-tetrahydro-1H-pyrazolo[3,4-g]isoquinolin-6(4H)-yl)sulfonyl)-N,N-dimethylbenzamide

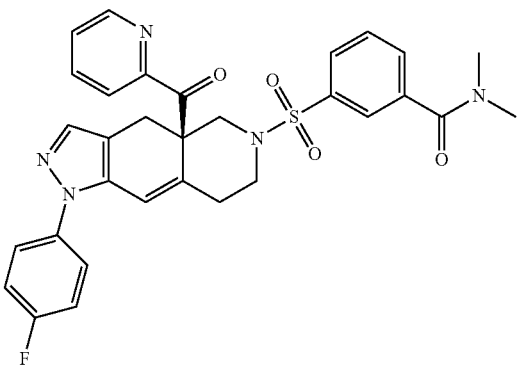 [SMILES: CN(C)C(=O)c1cccc(S(=O)(=O)N2CCC3=Cc4c(cnn4-c4ccc(F)cc4)C[C@]3(C(=O)c3ccccn3)C2)c1]

2-(1H-7-Azabenzotriazol-1-yl)-1,1,3,3-tetramethyl uronium hexafluorophosphate Methanaminium (HATU) (42.7 mg, 0.112 mmol) was added to a solution of (R)-3-((1-(4-fluorophenyl)-4a-picolinoyl-4a,5,7,8-tetrahydro-1H-pyrazolo[3,4-g]isoquinolin-6(4H)-yl)sulfonyl)benzoic acid (57 mg, 0.102 mmol), dimethylamine (51.0 µl, 0.102 mmol) and triethylamine (28.4 µl, 0.204 mmol) in dichloromethane (3 mL). The resultant mixture was stirred at room temperature for 1 hour. The reaction was diluted with dichloromethane (5 mL) and washed with a saturated solution of sodium hydrogen carbonate (aqueous, 5 mL). The organic phase was passed through a phase separator and solvent removed to give a yellow solid. The crude product was purified by chromatography on silica gel (gradient: 0-100% ethyl acetate in isohexane) to afford (R)-3-((1-(4-fluorophenyl)-4a-picolinoyl-4a,5,7,8-tetrahydro-1H-pyrazolo[3,4-g]isoquinolin-6(4H)-yl)sulfonyl)-N,N-dimethylbenzamide (7 mg) as a white solid. LCMS (Method F, ES-API): RT 2.24 min, m+H=586.1; 1H NMR (400 MHz, CDCl3): δ 8.68 (1H, ddd, J=4.7, 1.7, 0.9 Hz), 7.90 (1H, dt, J=7.9, 1.2 Hz), 7.84 (1H, td, J=7.7, 1.7 Hz), 7.74-7.71 (2H, m), 7.61 (1H, dt, J=7.7, 1.4 Hz), 7.57-7.39 (4H, m), 7.28 (1H, s), 7.20-7.13 (2H, m), 6.47 (1H, d, J=2.0 Hz), 5.52 (1H, dd, J=12.1, 2.0 Hz), 4.27 (1H, d, J=16.9 Hz), 3.86-3.77 (1H, m), 3.14 (3H, s), 2.94-2.76 (5H, m), 2.70 (1H, d, J=12.1 Hz), 2.50-2.43 (2H, m).

Example 15. (R)-(6-((1-ethyl-1H-pyrazol-4-yl)sulfonyl)-1-(4-fluorophenyl)-4,4a,5,6,7,8-hexahydro-1H-pyrazolo[3,4-g]isoquinolin-4a-yl)(4-(trifluoromethyl)pyridin-2-yl)methanone

Example 15A. (R)-pyridin-2-yl(1-(pyridin-3-yl)-6-((3-(trifluoromethyl)phenyl)sulfonyl)-4,4a,5,6,7,8-hexahydro-1H-pyrazolo[3,4-g]isoquinolin-4a-yl)methanone

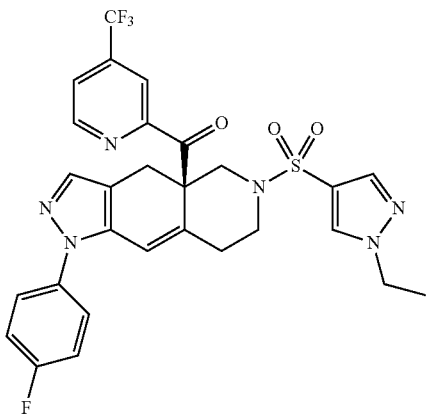 [SMILES: CCn1cc(S(=O)(=O)N2CCC3=Cc4c(cnn4-c4ccc(F)cc4)C[C@]3(C(=O)c3cc(C(F)(F)F)ccn3)C2)cn1]

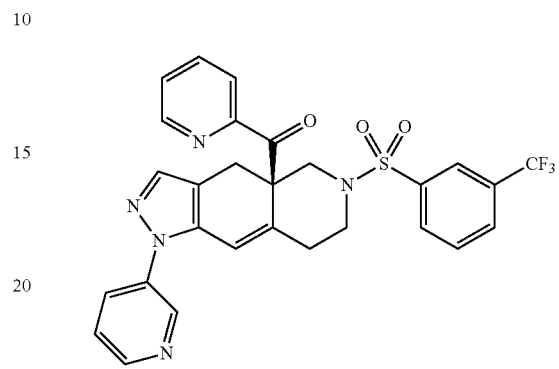

2-Bromo-4-(trifluoromethyl)pyridine (171 μl, 1.382 mmol) in dry tetrahydrofuran (1 mL) was added to butyllithium (2.5 M in Hexanes) (885 μl, 1.416 mmol) in dry tetrahydrofuran (2 mL) at −78° C. The reaction mixture was stirred at −78° C. for 45 minutes, then a solution of (R)-methyl 6-((1-ethyl-1H-pyrazol-4-yl)sulfonyl)-1-(4-fluorophenyl)-4,4a,5,6,7,8-hexahydro-1H-pyrazolo[3,4-g]isoquinoline-4a-carboxylate (220 mg, 0.453 mmol) in dry tetrahydrofuran (2 mL) was added dropwise and the reaction mixture stirred for 1 hour at −78° C. Water (10 mL) was added and the reaction mixture was stirred at room temperature for 10 minutes. The aqueous phase was extracted with ethyl acetate (2×15 mL), and the combined organic layers were washed with brine (20 mL), dried over magnesium sulfate, filtered and concentrated in vacuo to give an orange oil. The crude product was purified by chromatography on silica gel (gradient: 0-80% ethyl acetate in isohexane) and preparative HPLC (Waters, Acidic (0.1% Formic acid), Waters X-Select Prep-C18, 5 μm, 19×50 mm column, 35-70% acetonitrile in water) to afford (R)-(6-((1-ethyl-1H-pyrazol-4-yl)sulfonyl)-1-(4-fluorophenyl)-4,4a,5,6,7, 8-hexahydro-1H-pyrazolo[3,4-g]isoquinolin-4a-yl)(4-(trifluoromethyl)pyridin-2-yl)methanone (23 mg) as a white solid. LCMS (Method F, ES-API): RT 3.00 min, m+H=601.2; 1H NMR (400 MHz, CDCl3): δ 8.88-8.87 (1H, m), 8.15 (1H, m), 7.71-7.69 (2H, m), 7.67 (1H, d, J=0.6 Hz), 7.47-7.42 (2H, m), 7.30 (1H, s), 7.20-7.14 (2H, m), 6.51 (1H, d, J=2.0 Hz), 5.44 (1H, dd, J=12.0, 2.0 Hz), 4.22-4.16 (3H, m), 3.80-3.76 (1H, m), 2.94 (1H, d, J=16.9 Hz), 2.88-2.79 (1H, m), 2.67 (1H, d, J=12.3 Hz), 2.52-2.40 (2H, m), 1.51 (3H, t, J=7.3 Hz).

The following examples were similarly prepared from appropriate intermediates:

LCMS (Method F, ES-API): RT 2.33 min, m+H=566.0; 1H NMR (400 MHz, CDCl3): δ 8.78-8.76 (1H, m), 8.66 (1H, ddd, J=4.7, 1.6, 0.9 Hz), 8.61 (1H, dd, J=4.7, 1.6 Hz), 7.94 (1H, s), 7.90-7.79 (5H, m), 7.62 (1H, t, J=7.9 Hz), 7.48 (1H, ddd, J=8.8, 6.2, 1.5 Hz), 7.44 (1H, ddd, J=8.8, 4.8, 0.7 Hz), 7.36 (1H, s), 6.56 (1H, d, J=2.0 Hz), 5.57 (1H, dd, J=12.3, 2.0 Hz), 4.30 (1H, d, J=17.0 Hz), 3.92-3.85 (1H, m), 2.93-2.78 (3H, m), 2.62-2.50 (2H, m).

Example 15B. (R)-(6-((3,4-dichlorophenyl)sulfonyl)-1-phenyl-4,4a,5,6,7,8-hexahydro-1H-pyrazolo[3,4-g]isoquinolin-4a-yl)(pyridin-2-yl)methanone

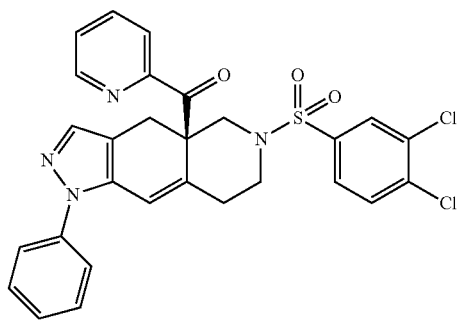 [SMILES: O=C(c1ccccn1)[C@]12Cc3cnn(-c4ccccc4)c3C=C1CCN(S(=O)(=O)c1ccc(Cl)c(Cl)c1)C2]

Quenching the reaction with acetic acid in place of water. LCMS (Method F, ES-API): RT 2.83 min, m+H=565.0; 1H NMR (400 MHz, CDCl3): δ 8.62-8.60 (1H, m), 7.88-7.81 (2H, m), 7.74 (1H, dd, J=1.8, 0.4 Hz), 7.52-7.44 (7H, m), 7.38-7.34 (1H, m), 7.29 (1H, s), 6.57 (1H, d, J=2.1 Hz), 5.54 (1H, dd, J=12.3, 1.9 Hz), 4.26 (1H, d, J=16.8 Hz), 3.91-3.85 (1H, m), 2.92-2.75 (3H, m), 2.64-2.49 (2H, m).

Example 15C. (R)-(6-((3,4-dichlorophenyl)sulfonyl)-1-(3,4-difluorophenyl)-4,4a,5,6,7,8-hexahydro-1H-pyrazolo[3,4-g]isoquinolin-4a-yl)(pyridin-2-yl)methanone

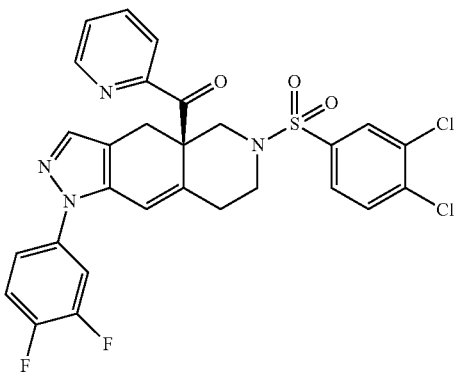 [SMILES: O=C(c1ccccn1)[C@]12Cc3cnn(-c4ccc(F)c(F)c4)c3C=C1CCN(S(=O)(=O)c1ccc(Cl)c(Cl)c1)C2]

Quenching the reaction with acetic acid in place of water. LCMS (Method F, ES-API): RT 2.93 min, m+H=600.9; 1H NMR (400 MHz, CDCl3): δ 8.59 (1H, dt, J=4.7, 1.4 Hz), 7.86-7.79 (2H, m), 7.73 (1H, d, J=1.9 Hz), 7.52-7.43 (3H, m), 7.34 (1H, ddd, J=10.7, 6.9, 2.5 Hz), 7.29-7.24 (2H, m), 7.22-7.18 (1H, m), 6.51 (1H, d, J=2.2 Hz), 5.50 (1H, d, J=12.5 Hz), 4.23 (1H, d, J=16.9 Hz), 3.90-3.84 (1H, m), 2.93-2.80 (3H, m), 2.64 (1H, td, J=11.7, 3.4 Hz), 2.53 (1H, dt, J=14.8, 2.3 Hz).

Example 15D. (R)-(6-((3,5-difluoro-4-methoxyphenyl)sulfonyl)-1-(4-fluorophenyl)-4,4a,5,6,7,8-hexahydro-1H-pyrazolo[3,4-g]isoquinolin-4a-yl)(pyridin-2-yl)methanone

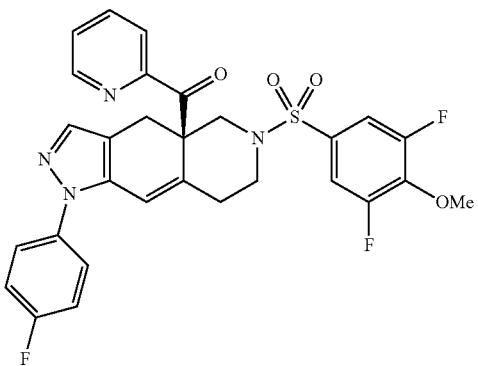 [SMILES: COc1c(F)cc(S(=O)(=O)N2CCC3=Cc4c(cnn4-c4ccc(F)cc4)C[C@]3(C(=O)c3ccccn3)C2)cc1F]

LCMS (Method F, ES-API): RT 2.65 min, m+H=581.2; 1H NMR (400 MHz, DMSO-d6): δ 8.72 (1H, ddd, J=4.7, 1.7, 0.9 Hz), 8.00 (1H, dt, J=7.7, 1.7 Hz), 7.76 (1H, dt, 7.7, 0.9 Hz), 7.66 (1H, ddd, J=7.7, 4.7, 1.2 Hz), 7.51-7.47 (2H, m), 7.44-7.42 (2H, m), 7.40-7.36 (3H, m), 6.65 (1H, s), 5.30 (1H, dd, J=12.5, 1.7 Hz), 4.09 (1H, d, J=16.9 Hz), 4.04 (3H, m), 3.75-3.73 (1H, m), 2.97-2.90 (2H, m), 2.64-2.54 (3H, m).

Example 16. (R)-(6-((6-(dimethylamino)pyridin-3-yl)sulfonyl)-1-(4-fluorophenyl)-4,4a,5,6,7,8-hexahydro-1H-pyrazolo[3,4-g]isoquinolin-4a-yl)(pyridin-2-yl)methanone

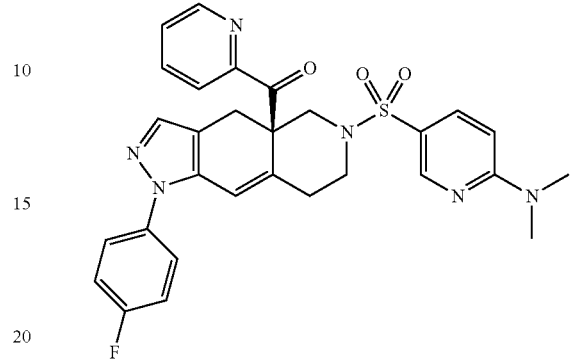

(R)-(6-((6-chloropyridin-3-yl)sulfonyl)-1-(4-fluorophenyl)-4,4a,5,6,7,8-hexahydro-1H-pyrazolo[3,4-g]isoquinolin-4a-yl)(pyridin-2-yl)methanone (30 mg, 0.055 mmol) was dissolved in a solution of dimethylamine in tetrahydrofuran (2M, 545 µl, 1.091 mmol), and the reaction mixture stirred at room temperature overnight. The solvent was removed in vacuo to give a yellow oil, which was purified by chromatography on silica gel (gradient: 10-100% ethyl acetate in isohexane) to afford (R)-(6-((6-(dimethylamino)pyridin-3-yl)sulfonyl)-1-(4-fluorophenyl)-4,4a,5,6,7,8-hexahydro-1H-pyrazolo[3,4-g]isoquinolin-4a-yl)(pyridin-2-yl)methanone (25 mg) as a pale yellow solid. LCMS (Method F, ES-API): RT 2.38 min, m+H=559.3; 1H NMR (400 MHz, CDCl3): δ 8.62 (1H, ddd, J=4.8, 1.8, 0.9 Hz), 8.43 (1H, d, J=2.5 Hz), 7.88 (1H, dt, J=8.0, 1.1 Hz), 7.81 (1H, td, J=7.7, 1.8 Hz), 7.60 (1H, dd, J=9.1, 2.5 Hz), 7.46-7.40 (3H, m), 7.28 (1H, s), 7.20-7.12 (2H, m), 6.47 (1H, d, J=2.2 Hz), 6.39 (1H, dd, J=9.1, 0.8 Hz), 5.47 (1H, dd, J=12.0, 2.2 Hz), 4.29 (1H, d, J=16.9 Hz), 3.84-3.79 (1H, m), 3.14 (6H, s), 2.92-2.75 (2H, m), 2.70 (1H, d, J=12.0 Hz), 2.51-2.44 (2H, m).

Example 17. (R)-5-((1-(4-fluorophenyl)-4a-picolinoyl-4a,5,7,8-tetrahydro-1H-pyrazolo[3,4-g]isoquinolin-6(4H)-yl)sulfonyl)-1-methylpyridin-2(1H)-one

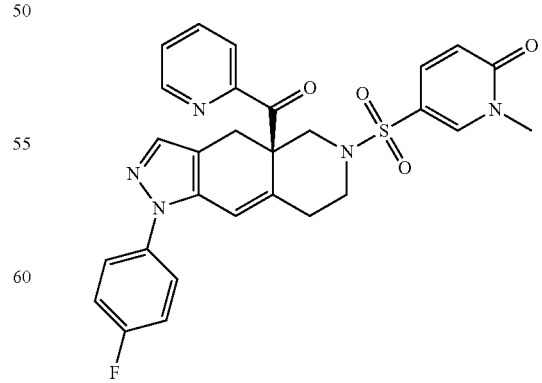

1-Methyl-6-oxo-1,6-dihydropyridine-3-sulfonic acid, ammonium salt (1 g, 4.85 mmol) was suspended in N,N- dimethylformamide (8 ml), and thionyl chloride (2.1 ml) was added. The reaction mixture was stirred at room temperature for 3 hours, giving a clear brown solution, before evaporation in vacuo to give crude sulphonyl chloride as a pale brown viscous oil. (R)-tert-butyl 1-(4-fluorophenyl)-4a-picolinoyl-4a,5,7,8-tetrahydro-1H-pyrazolo[3,4-g]isoquinoline-6(4H)-carboxylate (0.2 g, 0.421 mmol) was dissolved in HCl (4M in dioxane) (2.107 ml, 8.43 mmol), and the reaction mixture stirred at room temperature for 45 minutes, then evaporated to give a yellow solid. This intermediate was dissolved in dichloromethane (8 mL) and triethylamine (1.175 ml, 8.43 mmol), and 25% of the crude sulphonyl chloride added. The reaction mixture was stirred at room temperature for 72 hours, then diluted with dichloromethane (100 ml) and washed with 2M hydrochloric acid (2×50 ml), and the organic phase dried (magnesium sulfate), filtered and evaporated to give a brown gum. The crude product was purified first by chromatography on silica gel (gradient: 50-100% ethyl acetate in isohexane), followed by preparative HPLC (Gilson, Acidic (0.1% Formic acid), Agilent Prep C-18, 5 μm, 21.2×50 mm column, 25-40% acetonitrile in water) to afford (R)-54(1-(4-fluorophenyl)-4a-picolinoyl-4a,5,7,8-tetrahydro-1H-pyrazolo[3,4-g]isoquinolin-6(4H)-yl)sulfonyl)-1-methylpyridin-2(1H)-one (5 mg) as a white solid. LCMS (Method F, ES-API): RT 2.08 min, m+H=546.2; 1H NMR (400 MHz, CDCl3): δ 8.56 (1H, d, J=3.3 Hz), 7.88-7.79 (3H, m), 7.50-7.40 (3H, m), 7.33 (1H, d, J=9.2 Hz), 7.29-7.27 (1H, m), 7.17 (2H, t, J=8.3 Hz), 6.52 (1H, s), 6.35 (1H, d, J=9.6 Hz), 5.52 (1H, d, J=12.5 Hz), 4.23 (1H, d, J=16.7 Hz), 3.91-3.84 (1H, m), 3.51 (3H, s), 3.02-2.70 (4H, m), 2.55 (1H, d, J=14.4 Hz).

Example 18. (R)-(1-(4-fluorophenyl)-6-((1-methyl-1H-pyrazol-4-yl)sulfonyl)-4,4a,5,6,7,8-hexahydro-1H-pyrazolo[3,4-g]isoquinolin-4a-yl)(4-(trifluoromethyl)pyridin-2-yl)methanone

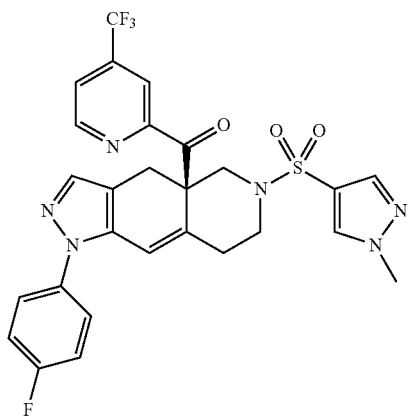 [SMILES: Cn1cc(S(=O)(=O)N2CCC3=Cc4c(cnn4-c4ccc(F)cc4)C[C@]3(C(=O)c3cc(C(F)(F)F)ccn3)C2)cn1]

HCl/Dioxane (4M) (25.3 ml, 101 mmol) was added to (R)-tert-butyl 1-(4-fluorophenyl)-4a-(4-(trifluoromethyl)picolinoyl)-4a,5,7,8-tetrahydro-1H-pyrazolo[3,4-g]isoquinoline-6(4H)-carboxylate (2.75 g, 5.07 mmol) and the reaction mixture was stirred at room temperature for 2 h. The solvent was removed in vacuo to give an orange gum. This was dissolved in dichloromethane (75 mL) and Hunig's base (4.43 ml, 25.3 mmol) was added followed by 1-methyl-1H-pyrazole-4-sulfonyl chloride (1.099 g, 6.08 mmol). The reaction mixture was stirred at room temperature for 1 h. The solvent was removed in vacuo to give an orange oil. The crude product was purified twice by chromatography on silica gel (gradient: 0-70% ethyl acetate in isohexane, followed by 0-60% ethyl acetate in dichloromethane), to give (R)-(1-(4-fluorophenyl)-6-((1-methyl-1H-pyrazol-4-yl)sulfonyl)-4,4a,5,6,7,8-hexahydro-1H-pyrazolo[3,4-g]isoquinolin-4a-yl)(4-(trifluoromethyl)pyridin-2-yl)methanone (1.89 g) as a pale yellow solid. LCMS (Method F, ES-API): RT 2.39 min, m+H=587.2; 1H NMR (400 MHz, CDCl3): δ 8.87 (1H, d, J=5.0 Hz), 8.16-8.15 (1H, m), 7.72-7.70 (1H, m), 7.69-7.66 (2H, m), 7.47-7.42 (2H, m), 7.30 (1H, s), 7.21-7.14 (2H, m), 6.51 (1H, d, J=2.1 Hz), 5.44 (1H, dd, J=12.0, 2.1 Hz), 4.21 (1H, d, J=16.9 Hz), 3.93 (3H, s), 3.80-3.76 (1H, m), 2.94 (1H, J=16.9 Hz), 2.88-2.79 (1H, m), 2.66 (1H, d, J=12.1 Hz), 2.53-2.48 (1H, m), 2.43 (1H, ddd, J=12.6, 10.5, 3.5 Hz).

Example 19. (R)-(6-((3,4-dichlorophenyl)sulfonyl)-1-(4-fluorophenyl)-4,4a,5,6,7,8-hexahydro-1H-pyrazolo[3,4-g]isoquinolin-4a-yl)(thiazol-4-yl)methanone

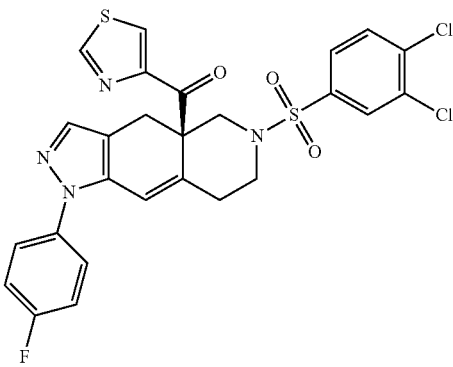 [SMILES: O=C(c1cscn1)[C@]12Cc3cnn(-c4ccc(F)cc4)c3C=C1CCN(S(=O)(=O)c1ccc(Cl)c(Cl)c1)C2]

To HCl 2M in ether (2809 μl, 5.62 mmol) was added (R)-tert-butyl 1-(4-fluorophenyl)-4a-(thiazole-4-carbonyl)-4a,5,7,8-tetrahydro-1H-pyrazolo[3,4-g]isoquinoline-6(4H)-carboxylate (135 mg, 0.281 mmol) as a solution in ether (1 mL). The resulting suspension was stirred at room temperature for 1 h. The solvent was removed to give a white solid. This was dissolved in dichloromethane (1.4 mL) and Hunig's base (245 μl, 1.405 mmol), and 3,4-dichlorobenzene-1-sulfonyl chloride (76 mg, 0.309 mmol) was added to the solution. The resulting solution was stirred at room temperature for 18 h. The crude product was purified by chromatography on silica gel (gradient: 5-95% ethyl acetate in isohexane to afford (R)-(6-((3,4-dichlorophenyl)sulfonyl)-1-(4-fluorophenyl)-4,4a,5,6,7,8-hexahydro-1H-pyrazolo[3,4-g]isoquinolin-4a-yl)(thiazol-4-yl)methanone (111 mg) as a pale yellow solid. LCMS (Method F, ES-API): RT 2.76 min, m+H=588.8; 1H NMR (400 MHz, CDCl3): δ 8.85 (1H, d, J=2.2 Hz), 8.22 (1H, d, J=2.2 Hz), 7.77 (1H, t, J=1.2 Hz), 7.52 (2H, d, J=1.2 Hz), 7.45-7.40 (2H, m), 7.28 (1H, s), 7.20-7.13 (2H, m), 6.52 (1H, d, J=2.2 Hz), 5.44 (1H, dd, J=12.6, 2.2 Hz), 4.13 (1H, d, J=16.8 Hz), 3.90-3.87 (1H, m), 2.92-2.81 (2H, m), 2.78 (1H, d, J=12.6 Hz), 2.62-2.50 (2H, m).

Example 20. Human Glucocorticoid Receptor (GR) Fluorescence Polarisation (FP) Binding Assay The following is a description of a FP assay for measuring compound inhibition of labelled glucocorticoid binding to the human recombinant GR.

The binding affinity of test compounds was determined using a FP binding assay using human recombinant GR (PanVera P2812) and a fluorescent labelled glucocorticoid ligand (Fluorome GS Red) (PanVera P2894). The presence of inhibitors prevents the formation of a GS Red/GR complex resulting in a decrease in the measured polarisation value. The change in polarisation value in the presence of test compounds is used to calculate the binding affinity of the compound for GR.

This assay was performed in 384 well, black, round-bottom, polypropylene micro titre plates in a final volume of 20 µl. The assay contained 5 µl 1 nM GR (final concentration), 5 µl 0.5 nM Fluorome GS Red (final concentration) in the presence of 10 µl test compounds. Positive control wells (high polarisation) receive, 10 µl 2% (v:v) DMSO vehicle (1% (v/v) final concentration)+5 µl 1 nM GR and 5 µl 0.5 nM Fluorome GS Red. Negative control wells (low polarisation) receive 10 µl 2 µM dexamethasone (1 µM final concentration)+5 µl 1 nM GR and 5 µl 0.5 nM Fluorome GS Red. Assay blank background wells (used for normalisation) receive 15 µl 1×GS screening buffer+5 µl GR.

For the $IC_{50}$ determination (concentration of compound that displaces 50% of the bound GS Red), compounds were tested at eight different concentrations in duplicate in two independently performed experiments. Compounds were prepared as solubilised solids at 10 mM in DMSO. On the day of assay, an 8 point half-log serial dilution (55 µl DMSO+25 µl compound solution) was prepared. A 1:50 dilution (1 µl compound solution+49 µl 1×GR screening buffer) was prepared for each compound. The compounds were prepared at 2× final assay concentration.

The reagents were added to the 384 well micro titre plates in the following order: 10 µl test compound/vehicle/1 µM dexamethasone, 5 µl Fluorome GS Red and 5 µl GR. The plates were mixed and incubated for 4 hour at room temperature. FP was measured using an Envision Excite plate reader with 535 nm excitation and 590 nm emission interference filters.

Milli-polarisation (mP) values were calculated using the below equation:

$$mP = 1000 * (S - G*P)/(S + G*P)$$

where S and P are assay blank background subtracted fluorescence units, G=G-factor (1.07).

Compound $IC_{50}$ values were calculated by plotting a [compound] v. % inhibition curve and fitting the data to a 4-parameter logistic fit equation. Compound $K_i$ (equilibrium dissociation constant) values were determined from the experimental $IC_{50}$ values using a ligand depletion correction equation (see below) assuming the antagonists were competitive inhibitors with respect to dexamethasone (Pharmacologic Analysis of Drug Receptor Interactions, $2^{nd}$ Ed., p 385-410, 1993, Raven Press, New York).

$$K_i = \frac{(L_b) * (IC_{50}) * (K_d)}{(L_o) * (R_o) + L_b * (R_o - L_o + L_b - K_d)}$$

| | |
|---|---|
| Equilibrium dissociation constant of GS red ligand ($K_d$) | 0.3 nM |
| Bound tracer concentration ($L_b$) | 0.3 nM |
| Total tracer concentration ($L_o$) | 0.5 nM |
| Total receptor concentration ($R_o$) | 1.0 nM |

Reagents:

10×GR screening buffer (100 mM potassium phosphate pH 7.4, 200 mM $Na_2MoO_4$, 1 mM EDTA, 20% (v/v) DMSO). To prepare 1×GR screening buffer, combine 1 ml 10×GR screening buffer (PanVera P2814)+1 ml stabilising peptide (PanVera P2815)+7.95 ml 4° C. MQ water. Add 50 µl 1M DTT, vortex and place on ice until use.

Example 21. HepG2 Tyrosine Aminotransferase (TAT) Assay

Glucocorticoid mediated activation of TAT occurs by transactivation of glucocorticoid response elements in the TAT promoter by glucocorticoid receptoragonist complex. The following protocol describes an assay for measuring induction of TAT by dexamethasone in HepG2 cells (a human liver hepatocellular carcinoma cell line; ECACC, UK).

TAT activity was measured as outlined in the literature by A. Ali et al., J. Med. Chem., 2004, 47, 2441-2452. Dexamethasone induced TAT production with an average $EC_{50}$ value (half-maximal effect) of 20 nM.

HepG2 cells were cultured using MEME media supplemented with 10% (v/v) foetal bovine serum; 2 mM L-glutamine and 1% (v/v) NEAA at 37° C., 5%/95% (v/v) $CO_2$/air. The HepG2 cells were counted and adjusted to yield a density of $0.125 \times 10^6$ cells/ml in RPMI 1640 without phenol red, 10% (v/v) charcoal stripped FBS, 2 mM L-glutamine and seeded at 25,000 cells/well in 200 µl into 96 well, sterile, tissue culture micro titre plates, and incubated at 37° C., 5% $CO_2$ for 24 hours Growth media was removed and replaced with assay media {RPMI 1640 without phenol red, 2 mM L-glutamine+ 10 µM forskolin}. Test compounds were screened against a challenge of 100 nM dexamethasone. Compounds were serially half log diluted in 100% (v/v) dimethylsulfoxide from a 10 mM stock. Then an 8-point half-log dilution curve was generated followed by a 1:100 dilution into assay media to give a 10× final assay [compound]: this resulted in final assay [compound] that ranged 10 to 0.003 µM in 0.1% (v/v) dimethylsulfoxide.

Test compounds were pre-incubated with cells in microtitre plates for 30 minutes at 37° C., 5/95 (v/v) $CO_2$/air, before the addition of 100 nM dexamethasone and then subsequently for 20 hours to allow optimal TAT induction.

HepG2 cells were then lysed with 30 µl of cell lysis buffer containing a protease inhibitor cocktail for 15 minutes at 4° C. 155 µl of substrate mixture was then added containing 5.4 mM Tyrosine sodium salt, 10.8 mM alpha ketoglutarate and 0.06 mM pyridoxal 5' phosphate in 0.1M potassium phosphate buffer (pH 7.4). After 2 hours incubation at 37° C. the reaction was terminated by the addition of 15 µl of 10M aqueous potassium hydroxide solution, and the plates incubated for a further 30 minutes at 37° C. The TAT activity product was measured by absorbance at λ340 nm.

$IC_{50}$ values were calculated by plotting % inhibition (normalised to 100 nM dexamethasone TAT stimulation) v. [compound] and fitting the data to a 4 parameter logistic equation. $IC_{50}$ values were converted to Ki (equilibrium dissociation constant) using the Cheng and Prusoff equation, assuming the antagonists were competitive inhibitors with respect to dexamethasone.

TABLE 1

Activity Data

| Example | R¹ | R¹ᵃ | Ring J | R² | n | R³ | GR binding | TAT |
|---|---|---|---|---|---|---|---|---|
| Int. 13 | pyridin-2-yl | | pyridin-3-yl | 6-Cl | 0 | 4-F-phenyl | | |
| Int. 14 | thiazol-2-yl | | pyridin-3-yl | 6-Cl | 0 | 4-F-phenyl | | |
| 1 | pyridin-2-yl | | phenyl | 4-CF₃ | 0 | 4-F-phenyl | +++ | +++ |
| 1A | 1H-imidazol-2-yl | 1-Me | phenyl | 4-CF₃ | 0 | 4-F-phenyl | ++ | ++ |
| 1B | pyridin-3-yl | | phenyl | 4-CF₃ | 0 | 4-F-phenyl | ++ | + |
| 1C | thiazol-2-yl | | phenyl | 4-CF₃ | 0 | 4-F-phenyl | +++ | +++ |
| 1D | 1,3,4-oxadiazol-2-yl | 5-Me | phenyl | 4-CF₃ | 0 | 4-F-phenyl | + | + |
| 1E | oxazol-4-l | | phenyl | 4-CF₃ | 0 | 4-F-phenyl | +++ | ++ |
| 1F | oxazol-2-yl | | phenyl | 4-CF₃ | 0 | 4-F-phenyl | +++ | ++ |
| 1G | furan-2-yl | | phenyl | 4-CF₃ | 0 | 4-F-phenyl | +++ | ++ |
| 1H | thiophen-2-yl | | phenyl | 4-CF₃ | 0 | 4-F-phenyl | +++ | ++ |
| 1I | oxazol-2-yl | | phenyl | 3-Me | 0 | 4-F-phenyl | +++ | ++ |
| 1J | pyrimidin-2-yl | | phenyl | 3-Me | 0 | 4-F-phenyl | +++ | ++ |
| 1K | pyridin-2-yl | 4-OMe | phenyl | 3,5-difluoro | 0 | 4-F-phenyl | +++ | +++ |
| 1L | pyridin-2-yl | 4-Et | phenyl | 3,4,5-trifluoro | 0 | 4-F-phenyl | +++ | +++ |
| 1M | pyridin-2-yl | 4-OMe | phenyl | 3,4,5-trifluoro | 0 | 4-F-phenyl | +++ | +++ |
| 2 | pyridin-2-yl | | phenyl | 4-F | 0 | 4-F-phenyl | +++ | +++ |
| 2A | thiazol-2-yl | | phenyl | 3-F | 1 | 4-F-phenyl | +++ | + |
| 2B | thiazol-2-yl | | tetrahydrofuran-2-yl | | 1 | 4-F-phenyl | ++ | + |
| 2C | pyridin-2-yl | | phenyl | 2-Me | 0 | 4-F-phenyl | +++ | +++ |
| 2D | pyridin-2-yl | | phenyl | 4-Et | 0 | 4-F-phenyl | +++ | +++ |
| 2E | pyridin-2-yl | | phenyl | 3-Me | 0 | 4-F-phenyl | +++ | +++ |
| 2F | pyridin-2-yl | | phenyl | 3-Cl | 0 | 4-F-phenyl | +++ | +++ |
| 2G | pyridin-2-yl | | phenyl | 3-OMe | 0 | 4-F-phenyl | +++ | +++ |
| 2H | pyridin-2-yl | | phenyl | 3-F, 4-Cl | 0 | 4-F-phenyl | +++ | +++ |
| 2I | pyridin-2-yl | | phenyl | 4-OMe | 0 | 4-F-phenyl | +++ | +++ |
| 2J | pyridin-2-yl | | phenyl | 3-F, 4-Me | 0 | 4-F-phenyl | +++ | +++ |
| 2K | pyridin-2-yl | | phenyl | | 0 | 4-F-phenyl | +++ | +++ |
| 2L | pyridin-2-yl | | phenyl | 2-F | 0 | 4-F-phenyl | +++ | +++ |
| 2M | pyridin-2-yl | | 1H-pyrazol-4-yl | 1-Me | 0 | 4-F-phenyl | +++ | ++ |
| 2N | pyridin-2-yl | | pyridin-3-yl | 6-CF₃ | 0 | 4-F-phenyl | +++ | +++ |
| 2O | pyridin-2-yl | | phenyl | 4-Me | 0 | 4-F-phenyl | +++ | +++ |
| 2P | pyridin-2-yl | | phenyl | 3-CF₃, 4-F | 0 | 4-F-phenyl | ++ | +++ |
| 2Q | pyridin-2-yl | | phenyl | 4-CN | 0 | 4-F-phenyl | +++ | ++ |
| 2R | pyridin-2-yl | | pyridin-3-yl | 6-OMe | 0 | 4-F-phenyl | +++ | +++ |
| 2S | pyridin-2-yl | | tetrahydro-2H-pyran-4-yl | | 0 | 4-F-phenyl | + | + |
| 2T | pyridin-2-yl | | cyclohexyl | | 0 | 4-F-phenyl | + | + |
| 2U | pyridin-2-yl | 4-CF₃ | 1H-pyrazol-5-yl | 1-Et | 0 | 4-F-phenyl | + | +++ |
| 2V | pyridin-2-yl | 4-CF₃ | 1H-pyrazol-4-yl | 3,5-dimethyl | 0 | 4-F-phenyl | + | ++ |
| 2W | pyridin-2-yl | 4-CF₃ | 1H-imidazol-4-yl | | 0 | 4-F-phenyl | + | ++ |
| 3 | pyridin-2-yl | | pyridin-3-yl | 6-morpholine | 0 | 4-F-phenyl | +++ | ++ |
| 4 | thiazol-2-yl | | pyridin-3-yl | 6-pyrrolidin-1-yl | 0 | 4-F-phenyl | +++ | + |
| 5 | thiazol-2-yl | | phenyl | 4-F | 0 | 4-F-phenyl | +++ | ++ |
| 5A | thiazol-2-yl | | phenyl | 3-F | 0 | 4-F-phenyl | +++ | +++ |
| 5B | thiazol-2-yl | | phenyl | 4-CN | 1 | 4-F-phenyl | +++ | + |
| 5C | pyridin-2-yl | | phenyl | 3-CF₃ | 0 | 4-F-phenyl | +++ | +++ |
| 5D | 1H-1,2,4-triazol-5-yl | 1-Me | phenyl | 4-CF₃ | 0 | 4-F-phenyl | +++ | + |
| 5E | pyrazin-2-yl | | phenyl | 4-CF₃ | 0 | 4-F-phenyl | +++ | ++ |
| 5F | pyridin-2-yl | | pyridin-3-yl | 5-F | 0 | 4-F-phenyl | +++ | ++ |
| 5G | pyridin-2-yl | | phenyl | 3-F | 0 | 4-F-phenyl | +++ | +++ |
| 5H | pyridin-2-yl | 5-OMe | phenyl | 4-CF₃ | 0 | 4-F-phenyl | ++ | +++ |
| 5I | thiazol-5-yl | | phenyl | 4-CF₃ | 0 | 4-F-phenyl | +++ | + |
| 5J | thiazol-2-yl | | pyridin-3-yl | 5-F | 0 | 4-F-phenyl | | |
| 6 | thiazol-2-yl | | phenyl | 4-pyrrolidin-1-yl | 0 | 4-F-phenyl | ++ | ++ |
| 6A | thiazol-2-yl | | phenyl | 3-pyrrolidin-1-yl | 0 | 4-F-phenyl | +++ | + |

TABLE 1-continued

Activity Data

| Example | R¹ | R¹ᵃ | Ring J | R² | n | R³ | GR binding | TAT |
|---|---|---|---|---|---|---|---|---|
| 7 | thiaozl-2-yl | | pyridin-3-yl | 5-piperidin-1-yl | 0 | 4-F-phenyl | +++ | ++ |
| 7A | thiazol-2-yl | | pyridin-3-yl | 5-pyrrolidin-1-yl | 0 | 4-F-phenyl | +++ | ++ |
| 8 | pyridin-2-yl | | pyridin-3-yl | 6-pyrrolidin-1-yl | 0 | 4-F-phenyl | +++ | + |
| 9 | thiazol-2-yl | | pyridin-3-yl | 6-((R)-3-fluoropyrrolidin-1-yl) | 0 | 4-F-phenyl | +++ | + |
| 10 | pyridin-2-yl | | phenyl | 4-pyrrolidin-1-yl | 0 | 4-F-phenyl | +++ | + |
| 10A | pyridin-2-yl | | pyridin-3-yl | 5-piperidin-1-yl | 0 | 4-F-phenyl | +++ | +++ |
| 10B | pyridin-2-yl | | pyridin-3-yl | 5-pyrrolidin-1-yl | 0 | 4-F-phenyl | +++ | +++ |
| 11 | thiazol-4-yl | | phenyl | 4-CF₃ | 0 | 4-F-phenyl | +++ | ++ |
| 11A | pyridin-2-yl | | phenyl | 4-Cl | 0 | 4-F-phenyl | +++ | +++ |
| 11B | pyridin-2-yl | | phenyl | 3-Me, 4-OMe | 0 | 4-F-phenyl | +++ | +++ |
| 11C | pyridin-2-yl | | phenyl | 3-Cl, 4-OMe | 0 | 4-F-phenyl | +++ | ++ |
| 11D | pyridin-2-yl | | phenyl | 3-F, 4-OMe | 0 | 4-F-phenyl | +++ | +++ |
| 11E | pyridin-2-yl | | phenyl | 2-F, 4-Me | 0 | 4-F-phenyl | +++ | ++ |
| 11F | thiazol-4-yl | | phenyl | 3-Me | 0 | 4-F-phenyl | +++ | ++ |
| 11G | pyridin-2-yl | | phenyl | 3-CN | 0 | 4-F-phenyl | +++ | +++ |
| 11H | pyridin-2-yl | | phenyl | 4-OCHF₂ | 0 | 4-F-phenyl | +++ | +++ |
| 11I | pyridin-2-yl | | phenyl | 3-OCF₃ | 0 | 4-F-phenyl | +++ | +++ |
| 11J | pyridin-2-yl | | phenyl | 3,5-difluoro | 0 | 4-F-phenyl | +++ | +++ |
| 11K | thiazol-4-yl | | phenyl | 4-Me | 0 | 4-F-phenyl | +++ | +++ |
| 11L | pyridin-2-yl | | phenyl | 3-OCHF₂ | 0 | 4-F-phenyl | +++ | +++ |
| 11M | pyridin-2-yl | | phenyl | 3,4-dimethyl | 0 | 4-F-phenyl | +++ | +++ |
| 11N | pyridin-2-yl | | phenyl | 3,5-dimethyl | 0 | 4-F-phenyl | +++ | +++ |
| 11O | pyridin-2-yl | | pyridin-2-yl | 6-Me | 0 | 4-F-phenyl | +++ | +++ |
| 11P | pyridin-2-yl | | phenyl | 3,4-difluoro | 0 | 4-F-phenyl | +++ | +++ |
| 11Q | pyridin-2-yl | | phenyl | 3,4,5-trifluoro | 0 | 4-F-phenyl | +++ | +++ |
| 11R | pyridin-2-yl | | phenyl | 3-Cl, 4-F | 0 | 4-F-phenyl | +++ | +++ |
| 11S | pyridin-2-yl | 4-Me | phenyl | 3-CN | 0 | 4-F-phenyl | +++ | +++ |
| 11T | pyridin-2-yl | 4-Me | 1H-pyrazol-4-yl | 1-Me | 0 | 4-F-phenyl | +++ | +++ |
| 11U | pyridin-2-yl | 4-Me | phenyl | 3,4-difluoro | 0 | 4-F-phenyl | +++ | +++ |
| 11V | pyridin-2-yl | 4-Me | 1H-imidazol-4-yl | 1-Me | 0 | 4-F-phenyl | +++ | ++ |
| 11W | pyridin-2-yl | 4-Me | phenyl | 3,5-difluoro | 0 | 4-F-phenyl | +++ | +++ |
| 11X | pyridin-2-yl | 4-Me | phenyl | 3,4,5-trifluoro | 0 | 4-F-phenyl | +++ | +++ |
| 11Y | pyridin-2-yl | | phenyl | 3-SO₂Me | 0 | 4-F-phenyl | +++ | ++ |
| 11Z | pyridin-2-yl | | phenyl | 3-CO2H | 0 | 4-F-phenyl | | |
| 11AA | pyridin-2-yl | | phenyl | 3-CH₂OMe | 0 | 4-F-phenyl | +++ | ++ |
| 11AB | pyridin-2-yl | | 4-methyl-3,4-dihydro-2H-pyrido[3,2-b][1,4]oxazin-7-yl | | 0 | 4-F-phenyl | +++ | ++ |
| 11AC | pyridin-2-yl | | phenyl | 2,3,4-trifluoro | 0 | 4-F-phenyl | +++ | +++ |
| 11AD | pyridin-2-yl | | pyridin-2-yl | 6-CF₃ | 0 | 4-F-phenyl | +++ | +++ |
| 11AE | pyridin-2-yl | 4-Me | pyridin-2-yl | 6-CF₃ | 0 | 4-F-phenyl | +++ | +++ |
| 11AF | pyridin-2-yl | | phenyl | 3,4-dichloro | 0 | 4-F-phenyl | +++ | +++ |
| 11AG | pyridin-2-yl | 4-Me | phenyl | 3-CF₃ | 0 | 4-F-phenyl | +++ | +++ |
| 11AH | pyridin-2-yl | 4-Me | 1H-pyrazol-4-yl | 1-Et | 0 | 4-F-phenyl | +++ | +++ |
| 11AI | pyridin-2-yl | 4-Me | 1H-pyrazol-4-yl | 1,5-dimethyl | 0 | 4-F-phenyl | +++ | +++ |
| 11AJ | pyridin-2-yl | 4-Me | 1H-pyrazol-5-yl | 1-Me | 0 | 4-F-phenyl | +++ | +++ |
| 11AK | pyridin-2-yl | 4-Me | 1H-pyrazol-3-yl | 1-Me | 0 | 4-F-phenyl | +++ | +++ |
| 11AL | pyridin-2-yl | 4-Me | phenyl | 3-Me, 4-F | 0 | 4-F-phenyl | +++ | +++ |
| 11AM | pyridin-2-yl | 4-Me | 4-methyl-3,4-dihydro-2H-pyrido[3,2-b][1,4]oxazin-7-yl | | 0 | 4-F-phenyl | +++ | +++ |
| 11AN | pyridin-2-yl | 4-Me | 2,3-dihydrobenzofuran-5-yl | | 0 | 4-F-phenyl | +++ | +++ |
| 11AO | pyridin-2-yl | 4-Me | 1-methylindolin-2-one-5-yl | | 0 | 4-F-phenyl | +++ | +++ |
| 11AP | pyridin-2-yl | 4-Me | phenyl | 3-SO₂Me | 0 | 4-F-phenyl | +++ | +++ |
| 11AQ | pyridin-2-yl | 4-Me | 1H-pyrazol-4-yl | 1,3-dimethyl | 0 | 4-F-phenyl | +++ | ++ |
| 11AR | pyridin-2-yl | 4-Me | 2,3-dihydrobenzo[b][1,4]dioxin-6-yl | | 0 | 4-F-phenyl | +++ | +++ |
| 11AS | pyridin-2-yl | 4-Me | phenyl | 3-F, 4-CF₃ | 0 | 4-F-phenyl | +++ | +++ |
| 11AT | pyridin-2-yl | | phenyl | 3-F, 4-CF₃ | 0 | 4-F-phenyl | +++ | +++ |

TABLE 1-continued

Activity Data

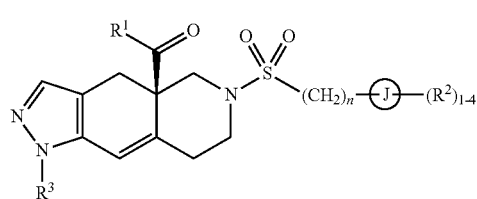

| Example | R$^1$ | R$^{1a}$ | Ring J | R$^2$ | n | R$^3$ | GR binding | TAT |
|---|---|---|---|---|---|---|---|---|
| 11AU | pyridin-2-yl | 4-Et | phenyl | 3-CN | 0 | 4-F-phenyl | +++ | +++ |
| 11AV | pyridin-2-yl | 4-Et | pyridin-2-yl | 6-CF$_3$ | 0 | 4-F-phenyl | +++ | +++ |
| 11AW | pyridin-2-yl | 4-Me | phenyl | 3-CO$_2$H | 0 | 4-F-phenyl | +++ | + |
| 11AX | pyridin-2-yl | 4-Me | isoxazol-4-yl | 3,5-dimethyl | 0 | 4-F-phenyl | +++ | ++ |
| 11AY | pyridin-2-yl |  | 1H-pyrazol-4-yl | 1-Et | 0 | 4-F-phenyl | +++ | ++ |
| 11AZ | pyridin-2-yl |  | phenyl | 3-CF$_3$ | 0 | phenyl | +++ | ++ |
| 11BA | pyridin-2-yl | 4-Me | 1H-pyrazol-5-yl | 1,3-dimethyl | 0 | 4-F-phenyl | +++ | +++ |
| 11BB | pyridin-2-yl | 4-Me | pyridin-4-yl | 2-CF$_3$ | 0 | 4-F-phenyl | +++ | +++ |
| 11BC | pyridin-2-yl | 4-Me | pyridin-2-yl | 4-CF$_3$ | 0 | 4-F-phenyl | +++ | +++ |
| 11BD | pyridin-2-yl | 4-Me | 1H-pyrazol-4-yl | 5-Me | 0 | 4-F-phenyl | +++ | ++ |
| 11BE | pyridin-2-yl |  | pyridin-4-yl | 2-CF$_3$ | 0 | 4-F-phenyl | +++ | ++ |
| 11BF | pyridin-2-yl |  | phenyl | 3-CF$_3$, 4-Cl | 0 | 4-F-phenyl | +++ | ++ |
| 11BG | pyridin-2-yl |  | phenyl | 3-Cl, 4-Me | 0 | 4-F-phenyl | +++ | +++ |
| 11BH | pyridin-4-yl | 2-pyrrolidin-1-yl | phenyl | 3,4-difluoro | 0 | 4-F-phenyl | + | + |
| 11BI | pyridin-2-yl | 4-CF$_3$ | 1H-pyrazol-3-yl | 1-Me | 0 | 4-F-phenyl | +++ | +++ |
| 11BJ | pyridin-2-yl |  | 1H-pyrazol-3-yl | 1-Me | 0 | 4-F-phenyl | +++ | ++ |
| 11BK | pyridin-2-yl | 4-CF$_3$ | 1H-pyrazol-4-yl | 5-Me | 0 | 4-F-phenyl | +++ | +++ |
| 11BL | pyridin-2-yl | 4-CF$_3$ | phenyl | 3-CN | 0 | 4-F-phenyl | +++ | +++ |
| 11BM | pyridin-2-yl | 4-CF$_3$ | 1H-pyrazol-5-yl | 1-Me | 0 | 4-F-phenyl | +++ | +++ |
| 11BN | pyridin-2-yl | 4-CF$_3$ | 1H-pyrazol-4-yl | 1,5-dimethyl | 0 | 4-F-phenyl | +++ | +++ |
| 11BO | pyridin-2-yl | 4-CF$_3$ | 1H-pyrazol-4-yl |  | 0 | 4-F-phenyl | +++ | +++ |
| 11BP | pyridin-2-yl |  | 1H-pyrazol-4-yl | 1-Me, 3-CF$_3$ | 0 | 4-F-phenyl | +++ | + |
| 11BQ | pyridin-2-yl | 4-CF$_3$ | phenyl | 3,4,5-trifluoro | 0 | 4-F-phenyl | + | +++ |
| 11BR | pyridin-2-yl | 4-CF$_3$ | 1H-pyrazol-3-yl | 1-Me | 0 | 4-Cl-phenyl | ++ | +++ |
| 11BS | pyridin-2-yl |  | 1H-pyrazol-4-yl |  | 0 | 4-F-phenyl | ++ | ++ |
| 11BT | pyridin-2-yl |  | 1H-pyrazol-3-yl | 1-Me | 0 | 4-CF$_3$-phenyl | + | + |
| 11BU | thiazol-4-yl |  | phenyl | 3,4-difluoro | 0 | 4-F-phenyl | + | ++ |
| 11BV | pyridin-2-yl | 4-CF3 | 1H-imidazol-4-yl | 1,2-dimethyl | 0 | 4-F-phenyl | +++ | +++ |
| 11BW | pyridin-2-yl | 4-CF3 | 1H-imdiazol-5-yl | 1,2-dimethyl | 0 | 4-F-phenyl | + | ++ |
| 11BX | pyridin-2-yl | 4-CF3 | 1H-imidazol-2-yl | 1-methyl | 0 | 4-F-phenyl | ++ | +++ |
| 11BY | pyridin-2-yl | 4-CF3 | 1H-imidazol-4-yl | 1-ethyl | 0 | 4-F-phenyl | +++ | +++ |
| 11BZ | thiazol-4-yl |  | 1H-pyrazol-4-yl | 1-ethyl | 0 | 4-F-phenyl | +++ | ++ |
| 11CA | pyridin-2-yl |  | 1H-pyrazol-4-yl | 1-propyl | 0 | 4-F-phenyl | +++ | +++ |
| 11CB | pyridin-2-yl |  | 1H-pyrazol-4-yl | 1-(2-methoxyethyl) | 0 | 4-F-phenyl | +++ | +++ |
| 11CC | pyrazol-4-yl | 1-Me | phenyl | 3,4-dichloro | 0 | 4-F-phenyl | + | ++ |
| 11CD | pyridin-2-yl |  | 1H-pyrazol-4-yl | 1-isopropyl | 0 | 4-F-phenyl | +++ | +++ |
| 11CE, 11CF, 11CG | pyridin-2-yl | 4-CF3 | 1,2,3-triazolyl | methyl | 0 |  | +++ + +++ | +++ ++ +++ |
| 11CH, 11CI, 11CJ | pyridin-2-yl |  | 1,2,3-triazolyl | ethyl | 0 | 4-F-phenyl | +++ + +++ | +++ ++ ++ |
| 11CK, 11CL, 11CM | pyridin-2-yl | 4-CF3 | 1,2,3-triazolyl | ethyl | 0 | 4-F-phenyl | +++ + +++ | +++ ++ +++ |
| 11CN, 11CO, 11CP | pyridin-2-yl |  | 1,2,3-triazolyl | propyl | 0 | 4-F-phenyl | +++ + +++ | +++ ++ +++ |
| 11CQ, 11CR, 11CS | thiazol-4-yl |  | 1,2,3-triazolyl | propyl | 0 | 4-F-phenyl | +++ ++ +++ | +++ ++ +++ |
| 11CT, 11CU, 11CV | pyridin-2-yl |  | 1,2,3-triazolyl | isopropyl | 0 | 4-F-phenyl | +++ ++ +++ | +++ ++ ++ |
| 11CW | thiazol-4-yl |  | 1H-pyrazol-5-yl | 1-ethyl | 0 | 4-F-phenyl | +++ | ++ |
| 11CX | pyridin-2-yl | 4-CF3 | 1H-pyrazol-4-yl | 1-propyl | 0 | 4-F-phenyl | +++ | +++ |
| 11CY | thiazol-4-yl |  | 1H-pyrazol-4-yl | 1-methyl | 0 | 4-F-phenyl | ++ | ++ |
| 11CZ | thiazol-4-yl |  | 1H-pyrazol-4-yl | 1-propyl | 0 | 4-F-phenyl | +++ | +++ |
| 11DA | thiazol-4-yl |  | 1,2,3-triazolyl | methyl | 0 | 4-F-phenyl | +++ | +++ |
| 11CB | pyridin-2-yl |  | 1,2,3-triazolyl | methyl | 0 | 4-F-phenyl | +++ | +++ |
| 11DC | pyridin-2-yl | 4-CF3 | 1,2,3-triazolyl | propyl | 0 | 4-F-phenyl | ++ | +++ |
| 12 | thiazol-2-yl |  | phenyl | 3-CF$_3$ | 0 | 4-F-phenyl | +++ | +++ |

TABLE 1-continued

Activity Data

| Example | R¹ | R¹ᵃ | Ring J | R² | n | R³ | GR binding | TAT |
|---|---|---|---|---|---|---|---|---|
| 12A | thiazol-2-yl | | phenyl | 3-Me | 0 | 4-F-phenyl | +++ | +++ |
| 12B | thiazol-2-yl | | phenyl | 3-OMe | 0 | 4-F-phenyl | ++ | ++ |
| 12C | thiazol-2-yl | | Phenyl | 4-Me, 3-F | 0 | 4-F-phenyl | +++ | ++ |
| 12D | thiazol-2-yl | | phenyl | | 0 | 4-F-phenyl | +++ | +++ |
| 12E | thiazol-2-yl | | phenyl | 3-Cl | 0 | 4-F-phenyl | +++ | ++ |
| 12F | pyridin-2-yl | 5-Me | phenyl | 3-Me | 0 | 4-F-phenyl | +++ | +++ |
| 12G | pyridin-2-yl | 4-Me | phenyl | 3-Me | 0 | 4-F-phenyl | +++ | +++ |
| 12H | pyridin-2-yl | 6-Me | phenyl | 3-Me | 0 | 4-F-phenyl | +++ | +++ |
| 12I | thiazol-2-yl | | phenyl | 3-CF₃, 4-F | 0 | 4-F-phenyl | +++ | ++ |
| 12J | thiazol-2-yl | | phenyl | 3,4,5-trifluoro | 0 | 4-F-phenyl | +++ | ++ |
| 12K | thiazol-2-yl | | phenyl | 3-F, 4-CF₃ | 0 | 4-F-phenyl | +++ | ++ |
| 12L | thiazol-2-yl | 5-Me | phenyl | 3-CF₃ | 0 | 4-F-phenyl | +++ | +++ |
| 12M | thiazol-2-yl | 4-Me | phenyl | 3-CF₃ | 0 | 4-F-phenyl | ++ | ++ |
| 12N | thiazol-2-yl | | phenyl | 3,4-dichloro | 0 | 4-F-phenyl | ++ | +++ |
| 12O | thiazol-2-yl | 5-Me | phenyl | 3,4-dichloro | 0 | 4-F-phenyl | +++ | +++ |
| 12P | thiazol-2-yl | | phenyl | 3,4-difluoro | 0 | 4-F-phenyl | +++ | ++ |
| 12Q | thiazol-2-yl | 5-Me | phenyl | 3,4-difluoro | 0 | 4-F-phenyl | + | +++ |
| 12R | thiazol-2-yl | 5-Me | phenyl | 3-F, 4-Cl | 0 | 4-F-phenyl | ++ | +++ |
| 12S | thiazol-2-yl | 5-Me | 1H-pyraozl-3-yl | 1-Me | 0 | 4-F-phenyl | +++ | +++ |
| 12T | thiazol-2-yl | 5-Me | 1H-pyrazol-4-yl | 1Me | 0 | 4-F-phenyl | +++ | +++ |
| 12U | thiazol-2-yl | 5-Me | 1H-pyrazol-5-yl | 1,3-dimethyl | 0 | 4-F-phenyl | + | ++ |
| 12V | thiazol-2-yl | 5-Me | 1H-pyrazol-5-yl | 1-Me | 0 | 4-F-phenyl | ++ | ++ |
| 12W | thiazol-2-yl | | 1H-pyrazol-5-yl | 1-ethyl | 0 | 4-F-phenyl | + | + |
| 12X | thiazol-2-yl | | 1H-pyrazol-4-yl | 1-ethyl | 0 | 4-F-phenyl | +++ | ++ |
| 12Y | thiazol-2-yl | | 1H-pyrazol-4-yl | 1-propyl | 0 | 4-F-phenyl | +++ | +++ |
| 12Z | thiazol-2-yl | | 1,2,3-triazolyl | methyl | 0 | 4-F-phenyl | +++ | + |
| 12AA | thiazol-2-yl | | 1,2,3-triazolyl | propyl | 0 | 4-F-phenyl | +++ | ++ |
| 13 | 1H-imideazol-2-yl | 1-Me | phenyl | 4-Me | 0 | 4-F-phenyl | ++ | ++ |
| 13A | 1H-imidazol-2-yl | 1-Me | phenyl | 3-Me | 0 | 4-F-phenyl | +++ | ++ |
| 14 | pyridin-2-yl | | phenyl | 3-CONMe2 | 0 | 4-F-phenyl | +++ | ++ |
| 15 | pyridin-2-yl | 4-CF₃ | 1H-pyrazol-4-yl | 1-Et | 0 | 4-F-phenyl | +++ | +++ |
| 15A | pyridin-2-yl | | phenyl | 3-CF₃ | 0 | pyridin-3-yl | +++ | ++ |
| 15B | pyridin-2-yl | | phenyl | 3,4-dichloro | 0 | phenyl | +++ | +++ |
| 15C | pyridin-2-yl | | phenyl | 3,4-dichloro | 0 | 3,4-difluorophenyl | +++ | ++ |
| 15D | pyridin-2-yl | | phenyl | 3,5-difluoro, 4-methoxy | 0 | 4-F-phenyl | ++ | +++ |
| 16 | pyridin-2-yl | | pyridin-3-yl | 6-NMe₂ | 0 | 4-F-phenyl | +++ | ++ |
| 17 | pyridin-2-yl | | pyridin-2(1H)-one-5-yl | 1-Me | 0 | 4-F-phenyl | | + |
| 18 | pyridin-2-yl | 4-CF₃ | 1H-pyrazol-4-yl | 1-Me | 0 | 4-F-phenyl | +++ | +++ |
| 19 | thiazol-4-yl | | phenyl | 3,4-dichloro | 0 | 4-F-phenyl | +++ | +++ |

In Table 1, GR Binding compounds with a $K_i$ value of less than 0.5 nM are designated with +++; compounds with a $K_i$ value from 0.5 nM to less than 1.0 nM are designated with ++; and compounds with a $K_i$ value of at least 1.0 nM are designated with +. TAT activity with a $K_i$ value of less than 20 nM are designated with +++, compounds with a $K_i$ value from 20 nM to less than 100 nM are designated with ++; and compounds with a $K_i$ value of at least 100 nM are designated with +.

Example 22. Cell Transrepression Assays

The following protocol describes assays for measuring the effect of either GR agonists or antagonists on IL-1β stimulated IL-6 production by A549 cells.

In the GR antagonist mode of the assay compounds are tested for their ability to reverse the suppression of IL-1β stimulated IL-6 production by dexamethasone. Conversely, in the GR agonist mode of the assay compounds are tested for their ability to directly inhibit IL-1β stimulated IL-6 production. These assays were adapted from a protocol outlined by Ali et al., J. Med. Chem. (2004), 47, 2441-2452.

A549 cells were routinely cultured in DMEM media supplemented with 10% (v/v) foetal bovine serum and 2 mM L-glutamine at 37° C., 5%/95% (v/v) $CO_2$/air (Standard Incubation Conditions). For assay use, cells were counted and the suspension diluted in DMEM supplemented with 2 mM L-glutamine (Assay Media) to 0.66×10⁶ cells/ml. This cell preparation was then used to seed sterile, tissue culture treated, 384 well plates (20,000 cells/well), which were subsequently kept under Standard Incubation Conditions for 1 hour.

Compounds were solubilised in DMSO to generate a 10 mM stock solution. A range of 8 test concentrations were generated by diluting the stock solution in DMSO to 240 µM, followed by 7 serial half log dilutions in DMSO. These test compound solutions were diluted 40-fold into Assay Media prior to addition to the cells to give a range of final assay compound concentrations of 10 to 0.003 µM in 0.25% (v/v) DMSO.

Note that the standard GR agonist dexamethasone was tested at concentrations ranging from 100 to 0.03 nM. Compounds were screened for GR antagonism of an $EC_{80}$ (10 nM) dexamethasone stimulation.

Compounds were pre-incubated with cells for 1 hour using Standard Conditions as previously described, prior to the addition of 10 nM dexamethasone (antagonist mode) or Assay Media (agonist mode) and then incubated for a further hour.

Cells were then stimulated with IL-1β (final assay concentration 3 ng/µL) and incubated for 18 hours to allow sufficient IL-6 to be produced.

IL-6 in the cell media was measured using an AlphaLISA detection assay (Perkin Elmer). Raw data were converted to IL-6 concentrations by interpolation of test data against an IL-6 standard curve using GraphPad Prism software.

For the agonist mode assay, IL-6 values were normalised to the maximal effect of the full agonist dexamethasone and compound concentration effect curves were fitted to a 4 parameter logistic equation to determine $EC_{50}$ and maximal effect values.

For the antagonist mode assay, IL-6 values were normalised to the effect of 10 nM dexamethasone inhibition of IL-6 production, such that 100% inhibition represented complete reversal of the dexamethasone suppression of IL-6. Compound $IC_{50}$ values were determined by plotting compound concentrations against % inhibition and fitting the data to a 4 parameter logistic equation. Compound Ki (inhibitor dissociation constant) values were estimated by correcting the $IC_{50}$ values using the Cheng-Prusoff equation, assuming that all compounds were competitive GR antagonists with respect to dexamethasone.

Although the foregoing invention has been described in some detail by way of illustration and Example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A method of treating antipsychotic induced weight gain, the method comprising administering to a subject in need thereof, a therapeutically effective amount of a compound of Formula I, thereby treating the antipsychotic induced weight gain, wherein the compound of Formula I has the formula:

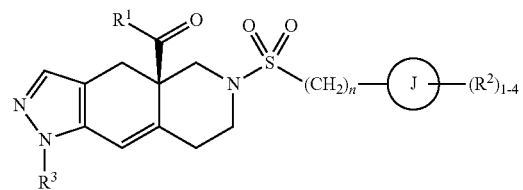

wherein
  $R^1$ is a heteroaryl ring having from 5 to 6 ring members and from 1 to 4 heteroatoms each independently selected from the group consisting of N, O and S, optionally substituted with 1-4 groups each independently selected from $R^{1a}$;
  each $R^{1a}$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, —CN, N-oxide, $C_{3-8}$ cycloalkyl, and $C_{3-8}$ heterocycloalkyl;
  ring J is selected from the group consisting of a cycloalkyl ring, a heterocycloalkyl ring, an aryl ring and a heteroaryl ring, wherein the heterocycloalkyl and heteroaryl rings have from 5 to 6 ring members and from 1 to 4 heteroatoms each independently selected from the group consisting of N, O and S;
  each $R^2$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, $C_{1-6}$ alkyl-$C_{1-6}$ alkoxy, —CN, —OH, —$NR^{2a}R^{2b}$, —$C(O)R^{2a}$, —$C(O)OR^{2a}$, —$C(O)NR^{2a}R^{2b}$, —$SR^{2a}$, —$S(O)R^{2a}$, —$S(O)_2R^{2a}$, $C_{3-8}$ cycloalkyl, and $C_{3-8}$ heterocycloalkyl, wherein the heterocycloalkyl groups are optionally substituted with 1-4 $R^{2c}$ groups;
  alternatively, two $R^2$ groups linked to the same carbon are combined to form an oxo group (=O);
  alternatively, two $R^2$ groups are combined to form a heterocycloalkyl ring having from 5 to 6 ring members and from 1 to 3 heteroatoms each independently selected from the group consisting of N, O and S, wherein the heterocycloalkyl ring is optionally substituted with from 1 to 3 $R^{2d}$ groups;
  $R^{2a}$ and $R^{2b}$ are each independently selected from the group consisting of hydrogen and $C_{1-6}$ alkyl;
  each $R^{2c}$ is independently selected from the group consisting of hydrogen, halogen, hydroxy, $C_{1-6}$ alkoxy, $C_{1-6}$ haloalkoxy, —CN, and —$NR^{2a}R^{2b}$;
  each $R^{2d}$ is independently selected from the group consisting of hydrogen and $C_{1-6}$ alkyl, or two $R^{2d}$ groups attached to the same ring atom are combined to form (=O);
  $R^3$ is selected from the group consisting of phenyl and pyridyl, each optionally substituted with 1-4 $R^{3a}$ groups;
  each $R^{3a}$ is independently selected from the group consisting of hydrogen, halogen, and $C_{1-6}$ haloalkyl;
  subscript n is an integer from 0 to 3;
  or salts thereof.

2. The method of claim 1, wherein $R^1$ is selected from the group consisting of pyrrole, pyrazole, imidazole, triazole, tetrazole, furan, oxazole, isoxazole, oxadiazole, thiophene, thiazole, isothiazole, thiadiazole, pyridine, pyrazine, pyrimidine, and pyridazine.

3. The method of claim 1, wherein $R^1$ is selected from the group consisting of 2-pyrrole, 3-pyrrole, 3-pyrazole, 4-pyrazole, 5-pyrazole, 2-imidazole, 4-imidazole, 5-imidazole, 1,2,3-triazol-4-yl, 1,2,3,-triazol-5-yl, 1,2,4-triazol-3-yl, 1,2,4-triazol-5-yl, 1,2,3,4-tetrazol-1-yl, 1,2,3,4,tetrazol-5-yl, 2-furan, 3-furan, 2-oxazole, 4-oxazole, 5-oxazole, 3-isoxazole, 4-isooxazole, 5-isooxazole, 1,2,4-oxadiazol-3-yl, 1,2,4-oxadiazol-5-yl, 1,2,5-oxadiazol-3-yl, 1,3,4-oxadiazol-2-yl, 2-thiophene, 3-thiophene, 2-thiazole, 4-thiazole, 5-thiazole, 3-isothiazole, 4-isothiazole, 5-isothiazole, 1,2,3-thiadiazol-4-yl, 1,2,3-thiadiazol-5-yl, 1,2,4-thiadiazol-3-yl, 1,2,4-thiadiazol-5-yl, 1,2,5-thiadiazol-3-yl, 1,3,4-thiadiazol-2-yl, 2-pyridine, 3-pyridine, 4-pyridine, pyrazine, 2-pyrimidine, 4-pyrimidine, 5-pyrimidine, 6-pyrimidine, 3-pyridazine, 4-pyridazine, 5-pyridazine, and 6-pyridazine.

4. The method of claim 1, wherein $R^1$ is selected from the group consisting of pyrazole, imidazole, triazole, furan, oxazole, oxadiazole, thiophene, thiazole, pyridine, pyrazine and pyrimidine.

5. The method of claim 1, wherein $R^1$ selected from the group consisting of 1-pyrazole, 3-pyrazole, 4-pyrazole, 5-pyrazole, 2-imidazole, 4-imidazole, 5-imidazole, 1,2,3-triazol-4-yl, 1,2,3,-triazol-5-yl, 1,2,4-triazol-3-yl, 1,2,4-triazol-5-yl, 2-furan, 3-furan, 2-oxazole, 4-oxazole, 5-oxazole, 1,2,4-oxadiazol-3-yl, 1,2,4-oxadiazol-5-yl, 1,2,5-oxadiazol-3-yl, 1,3,4-oxadiazol-2-yl, 2-thiophene, 3-thiophene, 2-thiazole, 4-thiazole, 5-thiazole, 2-pyridine, 3-pyridine, 4-pyridine, pyrazine, 2-pyrimidine, 4-pyrimidine, 5-pyrimidine, and 6-pyrimidine.

6. The method of claim 1, wherein each $R^{1a}$ is independently selected from the group consisting of hydrogen, $C_{1-6}$ alkyl, $C_{1-6}$ haloalkyl, $C_{1-6}$ alkoxy and $C_{3-8}$ heterocycloalkyl.

7. The method of claim 1, wherein each $R^{1a}$ is independently selected from the group consisting of hydrogen, methyl, ethyl, trifluoromethyl, and methoxy.

8. The method of claim 1, wherein ring J is selected from the group consisting of heterocycloalkyl, aryl and heteroaryl.

9. The method of claim 1, wherein ring J is selected from the group consisting of aryl and heteroaryl.

10. The method of claim 1, wherein ring J is selected from the group consisting of phenyl, pyridine, imidazole, pyrazole, triazole, tetrazole, thiadiazole, isothiazole, cyclohexyl, tetrahydrofuran and tetrahydro-2H-pyran.

11. The method of claim 1, wherein ring J is phenyl.

12. The method of claim 1, wherein ring J is pyridyl.

13. The method of claim 1, wherein each $R^2$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, $C_{1-6}$ alkyl-$C_{1-6}$ alkoxy, —CN, —NR$^{2a}$R$^{2b}$, —C(O)OR$^{2a}$, —S(O)$_2$R$^{2a}$, $C_{3-8}$ cycloalkyl, and $C_{3-8}$ heterocycloalkyl, wherein the heterocycloalkyl group has 5-6 ring members and 1 to 2 heteroatoms.

14. The method of claim 1, wherein each $R^2$ is independently selected from the group consisting of hydrogen, methyl, ethyl, F, Cl, —CF$_3$, OMe, OCHF$_2$, —CN, —NMe$_2$, —S(O)$_2$Me, pyrrolidine, piperidine and morpholine.

15. The method of claim 1, wherein $R^3$ is 4-F-phenyl.

16. The method of claim 1, wherein the compound is selected from the group consisting of:

(R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(pyridin-2-yl)methanone, (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(1-methyl-1H-imidazol-2-yl)methanone, (R)-(1-(4-fluorophenyl)-6-((4-fluorophenyl)sulfonyl)-4,4a,5,6,7,8-hexahydro-1H-pyrazolo[3,4-g]isoquinolin-4a-yl)(pyridin-2-yl)methanone, (R)-(6-((6-chloropyridin-3-yl)sulfonyl)-1-(4-fluorophenyl)-4,4a,5,6,7,8-hexahydro-1H-pyrazolo[3,4-g]isoquinolin-4a-yl)(pyridin-2-yl)methanone, (R)-(1-(4-fluorophenyl)-6-((6-morpholinopyridin-3-yl)sulfonyl)-4,4a, 5,6,7,8-hexahydro-1H-pyrazolo[3,4-g]isoquinolin-4a-yl)(pyridin-2-yl)methanone, (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(pyridin-3-yl)methanone, (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(thiazol-2-yl)methanone, (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(5-methyl-1,3,4-oxadiazol-2-yl)methanone, (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(oxazol-4-yl)methanone, (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(oxazol-2-yl)methanone, (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(furan-2-yl)methanone, (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(thiophen-2-yl)methanone, (R)-(6-((6-chloropyridin-3-yl)sulfonyl)-1-(4-fluorophenyl)-4,4a,5,6,7,8-hexahydro-1H-pyrazolo[3,4-g]isoquinolin-4a-yl)(thiazol-2-yl)methanone, (R)-(1-(4-fluorophenyl)-6-((6-(pyrrolidin-1-yl)pyridin-3-yl)sulfonyl)-4,4a, 5,6,7,8-hexahydro-1H-pyrazolo[3,4-g]isoquinolin-4a-yl)(thiazol-2-yl)methanone, (R)-(6-((3-fluorobenzyl)sulfonyl)-1-(4-fluorophenyl)-4,4a,5,6,7,8-hexahydro-1H-pyrazolo[3,4-g]isoquinolin-4a-yl)(thiazol-2-yl)methanone, ((4aR)-1-(4-fluorophenyl)-6-(((((R/S)-tetrahydrofuran-2-yl)methyl)sulfonyl)-4,4a,5,6,7,8-hexahydro-1H-pyrazolo[3,4-g]isoquinolin-4a-yl)(thiazol-2-yl)methanone, (R)-(1-(4-fluorophenyl)-6-((4-fluorophenyl)sulfonyl)-4,4a,5,6,7,8-hexahydro-1H-pyrazolo[3,4-g]isoquinolin-4a-yl)(thiazol-2-yl)methanone, (R)-(1-(4-fluorophenyl)-6-((4-(pyrrolidin-1-yl)phenyl)sulfonyl)-4,4a,5,6,7,8-hexahydro-1H-pyrazolo[3,4-g]isoquinolin-4a-yl)(thiazol-2-yl)methanone, (R)-(1-(4-fluorophenyl)-6-((3-fluorophenyl)sulfonyl)-4,4a,5,6,7,8-hexahydro-1H-pyrazolo[3,4-g]isoquinolin-4a-yl)(thiazol-2-yl)methanone, (R)-(1-(4-fluorophenyl)-6-((3-(pyrrolidin-1-yl)phenyl)sulfonyl)-4,4a,5,6,7,8-hexahydro-1H-pyrazolo[3,4-g]isoquinolin-4a-yl)(thiazol-2-yl)methanone, (R)-4-(((1-(4-fluorophenyl)-4a-(thiazole-2-carbonyl)-4a,5,7,8-tetrahydro-1H-pyrazolo[3,4-g]isoquinolin-6(4H)-yl)sulfonyl)methyl)benzonitrile, (R)-(1-(4-fluorophenyl)-6-((5-(piperidin-1-yl)pyridin-3-yl)sulfonyl)-4,4a,5,6,7,8-hexahydro-1H-pyrazolo[3,4-g]isoquinolin-4a-yl)(thiazol-2-yl)methanone, (R)-(1-(4-fluorophenyl)-6-((5-(pyrrolidin-1-yl)pyridin-3-yl)sulfonyl)-4,4a,5,6,7,8-hexahydro-1H-pyrazolo[3,4-g]isoquinolin-4a-yl)(thiazol-2-yl)methanone, (R)-(1-(4-fluorophenyl)-6-((3-(trifluoromethyl)phenyl)sulfonyl)-4,4a,5,6,7,8-hexahydro-1H-pyrazolo[3,4-g]isoquinolin-4a-yl)(pyridin-2-yl)methanone, (R)-(1-(4-fluorophenyl)-6-((6-(pyrrolidin-1-yl)pyridin-3-yl)sulfonyl)-4,4a,5,6,7,8-hexahydro-1H-pyrazolo[3,4-g]isoquinolin-4a-yl)(pyridin-2-yl)methanone,
((R)-1-(4-fluorophenyl)-6-((6-((R)-3-fluoropyrrolidin-1-yl)pyridin-3-yl)sulfonyl)-4,4a,5,6,7,8-hexahydro-1H-pyrazolo[3,4-g]isoquinolin-4a-yl)(thiazol-2-yl)methanone,
(R)-(1-(4-fluorophenyl)-6-((4-(pyrrolidin-1-yl)phenyl)sulfonyl)-4,4a,5,6,7,8-hexahydro-1H-pyrazolo[3,4-g]isoquinolin-4a-yl)(pyridin-2-yl)methanone,
(R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(1-methyl-1H-1,2,4-triazol-5-yl)methanone,
(R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(thiazol-4-yl)methanone,
(R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(pyrazin-2-yl)methanone,
(R)-(1-(4-fluorophenyl)-6-((5-fluoropyridin-3-yl)sulfonyl)-4,4a,5,6,7,8-hexahydro-1H-pyrazolo[3,4-g]isoquinolin-4a-yl)(pyridin-2-yl)methanone,
(R)-(1-(4-fluorophenyl)-6-((3-fluorophenyl)sulfonyl)-4,4a,5,6,7,8-hexahydro-1H-pyrazolo[3,4-g]isoquinolin-4a-yl)(pyridin-2-yl)methanone,
(R)-(1-(4-fluorophenyl)-6-((5-(piperidin-1-yl)pyridin-3-yl)sulfonyl)-4,4a,5,6,7,8-hexahydro-1H-pyrazolo[3,4-g]isoquinolin-4a-yl)(pyridin-2-yl)methanone,
(R)-(1-(4-fluorophenyl)-6-(o-tolylsulfonyl)-4,4a,5,6,7,8-hexahydro-1H-pyrazolo[3,4-g]isoquinolin-4a-yl)(pyridin-2-yl)methanone,
(R)-(6-((4-ethylphenyl)sulfonyl)-1-(4-fluorophenyl)-4,4a,5,6,7,8-hexahydro-1H-pyrazolo[3,4-g]isoquinolin-4a-yl)(pyridin-2-yl)methanone,
(R)-(1-(4-fluorophenyl)-6-(m-tolylsulfonyl)-4,4a,5,6,7,8-hexahydro-1H-pyrazolo[3,4-g]isoquinolin-4a-yl)(pyridin-2-yl)methanone,
(R)-(1-(4-fluorophenyl)-6-((5-(pyrrolidin-1-yl)pyridin-3-yl)sulfonyl)-4,4a,5,6,7,8-hexahydro-1H-pyrazolo[3,4-g]isoquinolin-4a-yl)(pyridin-2-yl)methanone,
(R)-(6-((3-chlorophenyl)sulfonyl)-1-(4-fluorophenyl)-4,4a,5,6,7,8-hexahydro-1H-pyrazolo[3,4-g]isoquinolin-4a-yl)(pyridin-2-yl)methanone,
(R)-(1-(4-fluorophenyl)-6-((3-methoxyphenyl)sulfonyl)-4,4a,5,6,7,8-hexahydro-1H-pyrazolo[3,4-g]isoquinolin-4a-yl)(pyridin-2-yl)methanone,
(R)-(6-((4-chloro-3-fluorophenyl)sulfonyl)-1-(4-fluorophenyl)-4,4a,5,6,7,8-hexahydro-1H-pyrazolo[3,4-g]isoquinolin-4a-yl)(pyridin-2-yl)methanone,
(R)-(1-(4-fluorophenyl)-6-((4-methoxyphenyl)sulfonyl)-4,4a,5,6,7,8-hexahydro-1H-pyrazolo[3,4-g]isoquinolin-4a-yl)(pyridin-2-yl)methanone,
(R)-(6-((3-fluoro-4-methylphenyl)sulfonyl)-1-(4-fluorophenyl)-4,4a,5,6,7,8-hexahydro-1H-pyrazolo[3,4-g]isoquinolin-4a-yl)(pyridin-2-yl)methanone,
(R)-(1-(4-fluorophenyl)-6-(phenylsulfonyl)-4,4a,5,6,7,8-hexahydro-1H-pyrazolo[3,4-g]isoquinolin-4a-yl)(pyridin-2-yl)methanone,
(R)-(1-(4-fluorophenyl)-6-((2-fluorophenyl)sulfonyl)-4,4a,5,6,7,8-hexahydro-1H-pyrazolo[3,4-g]isoquinolin-4a-yl)(pyridin-2-yl)methanone,
(R)-(1-(4-fluorophenyl)-6-((1-methyl-1H-pyrazol-4-yl)sulfonyl)-4,4a,5,6,7,8-hexahydro-1H-pyrazolo[3,4-g]isoquinolin-4a-yl)(pyridin-2-yl)methanone,
(R)-(1-(4-fluorophenyl)-6-((6-(trifluoromethyl)pyridin-3-yl)sulfonyl)-4,4a,5,6,7,8-hexahydro-1H-pyrazolo[3,4-g]isoquinolin-4a-yl)(pyridin-2-yl)methanone,
(R)-(1-(4-fluorophenyl)-6-tosyl-4,4a,5,6,7,8-hexahydro-1H-pyrazolo[3,4-g]isoquinolin-4a-yl)(pyridin-2-yl)methanone,
(R)-(6-((4-fluoro-3-(trifluoromethyl)phenyl)sulfonyl)-1-(4-fluorophenyl)-4,4a,5,6,7,8-hexahydro-1H-pyrazolo[3,4-g]isoquinolin-4a-yl)(pyridin-2-yl)methanone,
(R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(5-methoxypyridin-2-yl)methanone,
(R)-(1-(4-fluorophenyl)-6-((3-(trifluoromethyl)phenyl)sulfonyl)-4,4a,5,6,7,8-hexahydro-1H-pyrazolo[3,4-g]isoquinolin-4a-yl)(thiazol-2-yl)methanone,
(R)-(1-(4-fluorophenyl)-6-(m-tolylsulfonyl)-4,4a,5,6,7,8-hexahydro-1H-pyrazolo[3,4-g]isoquinolin-4a-yl)(thiazol-2-yl)methanone,
(R)-4-((1-(4-fluorophenyl)-4a-picolinoyl-4a,5,7,8-tetrahydro-1H-pyrazolo[3,4-g]isoquinolin-6(4H)-yl)sulfonyl)benzonitrile,
(R)-(1-(4-fluorophenyl)-6-((6-methoxypyridin-3-yl)sulfonyl)-4,4a,5,6,7,8-hexahydro-1H-pyrazolo[3,4-g]isoquinolin-4a-yl)(pyridin-2-yl)methanone,
(R)-(1-(4-fluorophenyl)-6-((tetrahydro-2H-pyran-4-yl)sulfonyl)-4,4a,5,6,7,8-hexahydro-1H-pyrazolo[3,4-g]isoquinolin-4a-yl)(pyridin-2-yl)methanone,
(R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(thiazol-5-yl)methanone,
(R)-(6-(cyclohexylsulfonyl)-1-(4-fluorophenyl)-4,4a,5,6,7,8-hexahydro-1H-pyrazolo[3,4-g]isoquinolin-4a-yl)(pyridin-2-yl)methanone,
(R)-(1-(4-fluorophenyl)-6-((3-methoxyphenyl)sulfonyl)-4,4a,5,6,7,8-hexahydro-1H-pyrazolo[3,4-g]isoquinolin-4a-yl)(thiazol-2-yl)methanone,
(R)-(6-((4-chlorophenyl)sulfonyl)-1-(4-fluorophenyl)-4,4a,5,6,7,8-hexahydro-1H-pyrazolo[3,4-g]isoquinolin-4a-yl)(pyridin-2-yl)methanone,
(R)-(1-(4-fluorophenyl)-6-((4-methoxy-3-methylphenyl)sulfonyl)-4,4a,5,6,7,8-hexahydro-1H-pyrazolo[3,4-g]isoquinolin-4a-yl)(pyridin-2-yl)methanone,
(R)-(6-((3-chloro-4-methoxyphenyl)sulfonyl)-1-(4-fluorophenyl)-4,4a,5,6,7,8-hexahydro-1H-pyrazolo[3,4-g]isoquinolin-4a-yl)(pyridin-2-yl)methanone,
(R)-(6-((3-fluoro-4-methylphenyl)sulfonyl)-1-(4-fluorophenyl)-4,4a,5,6,7,8-hexahydro-1H-pyrazolo[3,4-g]isoquinolin-4a-yl)(thiazol-2-yl)methanone,
(R)-(1-(4-fluorophenyl)-6-(phenylsulfonyl)-4,4a,5,6,7,8-hexahydro-1H-pyrazolo[3,4-g]isoquinolin-4a-yl)(thiazol-2-yl)methanone,
(R)-(6-((3-chlorophenyl)sulfonyl)-1-(4-fluorophenyl)-4,4a,5,6,7,8-hexahydro-1H-pyrazolo[3,4-g]isoquinolin-4a-yl)(thiazol-2-yl)methanone,
(R)-(6-((3-fluoro-4-methoxyphenyl)sulfonyl)-1-(4-fluorophenyl)-4,4a,5,6,7,8-hexahydro-1H-pyrazolo[3,4-g]isoquinolin-4a-yl)(pyridin-2-yl)methanone,
(R)-(6-((2-fluoro-4-methylphenyl)sulfonyl)-1-(4-fluorophenyl)-4,4a,5,6,7,8-hexahydro-1H-pyrazolo[3,4-g]isoquinolin-4a-yl)(pyridin-2-yl)methanone,
(R)-(1-(4-fluorophenyl)-6-(m-tolylsulfonyl)-4,4a,5,6,7,8-hexahydro-1H-pyrazolo[3,4-g]isoquinolin-4a-yl)(thiazol-2-yl)methanone,
(R)-(1-(4-fluorophenyl)-6-tosyl-4,4a,5,6,7,8-hexahydro-1H-pyrazolo[3,4-g]isoquinolin-4a-yl)(1-methyl-1H-imidazol-2-yl)methanone, (R)-3-((1-(4-fluorophenyl)-4a-picolinoyl-4a,5,7,8-tetrahydro-1H-pyrazolo[3,4-g]isoquinolin-6(4H)-yl)sulfonyl)benzonitrile, (R)-(6-((4-(difluoromethoxy)phenyl)sulfonyl)-1-(4-fluorophenyl)-4,4a,5,6,7,8-hexahydro-1H-pyrazolo[3,4-g]isoquinolin-4a-yl)(pyridin-2-yl)methanone, (R)-(1-(4-fluorophenyl)-6-((3-(trifluoromethoxy)phenyl)sulfonyl)-4,4a, 5,6,7,8-hexahydro-1H-pyrazolo[3,4-g]isoquinolin-4a-yl)(pyridin-2-yl)methanone, (R)-(1-(4-fluorophenyl)-6-(m-tolylsulfonyl)-4,4a,5,6,7,8-hexahydro-1H-pyrazolo[3,4-g]isoquinolin-4a-yl)(1-methyl-1H-imidazol-2-yl)methanone, (R)-(6-((3,5-difluorophenyl)sulfonyl)-1-(4-fluorophenyl)-4,4a,5,6,7,8-hexahydro-1H-pyrazolo[3,4-g]isoquinolin-4a-yl)(pyridin-2-yl)methanone, (R)-(1-(4-fluorophenyl)-6-tosyl-4,4a,5,6,7,8-hexahydro-1H-pyrazolo[3,4-g]isoquinolin-4a-yl)(thiazol-4-yl)methanone, (R)-(1-(4-fluorophenyl)-6-(m-tolylsulfonyl)-4,4a,5,6,7,8-hexahydro-1H-pyrazolo[3,4-g]isoquinolin-4a-yl)(5-methylpyridin-2-yl)methanone, (R)-(1-(4-fluorophenyl)-6-(m-tolylsulfonyl)-4,4a,5,6,7,8-hexahydro-1H-pyrazolo[3,4-g]isoquinolin-4a-yl)(4-methylpyridin-2-yl)methanone, (R)-(6-((3-(difluoromethoxy)phenyl)sulfonyl)-1-(4-fluorophenyl)-4,4a,5,6,7,8-hexahydro-1H-pyrazolo[3,4-g]isoquinolin-4a-yl)(pyridin-2-yl)methanone, (R)-(6-((3,4-dimethylphenyl)sulfonyl)-1-(4-fluorophenyl)-4,4a,5,6,7,8-hexahydro-1H-pyrazolo[3,4-g]isoquinolin-4a-yl)(pyridin-2-yl)methanone, (R)-(6-((3,5-dimethylphenyl)sulfonyl)-1-(4-fluorophenyl)-4,4a,5,6,7,8-hexahydro-1H-pyrazolo[3,4-g]isoquinolin-4a-yl)(pyridin-2-yl)methanone, (R)-(1-(4-fluorophenyl)-6-(m-tolylsulfonyl)-4,4a,5,6,7,8-hexahydro-1H-pyrazolo[3,4-g]isoquinolin-4a-yl)(oxazol-2-yl)methanone, (R)-(1-(4-fluorophenyl)-6-((6-methylpyridin-2-yl)sulfonyl)-4,4a,5,6,7,8-hexahydro-1H-pyrazolo[3,4-g]isoquinolin-4a-yl)(pyridin-2-yl)methanone, (R)-(6-((3,4-difluorophenyl)sulfonyl)-1-(4-fluorophenyl)-4,4a,5,6,7,8-hexahydro-1H-pyrazolo[3,4-g]isoquinolin-4a-yl)(pyridin-2-yl)methanone, (R)-(1-(4-fluorophenyl)-6-((3,4,5-trifluorophenyl)sulfonyl)-4,4a,5,6,7, 8-hexahydro-1H-pyrazolo[3,4-g]isoquinolin-4a-yl)(pyridin-2-yl)methanone, (R)-(1-(4-fluorophenyl)-6-(m-tolylsulfonyl)-4,4a,5,6,7,8-hexahydro-1H-pyrazolo[3,4-g]isoquinolin-4a-yl)(6-methylpyridin-2-yl)methanone, (R)-(6-((3-chloro-4-fluorophenyl)sulfonyl)-1-(4-fluorophenyl)-4,4a,5,6,7,8-hexahydro-1H-pyrazolo[3,4-g]isoquinolin-4a-yl)(pyridin-2-yl)methanone, (R)-3-((1-(4-fluorophenyl)-4a-(4-methylpicolinoyl)-4a,5,7,8-tetrahydro-1H-pyrazolo[3,4-g]isoquinolin-6(4H)-yl)sulfonyl)benzonitrile, (R)-(1-(4-fluorophenyl)-6-((1-methyl-1H-pyrazol-4-yl)sulfonyl)-4,4a, 5,6,7,8-hexahydro-1H-pyrazolo[3,4-g]isoquinolin-4a-yl)(4-methylpyridin-2-yl)methanone, (R)-(6-((3,4-difluorophenyl)sulfonyl)-1-(4-fluorophenyl)-4,4a,5,6,7,8-hexahydro-1H-pyrazolo[3,4-g]isoquinolin-4a-yl)(4-methylpyridin-2-yl)methanone, (R)-(1-(4-fluorophenyl)-6-((1-methyl-1H-imidazol-4-yl)sulfonyl)-4,4a,5,6,7,8-hexahydro-1H-pyrazolo[3,4-g]isoquinolin-4a-yl)(4-methylpyridin-2-yl)methanone, (R)-(1-(4-fluorophenyl)-6-(m-tolylsulfonyl)-4,4a,5,6,7,8-hexahydro-1H-pyrazolo[3,4-g]isoquinolin-4a-yl)(pyrimidin-2-yl)methanone, (R)-(6-((4-fluoro-3-(trifluoromethyl)phenyl)sulfonyl)-1-(4-fluorophenyl)-4,4a,5,6,7,8-hexahydro-1H-pyrazolo[3,4-g]isoquinolin-4a-yl)(thiazol-2-yl)methanone, (R)-(6-((3,5-difluorophenyl)sulfonyl)-1-(4-fluorophenyl)-4,4a,5,6,7,8-hexahydro-1H-pyrazolo[3,4-g]isoquinolin-4a-yl)(4-methylpyridin-2-yl)methanone, (R)-(1-(4-fluorophenyl)-6-((3,4,5-trifluorophenyl)sulfonyl)-4,4a,5,6,7,8-hexahydro-1H-pyrazolo[3,4-g]isoquinolin-4a-yl)(4-methylpyridin-2-yl)methanone, (R)-(1-(4-fluorophenyl)-6-((3-(methylsulfonyl)phenyl)sulfonyl)-4,4a,5,6,7,8-hexahydro-1H-pyrazolo[3,4-g]isoquinolin-4a-yl)(pyridin-2-yl)methanone, (R)-3-((1-(4-fluorophenyl)-4a-picolinoyl-4a,5,7,8-tetrahydro-1H-pyrazolo[3,4-g]isoquinolin-6(4H)-yl)sulfonyl)benzoic acid, (R)-3-((1-(4-fluorophenyl)-4a-picolinoyl-4a,5,7,8-tetrahydro-1H-pyrazolo[3,4-g]isoquinolin-6(4H)-yl)sulfonyl)-N,N-dimethylbenzamide, (R)-(1-(4-fluorophenyl)-6-((3-(methoxymethyl)phenyl)sulfonyl)-4,4a,5,6,7,8-hexahydro-1H-pyrazolo[3,4-g]isoquinolin-4a-yl)(pyridin-2-yl)methanone, (R)-(1-(4-fluorophenyl)-6-((4-methyl-3,4-dihydro-2H-pyrido[3,2-b][1,4]oxazin-7-yl)sulfonyl)-4,4a,5,6,7, 8-hexahydro-1H-pyrazolo[3,4-g]isoquinolin-4a-yl)(pyridin-2-yl)methanone, (R)-(1-(4-fluorophenyl)-6-((2,3,4-trifluorophenyl)sulfonyl)-4,4a,5,6,7,8-hexahydro-1H-pyrazolo[3,4-g]isoquinolin-4a-yl)(pyridin-2-yl)methanone, (R)-(1-(4-fluorophenyl)-6-((3,4,5-trifluorophenyl)sulfonyl)-4,4a,5,6,7,8-hexahydro-1H-pyrazolo[3,4-g]isoquinolin-4a-yl)(thiazol-2-yl)methanone, (R)-(1-(4-fluorophenyl)-6-((6-(trifluoromethyl)pyridin-2-yl)sulfonyl)-4,4a,5,6,7,8-hexahydro-1H-pyrazolo[3,4-g]isoquinolin-4a-yl)(pyridin-2-yl)methanone, (R)-(1-(4-fluorophenyl)-6-((6-(trifluoromethyl)pyridin-2-yl)sulfonyl)-4,4a,5,6,7,8-hexahydro-1H-pyrazolo[3,4-g]isoquinolin-4a-yl)(4-methylpyridin-2-yl)methanone, (R)-(6-((3,4-dichlorophenyl)sulfonyl)-1-(4-fluorophenyl)-4,4a,5,6,7,8-hexahydro-1H-pyrazolo[3,4-g]isoquinolin-4a-yl)(pyridin-2-yl)methanone, (R)-(1-(4-fluorophenyl)-6-((3-(trifluoromethyl)phenyl)sulfonyl)-4,4a,5,6,7,8-hexahydro-1H-pyrazolo[3,4-g]isoquinolin-4a-yl)(4-methylpyridin-2-yl)methanone, (R)-(6-((1-ethyl-1H-pyrazol-4-yl)sulfonyl)-1-(4-fluorophenyl)-4,4a,5,6,7,8-hexahydro-1H-pyrazolo[3,4-g]isoquinolin-4a-yl)(4-methylpyridin-2-yl)methanone, (R)-(6-((1,5-dimethyl-1H-pyrazol-4-yl)sulfonyl)-1-(4-fluorophenyl)-4,4a,5,6,7,8-hexahydro-1H-pyrazolo[3,4-g]isoquinolin-4a-yl)(4-methylpyridin-2-yl)methanone, (R)-(1-(4-fluorophenyl)-6-((1-methyl-1H-pyrazol-5-yl)sulfonyl)-4,4a, 5,6,7,8-hexahydro-1H-pyrazolo[3,4-g]isoquinolin-4a-yl)(4-methylpyridin-2-yl)methanone, (R)-(1-(4-fluorophenyl)-6-((1-methyl-1H-pyrazol-3-yl)sulfonyl)-4,4a, 5,6,7,8-hexahydro-1H-pyrazolo[3,4-g]isoquinolin-4a-yl)(4-methylpyridin-2-yl)methanone, (R)-(6-((4-fluoro-3-methylphenyl)sulfonyl)-1-(4-fluorophenyl)-4,4a,5,6,7,8-hexahydro-1H-pyrazolo[3,4-g]isoquinolin-4a-yl)(4-methylpyridin-2-yl)methanone, (R)-(1-(4-fluorophenyl)-6-((1-methyl-1H-pyrazol-4-yl)sulfonyl)-4,4a,5,6,7,8-hexahydro-1H-pyrazolo[3,4-g]isoquinolin-4a-yl)(4-(trifluoromethyl)pyridin-2-yl)methanone, (R)-(1-(4-fluorophenyl)-6-((4-methyl-3,4-dihydro-2H-pyrido[3,2-b][1,4]oxazin-7-yl)sulfonyl)-4,4a,5,6,7, 8-hexahydro-1H-pyrazolo[3,4-g]isoquinolin-4a-yl)(4-methylpyridin-2-yl)methanone, (R)-(6-((2,3-dihydrobenzofuran-5-yl)sulfonyl)-1-(4-fluorophenyl)-4,4a,5,6,7,8-hexahydro-1H-pyrazolo[3,4-g]isoquinolin-4a-yl)(4-methylpyridin-2-yl)methanone, (R)-5-((1-(4-fluorophenyl)-4a-(4-methylpicolinoyl)-4a,5,7,8-tetrahydro-1H-pyrazolo[3,4-g]isoquinolin-6(4H)-yl)sulfonyl)-1-methylindolin-2-one, (R)-(1-(4-fluorophenyl)-6-((3-(methylsulfonyl)phenyl)sulfonyl)-4,4a,5,6,7,8-hexahydro-1H-pyrazolo[3,4-g]isoquinolin-4a-yl)(4-methylpyridin-2-yl)methanone, (R)-(6-((3,5-difluorophenyl)sulfonyl)-1-(4-fluorophenyl)-4,4a,5,6,7,8-hexahydro-1H-pyrazolo[3,4-g]isoquinolin-4a-yl)(4-methoxypyridin-2-yl)methanone, (R)-(6-((1,3-dimethyl-1H-pyrazol-4-yl)sulfonyl)-1-(4-fluorophenyl)-4,4a,5,6,7,8-hexahydro-1H-pyrazolo[3,4-g]isoquinolin-4a-yl)(4-methylpyridin-2-yl)methanone, (R)-(6-((2,3-dihydrobenzo[b][1,4]dioxin-6-yl)sulfonyl)-1-(4-fluorophenyl)-4,4a,5,6,7,8-hexahydro-1H-pyrazolo[3,4-g]isoquinolin-4a-yl)(4-methylpyridin-2-yl)methanone, (R)-(6-((3-fluoro-4-(trifluoromethyl)phenyl)sulfonyl)-1-(4-fluorophenyl)-4,4a,5,6,7,8-hexahydro-1H-pyrazolo[3,4-g]isoquinolin-4a-yl)(4-methylpyridin-2-yl)methanone, (R)-(6-((3-fluoro-4-(trifluoromethyl)phenyl)sulfonyl)-1-(4-fluorophenyl)-4,4a,5,6,7,8-hexahydro-1H-pyrazolo[3,4-g]isoquinolin-4a-yl)(pyridin-2-yl)methanone, (R)-(6-((3-fluoro-4-(trifluoromethyl)phenyl)sulfonyl)-1-(4-fluorophenyl)-4,4a,5,6,7,8-hexahydro-1H-pyrazolo[3,4-g]isoquinolin-4a-yl)(thiazol-2-yl)methanone, (R)-3-((4a-(4-ethylpicolinoyl)-1-(4-fluorophenyl)-4a,5,7,8-tetrahydro-1H-pyrazolo[3,4-g]isoquinolin-6(4H)-yl)sulfonyl)benzonitrile, (R)-(4-ethylpyridin-2-yl)(1-(4-fluorophenyl)-6-((6-(trifluoromethyl)pyridin-2-yl)sulfonyl)-4,4a,5,6,7,8-hexahydro-1H-pyrazolo[3,4-g]isoquinolin-4a-yl)methanone, (R)-3-((1-(4-fluorophenyl)-4a-(4-methylpicolinoyl)-4a,5,7,8-tetrahydro-1H-pyrazolo[3,4-g]isoquinolin-6(4H)-yl)sulfonyl)benzoic acid, (R)-(6-((3,5-dimethylisoxazol-4-yl)sulfonyl)-1-(4-fluorophenyl)-4,4a,5,6,7,8-hexahydro-1H-pyrazolo[3,4-g]isoquinolin-4a-yl)(4-methylpyridin-2-yl)methanone, (R)-(1-(4-fluorophenyl)-6-((3-(trifluoromethyl)phenyl)sulfonyl)-4,4a,5,6,7,8-hexahydro-1H-pyrazolo[3,4-g]isoquinolin-4a-yl)(5-methylthiazol-2-yl)methanone, (R)-(6-((1-ethyl-1H-pyrazol-4-yl)sulfonyl)-1-(4-fluorophenyl)-4,4a,5,6,7,8-hexahydro-1H-pyrazolo[3,4-g]isoquinolin-4a-yl)(pyridin-2-yl)methanone, (R)-(1-phenyl-6-((3-(trifluoromethyl)phenyl)sulfonyl)-4,4a,5,6,7,8-hexahydro-1H-pyrazolo[3,4-g]isoquinolin-4a-yl)(pyridin-2-yl)methanone, (R)-(6-((1,3-dimethyl-1H-pyrazol-5-yl)sulfonyl)-1-(4-fluorophenyl)-4,4a,5,6,7,8-hexahydro-1H-pyrazolo[3,4-g]isoquinolin-4a-yl)(4-methylpyridin-2-yl)methanone, (R)-(1-(4-fluorophenyl)-6-((2-(trifluoromethyl)pyridin-4-yl)sulfonyl)-4,4a,5,6,7,8-hexahydro-1H-pyrazolo[3,4-g]isoquinolin-4a-yl)(4-methylpyridin-2-yl)methanone, (R)-(4-ethylpyridin-2-yl)(1-(4-fluorophenyl)-6-((3,4,5-trifluorophenyl)sulfonyl)-4,4a,5,6,7,8-hexahydro-1H-pyrazolo[3,4-g]isoquinolin-4a-yl)methanone, (R)-(1-(4-fluorophenyl)-6-((3,4,5-trifluorophenyl)sulfonyl)-4,4a,5,6,7,8-hexahydro-1H-pyrazolo[3,4-g]isoquinolin-4a-yl)(4-methoxypyridin-2-yl)methanone, (R)-(1-(4-fluorophenyl)-6-((3-(trifluoromethyl)phenyl)sulfonyl)-4,4a,5,6,7,8-hexahydro-1H-pyrazolo[3,4-g]isoquinolin-4a-yl)(4-methylthiazol-2-yl)methanone, (R)-(1-(4-fluorophenyl)-6-((4-(trifluoromethyl)pyridin-2-yl)sulfonyl)-4,4a,5,6,7,8-hexahydro-1H-pyrazolo[3,4-g]isoquinolin-4a-yl)(4-methylpyridin-2-yl)methanone, (R)-(1-(4-fluorophenyl)-6-((5-methyl-1H-pyrazol-4-yl)sulfonyl)-4,4a,5,6,7,8-hexahydro-1H-pyrazolo[3,4-g]isoquinolin-4a-yl)(4-methylpyridin-2-yl)methanone, (R)-(6-((1-ethyl-1H-pyrazol-4-yl)sulfonyl)-1-(4-fluorophenyl)-4,4a,5,6,7,8-hexahydro-1H-pyrazolo[3,4-g]isoquinolin-4a-yl)(4-(trifluoromethyl)pyridin-2-yl)methanone, (R)-(6-((3,4-dichlorophenyl)sulfonyl)-1-(4-fluorophenyl)-4,4a,5,6,7,8-hexahydro-1H-pyrazolo[3,4-g]isoquinolin-4a-yl)(thiazol-2-yl)methanone, (R)-(1-(4-fluorophenyl)-6-((2-(trifluoromethyl)pyridin-4-yl)sulfonyl)-4,4a,5,6,7,8-hexahydro-1H-pyrazolo[3,4-g]isoquinolin-4a-yl)(pyridin-2-yl)methanone, (R)-pyridin-2-yl(1-(pyridin-3-yl)-6-((3-(trifluoromethyl)phenyl)sulfonyl)-4,4a,5,6,7,8-hexahydro-1H-pyrazolo[3,4-g]isoquinolin-4a-yl)methanone, (R)-(6-((3,4-dichlorophenyl)sulfonyl)-1-(4-fluorophenyl)-4,4a,5,6,7,8-hexahydro-1H-pyrazolo[3,4-g]isoquinolin-4a-yl)(5-methylthiazol-2-yl)methanone, (R)-(6-((4-chloro-3-(trifluoromethyl)phenyl)sulfonyl)-1-(4-fluorophenyl)-4,4a,5,6,7,8-hexahydro-1H-pyrazolo[3,4-g]isoquinolin-4a-yl)(pyridin-2-yl)methanone, (R)-(6-((3-chloro-4-methylphenyl)sulfonyl)-1-(4-fluorophenyl)-4,4a,5,6,7,8-hexahydro-1H-pyrazolo[3,4-g]isoquinolin-4a-yl)(pyridin-2-yl)methanone, (R)-(6-((3,4-dichlorophenyl)sulfonyl)-1-phenyl-4,4a,5,6,7,8-hexahydro-1H-pyrazolo[3,4-g]isoquinolin-4a-yl)(pyridin-2-yl)methanone, (R)-(6-((3,4-difluorophenyl)sulfonyl)-1-(4-fluorophenyl)-4,4a,5,6,7,8-hexahydro-1H-pyrazolo[3,4-g]isoquinolin-4a-yl)(thiazol-2-yl)methanone, (R)-(6-((3,4-difluorophenyl)sulfonyl)-1-(4-fluorophenyl)-4,4a,5,6,7,8-hexahydro-1H-pyrazolo[3,4-g]isoquinolin-4a-yl)(2-(pyrrolidin-1-yl)pyridin-4-yl)methanone, (R)-(1-(4-fluorophenyl)-6-((1-methyl-1H-pyrazol-3-yl)sulfonyl)-4,4a, 5,6,7,8-hexahydro-1H-pyrazolo[3,4-g]isoquinolin-4a-yl)(4-(trifluoromethyl)pyridin-2-yl)methanone, (R)-(1-(4-fluorophenyl)-6-((1-methyl-1H-pyrazol-3-yl)sulfonyl)-4,4a, 5,6,7,8-hexahydro-1H-pyrazolo[3,4-g]isoquinolin-4a-yl)(pyridin-2-yl)methanone, (R)-(1-(4-fluorophenyl)-6-((5-methyl-1H-pyrazol-4-yl)sulfonyl)-4,4a,5,6,7,8-hexahydro-1H-pyrazolo[3,4-g]isoquinolin-4a-yl)(4-(trifluoromethyl)pyridin-2-yl)methanone, (R)-3-((1-(4-fluorophenyl)-4a-(4-(trifluoromethyl)picolinoyl)-4a,5,7,8-tetrahydro-1H-pyrazolo[3,4-g]isoquinolin-6(4H)-yl)sulfonyl)benzonitrile, (R)-(6-((3,4-dichlorophenyl)sulfonyl)-1-(3,4-difluorophenyl)-4,4a,5,6,7,8-hexahydro-1H-pyrazolo[3,4-g]isoquinolin-4a-yl)(pyridin-2-yl)methanone, (R)-(6-((3,4-dichlorophenyl)sulfonyl)-1-(4-fluorophenyl)-4,4a,5,6,7,8-hexahydro-1H-pyrazolo[3,4-g]isoquinolin-4a-yl)(thiazol-4-yl)methanone, (R)-(1-(4-fluorophenyl)-6-((1-methyl-1H-pyrazol-5-yl)sulfonyl)-4,4a, 5,6,7,8-hexahydro-1H-pyrazolo[3,4-g]isoquinolin-4a-yl)(4-(trifluoromethyl)pyridin-2-yl)methanone, (R)-(6-((1,5-dimethyl-1H-pyrazol-4-yl)sulfonyl)-1-(4-fluorophenyl)-4,4a,5,6,7,8-hexahydro-1H-pyrazolo[3,4-g]isoquinolin-4a-yl)(4-(trifluoromethyl)pyridin-2-yl)methanone,
(R)-(6-((1H-pyrazol-4-yl)sulfonyl)-1-(4-fluorophenyl)-4,4a,5,6,7,8-hexahydro-1H-pyrazolo[3,4-g]isoquinolin-4a-yl)(4-(trifluoromethyl)pyridin-2-yl)methanone,
(R)-(1-(4-fluorophenyl)-6-((1-methyl-3-(trifluoromethyl)-1H-pyrazol-4-yl)sulfonyl)-4,4a,5,6,7,8-hexahydro-1H-pyrazolo[3,4-g]isoquinolin-4a-yl)(pyridin-2-yl)methanone,
(R)-(6-((3,4-difluorophenyl)sulfonyl)-1-(4-fluorophenyl)-4,4a,5,6,7,8-hexahydro-1H-pyrazolo[3,4-g]isoquinolin-4a-yl)(5-methylthiazol-2-yl)methanone,
(R)-(6-((4-chloro-3-fluorophenyl)sulfonyl)-1-(4-fluorophenyl)-4,4a,5,6,7,8-hexahydro-1H-pyrazolo[3,4-g]isoquinolin-4a-yl)(5-methylthiazol-2-yl)methanone,
(R)-(1-(4-fluorophenyl)-6-((1-methyl-1H-pyrazol-3-yl)sulfonyl)-4,4a,5,6,7,8-hexahydro-1H-pyrazolo[3,4-g]isoquinolin-4a-yl)(5-methylthiazol-2-yl)methanone,
(R)-(6-((6-(dimethylamino)pyridin-3-yl)sulfonyl)-1-(4-fluorophenyl)-4,4a,5,6,7,8-hexahydro-1H-pyrazolo[3,4-g]isoquinolin-4a-yl)(pyridin-2-yl)methanone,
(R)-(1-(4-fluorophenyl)-6-((3,4,5-trifluorophenyl)sulfonyl)-4,4a,5,6,7,8-hexahydro-1H-pyrazolo[3,4-g]isoquinolin-4a-yl)(4-(trifluoromethyl)pyridin-2-yl)methanone,
(R)-(1-(4-chlorophenyl)-6-((1-methyl-1H-pyrazol-3-yl)sulfonyl)-4,4a,5,6,7,8-hexahydro-1H-pyrazolo[3,4-g]isoquinolin-4a-yl)(4-(trifluoromethyl)pyridin-2-yl)methanone,
(R)-(1-(4-fluorophenyl)-6-((1-methyl-1H-pyrazol-4-yl)sulfonyl)-4,4a,5,6,7,8-hexahydro-1H-pyrazolo[3,4-g]isoquinolin-4a-yl)(5-methylthiazol-2-yl)methanone,
(R)-(6-((1-ethyl-1H-pyrazol-5-yl)sulfonyl)-1-(4-fluorophenyl)-4,4a,5,6,7,8-hexahydro-1H-pyrazolo[3,4-g]isoquinolin-4a-yl)(4-(trifluoromethyl)pyridin-2-yl)methanone,
(R)-(6-((3,5-dimethyl-1H-pyrazol-4-yl)sulfonyl)-1-(4-fluorophenyl)-4,4a,5,6,7,8-hexahydro-1H-pyrazolo[3,4-g]isoquinolin-4a-yl)(4-(trifluoromethyl)pyridin-2-yl)methanone,
(R)-(6-((1H-imidazol-4-yl)sulfonyl)-1-(4-fluorophenyl)-4,4a,5,6,7,8-hexahydro-1H-pyrazolo[3,4-g]isoquinolin-4a-yl)(4-(trifluoromethyl)pyridin-2-yl)methanone,
(R)-(6-((1,3-dimethyl-1H-pyrazol-5-yl)sulfonyl)-1-(4-fluorophenyl)-4,4a,5,6,7,8-hexahydro-1H-pyrazolo[3,4-g]isoquinolin-4a-yl)(5-methylthiazol-2-yl)methanone,
(R)-(1-(4-fluorophenyl)-6-((1-methyl-1H-pyrazol-5-yl)sulfonyl)-4,4a,5,6,7,8-hexahydro-1H-pyrazolo[3,4-g]isoquinolin-4a-yl)(5-methylthiazol-2-yl)methanone,
(R)-(6-((1H-pyrazol-4-yl)sulfonyl)-1-(4-fluorophenyl)-4,4a,5,6,7,8-hexahydro-1H-pyrazolo[3,4-g]isoquinolin-4a-yl)(pyridin-2-yl)methanone,
(R)-5-((1-(4-fluorophenyl)-4a-picolinoyl-4a,5,7,8-tetrahydro-1H-pyrazolo[3,4-g]isoquinolin-6(4H)-yl)sulfonyl)-1-methylpyridin-2(1H)-one,
(R)-(6-((1-methyl-1H-pyrazol-3-yl)sulfonyl)-1-(4-(trifluoromethyl)phenyl)-4,4a,5,6,7,8-hexahydro-1H-pyrazolo[3,4-g]isoquinolin-4a-yl)(pyridin-2-yl)methanone, or salts thereof.

17. The method of claim 1, wherein the compound is selected from the group consisting of:
(R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(pyridin-2-yl)methanone,
(R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(thiazol-2-yl)methanone, and
(R)-(1-(4-fluorophenyl)-6-((3-(trifluoromethyl)phenyl)sulfonyl)-4,4a,5,6,7,8-hexahydro-1H-pyrazolo[3,4-g]isoquinolin-4a-yl)(pyridin-2-yl)methanone.

18. The method of claim 1, wherein the compound is selected from the group consisting of:
(R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(pyridin-2-yl)methanone, and
(R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(thiazol-2-yl)methanone.

19. The method of claim 1, wherein the compound is selected from the group consisting of:
(R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(pyridin-2-yl)methanone,
(R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(thiazol-2-yl)methanone,
(R)-(6-((3,4-difluorophenyl)sulfonyl)-1-(4-fluorophenyl)-4,4a,5,6,7,8-hexahydro-1H-pyrazolo[3,4-g]isoquinolin-4a-yl)(pyridin-2-yl)methanone,
(R)-(6-((3,4-dichlorophenyl)sulfonyl)-1-(4-fluorophenyl)-4,4a,5,6,7,8-hexahydro-1H-pyrazolo[3,4-g]isoquinolin-4a-yl)(pyridin-2-yl)methanone,
(R)-(1-(4-fluorophenyl)-6-((1-methyl-1H-pyrazol-4-yl)sulfonyl)-4,4a,5,6,7,8-hexahydro-1H-pyrazolo[3,4-g]isoquinolin-4a-yl)(4-(trifluoromethyl)pyridin-2-yl)methanone,
(R)-(6-((3,4-dichlorophenyl)sulfonyl)-1-(4-fluorophenyl)-4,4a,5,6,7,8-hexahydro-1H-pyrazolo[3,4-g]isoquinolin-4a-yl)(thiazol-2-yl)methanone, and
(R)-(6-((3,4-dichlorophenyl)sulfonyl)-1-(4-fluorophenyl)-4,4a,5,6,7,8-hexahydro-1H-pyrazolo[3,4-g]isoquinolin-4a-yl)(5-methylthiazol-2-yl)methanone.

* * * * *